US011452275B2

(12) United States Patent
Frederick et al.

(10) Patent No.: US 11,452,275 B2
(45) Date of Patent: Sep. 27, 2022

(54) TOBACCO PLANTS HAVING ALTERED AMOUNTS OF ONE OR MORE ALKALOIDS IN LEAF AND METHODS OF USING SUCH PLANTS

(71) Applicant: ALTRIA CLIENT SERVICES LLC, Richmond, VA (US)

(72) Inventors: Jesse Frederick, Richmond, VA (US); Yanxin Shen, Glen Allen, VA (US); Dongmei Xu, Glen Allen, VA (US); Ujwala Warek, Chester, VA (US); James Arthur Strickland, Richmond, VA (US)

(73) Assignee: Altria Client Services LLC, Richmond, VA (US)

( * ) Notice: Subject to any disclaimer, the term of this patent is extended or adjusted under 35 U.S.C. 154(b) by 0 days.

(21) Appl. No.: 17/005,942

(22) Filed: Aug. 28, 2020

(65) Prior Publication Data

US 2021/0084852 A1 Mar. 25, 2021

Related U.S. Application Data

(60) Continuation of application No. 15/914,033, filed on Mar. 7, 2018, now Pat. No. 10,813,318, which is a division of application No. 14/563,211, filed on Dec. 8, 2014, now abandoned.

(60) Provisional application No. 62/011,304, filed on Jun. 12, 2014, provisional application No. 61/912,752, filed on Dec. 6, 2013.

(51) Int. Cl.
*A01H 5/12* (2018.01)
*A24B 15/20* (2006.01)
*C12N 15/82* (2006.01)
*A01H 6/82* (2018.01)
*C07K 14/415* (2006.01)
*A01H 1/02* (2006.01)
*A01H 1/06* (2006.01)
*C12Q 1/6895* (2018.01)
*G01N 33/00* (2006.01)

(52) U.S. Cl.
CPC .............. *A01H 6/823* (2018.05); *A01H 1/02* (2013.01); *A01H 1/06* (2013.01); *A01H 5/12* (2013.01); *A24B 15/20* (2013.01); *C07K 14/415* (2013.01); *C12N 15/8243* (2013.01); *C12Q 1/6895* (2013.01); *G01N 33/0098* (2013.01); *C12Q 2600/13* (2013.01); *C12Q 2600/156* (2013.01); *C12Q 2600/16* (2013.01)

(58) Field of Classification Search
CPC .......... A01H 5/12; A01H 6/823; A24B 15/10; A24B 15/20; A24B 15/243; A24B 15/245
See application file for complete search history.

(56) References Cited

U.S. PATENT DOCUMENTS

| | | | |
|---|---|---|---|
| 3,927,682 A | 12/1975 | Matsuyama | |
| 4,528,993 A | 7/1985 | Sensabaugh, Jr. et al. | |
| 4,660,577 A | 4/1987 | Sensabaugh, Jr. et al. | |
| 4,683,195 A | 7/1987 | Mullis et al. | |
| 4,683,202 A | 7/1987 | Kary | |
| 4,761,373 A | 9/1988 | Anderson et al. | |
| 4,769,061 A | 9/1988 | Comai | |
| 4,800,159 A | 1/1989 | Mullis et al. | |
| 4,810,648 A | 3/1989 | Stalker | |
| 4,848,373 A | 7/1989 | Lenkey | |
| 4,940,835 A | 7/1990 | Shah et al. | |
| 4,965,188 A | 10/1990 | Mullis et al. | |
| 4,975,374 A | 12/1990 | Goodman et al. | |
| 5,013,659 A | 5/1991 | Bedbrook et al. | |
| 5,162,602 A | 11/1992 | Somers et al. | |
| 5,164,180 A | 11/1992 | Payne et al. | |
| 5,276,268 A | 1/1994 | Strauch et al. | |
| 5,372,149 A | 12/1994 | Roth et al. | |
| 5,545,565 A | 8/1996 | De Greve et al. | |
| 5,561,236 A | 10/1996 | Leemans et al. | |
| 5,767,366 A | 6/1998 | Sathasivan et al. | |
| 5,879,903 A | 3/1999 | Strauch et al. | |
| 5,928,937 A | 7/1999 | Kakefuda et al. | |
| 6,084,155 A | 7/2000 | Volrath et al. | |
| 6,166,302 A | 12/2000 | Merlo et al. | |
| 6,451,732 B1 | 9/2002 | Beckett et al. | |
| 6,451,735 B1 | 9/2002 | Ottaway et al. | |
| 2001/0016956 A1 | 8/2001 | Ward et al. | |
| 2005/0244521 A1 | 11/2005 | Strickland et al. | |
| 2006/0191548 A1 | 8/2006 | Strickland et al. | |
| 2010/0218270 A1* | 8/2010 | Xu | C12N 9/0073 800/317.3 |

(Continued)

FOREIGN PATENT DOCUMENTS

| | | |
|---|---|---|
| EP | 0242246 | 10/1987 |
| WO | WO 2009/061422 | 5/2009 |

OTHER PUBLICATIONS

Bienert, Manuela D., et al. "A pleiotropic drug resistance transporter in Nicotiana tabacum is involved in defense against the herbivore Manduca sexta." The Plant Journal 72.5 (2012): 745-757. (Year: 2012).*

(Continued)

*Primary Examiner* — Weihua Fan
(74) *Attorney, Agent, or Firm* — Arnold & Porter Kaye Scholer

(57) ABSTRACT

This disclosure provides a number of sequences involved in the transport of alkaloids from the root to the leaf in tobacco, methods of using such sequences, tobacco plants carrying modifications to such sequences, and tobacco products made from such plants.

13 Claims, 19 Drawing Sheets

Specification includes a Sequence Listing.

(56) References Cited

U.S. PATENT DOCUMENTS

| | | |
|---|---|---|
| 2012/0024301 A1 | 2/2012 | Carroll et al. |
| 2012/0031414 A1 | 2/2012 | Atchley et al. |
| 2012/0031416 A1 | 2/2012 | Atchley et al. |

OTHER PUBLICATIONS

Zhang, Yong, et al. "Transcription activator-like effector nucleases enable efficient plant genome engineering." Plant physiology 161.1 (2013): 20-27 (Year: 2013).*
GenBank: AFN42938.1. Retrieved from https://www.ncbi.nlm.nih.gov/protein/AFN42938.1?report=genpept (Year: 2012).*
AbuQamar et al., "Expression profiling and mutant analysis reveals complex regulatory networks involved in *Arabidopsis* response to Botrytis infection," The Plant Journal 48(1):28-44, 2006.
Brown et al., "Identification of novel genes in *Arabidopsis* involved in secondary cell wall formation using expression profiling and reverse genetics," The Plant Cell 17(8):2281-2295, 2005.
Brown et al., "The multidrug efflux protein NorM is a prototype of a new family of transporters," Mol. Microbiol., 31:394-5, Jan. 1999.
Chenna et al., "Multiple sequence alignment with the Clustal series of programs," Nucleic Acids Res., 31:13, 3497-3500, Jul. 2003.
Dayhoff et al., "A Model of Evolutionary Change in Proteins," Atlas of Protein Sequence and Structure, 5:3, 345-352, 1978.
European Examination in Application No. 14821961.1, dated Oct. 18, 2017, 15 pages.
Fischhoff et al., "Insect Tolerant Transgenic Tomato Plants," Nature Biotechnology, 5, 807-813, 1987.
Galle et al., "The role of mesophyll conductance during water stress and recovery in tobacco (*Nicotiana sylvestris*): acclimation or limitation?," journal of Experimental Botany 60(8):2379-2390, 2009.
GenBank Accession No. EB444445 GI: 92032740, "KR2B.103N01F.051227T7 KR2B Nicotiana tabacum cDNA clone KR2B.103N01, mRNA sequence," Apr. 13, 2006, 1 page.
GenBank Accession No. ET901945 GI: 191552991, "CHO_OF131xd13fl.ab 1 CHO_of Nicotiana tabacum genomic 5-, genomic survey sequence," Jun. 21, 2008, 1 page.
Hashimoto et al., "New genes in alkaloid metabolism and transport," Current Opinion in Biotechnology, 14(2): 163-168, Apr. 2003.
Hildreth et al., "Tobacco nicotine uptake permease (NUP1) affects alkaloid metabolism," PNAS USA, 108:44, 18179-18184, Nov. 1, 2011.
International Preliminary Report on Patentability in International Application No. PCT/US2014/069074, dated Jun. 16, 2016, 14 pages.
International Search Report and Written Opinion in International Application No. PCT/US2014/069074, dated May 19, 2015, 20 pages.
Li et al., "A fast neutron deletion mutagenesis-based reverse genetics system for plants," Plant J., 27:3, 235-242, Dec. 2001.
Li et al., "Modularly assembled designer TAL effector nucleases for targeted gene knockout and gene replacement in eukaryotes," Nucleic Acids Res., 39:14, 6315-3625, Aug. 2011.
Lorkovic and Barta, "Genome analysis: RNA recognition motif (RRM) and K homology (KH) domain RNA-binding proteins from the flowering plant *Arabidopsis thaliana*," Nuc. Acids Res., 30:3, 623-635, Feb. 2002.
Moons, "Transcriptional profiling of the PDR gene family in rice roots in response to plant growth regulators, redox perturbations and weak organic acid stresses," Planta, 229:1, 53-71, Dec. 2008.
Morita et al., "Vacuolar transport of nicotine is mediated by a multidrug and toxic compound extrusion (MATE) transporter in Nicotiana tabacum," Proceedings of the National Academy of Sciences of the United States of America, 106(7):2447-2452, Feb. 2009.
Office Action issued Japanese Patent Application No. 2016-536526 dated Nov. 12, 2018, with English translation.
Okuzaki and Tabei, "Improvement of the plastid transformation protocol by modifying tissue treatment at pre- and post-bombardment in tobacco," Plant Biotechnology, 29, 307-310, Jun. 2012.
Pakdeechanuan et al., "Root-to-shoot Translocation of Alkaloids is Dominantly Suppressed in Nicotiana alata," Plant and Cell Physiology 53(7):1247-1254, Jul. 2012.
Seguin et al., "Characterization of a gene encoding a DNA-binding protein that interacts in vitro with vascular specific cis elements of the phenylalanine ammonia-lyase promoter," Plant Mol. Biol., 35:3, 281-91, Oct. 1997.
Shitan et al., "Identification of a nicotine transporter in leaf vacuoles of Nicotiana tabacum," Plant Signaling and Behavior 4(6):530-532, 2009.
Shoji et al., "Multidrag and toxic compound extrusion-type transporters implicated in vacuolar sequestration of nicotine in tobacco roots," Plant Physiology 149(2):708-718, 2009.
Wright et al., "High-frequency homologous recombination in plants mediated by zinc-finger nucleases," The Plant J., 44:4, 693-705, Nov. 2005.
Yoo et al., "*Arabidopsis* mesophyll protoplasts: a versatile cell system for transient gene expression analysis," Nature Protocols, 2:7, 1565-1572, Jun. 2007.

* cited by examiner

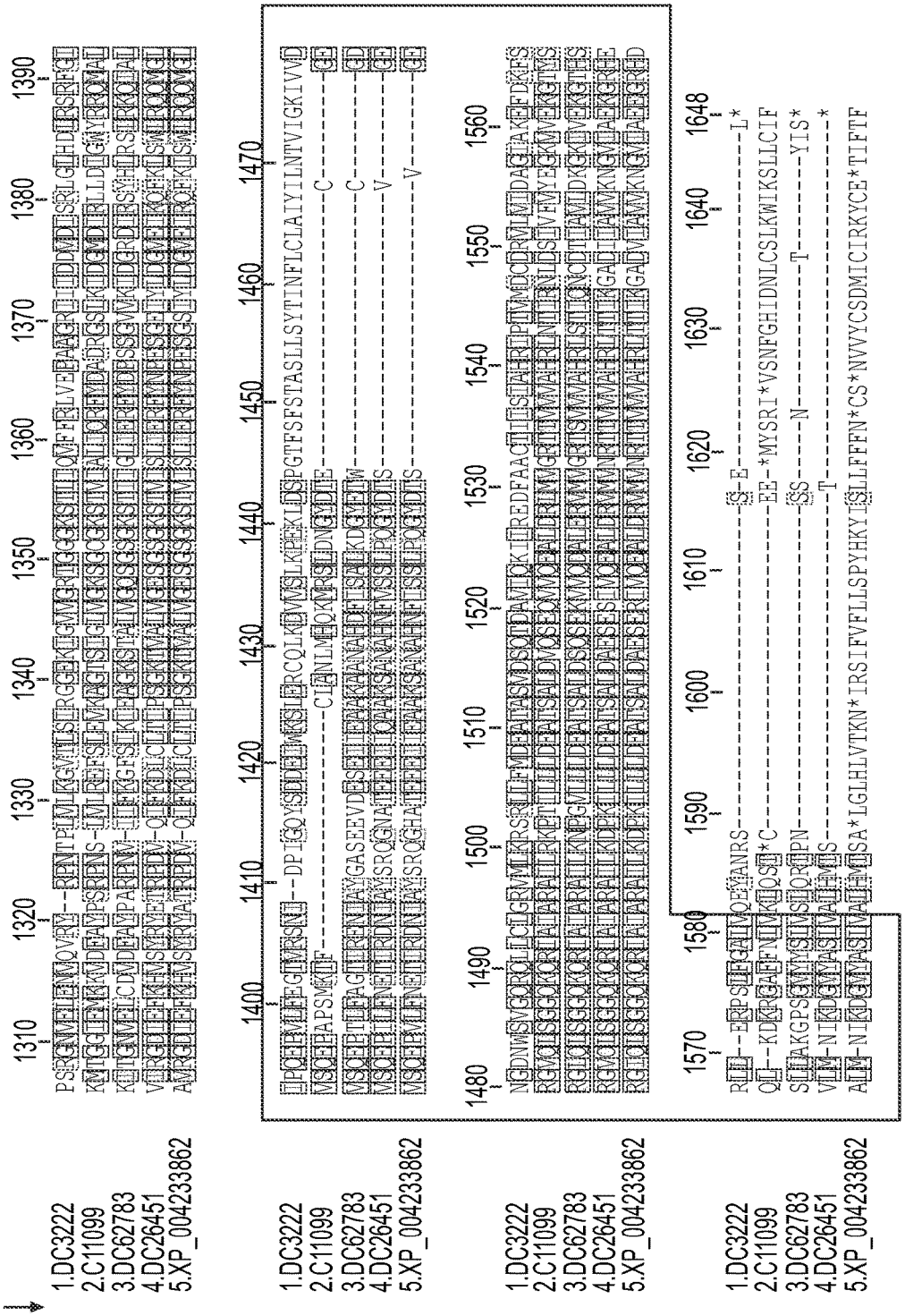
FIGURE 2 (CONT.-3)

Transformation cassette sequence (SEQ ID NO:57):

```
               ┌ aagcttCCAG AAGGTAATTA TCCAAGATGT AGCATCAAGA ATCCAATGTT TACGGGAAAA    60
               │ ACTATGGAAG TATTATGTGA GCTCAGCAAG AAGCAGATCA ATATGCGGCA CATATGCAAC   120
               │ CTATGTTCAA AAATGAAGAA TGTACAGATA CAAGATCCTA TACTGCCAGA ATACGAAGAA   180
pCSVMV         │ GAATACGTAG AAATTGAAAA AGAAGAACCA GGCGAAGAAA AGAATCTTGA AGACGTAAGC   240
Promoter       │ ACTGACGACA ACAATGAAAA GAAGAAGATA AGGTCGGTGA TTGTGAAAGA GACATAGAGG   300
               │ ACACATGTAA GGTGGAAAAT GTAAGGGCGG AAAGTAACCT TATCACAAAG GAATCTTATC   360
               │ CCCCACTACT TATCCTTTTA TATTTTTCCG TGTCATTTTT GCCCTTGAGT TTTCCTATAT   420
               │ AAGGAACCAA GTTCGGCATT TGTGAAAACA AGAAAAAATT TGGTGTAAGC TATTTTCTTT   480
               └ GAAGTACTGA GGATACAACT TCAGAGAAAT TTGTAAGTTT GTggatcctg caggctagcg   540
Cloning ──▶      tgcactctag aCTCGACGAA CTGACGAGCT CGAATTTCCC CGATCGTTCA AACATTTGGC   600
               ┌ AATAAAGTTT CTTAAGATTG AATCCTGTTG CCGGTCTTGC GATGATTATC ATATAATTTC   660
NOS            │ TGTTGAATTA CGTTAAGCAT GTAATAATTA ACATGTAATG CATGACGTTA TTTATGAGAT   720
terminator     │ GGGTTTTTAT GATTAGAGTC CCGCAATTAT ACATTTAATA CGCGATAGAA AACAAAATAT   780
               └ AGCGCGCAAA CTATGATAAA TTATCGCGCG CGGTGTCATC TATGTTACTA GATCGGgaat   840
               ┌ tcctcgagCA ACTATTTTTA TGTATGCAAG AGTCAGCATA TGTATAATTG ATTCAGAATC   900
               │ GTTTTGACGA GTTCGGATGT AGTAGTAGCC ATTATTTAAT GTACATACTA ATCGTGAATA   960
               │ GTGAATATGA TGAAACATTG TATCTTATTG TATAAATATC CATAAACACA TCATGAAAGA  1020
               │ CACTTTCTTT CACGGTCTGA ATTAATTATG ATACAATTCT AATAGAAAAC GAATTAAATT  1080
               │ ACGTTGAATT GTATGAAATC TAATTGAACA AGCCAACCAC GACGACGACT AACGTTGCCT  1140
               │ GGATTGACTC GGTTTAAGTT AACCACTAAA AAAACGGAGC TGTCATGTAA CACGCGGATC  1200
               │ GAGCAGGTCA CAGTCATGAA GCCATCAAAG CAAAAGAACT AATCCAAGGG CTGAGATGAT  1260
               │ TAATTAGTTT AAAAATTAGT TAACACGAGG GAAAAGGCTG TCTGACAGCC AGGTCACGTT  1320
               │ ATCTTTACCT GTGGTCGAAA TGATTCGTGT CTGTCGATTT TAATTATTTT TTTGAAAGGC  1380
               │ CGAAAATAAA GTTGTAAGAG ATAAACCCGC CTATATAAAT TCATATATTT TCCTCTCCGC  1440
ACTII          │ TTTGAATTGT CTCGTTGTCC TCCTCACTTT CATCAGCCGT TTTGAATCTC CGGCGACTTG  1500
Promoter       │ ACAGAGAAGA ACAAGGAAGA AGACTAAGAG AGAAAGTAAG AGATAATCCA GGAGATTCAT  1560
               │ TCTCCGTTTT GAATCTTCCT CAATCTCATC TTCTTCCGCT CTTTCTTTCC AAGGTAATAG  1620
               │ GAACTTTCTG GATCTACTTT ATTTGCTGGA TCTCGATCTT GTTTTCTCAA TTTCCTTGAG  1680
               │ ATCTGGAATT CGTTTAATTT GGATCTGTGA ACCTCCACTA AATCTTTTGG TTTTACTAGA  1740
               │ ATCGATCTAA GTTGACCGAT CAGTTAGCTC GATTATAGCT ACCAGAATTT GGCTTGACCT  1800
               │ TGATGGAGAG ATCCATGTTC ATGTTACCTG GGAAATGATT TGTATATGTG AATTGAAATC  1860
               │ TGAACTGTTG AAGTTAGATT GAATCTGAAC ACTGTCAATG TTAGATTGAA TCTGAACACT  1920
               │ GTTTAAGGTT AGATGAAGTT TGTGTATAGA TTCTTCGAAA CTTTAGGATT TGTAGTGTCG  1980
               │ TACGTTGAAC AGAAAGCTAT TTCTGATTCA ATCAGGGTTT ATTTGACTGT ATTGAACTCT  2040
               └ TTTTGTGTGT TTGCAGCTCA TAAAAggtac cAAACAATGA TTGAACAAGA TGGATTGCAC  2100
               ┌ GCAGGTTCTC CGGCCGCTTG GGTGGAGAGG CTATTCGGCT ATGACTGGGC ACAACAGACA  2160
               │ ATCGGCTGCT CTGATGCCGC CGTGTTCCGG CTGTCAGCGC AGGGGCGCCC GGTTCTTTTT  2220
               │ GTCAAGACCG ACCTGTCCGG TGCCCTGAAT GAACTGCAGG ACGAGGCAGC GCGGCTATCG  2280
               │ TGGCTGGCCA CGACGGGCGT TCCTTGCGCA GCTGTGCTCG ACGTTGTCAC TGAAGCGGGA  2340
               │ AGGGACTGGC TGCTATTGGG CGAAGTGCCG GGGCAGGATC TCCTGTCATC TCACCTTGCT  2400
NPT II         │ CCTGCCGAGA AAGTATCCAT CATGGCTGAT GCAATGCGGC GGCTGCATAC GCTTGATCCG  2460
Kan            │ GCTACCTGCC CATTCGACCA CCAAGCGAAA CATCGCATCG AGCGAGCACG TACTCGGATG  2520
Resistance     │ GAAGCCGGTC TTGTCGATCA GGATGATCTG GACGAAGAGC ATCAGGGGCT CGCGCCAGCC  2580
               │ GAACTGTTCG CCAGGCTCAA GGCGCGCATG CCCGACGGCG AGGATCTCGT CGTGACCCAT  2640
               │ GGCGATGCCT GCTTGCCGAA TATCATGGTG GAAAATGGCC GCTTTTCTGG ATTCATCGAC  2700
               │ TGTGGCCGGC TGGGTGTGGC GGACCGCTAT CAGGACATAG CGTTGGCTAC CCGTGATATT  2760
               │ GCTGAAGAGC TTGGCGGCGA ATGGGCTGAC CGCTTCCTCG TGCTTTACGG TATCGCCGCT  2820
               │ CCCGATTCGC AGCGCATCGC CTTCTATCGC CTTCTTGACG AGTTCTTTTG AGCGGGACTC  2880
               └ TGGcGaTCGc CCCGATCGTT CAAACATTTG GCAATAAAGT TTCTTAAGAT TGAATCCTGT  2940
               ┌ TGCCGGTCTT GCGATGATTA TCATATAATT TCTGTTGAAT TACGTTAAGC ATGTAATAAT  3000
NOS            │ TAACATGTAA TGCATGACGT TATTTATGAG ATGGGTTTTT ATGATTAGAG TCCCGCAATT  3060
Terminator     │ ATACATTTAA TACGCGATAG AAAACAAAAT ATAGCGCGCA AACTAGGATA AATTATCGCG  3120
               └ CGCGGTGTCA TCTATGTTAC TAGATCGGGa ctagt                             3180
```

TOBACCO PLANTS HAVING ALTERED AMOUNTS OF ONE OR MORE ALKALOIDS IN LEAF AND METHODS OF USING SUCH PLANTS

CROSS-REFERENCE TO RELATED APPLICATIONS AND INCORPORATION OF SEQUENCE LISTING

This application is a continuation of U.S. patent application Ser. No. 15/914,033, filed Mar. 7, 2018, which is a divisional of U.S. patent application Ser. No. 14/563,211, filed Dec. 8, 2014, which claims the benefit of U.S. Provisional Application No. 62/011,304, filed Jun. 12, 2014, and U.S. Provisional Application No. 61/912,752, filed Dec. 6, 2013, all of which are incorporated by reference in their entireties herein. A sequence listing contained in the file named "P34632US04_SL.TXT" which is 322,834 bytes (measured in MS-Windows®) and created on Aug. 28, 2020, is filed electronically herewith and incorporated by reference in its entirety.

TECHNICAL FIELD

This disclosure generally relates to tobacco plants.

BACKGROUND

Attempts have been made to produce low alkaloid varieties of tobacco. However, most such varieties result in low quality leaf and there are no commercial tobacco lines available with reduced leaf alkaloid content. Accordingly, there is a need to identify tobacco genes whose expression can be modulated such that the alkaloid profile in tobacco leaf can be altered, in particular, the profile of leaf nicotinic alkaloids.

SUMMARY

A number of sequences that are involved in the transport of alkaloids from the root to the leaf in tobacco are described. Methods of using such sequences also are described.

In one aspect, a tobacco hybrid, variety, line, or cultivar is provided. Such a tobacco hybrid, variety, line, or cultivar includes plants having a mutation in one or more endogenous nucleic acids such as SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90. In some embodiments, tobacco leaf from the plants exhibits a reduced amount of at least one alkaloid relative to tobacco leaf from a plant lacking the mutation. In some embodiments, cured leaf from the plants exhibits a reduced amount of at least one tobacco specific nitrosamine (TSNA) relative to cured leaf from a plant lacking the mutation. Seed produced by such a tobacco hybrid, variety, line, or cultivar also is provided, where the seed includes the mutation in one or more endogenous nucleic acids having a sequence such as SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90.

In another aspect, a method of making a tobacco plant is provided. Such a method typically includes the steps of inducing mutagenesis in *Nicotiana tabacum* cells to produce mutagenized cells, obtaining one or more plants from the mutagenized cells, and identifying at least one of the plants that contains a mutation in one or more endogenous nucleic acids such as SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90. Such a method can further include identifying at least one of the plants that contains leaf exhibiting a reduced amount of at least one alkaloid relative to leaf from a plant lacking the mutation. Such a method can also include identifying at least one of the plants where the resulting cured leaf exhibits a reduced amount of at least one TSNA relative to cured leaf from a plant lacking the mutation.

Mutagenesis can be induced using a chemical mutagen or ionizing radiation. Representative chemical mutagens include, without limitation, nitrous acid, sodium azide, acridine orange, ethidium bromide, and ethyl methane sulfonate (EMS). Representative ionizing radiation includes, without limitation, x-rays, gamma rays, fast neutron irradiation, and UV irradiation. Mutagenesis can be induced using TALEN or zinc-finger technology.

In another aspect, a method of producing a tobacco plant is provided. Such a method also can include the steps of crossing at least one plant of a first tobacco line with at least one plant of a second tobacco line and selecting for progeny tobacco plants that have the mutation. Generally, the plant of the first tobacco line has a mutation in one or more endogenous nucleic acids having a sequence such as SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90. Such a method further can include selecting for progeny tobacco plants that have leaf exhibiting a reduced amount of at least one alkaloid relative to leaf from a plant lacking the mutation. Such a method also can include selecting for progeny tobacco plants where the cured leaf exhibits a reduced amount of at least one TSNA relative to cured leaf from a plant lacking the mutation.

In another aspect, a tobacco product is provided. Such a tobacco product typically includes cured leaf from a tobacco plant having a mutation in one or more endogenous nucleic acids having a sequence such as SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90. In some embodiments, the cured leaf contained within the tobacco product exhibits a reduced amount of at least one alkaloid relative to cured leaf contained within a tobacco product that is from a plant lacking the mutation. In some embodiments, the cured leaf within the tobacco product exhibits a reduced amount of at least one TSNA relative to cured leaf contained within a tobacco product that is from a plant lacking the mutation.

In another aspect, a method of producing a tobacco product is provided. Such a method generally includes providing cured leaf from a tobacco plant having a mutation in one or more endogenous nucleic acids having a sequence such as SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90, and manufacturing a tobacco product using the cured leaves. In some embodiments, the cured leaf exhibits a reduced amount of at least one alkaloid relative to cured leaf from a plant lacking the mutation. In some embodiments, the cured leaf exhibits a reduced amount of at least one TSNA relative to cured leaf from a plant lacking the mutation.

A mutation as described herein can be, without limitation, a point mutation, an insertion, a deletion, or a substitution.

In still another aspect, a transgenic tobacco plant is provided that includes a plant expression vector. Typically, the expression vector includes a nucleic acid molecule that is at least 25 nucleotides in length and has at least 91% sequence identity to a sequence such as SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90. In some embodiments, expression of the nucleic acid molecule results in leaf exhibiting a reduced amount of at least one alkaloid relative to leaf from a tobacco plant not expressing the nucleic acid molecule. In some embodiments, expression of the nucleic acid molecule results in cured leaf exhibiting a reduced amount of at least one TSNA relative to cured leaf from a tobacco plant not expressing the nucleic acid molecule. Seed produced by such a transgenic tobacco plant also is provided, where the seed includes the expression vector.

In one aspect, a transgenic tobacco plant is provided that includes a heterologous nucleic acid molecule of at least 25 nucleotides in length, wherein the nucleic acid molecule hybridizes under stringent conditions to a nucleic acid sequence such as SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90. In some embodiments, expression of the heterologous nucleic acid molecule results in leaf exhibiting a reduced amount of at least one alkaloid relative to leaf from a tobacco plant not expressing the nucleic acid molecule. In some embodiments, expression of the heterologous nucleic acid molecule results in cured leaf exhibiting a reduced amount of at least one TSNA relative to cured leaf from a tobacco plant not expressing the nucleic acid molecule. Seed produced by such a transgenic tobacco plant also is provided, where the seed includes the heterologous nucleic acid molecule.

In one aspect, a leaf from a transgenic tobacco plant is provided that includes a vector. Generally, the vector includes a nucleic acid molecule having at least 91% sequence identity to 25 or more contiguous nucleotides of a nucleic acid sequence such as SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90. In some embodiments, expression of the nucleic acid molecule results in the leaf exhibiting a reduced amount of at least one alkaloid relative to leaf from a tobacco plant not expressing the nucleic acid molecule. In some embodiments, expression of the nucleic acid molecule results in cured leaf exhibiting a reduced amount of at least one TSNA relative to cured leaf from a tobacco plant not expressing the nucleic acid molecule.

In another aspect, a method of making a transgenic plant is provided. Such a method typically includes expressing a transgene in the plant. The transgene encodes a double-stranded RNA molecule that inhibits expression from a nucleic acid sequence such as SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90. The double-stranded RNA molecule includes at least 25 consecutive nucleotides having 91% or greater sequence identity to a sequence such as SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90. In some embodiments, expression of the transgene results in leaf from the plant exhibiting a reduced amount of at least one alkaloid relative to leaf from a plant not expressing the transgene. In some embodiments, expression of the transgene results in cured leaf exhibiting a reduced amount of at least one TSNA relative to cured leaf from a plant not expressing the nucleic acid molecule. In some embodiments, the double-stranded RNA molecule has a sequence such as SEQ ID NOs: 51-56.

In another aspect, a method of altering leaf constituents in a tobacco plant is provided. Such a method generally includes the steps of introducing a heterologous nucleic acid molecule operably linked to a promoter into tobacco cells to produce transgenic tobacco cells, and regenerating transgenic tobacco plants from the transgenic tobacco cells. Typically, the heterologous nucleic acid molecule includes at least 25 nucleotides in length and has at least 91% sequence identity to a nucleic acid sequence such as SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90. Such transgenic tobacco plants exhibit altered leaf constituents. Such a method further can include selecting at least one of the transgenic tobacco plants having leaf that exhibits a reduced amount of at least one alkaloid relative to leaf from a tobacco plant not expressing the heterologous nucleic acid molecule. Such a method further can include selecting at least one of the transgenic tobacco plants having cured leaf exhibiting a reduced amount of at least one TSNA relative to cured leaf from a tobacco plant not expressing the heterologous nucleic acid molecule.

In another aspect, a cured tobacco leaf from a transgenic tobacco plant is provided that includes a vector. Generally, the vector includes a nucleic acid molecule having at least 91% sequence identity (e.g., at least 92, 93, 94, 95, 96, 97, 98, 99 or 100% sequence identity) to 25 or more contiguous nucleotides of a nucleic acid sequence such as SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90. In some embodiments, expression of the nucleic acid molecule results in leaf exhibiting a reduced amount of at least one alkaloid relative to leaf from a tobacco plant not expressing the nucleic acid molecule. In some embodiments, expression of the nucleic acid molecule results in cured leaf exhibiting a reduced amount of at least one TSNA relative to cured leaf from a tobacco plant not expressing the nucleic acid molecule. In some embodiments, the nucleic acid is in sense orientation, while, in some embodiments, the nucleic acid is in antisense orientation.

In still another aspect, a transgenic tobacco plant is provided that includes a plant expression vector. Generally, the expression vector includes a nucleic acid molecule having at least 95% sequence identity to a sequence such as SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90, or a fragment of any of those sequences encoding a functional polypeptide. In some embodiments, expression of the nucleic acid molecule or a functional fragment thereof results in leaf exhibiting an increased amount of at least one alkaloid relative to leaf from a tobacco plant not expressing the nucleic acid molecule or functional fragment thereof. Seed produced by such a transgenic tobacco plant also is provided, where the seed includes the expression vector.

In another aspect, a transgenic tobacco plant is provided that includes a heterologous nucleic acid molecule. Generally, the nucleic acid molecule hybridizes under stringent conditions to a nucleic acid sequence such as SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90, or a fragment thereof encoding a functional polypeptide. In some embodiments, expression of the heterologous nucleic acid molecule or functional fragment thereof results in leaf exhibiting an increased amount of at least one alkaloid relative to leaf from a tobacco plant not expressing the nucleic acid molecule or functional fragment thereof. Seed produced by such a transgenic tobacco plant also is provided, where the seed includes the heterologous nucleic acid molecule.

In one aspect, a leaf from a transgenic tobacco plant is provided that includes a vector. Typically, such a vector includes a nucleic acid molecule having at least 95% sequence identity to a nucleic acid sequence such as SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90, or a fragment thereof encoding a functional polypeptide. In some embodiments, expression of the nucleic acid molecule or functional fragment thereof results in the leaf exhibiting an increased amount of at least one alkaloid relative to leaf from a tobacco plant not expressing the nucleic acid molecule or functional fragment thereof.

In another aspect, a method of altering leaf constituents in a tobacco plant is provided. Such a method typically includes the steps of introducing a heterologous nucleic acid molecule operably linked to a promoter into tobacco cells to produce transgenic tobacco cells, and regenerating transgenic tobacco plants from the transgenic tobacco cells, wherein the transgenic tobacco plants have altered leaf constituents. The heterologous nucleic acid molecule typically has at least 95% sequence identity to a nucleic acid sequence such as SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90, or a fragment thereof encoding a functional polypeptide. Such a method further can include selecting at least one of the transgenic tobacco plants having leaf that exhibits an increased amount of at least one alkaloid relative to leaf from a tobacco plant not expressing the heterologous nucleic acid molecule or functional fragment thereof In some embodiments, the heterologous nucleic acid molecule is introduced into the tobacco cells using particle bombardment, Agrobacterium-mediated transformation, microinjection, polyethylene glycol-mediated transformation, liposome-mediated DNA uptake, or electroporation.

In one aspect, a cured tobacco leaf from a transgenic tobacco plant is provided that includes a vector. Typically, the vector includes a nucleic acid molecule having at least 95% sequence identity to a nucleic acid sequence such as SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90, or a fragment thereof encoding a functional polypeptide. In some embodiments, expression of the nucleic acid molecule or functional fragment thereof results in tobacco leaf exhibiting an increased amount of at least one alkaloid relative to leaf from a tobacco plant not expressing the nucleic acid molecule or functional fragment thereof.

Representative alkaloids include, without limitation, nicotine, nornicotine, anabasine, myosmine, and anatabine. Typically, the amount of one or more alkaloids is determined using high performance liquid chromatography (HPLC)—mass spectroscopy (MS) or high performance thin layer chromatography (HPTLC).

Suitable tobacco plants for use in the methods described herein can be a Burley type, a dark type, a flue-cured type, a Maryland type, or an Oriental type. Suitable tobacco plants for use in the methods described herein typically are from *N. tabacum*, and can be from any number of *N. tabacum* varieties. A variety can be BU 64, CC 101, CC 200, CC 13, CC 27, CC 33, CC 35,CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpao tobacco, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119,, KDH 959, KT 200, KT204LC, KY 10, KY 14, KY 160, KY 17, KY 171, KY 907, KY907LC, KTY14xL8 LC, Little Crittenden, McNair 373, McNair 944, msKY 14xL8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, TR (Tom Rosson) Madole, VA 309, or VA359.

In another aspect, a method of screening plants is provided. Such a method typically includes providing plant material from a mutant plant as described herein, and determining the amount of one or more alkaloids in plant tissue. In some embodiments, the plant tissue is leaf In some embodiments, the plant tissue is root. Such a method can further include determining the amount of one or more TSNAs in plant tissue.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 2 is an alignment of the four novel MDR sequences described herein (DC3222 (SEQ ID NO:10); C11099 (SEQ ID NO:16): DC62783 (SEQ ID NO:12); DC26451 (SEQ ID NO:14)) with a representative MDR polypeptide (Accession # XP_004233862; SEQ ID NO:94). The boxed regions denote the conserved ATPase domain.

FIG. 4A is an alignment of one of the novel MDR sequences, C11099 (SEQ ID NO:16), with a putative ABC transporter B family member 8-like from *Solanum lycopersicum* (ABCB-8 (SEQ ID NO:96))

FIG. 10 describes regions of a transformation cassette sequence (SEQ ID NO:57).

DETAILED DESCRIPTION

Figure 1:
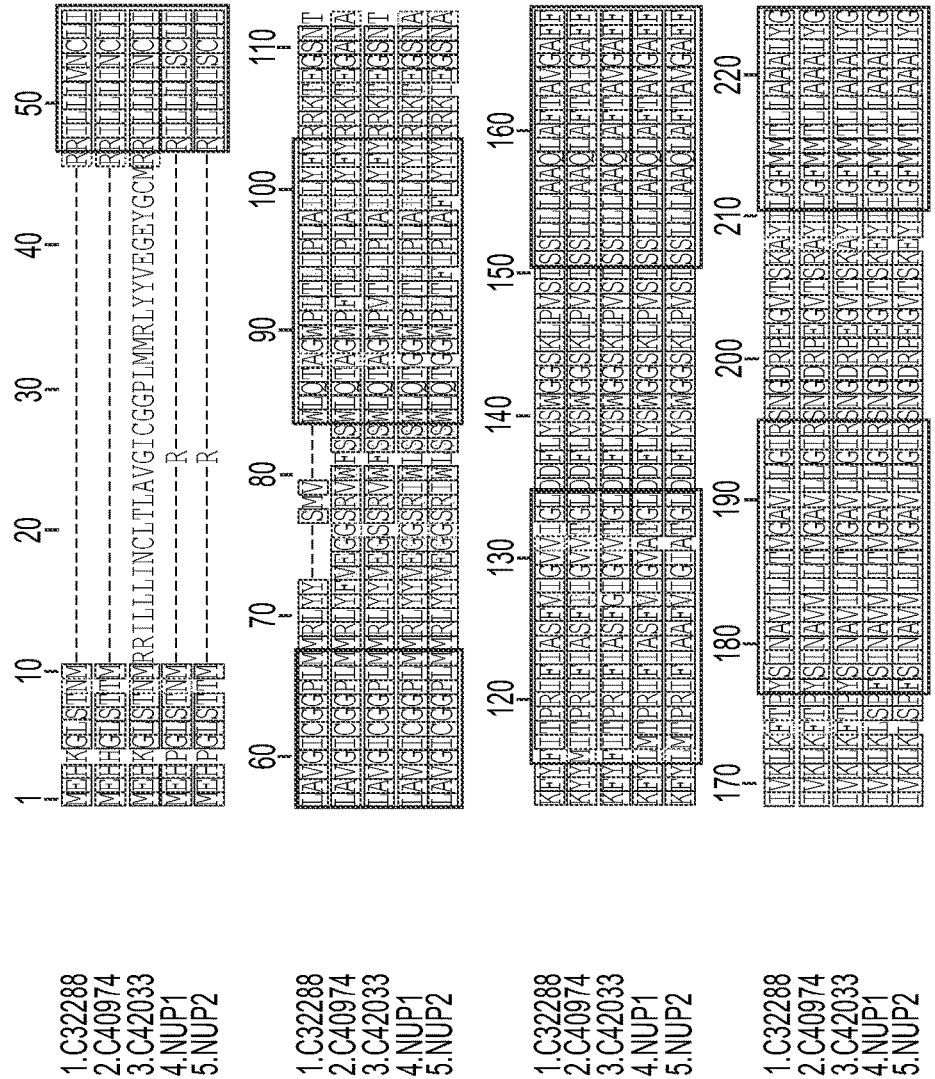
FIG. 1 is an alignment of the novel Nup sequences described herein with previously known *N. tabacum* Nup1 and Nup2. C32288 (SEQ ID NO:2); C40974 (SEQ ID NO:4); C42033 (SEQ ID NO:6); Nup1 (SEQ ID NO:92); Nup2 (SEQ ID NO:93). Nup1-predicted transmembrane helices are denoted by boxes.
Figure 1:
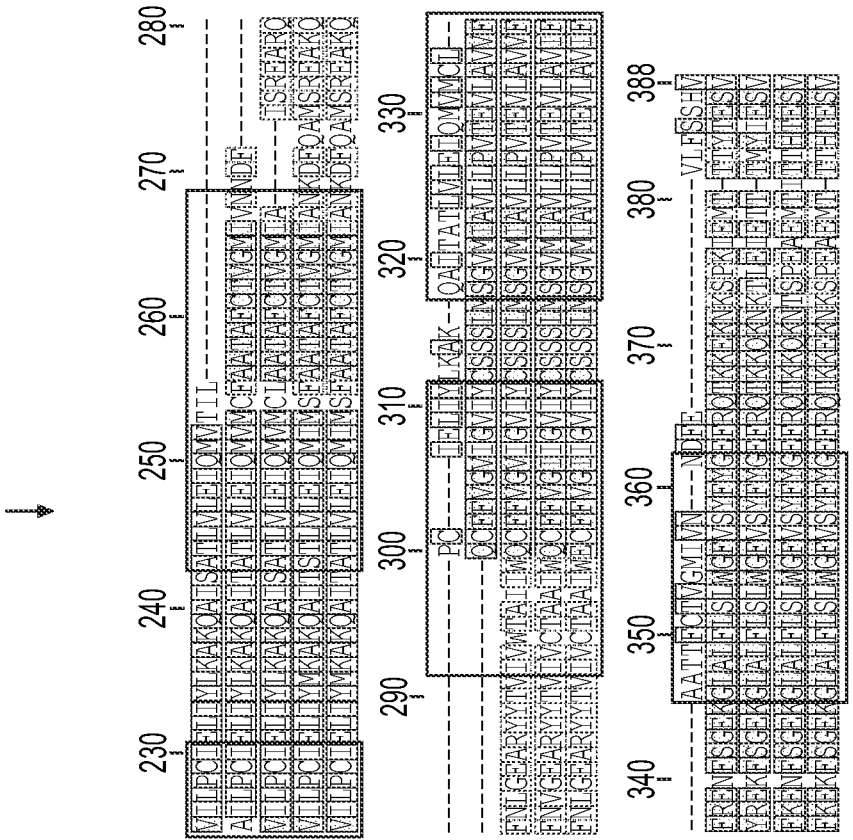

Previous attempts to modify the pathway to produce low alkaloid varieties of tobacco sometimes resulted in low quality leaf. Currently, there are no commercial tobacco lines with reduced leaf alkaloid content that provide the same quality of cured leaf as those containing standard alkaloid content (e.g., from wild type tobacco plants).

This disclosure is based on the discovery of novel nucleic acids encoding alkaloid transporter and regulatory polypeptides from *N. tabacum*. Such nucleic acids, SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90, and the polypeptides encoded thereby, SEQ ID NOs: 2, 4, 6, 8, 10, 12, 14, 16, 18, 20, 22, 24, 26, 28, 30, 32, 34, 36, 38, 40, 42, 44, 46, 48, 50, 71, 73, 75, 77, 79, 81, 83, 85, 87, 89, or 91, are described and characterized herein. Based on this discovery, the level of expression of such nucleic acid sequences and/or the function of such polypeptides can be modulated in *N. tabacum* and the resulting effect on alkaloid transport in plants can be evaluated. Modulating polypeptide function and/or genes expression can permit improved control of the alkaloid composition in tobacco leaf and resulting tobacco products.

Nucleic Acids and Polypeptides

Novel nucleic acids are provided herein (see, for example, SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90). As used herein, nucleic acids can include DNA and RNA, and includes nucleic acids that contain one or more nucleotide analogs or backbone modifications. A nucleic acid can be single stranded or double stranded, which usually depends upon its intended use. The novel nucleic acids provided herein encode novel polypeptides (see, for example, SEQ ID NOs: 2, 4, 6, 8, 10, 12, 14, 16, 18, 20, 22, 24, 26, 28, 30, 32, 34, 36, 38, 40, 42, 44, 46, 48, 50, 71, 73, 75, 77, 79, 81, 83, 85, 87, 89, or 91).

Also provided are nucleic acids and polypeptides that differ from SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90 and SEQ ID NOs: 2, 4, 6, 8, 10, 12, 14, 16, 18, 20, 22, 24, 26, 28, 30, 32, 34, 36, 38, 40, 42, 44, 46, 48, 50, 71, 73, 75, 77, 79, 81, 83, 85, 87, 89, or 91, respectively. Nucleic acids and polypeptides that differ in sequence from SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90 and SEQ ID NOs: 2, 4, 6, 8, 10, 12, 14, 16, 18, 20, 22, 24, 26, 28, 30, 32, 34, 36, 38, 40, 42, 44, 46, 48, 50, 71, 73, 75, 77, 79, 81, 83, 85, 87, 89, or 91, can have at least 50% sequence identity (e.g., at least 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity) to SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90 and SEQ ID NOs: 2, 4, 6, 8, 10, 12, 14, 16, 18, 20, 22, 24, 26, 28, 30, 32, 34, 36, 38, 40, 42, 44, 46, 48, 50, 71, 73, 75, 77, 79, 81, 83, 85, 87, 89, or 91, respectively.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the computer program ClustalW and default parameters, which allows alignments of nucleic acid or polypeptide sequences to be carried out across their entire length (global alignment). Chenna et al., 2003, Nucleic Acids Res., 31(13): 3497-500. ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of polypeptide sequences, the following parameters can be used: word size: 1; window size: 5; scoring method: percentage; number of top diagonals: 5; and gap penalty: 3. For multiple alignment of polypeptide sequences, the following parameters can be used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

Changes can be introduced into a nucleic acid molecule (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90), thereby leading to changes in the amino acid sequence of the encoded polypeptide (e.g., SEQ ID NOs: 2, 4, 6, 8, 10, 12, 14, 16, 18, 20, 22, 24, 26, 28, 30, 32, 34, 36, 38, 40, 42, 44, 46, 48, 50, 71, 73, 75, 77, 79, 81, 83, 85, 87, 89, or 91). For example, changes can be introduced into nucleic acid coding sequences using mutagenesis (e.g., site-directed mutagenesis, PCR-mediated mutagenesis) or by chemically synthesizing a nucleic acid molecule having such changes. Such nucleic acid changes can lead to conservative and/or non-conservative amino acid substitutions at one or more amino acid residues. A "conservative amino acid substitution" is one in which one amino acid residue is replaced with a different amino acid residue having a similar side chain (see, for example, Dayhoff et al. (1978, in Atlas of Protein Sequence and Structure, 5(Suppl. 3):345-352), which provides frequency tables for amino acid substitutions), and a non-conservative substitution is one in which an amino acid residue is replaced with an amino acid residue that does not have a similar side chain.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is "purified."

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

A vector containing a nucleic acid (e.g., a nucleic acid that encodes a polypeptide) also is provided. Vectors, including expression vectors, are commercially available or can be produced by recombinant DNA techniques routine in the art. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6xHis tag, glutathione S-transferase (GST))

Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins. As used herein, operably linked means that a promoter or other expression element(s) are positioned in a vector relative to a nucleic acid in such a way as to direct or regulate expression of the nucleic acid (e.g., in-frame). Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer.

Vectors as described herein can be introduced into a host cell. As used herein, "host cell" refers to the particular cell into which the nucleic acid is introduced and also includes the progeny of such a cell that carry the vector. A host cell can be any prokaryotic or eukaryotic cell. For example, nucleic acids can be expressed in bacterial cells such as $E.$ $coli$, or in insect cells, yeast or mammalian cells (such as Chinese hamster ovary cells (CHO) or COS cells). Other suitable host cells are known to those skilled in the art.

Nucleic acids can be detected using any number of amplification techniques (see, e.g., PCR Primer: A Laboratory Manual, 1995, Dieffenbach & Dveksler, Eds., Cold Spring Harbor Laboratory Press, Cold Spring Harbor, N.Y.; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid.

Nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.; Sections 7.37-7.57, 9.47-9.57, 11.7-11.8, and 11.45-11.57). Sambrook et al. discloses suitable Southern blot conditions for oligonucleotide probes less than about 100 nucleotides (Sections 11.45-11.46). The Tm between a sequence that is less than 100 nucleotides in length and a second sequence can be calculated using the formula provided in Section 11.46. Sambrook et al. additionally discloses Southern blot conditions for oligonucleotide probes greater than about 100 nucleotides (see Sections 9.47-9.54). The Tm between a sequence greater than 100 nucleotides in length and a second sequence can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2X SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a nucleic acid but not to another nucleic acid if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantitated directly on a membrane or from an autoradiograph using, for example, a PhosphorImager or a Densitometer (Molecular Dynamics, Sunnyvale, Calif.).

Polypeptides can be detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide can be generated using methods well known in the art. The antibody can be attached to a solid support such as a microtiter plate using methods known in the art. In the presence of a polypeptide, an antibody-polypeptide complex is formed.

Detection (e.g., of an amplification product, a hybridization complex, or a polypeptide) is usually accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

Certain nucleic acids described herein (e.g., SEQ ID NOs: 1, 3, 5, 7, or 82) are predicted to encode polypeptides (e.g., SEQ ID NOs: 2, 4, 6, 8, or 83) that belong to the nicotine uptake permease (Nup) family of sequences. Nup polypeptides are members of the larger family of purine permeases. See, for example, Hildreth et al., 2011, PNAS USA, 108: 18279-84. In addition to the novel Nup nucleic acid and polypeptide sequences disclosed herein, representative Nup1 and Nup2 sequences from *Nicotiana tabacum* are shown in Accession Nos. GU174268.1 and GU174267.1.

Certain nucleic acids described herein (e.g., SEQ ID NOs: 9, 11, 13, 15, 70, 72, 74, 76, 78, or 80) are predicted to encode polypeptides (e.g., SEQ ID NOs: 10, 12, 14, 16, 71, 73, 75, 77, 79, or 81) that belong to the multiple drug resistance (MDR) family of sequences. Multidrug transporters form a large class of membrane proteins present in the cells of most organisms. These proteins bind to a variety of potentially cytotoxic compounds and remove them from the cell in an ATP- or proton-dependent process (Zhelenova et al., 2000, Trends Biochem. Sci., 25:39-43). Multidrug transporters previously have been divided into four superfamilies: the ATP binding cassette (ABC) superfamily, the major facilitator superfamily, the small multidrug resistance family, and the resistance-nodulation-cell division family (the MATE family discussed in more detail below was recently identified as a fifth superfamily of multidrug transporters). The efflux pump proteins which belong to the ATP-binding cassette superfamily and the major facilitator superfamily are the most prominent contributors to multidrug resistance (MDR).

Certain nucleic acids described herein (e.g., SEQ ID NOs: 17, 19, 21, 23, 25, 27, 29, 31, 86, 88, or 90) are predicted to encode polypeptides (e.g., SEQ ID NOs: 18, 20, 22, 24, 26, 28, 30, 32, 87, 89, or 91) that belong to the multidrug and toxic compound extrusion-type (MATE) family of sequences. The MATE family of polypeptides is characterized by the presence of 12 putative transmembrane segments and by the absence of "signature sequences" specific to the other multidrug transporter superfamilies (Brown et al., 1999, Mol. Microbiol., 31:394-5). MATE proteins are believed to function as proton-dependent efflux transporters, and are abundant in bacteria and plants.

Certain nucleic acids described herein (e.g., SEQ ID NOs: 33 and 35) are predicted to encode polypeptides (e.g., SEQ ID NOs: 34 and 36) that belong to the pleiotropic drug resistance (PDR) family of sequences. See, for example, Moons, 2008, *Planta,* 229:53-71. The PDR family is only found in fungi and plants, and was first characterized in *Saccharomyces cerevisiae* by the increased expression of genes that encode for nonspecific drug-efflux transporter proteins. PDR polypeptides have been identified that confer resistance to a large set of functionally and structurally unrelated toxic compounds (e.g., antifungal and anticancer drugs) and that transport weak organic acids. In addition, a number of PDR genes have been identified in several plant species, including, for example, *Arabidopsis* and rice.

Plants Having Reduced Amounts of Alkaloids in Leaf and Methods of Making

Tobacco hybrids, varieties, lines, or cultivars are provided that have a mutation in one or more endogenous nucleic acids described herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90). As described herein, leaf from plants having a mutation in one or more of the endogenous nucleic acids (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90) can exhibit a reduced amount of at least one alkaloid (e.g., compared to leaf from a plant that lacks the mutation). In addition, leaf from plants having a mutation in one or more of the endogenous nucleic acids (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90) can exhibit a reduced amount of at least one tobacco specific nitrosamine (TSNA) (e.g., compared to leaf from a plant lacking the mutation).

The alkaloids referred to herein are typically pyridine alkaloids, which includes nicotine, nornicotine, anabasine, myosmine, and anatabine. See, for example, Sheng et al., 2005, Chromatographia, 62:63-8. TSNAs are produced during curing. Nitrite may accumulate as a result of nitrate reduction by bacteria, and TSNAs are formed by chemical reactions between nitrite (source of nitrosating species) and alkaloids. Representative TSNAs include, for example, N'-nitrosonornicotine (NNN), 4-(methylnitrosoamino)-1-(3-pyridyl)-1-butanone (NNK), N'-nitrosoanatabine (NAT), N'-nitrosoanabasine (NAB), and 4-(methylnitrosoamino)-1-(3-pyridyl)-1-butanal (NNAL).

Methods of detecting alkaloids or TSNAs, and methods of determining the amount of one or more alkaloids or TSNAs are known in the art. For example, high performance liquid chromatography (HPLC)—mass spectroscopy (MS) (HPLC-MS) or high performance thin layer chromatography (HPTLC) can be used to detect the presence of one or more alkaloids and/or determine the amount of one or more alkaloids. In addition, any number of chromatography methods (e.g., gas chromatography/thermal energy analysis (GC/TEA), liquid chromatography/mass spectrometry (LC/MS), and ion chromatography (IC)) can be used to detect the presence of one or more TSNAs and/or determine the amount of one or more TSNAs.

Methods of making a tobacco plant having a mutation are known in the art. Mutations can be random mutations or targeted mutations. For random mutagenesis, cells (e.g., *Nicotiana tabacum* cells) can be mutagenized using, for example, a chemical mutagen, ionizing radiation, or fast neutron bombardment (see, e.g., Li et al., 2001, *Plant J.*, 27:235-42). Representative chemical mutagens include, without limitation, nitrous acid, sodium azide, acridine orange, ethidium bromide, and ethyl methane sulfonate (EMS), while representative ionizing radiation includes, without limitation, x-rays, gamma rays, fast neutron irradiation, and UV irradiation. The dosage of the mutagenic chemical or radiation is determined experimentally for each type of plant tissue such that a mutation frequency is obtained that is below a threshold level characterized by lethality or reproductive sterility. The number of $M_1$ generation seed or the size of $M_1$ plant populations resulting from the mutagenic treatments are estimated based on the expected frequency of mutations. For targeted mutagenesis, representative technologies include TALEN (see, for example, Li et al., 2011, Nucleic Acids Res., 39(14):6315-25) or zinc-finger (see, for example, Wright et al., 2005, *The Plant J.*, 44:693-705). Whether random or targeted, a mutation can be a point mutation, an insertion, a deletion, a substitution, or combinations thereof.

Figure 2:
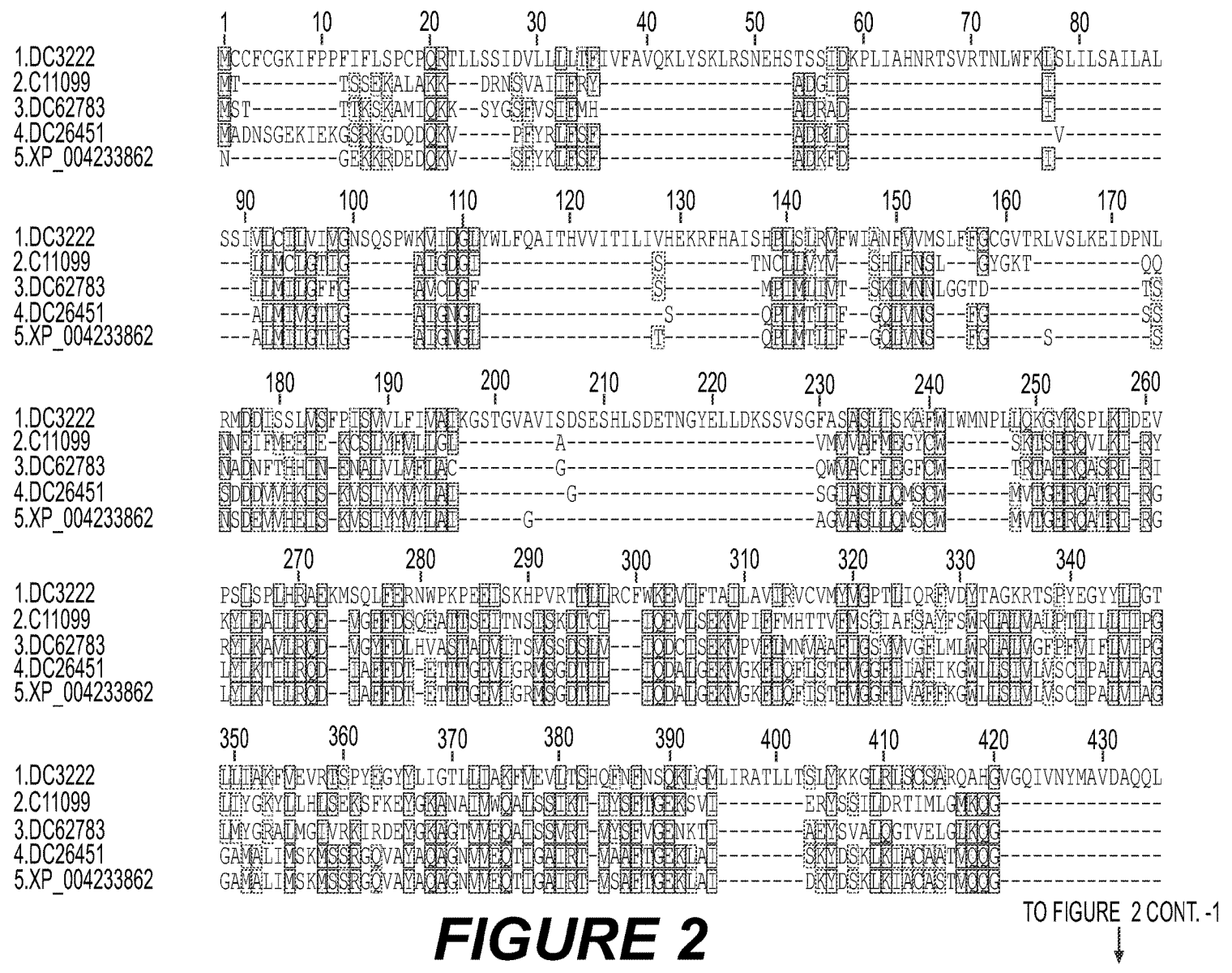
Figure 2:
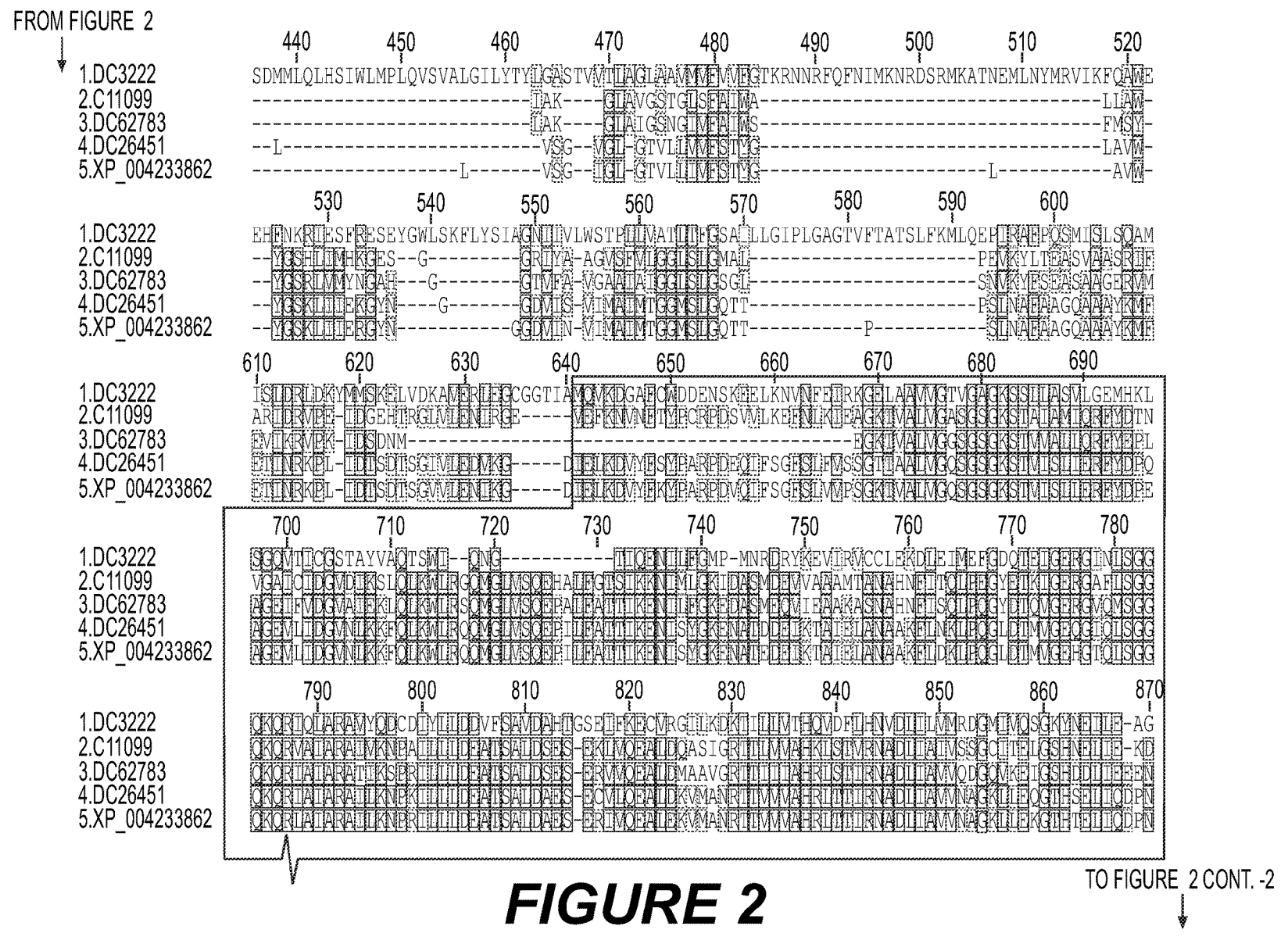
Figure 2:
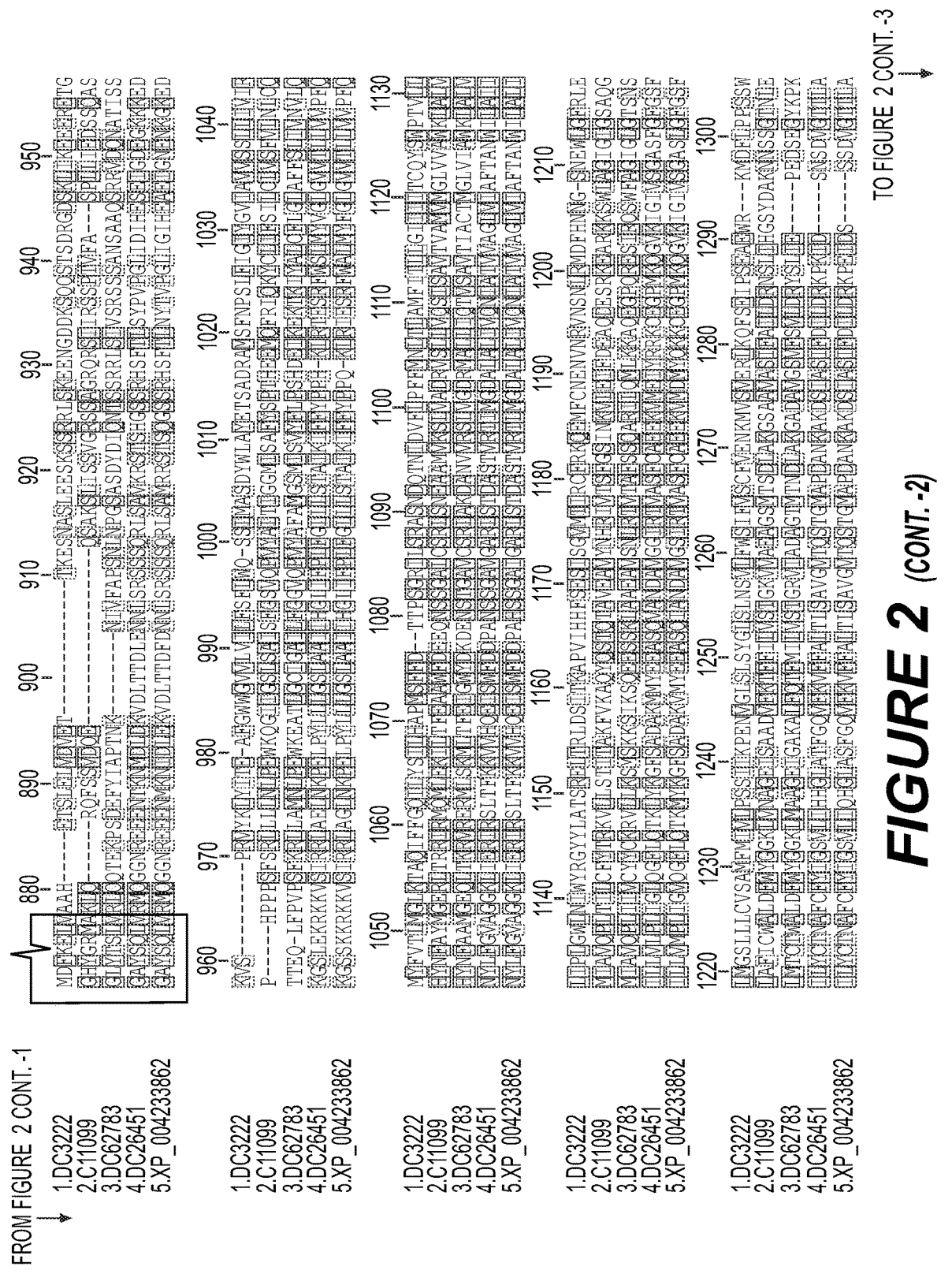
Figure 3:
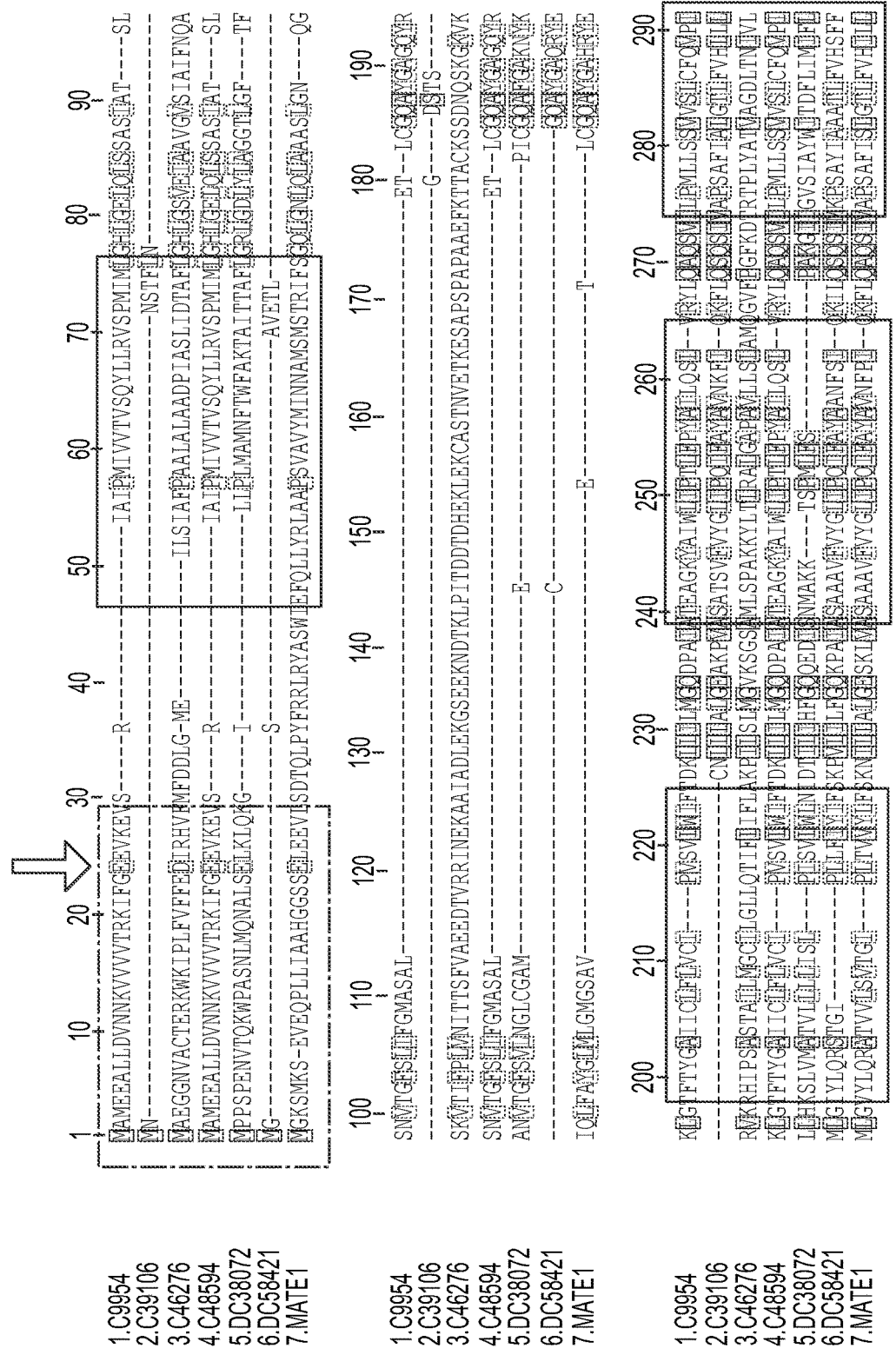
FIG. 3 is an alignment of the novel MATE sequences (C9954 (SEQ ID NO:26); C39106 (SEQ ID NO:28); C46276 (SEQ ID NO:22); C48594 (SEQ ID NO:24); DC38072 (SEQ ID NO:20); DC58421 (SEQ ID NO:18)) with *N. tabacum* MATE1. The boxes indicate predicted transmembrane domains; the predicted N-terminal localization is shaded, with the predicted conserved cleavage site shown with the arrow.
Figure 4A:
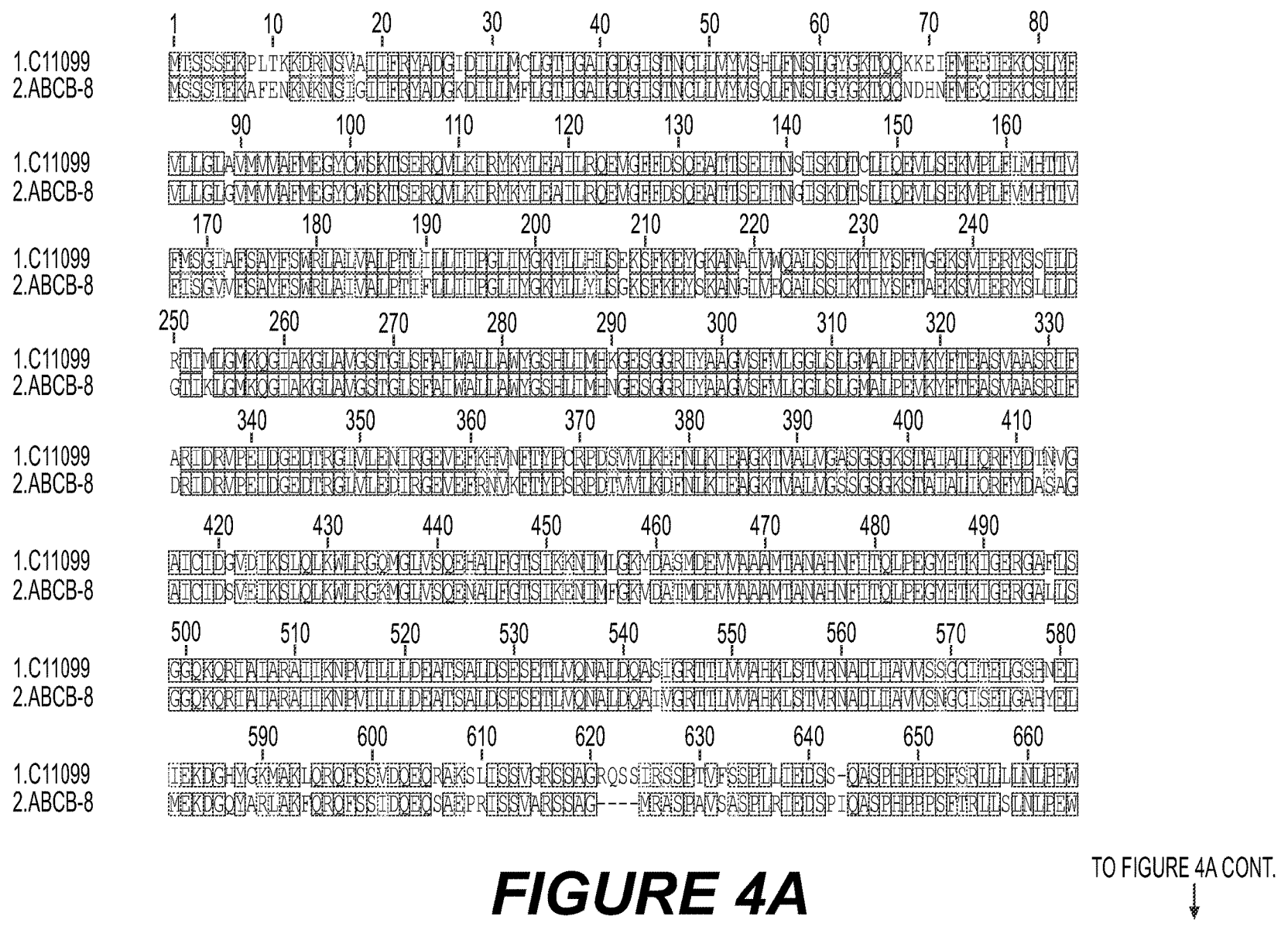
Figure 4A:
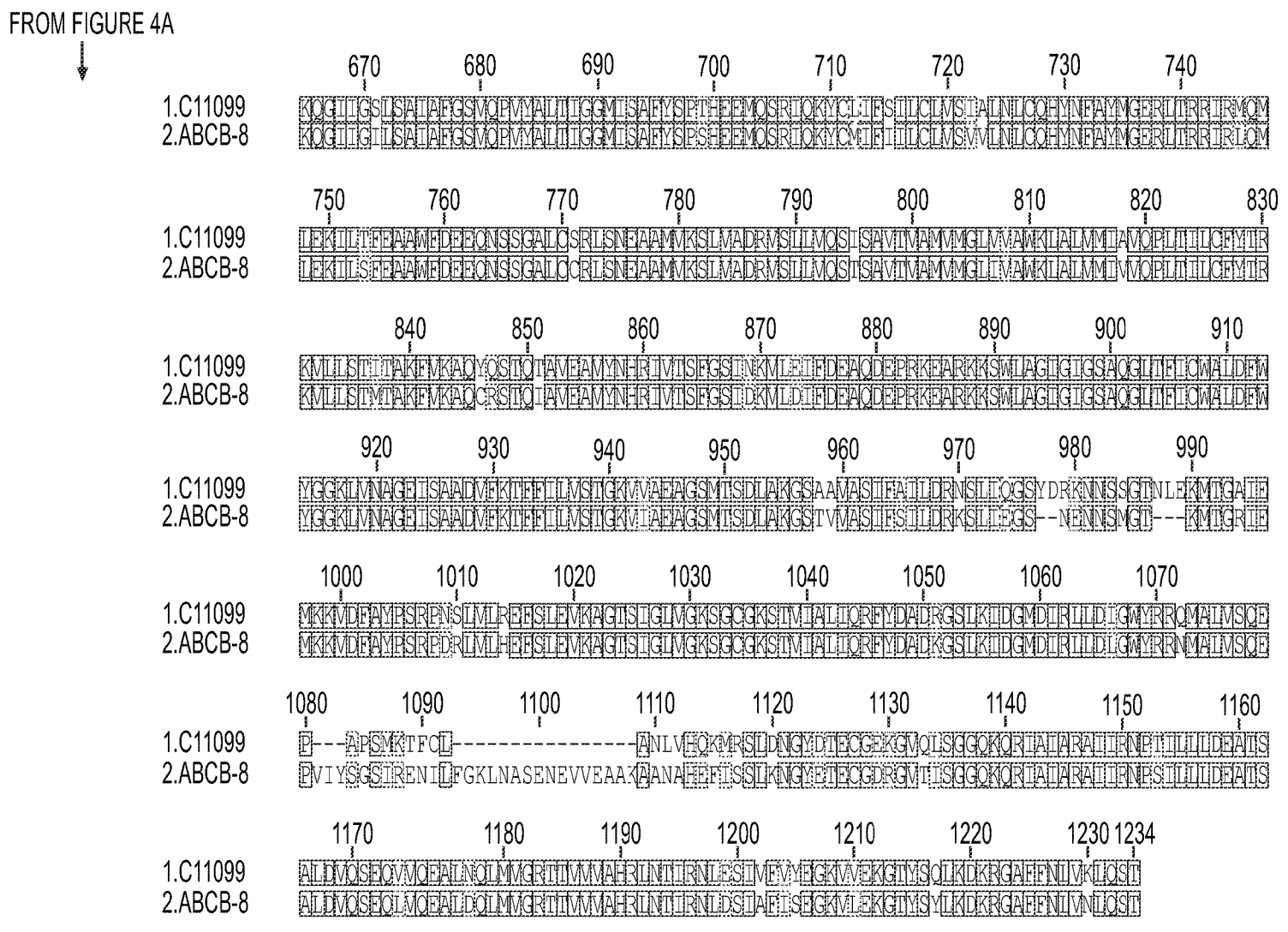
Figure 4B:
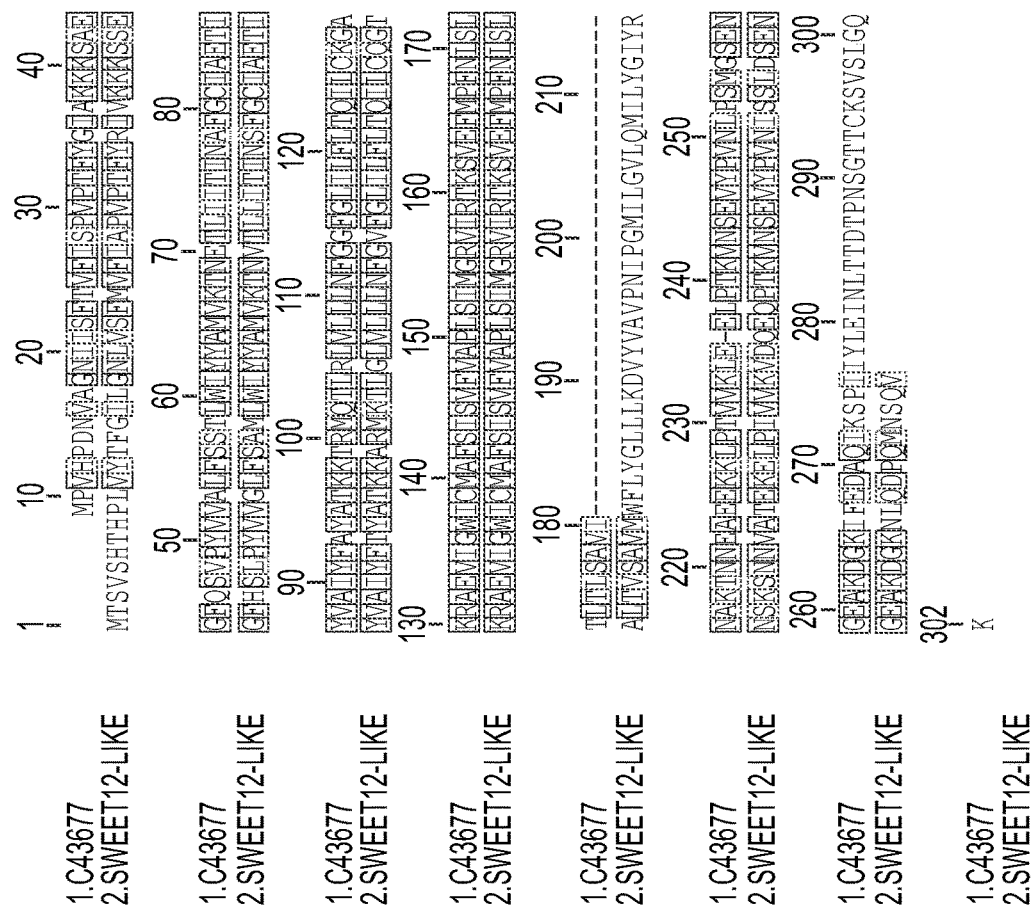
FIG. 4B is an alignment of one of the other transporter sequences identified, C43677 (SEQ ID NO:40), with a bidirectional sugar transporter SWEET12-like from *Solanum lycopersicum* (SEQ ID NO:97).

Conserved domains in polypeptides can be important for polypeptide function as well as cellular or subcellular location. FIG. 1 shows an alignment of Nup sequences, including the novel Nup sequences described herein, with the predicted transmembrane helices indicated by boxes. FIG. 2 shows an alignment of MDR sequences, including the novel MDR sequences described herein, with the conserved ATPase domains indicated by boxes. FIG. 3 shows an alignment of MATE sequences, including the novel MATE sequences described herein. The boxes in FIG. 3 indicate predicted transmembrane domains, with the predicted N-terminal signal peptide shown as shaded, and the predicted conserved cleavage site shown with an arrow. In addition, FIG. 4A shows an alignment between one of the novel MDR sequences, C11099, and a putative ABC transporter B family member 8-like sequence from *Solanum lycopersicum*. As indicated below in Table 5, these sequences have 84% sequence identity at the nucleotide level and 85% sequence identity at the amino acid level. Further, FIG. 4B shows an alignment between one of the novel sequence indicated as an "other" transporter sequence, C43677, and a bidirectional sugar transporter SWEET12-like sequence from *Solanum lycopersicum*. As indicated below in Table 8, these sequences have 71% sequence identity at the nucleotide level and 67% sequence identity at the amino acid level.

As discussed herein, one or more nucleotides can be mutated to alter the expression and/or function of the encoded polypeptide, relative to the expression and/or function of the corresponding wild type polypeptide. It will be appreciated, for example, that a mutation in one or more of the highly conserved regions (see, for example, the alignments shown in FIGS. 1, 2, 3, and 4) would likely alter polypeptide function, while a mutation outside of those conserved regions would likely have little to no effect on polypeptide function. In addition, a mutation in a single nucleotide can create a stop codon, which would result in a truncated polypeptide and, depending on the extent of truncation, loss-of-function.

Preferably, a mutation in one of the novel nucleic acids disclosed herein results in reduced or even complete elimination of transporter activity in a tobacco plant comprising the mutation. Suitable types of mutations in a transporter coding sequence include, without limitation, insertions of nucleotides, deletions of nucleotides, or transitions or transversions in the wild-type transporter coding sequence. Mutations in the coding sequence can result in insertions of one or more amino acids, deletions of one or more amino acids, and/or non-conservative amino acid substitutions in the encoded polypeptide. In some cases, the coding sequence of a transporter comprises more than one mutation or more than one type of mutation.

Insertion or deletion of amino acids in a coding sequence, for example, can disrupt the conformation of the encoded polypeptide. Amino acid insertions or deletions also can disrupt sites important for recognition of the binding ligand (i.e., the molecule(s) that are transported) or for activity of the polypeptide (i.e., transporter activity). It is known in the art that the insertion or deletion of a larger number of contiguous amino acids is more likely to render the gene product non-functional, compared to a smaller number of inserted or deleted amino acids. In addition, one or more mutations (e.g., a point mutation) can change the localization of the transporter polypeptide, introduce a stop codon to produce a truncated polypeptide, or disrupt an active site or domain (e.g., a catalytic site or domain, a binding site or domain) within the polypeptide.

Simply by way of example, a MATE transporter sequence (e.g., FIG. 3; e.g., C9954 (SEQ ID NO:26), C46276 (SEQ ID NO:22), C48594 (SEQ ID NO:24), and DC38072 (SEQ ID NO:20)) can be mutated to change the charged amino acid at residue 24 to an uncharged amino acid. Such a mutation can disrupt the usual targeting of the transport polypeptide to the cell surface, which can alter the transport of one or more alkaloids within the plant (e.g., into the xylem and/or from the root to the leaf). In addition, a MDR transporter (e.g., C11099 (SEQ ID NO:16)) can be mutated to change the T at nucleotide 124 to an A, which would result in a stop codon after the eighth amino acid residue. Such a mutation would significantly reduce or essentially eliminate the transporter polypeptide in the plant; a mutation to introduce a stop codon can be similarly applied to any of the transporter sequences disclosed herein. Further, the MDR (e.g., FIGS. 2 and 4A) and PDR (e.g., SEQ ID NOs: 33-36) family of polypeptides require hydrolysis of ATP for transport; ATPase domains are highly conserved and the amino acid residues required for hydrolysis are known (e.g., the Walker A amino acid motif (GXXGXGK) at residues 676-682 of FIG. 2). Thus, a MDR polypeptide (e.g., DC3222 (SEQ ID NO:10), C11099 (SEQ ID NO:16), DC62783 (SEQ ID NO:12), and DC26451 (SEQ ID NO:14)) ora PDR polypeptide (e.g., C53160 (SEQ ID NO:34), C22474 (SEQ ID NO:36)) can be mutated within the Walker A motif (e.g., at the conserved lysine (K) amino acid), which would result in a polypeptide that is unable to hydrolyze ATP and unable to perform, or at least deficient in, its ability to transport.

Non-conservative amino acid substitutions can replace an amino acid of one class with an amino acid of a different class. Non-conservative substitutions can make a substantial change in the charge or hydrophobicity of the gene product. Non-conservative amino acid substitutions can also make a substantial change in the bulk of the residue side chain, e.g., substituting an alanine residue for an isoleucine residue. Examples of non-conservative substitutions include a basic amino acid for a non-polar amino acid, or a polar amino acid for an acidic amino acid.

Transmembrane polypeptides such as transporter polypeptides contain particular sequences that determine where the polypeptide is localized within the cell. For example, while the previously described MATE1 protein contains sequences that target it to the vacuole, the novel MATE sequences described here have different N terminal domains (see the alignment in FIG. 3). The target peptide sequences often are cleaved (e.g., by specific proteases that recognize a specific nucleotide motif) after the polypeptide is inserted into the membrane. By mutating the target sequence or a cleavage motif, the targeting of the polypeptide can be altered.

Following mutagenesis, $M_0$ plants are regenerated from the mutagenized cells and those plants, or a subsequent generation of that population (e.g., $M_1$, $M_2$, $M_3$, etc.), can be screened for a mutation in a sequence of interest (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90). Screening for plants carrying a mutation in a sequence of interest can be performed using methods routine in the art (e.g., hybridization, amplification, combinations thereof) or by evaluating the phenotype (e.g., detecting and/or determining the amount of one or more alkaloids and/or one or more TSNAs in the roots and/or the leaf). Generally, the presence of a mutation in one or more of the nucleic acid sequences disclosed herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90) results in a reduction of one or more alkaloids in the leaf of the mutant plants and/or one or more TSNAs in the cured leaf of the mutant plants compared to a corresponding plant (e.g., having the same varietal background) lacking the mutation.

As used herein, "reduced" or "reduction" refers to a decrease (e.g., a statistically significant decrease) in the amount of one or more alkaloids in tobacco leaf, either green or cured, and/or one or more TSNAs in green or cured leaf by at least about 5% up to about 95% (e.g., about 5% to about 10%, about 5% to about 20%, about 5% to about 50%, about 5% to about 75%, about 10% to about 25%, about 10% to about 50%, about 10% to about 90%, about 20% to about 40%, about 20% to about 60%, about 20% to about 80%, about 25% to about 75%, about 50% to about 75%, about 50% to about 85%, about 50% to about 95%, and about 75% to about 95%) relative to similarly-treated leaf (e.g., green or cured) from a tobacco plant lacking the mutation. As used herein, statistical significance refers to a p-value of less than 0.05, e.g., a p-value of less than 0.025 or a p-value of less than 0.01, using an appropriate measure of statistical significance, e.g., a one-tailed two sample t-test.

An $M_1$ tobacco plant may be heterozygous for a mutant allele and exhibit a wild type phenotype. In such cases, at least a portion of the first generation of self-pollinated progeny of such a plant exhibits a wild type phenotype. Alternatively, an $M_1$ tobacco plant may have a mutant allele and exhibit a mutant phenotype. Such plants may be heterozygous and exhibit a mutant phenotype due to a phenomenon such as dominant negative suppression, despite the presence of the wild type allele, or such plants may be homozygous due to independently induced mutations in both alleles.

A tobacco plant carrying a mutant allele can be used in a plant breeding program to create novel and useful cultivars, lines, varieties and hybrids. Thus, in some embodiments, an $M_1$, $M_2$, $M_3$ or later generation tobacco plant containing at least one mutation is crossed with a second *Nicotiana tabacum* plant, and progeny of the cross are identified in which the mutation(s) is present. It will be appreciated that the second *Nicotiana tabacum* plant can be one of the species and varieties described herein. It will also be appreciated that the second *Nicotiana tabacum* plant can contain the same mutation as the plant to which it is crossed, a different mutation, or be wild type at the locus. Additionally or alternatively, a second tobacco line can exhibit a phenotypic trait such as, for example, disease resistance, high yield, high grade index, curability, curing quality, mechanical harvesting, holding ability, leaf quality, height, plant maturation (e.g., early maturing, early to medium maturing, medium maturing, medium to late maturing, or late maturing), stalk size (e.g., small, medium, or large), and/or leaf number per plant (e.g., a small (e.g., 5-10 leaves), medium (e.g., 11-15 leaves), or large (e.g., 16-21 leaves) number of leaves).

Breeding is carried out using known procedures. DNA fingerprinting, SNP or similar technologies may be used in a marker-assisted selection (MAS) breeding program to transfer or breed mutant alleles into other tobaccos, as described herein. Progeny of the cross can be screened for a mutation using methods described herein, and plants having a mutation in a nucleic acid sequence disclosed herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90) can be selected. For example, plants in the $F_2$ or backcross generations can be screened using a marker developed from a sequence described herein or a fragment thereof, using one of the techniques listed herein. Leaf (green or cured, as appropriate) from progeny plants also can be screened for the amount of one or more alkaloids and/or one or more TSNAs, and those plants having reduced amounts, compared to a corresponding plant that lacks the mutation, can be selected. Plants identified as possessing the mutant allele and/or the mutant phenotype can be backcrossed or self-pollinated to create a second population to be screened. Backcrossing or other breeding procedures can be repeated until the desired phenotype of the recurrent parent is recovered.

Successful crosses yield $F_1$ plants that are fertile and that can be backcrossed with one of the parents if desired. In some embodiments, a plant population in the $F_2$ generation is screened for the mutation or variant gene expression using standard methods (e.g., PCR with primers based upon the nucleic acid sequences disclosed herein). Selected plants are then crossed with one of the parents and the first backcross ($BC_1$) generation plants are self-pollinated to produce a $BC_1F_2$ population that is again screened for variant gene expression. The process of backcrossing, self-pollination, and screening is repeated, for example, at least four times until the final screening produces a plant that is fertile and reasonably similar to the recurrent parent. This plant, if desired, is self-pollinated and the progeny are subsequently screened again to confirm that the plant contains the mutation and exhibits variant gene expression. Breeder's seed of the selected plant can be produced using standard methods including, for example, field testing, confirmation of the null condition, and/or chemical analyses of leaf (e.g., cured leaf) to determine the level of alkaloids.

The result of a plant breeding program using the mutant tobacco plants described herein are novel and useful cultivars, varieties, lines, and hybrids. As used herein, the term "variety" refers to a population of plants that share constant characteristics which separate them from other plants of the same species. A variety is often, although not always, sold commercially. While possessing one or more distinctive traits, a variety is further characterized by a very small overall variation between individual with that variety. A "pure line" variety may be created by several generations of self-pollination and selection, or vegetative propagation from a single parent using tissue or cell culture techniques. A "line," as distinguished from a variety, most often denotes a group of plants used non-commercially, for example, in plant research. A line typically displays little overall variation between individuals for one or more traits of interest, although there may be some variation between individuals for other traits.

A variety can be essentially derived from another line or variety. As defined by the International Convention for the Protection of New Varieties of Plants (Dec. 2, 1961, as revised at Geneva on Nov. 10, 1972, On Oct. 23, 1978, and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it confirms to the initial variety in the expression of the essential characteristics that result from the genotype or combination of genotypes of the initial variety. Essentially derived varieties can be obtained, for example, by the selection of a natural or induced mutant, a somaclonal variant, a variant individual plant from the initial variety, backcrossing, or transformation.

Tobacco hybrids can be produced by preventing self-pollination of female parent plants (i.e., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), nuclear male sterility, genetic male sterility, molecular male sterility wherein a transgene inhibits microsporogenesis and/or pollen formation, or self-incompatibility. Female parent plants containing CMS are particularly useful. In embodiments in which the female parent plants are CMS, the male parent plants typically contain a fertility restorer gene to ensure that the $F_1$ hybrids are fertile. In other embodiments in which the female parents are CMS, male parents can be used that do not contain a fertility restorer. $F_1$ hybrids produced from such parents are male sterile. Male sterile hybrid seed can be interplanted with male fertile seed to provide pollen for seed-set on the resulting male sterile plants.

Varieties, lines and cultivars described herein can be used to form single-cross tobacco $F_1$ hybrids. In such embodiments, the plants of the parent varieties can be grown as substantially homogeneous adjoining populations to facilitate natural cross-pollination from the male parent plants to the female parent plants. The $F_2$ seed formed on the female parent plants is selectively harvested by conventional means. One also can grow the two parent plant varieties in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

The tobacco plants used in the methods described herein can be a Burley type, a dark type, a flue-cured type, a Maryland type, or an Oriental type. The tobacco plants used in the methods described herein typically are from *N. tabacum*, and can be from any number of *N. tabacum* varieties. A variety can be BU 64, CC 101, CC 200, CC 13, CC 27, CC 33, CC 35,CC 37, CC 65, CC 67, CC 301, CC 400, CC 500, CC 600, CC 700, CC 800, CC 900, CC 1063, Coker 176, Coker 319, Coker 371 Gold, Coker 48, CU 263, DF911, Galpao tobacco, GL 26H, GL 338, GL 350, GL 395, GL 600, GL 737, GL 939, GL 973, GF 157, GF 318, RJR 901, HB 04P, K 149, K 326, K 346, K 358, K394, K 399, K 730, NC 196, NC 37NF, NC 471, NC 55, NC 92, NC2326, NC 95, NC 925, PVH 1118, PVH 1452, PVH 2110, PVH 2254, PVH 2275, VA 116, VA 119,, KDH 959, KT 200, KT204LC, KY 10, KY 14, KY 160, KY 17, KY 171, KY 907, KY907LC, KTY14×L8 LC, Little Crittenden, McNair 373, McNair 944, msKY 14×L8, Narrow Leaf Madole, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN90LC, TN 97, TN97LC, TN D94, TN D950, TR (Tom Rosson) Madole, VA 309, or VA359.

In addition to mutation, another way in which the amount of alkaloids in tobacco leaf can be reduced is to use inhibitory RNAs (e.g., RNAi). Therefore, transgenic tobacco plants are provided that contain a transgene encoding at least one RNAi molecule, which, when expressed, silences at least one of the endogenous nucleic acids described herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90). As described herein, leaf from such transgenic plants exhibit a reduced amount of at least one alkaloid (e.g., compared to leaf from a plant lacking or not expressing the RNAi). In addition, leaf from such transgenic plants exhibit a reduced amount of at least one tobacco specific nitrosamine (TSNA) (e.g., compared to leaf from a plant lacking or not expressing the RNAi).

RNAi technology is known in the art and is a very effective form of post-transcriptional gene silencing. RNAi molecules typically contain a nucleotide sequence (e.g., from about 18 nucleotides in length (e.g., about 19 or 20 nucleotides in length) up to about 700 nucleotides in length) that is complementary to the target gene in both the sense and antisense orientations. The sense and antisense strands can be connected by a short "loop" sequence (e.g., about 5 nucleotides in length up to about 800 nucleotides in length)

and expressed in a single transcript, or the sense and antisense strands can be delivered to and expressed in the target cells on separate vectors or constructs. A number of companies offer RNAi design and synthesis services (e.g., Life Technologies, Applied Biosystems), and representative RNAi molecules to a number of the novel sequences described herein are provided in SEQ ID NOs: 51-56.

The RNAi molecule can be expressed using a plant expression vector. The RNAi molecule typically is at least 25 nucleotides in length and has at least 91% sequence identity (e.g., at least 95%, 96%, 97%, 98% or 99% sequence identity) to one of the nucleic acid sequences disclosed herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90) or hybridizes under stringent conditions to one of the nucleic acid sequences disclosed herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90). Hybridization under stringent conditions is described above.

Methods of introducing a nucleic acid (e.g., a heterologous nucleic acid) into plant cells are known in the art and include, for example, particle bombardment, Agrobacterium-mediated transformation, microinjection, polyethylene glycol-mediated transformation (e.g., of protoplasts, see, for example, Yoo et al. (2007, *Nature Protocols,* 2(7):1565-72)), liposome-mediated DNA uptake, or electroporation. Following transformation, the transgenic plant cells can be regenerated into transgenic tobacco plants. As described herein, expression of the transgene results in leaf that exhibits a reduced amount of at least one alkaloid and/or at least one TSNA in the resulting cured leaf relative to leaf from a plant not expressing the transgene. The leaves of the regenerated transgenic plants can be screened for the amount of one or more alkaloids and/or one or more TSNAs in the resulting cured leaf, and plants having reduced amounts of at least one alkaloid and/or at least one TSNA in the resulting cured leaf, compared to the amount in a corresponding non-transgenic plant, can be selected for use in, for example, a breeding program as discussed herein.

Nucleic acids that confer traits such as herbicide resistance (sometimes referred to as herbicide tolerance), insect resistance, or stress tolerance, can also be present in the novel tobacco plants described herein. Genes conferring resistance to a herbicide that inhibits the growing point or meristem, such as an imidazolinone or a sulfonylurea, can be suitable. Exemplary genes in this category encode mutant ALS and AHAS enzymes as described, for example, in U.S. Pat. Nos. 5,767,366 and 5,928,937. U.S. Pat. Nos. 4,761,373 and 5,013,659 are directed to plants resistant to various imidazolinone or sulfonamide herbicides. U.S. Pat. No. 4,975,374 relates to plant cells and plants containing a gene encoding a mutant glutamine synthetase (GS), which is resistant to inhibition by herbicides that are known to inhibit GS, e.g. phosphinothricin and methionine sulfoximine. U.S. Pat. No. 5,162,602 discloses plants resistant to inhibition by cyclohexanedione and aryloxyphenoxypropanoic acid herbicides.

Genes for resistance to glyphosate also are suitable. See, for example, U.S. Pat. Nos. 4,940,835 and 4,769,061. Such genes can confer resistance to glyphosate herbicidal compositions, including, without limitation, glyphosate salts such as the trimethylsulphonium salt, the isopropylamine salt, the sodium salt, the potassium salt and the ammonium salt. See, e.g., U.S. Pat. Nos. 6,451,735 and 6,451,732. Genes for resistance to phosphono compounds such as glufosinate ammonium or phosphinothricin, and pyridinoxy or phenoxy propionic acids and cyclohexones also are suitable. See, e.g., U.S. Pat. Nos. 5,879,903; 5,276,268; and 5,561,236; and European Application No. 0 242 246.

Other suitable herbicides include those that inhibit photosynthesis, such as a triazine and a benzonitrile (nitrilase). See U.S. Pat. No. 4,810,648. Other suitable herbicides include 2,2-dichloropropionic acid, sethoxydim, haloxyfop, imidazolinone herbicides, sulfonylurea herbicides, triazolopyrimidine herbicides, s-triazine herbicides and bromoxynil. Also suitable are herbicides that confer resistance to a protox enzyme. See, e.g., U.S. Pat. No. 6,084,155 and US 20010016956.

A number of genes are available that confer resistance to insects, for example, insects in the order Lepidoptera. Exemplary genes include those that encode truncated Cry1A(b) and Cry1A(c) toxins. See, e.g., genes described in U.S. Pat. Nos. 5,545,565; 6,166,302; and 5,164,180. See also, Vaeck et al., 1997, *Nature,* 328:33-37 and Fischhoff et al., 1987, *Nature Biotechnology,* 5:807-813. Particularly useful are genes encoding toxins that exhibit insecticidal activity against *Manduca sexta* (tobacco hornworm); *Heliothis virescens* Fabricius (tobacco budworm) and/or *S. litura* Fabricius (tobacco cutworm).

Plants Having Increased Amounts of Alkaloids in Leaf and Methods of Making

The sequences described herein can be overexpressed in plants in order to increase the amount of one or more alkaloids (and/or one or more TSNAs) in the leaf. Therefore, transgenic tobacco plants, or leaf from such plants, are provided that are transformed with a nucleic acid molecule described herein (e.g., SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90) or a functional fragment thereof under control of a promoter that is able to drive expression in plants (e.g., a plant promoter). As discussed herein, a nucleic acid molecule used in a plant expression vector can have a different sequence than a sequence described herein, which can be expressed as a percent sequence identity (e.g., relative to SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90) or based on the conditions under which the sequence hybridizes to SEQ ID NOs: 1, 3, 5, 7, 9, 11, 13, 15, 17, 19, 21, 23, 25, 27, 29, 31, 33, 35, 37, 39, 41, 43, 45, 47, 49, 70, 72, 74, 76, 78, 80, 82, 84, 86, 88, or 90.

As an alternative to using a full-length sequence, a portion of the sequence can be used that encodes a polypeptide fragment having the desired functionality (referred to herein as a "functional fragment"). When used with respect to nucleic acids, it would be appreciated that it is not the nucleic acid fragment that possesses functionality but the encoded polypeptide fragment. Based on the disclosure herein and the alignments shown in FIGS. 1, 2, 3 and 4, one of skill in the art can predict the portion(s) of a polypeptide (e.g., one or more domains) that may impart the desired functionality.

Following transformation, the transgenic tobacco cells can be regenerated into transgenic tobacco plants. The leaves of the regenerated tobacco plants can be screened for the amount of one or more alkaloids, and plants having increased amounts of at least one alkaloid, compared to the amount in a corresponding non-transgenic plant, can be selected and used, for example, in a breeding program as discussed herein. Expression of the nucleic acid molecule or a functional fragment thereof may result in leaf that exhibits an increased amount of at least one alkaloid compared to leaf from a tobacco plant that does not express the nucleic acid molecule or functional fragment thereof. Nucleic acids conferring herbicide resistance, insect resistance, or stress tolerance, can also be introduced into such tobacco plants.

Tobacco Products and Methods of Making

The methods described herein allow for leaf constituents in a tobacco plant to be altered. As described herein, altering leaf constituents refers to reducing or increasing the amount of at least one alkaloid in the leaf. As described herein, such methods can include mutagenesis (e.g., random or targeted) or the production of transgenic plants (using, e.g., RNAi or overexpression).

Leaf from such tobacco (e.g., having reduced or increased amounts of one or more alkaloids) can be cured, aged, conditioned, and/or fermented. Methods of curing tobacco are well known and include, for example, air curing, fire curing, flue curing and sun curing. Aging also is known and typically is carried out in a wooden drum (e.g., a hogshead) or cardboard cartons in compressed conditions for several years (e.g., 2 to 5 years), at a moisture content of from about 10% to about 25% (see, for example, U.S. Pat. No. 4,516,590 and 5,372,149). Conditioning includes, for example, a heating, sweating or pasteurization step as described in US 2004/0118422 or US 2005/0178398, while fermenting typically is characterized by high initial moisture content, heat generation, and a 10 to 20% loss of dry weight. See, e.g., U.S. Pat. Nos. 4,528,993, 4,660,577, 4,848,373 and 5,372,149. The tobacco also can be further processed (e.g., cut, expanded, blended, milled or comminuted), if desired, and used in a tobacco product.

Tobacco products are known in the art and include any product made or derived from tobacco that is intended for human consumption, including any component, part, or accessory of a tobacco product. Representative tobacco products include, without limitation, smokeless tobacco products, tobacco-derived nicotine products, cigarillos, non-ventilated recess filter cigarettes, vented recess filter cigarettes, cigars, snuff, pipe tobacco, cigar tobacco, cigarette tobacco, chewing tobacco, leaf tobacco, shredded tobacco, and cut tobacco. Representative smokeless tobacco products include, for example, chewing tobacco, snus, pouches, films, tablets, coated dowels, rods, and the like. Representative cigarettes and other smoking articles include, for example, smoking articles that include filter elements or rod elements, where the rod element of a smokeable material can include cured tobacco within a tobacco blend. In addition to the reduced-alkaloid tobacco described herein, tobacco products also can include other ingredients such as, without limitation, binders, plasticizers, stabilizers, and/or flavorings. See, for example, US 2005/0244521, US 2006/0191548, US 2012/0024301, US 2012/0031414, and US 2012/0031416 for examples of tobacco products.

The invention will be further described in the following examples, which do not limit the scope of the methods and compositions of matter described in the claims.

EXAMPLES

Example 1—Transport of Alkaloids from Root to Leaf

Figure 5:
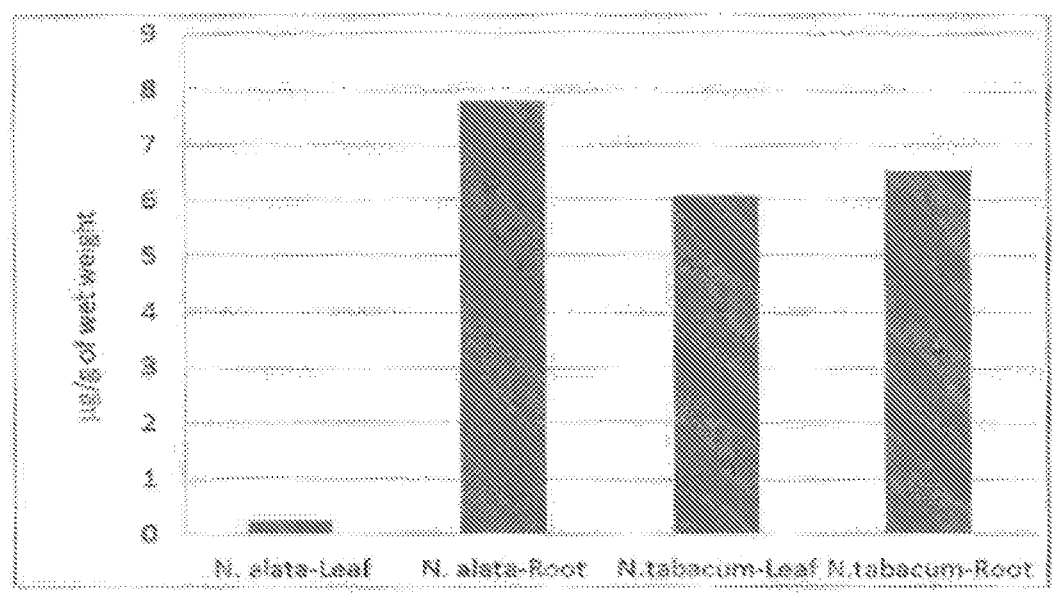
FIG. 5 is a graph showing the amount of nicotine in leaves and roots of *N. alata* and *N. tabacum*.

Previous studies have shown that *Nicotiana alata*, a relative of *Nicotiana tabacum*, does not transport alkaloids to the leaves (Pakdeechanuan et al., 2012, Plant Cell Physiol., 53(7):1247-54). This phenotype was confirmed as shown in FIG. 5. The possibility that *N. alata* is able to transport alkaloids after topping was also tested. See Table 1. Under no condition tested were alkaloids found to be transported to the leaf.

TABLE 1

Alkaloid content of *N. alata* leaves and roots with and without topping

| Code | Nicotine (µg/ml) | Nornicotine (µg/ml) | Anabasine (µg/ml) | Myosmine (µg/ml) | Anatabine (µg/ml) |
|---|---|---|---|---|---|
| Leaf from topped plants | <LOQ | ND | ND | ND | ND |
| Root from topped plants | 3.85 | 0.270 | <LOQ | 0.108 | 0.277 |
| Leaf from untopped plants | <LOQ | ND | ND | ND | ND |
| Root from untopped plants | 2.52 | 0.186 | ND | 0.0858 | <LOQ |
| Approx. limit of quantitation | 0.973 | 0.040 | 0.012 | 0.00823 | 0.128 |

LOQ, level of quantification; ND, not detected

Example 2—RNA Preparation and Sequencing

RNA from root tissue of *N. alata* plants before and after topping was collected and RNA-sequencing libraries were created using the True-Seq Library Construction Kit from Illumina. Sequencing of *N. alata* RNA was accomplished using the Illumina MiSeq platform. Sequencing runs were conducted with 150 cycle paired end read parameters, and library quality and average size were determined using an E-Gene capillary electrophoresis instrument. Root-specific gene expression in TN90 tobacco was determined by RNA deep sequencing performed by ArrayXpress (Raleigh, N.C.).

After sequencing, the resultant sequences were trimmed and reads with quality scores above 30 were assembled into contigs. Individual sequence reads were then mapped onto these contigs. Sequencing Run 1 generated 4.6 million mapped reads for a total of 69 Mb of sequence data, and Sequencing Run 2 generated 2.5 million mapped reads for a total of 37.5 Mb of sequence data. This resulted in 106.5 Mb of sequence reads used in the analysis of *N. alata* gene expression.

Full length coding sequences were determined by comparison to a *N. benthamiana* reference genome with a cutoff of 95% sequence identity. The full length coding sequences and the predicted polypeptides encoded thereby are shown in SEQ ID NOs:1-50 and 70-91.

Example 3—Analysis of Expression Levels

The TN90 and *N. alata* gene expression data were analyzed to identify transport related genes that are differentially expressed or undetected in *N. alata* compared to *N. tabacum*. The TN90 expression data was filtered for root specific expression based on differences in expression from other tissues (>9 fold higher gene expression, p-value<0.000001). Results were then filtered for high root expression (>100 reads after topping). Genes were then filtered for gene ontology (GO) terms that denote transporters of secondary metabolites (e.g., the term "transport"

coupled with "drug" or "purine" were used to filter the results). Genes that were not detected in *N. alata* in the two independent sequencing runs were filtered using the same GO criteria. These datasets then were compared to determine genes that fall into all three categories (i.e., (i) high root specific expression, (ii) GO criteria, and (iii) not expressed in *N. alata*).

These genes are listed, along with their expression level in TN90 tobacco, in Table 2.

Example 4—Sequence Alignments

The genes predicted to be involved with transport fall into five main categories: the nicotine uptake permease (Nup) family, the multidrug and toxic compound extrusion-type (MATE) family, the multiple drug resistance (MDR) family, and the pleiotropic drug resistance (PDR) family, as well as a group of unrelated genes. The nucleotide sequences and the predicted polypeptide sequences were compared with

TABLE 2

Gene expression in TN90

| | Gene Designation | Root (0 hr*) | Root (24 hr*) | Root (72 hr*) | Bud | Leaf | SEM | *N. alata* | SEQ ID NO (nt/prot) |
|---|---|---|---|---|---|---|---|---|---|
| NUP | C32288 | 495 | 229 | 359 | 13 | 25 | 23 | ND | 1/2 |
| | C40974 | 820 | 129 | 184 | 3 | 6 | 4 | ND | 3/4 |
| | C42033 | 382 | 91 | 147 | 16 | 12 | 15 | ND | 5/6 |
| | C29462 | 769 | 459 | 414 | 42 | 119 | 61 | ND | 7/8 |
| MDR | DC3222 | 224 | 296 | 180 | 759 | 2332 | 1058 | ND | 9/10 |
| | DC62783 | 255 | 225 | 176 | 7 | 4 | 2 | ND | 11/12 |
| | DC26451 | 192 | 205 | 174 | 14 | 67 | 11 | ND | 13/14 |
| | C11099 | 34 | 198 | 158 | 1 | 0 | 1 | ND | 15/16 |
| MATE | DC58421 | 149 | 320 | 221 | 15 | 16 | 5 | ND | 17/18 |
| | DC38072 | 153 | 134 | 147 | 11 | 39 | 12 | ND | 19/20 |
| | C46276 | 70 | 658 | 422 | 5 | 4 | 4 | ND | 21/22 |
| | C48594 | 188 | 307 | 321 | 9 | 3 | 9 | ND | 23/24 |
| | C9954 | 91 | 154 | 181 | 4 | 3 | 3 | ND | 25/26 |
| | C39106 | 308 | 502 | 527 | 12 | 9 | 10 | ND | 27/28 |
| | C3055 | 416 | 681 | 512 | 11 | 122 | 6 | ND | 29/30 |
| | DC14012 | 209 | 178 | 208 | 525 | 447 | 459 | ND | 31/32 |
| PDR | C53160 | 984 | 947 | 772 | 149 | 175 | 127 | ND | 33/34 |
| | C22474 | 916 | 906 | 599 | 84 | 76 | 64 | ND | 35/36 |
| Other | DC69629 | 267 | 396 | 480 | 17 | 5 | 10 | ND | 37/38 |
| | C43677 | 17 | 17 | 116 | 243 | 9 | 127 | ND | 39/40 |
| | C19125 | 138 | 252 | 177 | 8 | 32 | 17 | ND | 41/42 |

*, hrs after topping;

ND = not detected

The expression level of *N. alata* genes relative to TN90 expression also were analyzed to determine possible regulatory and/or biosynthetic genes that were highly expressed in *N. alata* but not in *N. tabacum*. Four targets were identified, which are listed in Table 3.

sequences deposited in public databases. The results of those comparisons are shown in Table 4 (Nup sequences), Table 5 (MDR sequences), Table 6 (MATE sequences), Table 7 (PDR sequences), Table 8 (other transporter sequences), and Table 9 (*N. alata* genes expressed at high levels).

TABLE 3

Expression of genes highly expressed in N. alata

| Gene | TN90[a] | N. alata[a] | Root (0 hr*) | Root (24 hr*) | Root (72 hr*) | Bud | Leaf | SEM | SEQ ID NO: |
|---|---|---|---|---|---|---|---|---|---|
| C31400 | 61 | 1469 | 355 | 735 | 584 | 182 | 437 | 276 | 43/44 |
| DC77221 | ND | 2754 | 1535 | 2313 | 1931 | 11 | 3 | 9 | 45/46 |
| C10055 | 150 | 1590 | 63 | 53 | 81 | 10 | 13 | 21 | 47/48 |
| C33728 | 1 | 8539 | 2328 | 2151 | 1677 | 2500 | 1298 | 2338 | 49/50 |

[a]root tissues collected 72 hours after topping;

*hrs after topping

TABLE 4

Nup sequences

| Gene | Nuc ID % | Prot ID % | Protein Accession | Description |
|---|---|---|---|---|
| C32288 | 77 | 75 | ADP30798 | nicotine uptake permease 1 [*Nicotiana tabacum*] |
| C40974 | 82 | 81 | ADP30798 | nicotine uptake permease 1 [*Nicotiana tabacum*] |
| C42033 | 83 | 85 | ADP30799 | nicotine uptake permease 2 [*Nicotiana tabacum*] |
| C29462 | 93 | 93 | ADP30798 | nicotine uptake permease 1 [*Nicotiana tabacum*] |

TABLE 5

MDR sequences

| Gene | Nuc ID % | Prot ID % | Protein Accession | Description |
|---|---|---|---|---|
| DC3222 | 86 | 87 | XP_004247427 | predicted: ABC transporter C family member 4-like [*Solanum lycopersicum*] |
| DC62783 | 87 | 89 | XP_004232253 | predicted: ABC transporter B family member 15-like [*Solanum lycopersicum*] |
| DC26451 | 90 | 91 | XP_004233862 | predicted: ABC transporter B family member 9-like, partial [*Solanum lycopersicum*] |
| C11099 | 84 | 85 | XP_004235187 | predicted: putative ABC transporter B family member 8-like [*Solanum lycopersicum*] |

TABLE 6

MATE sequences

| Gene | Nuc ID % | Prot ID % | Protein Accession | Description |
|---|---|---|---|---|
| DC58421 | 69 | 71 | XP_004231608 | predicted: protein TRANSPARENT TESTA 12-like [*Solanum lycopersicum*] |
| DC38072 | 79 | 78 | XP_004245689 | predicted: MATE efflux family protein DTX1-like [*Solanum lycopersicum*] |
| C46276 | 78 | 84 | XP_004229626 | predicted: MATE efflux family protein FRD3-like [*Solanum lycopersicum*] |
| C48594 | 76 | 87 | XP_004233485 | predicted: MATE efflux family protein 9-like [*Solanum lycopersicum*] |
| C9954 | 52 | 87 | XP_004233485 | predicted: MATE efflux family protein 9-like [*Solanum lycopersicum*] |
| C39106 | 63 | 67 | DAA50099 | TPA: putative MATE efflux family protein [*Zea mays*] |
| C3055 | 81 | 88 | XP_004239125 | predicted: protein TRANSPARENT TESTA 12-like [*Solanum lycopersicum*] |
| DC14012 | 86 | 85 | XP_004248692.1 | predicted: MATE efflux family protein 4, chloroplastic-like [*Solanum lycopersicum*] |

TABLE 7

PDR sequences

| Gene | Nuc ID % | Prot ID % | Protein Accession | Description |
|---|---|---|---|---|
| C53160 | 100 | 100 | BAD07484 | PDR-type ABC transporter 2 [*Nicotiana tabacum*] |
| C22474 | 100 | 100 | AFN42938 | pleiotropic drug resistance transporter 5b [*Nicotiana tabacum*] |

TABLE 8

Other transporter sequences

| Gene | Nuc ID % | Prot ID % | Protein Accession | Description |
|---|---|---|---|---|
| DC69629 | 89 | 92 | XP_004236321 | predicted: adenine/guanine permease AZG2-like [*Solanum lycopersicum*] |
| C43677 | 71 | 67 | XP_004235470.1 | predicted: bidirectional sugar transporter SWEET12-like [*Solanum lycopersicum*] |
| C19125 | 98 | 91 | CCQ77797 | heavy metal ATPase [*Nicotiana tabacum*] |

TABLE 9

Genes expressed at high levels in *N. alata*

| Query | Nuc ID % | Prot ID % | Protein Accession | Description |
|---|---|---|---|---|
| C31400 | 88 | 91 | NP_001234027 | spe4 protein [*Solanum lycopersicum*] |
| DC77221 | 82 | 81 | XP_004242860 | F-box/kelch-repeat protein [*Solanum lycopersicum*] |
| C10055 | 76 | 72 | XP_004239926 | proline transporter 2-like [*Solanum lycopersicum*] |
| C33728 | 100 | 100 | AAC49850.1 | DNA binding protein ACBF [*Nicotiana tabacum*] |

One of the genes that was highly expressed in *N. alata* relative to *N. tabacum*, C33728, appears to be an AC-rich binding factor (ACBF) regulatory protein. This polypeptide was shown to bind to AC-rich repeat regions in the promoter of heterologous xylem-related promoter from bean when transferred to tobacco, and was found to be expressed in all tissues but was most prevalent in the stem of the plant (Séguin et al., 1997, *Plant Mol. Biol.*, 35(3):281-91). The polypeptide contains three distinct predicted RNA binding domains and a glutamine rich region that may be involved in gene activation. These predicted domains are shown with underlining in SEQ ID NO:50 below. The N-terminal domain is glutamine rich. This type of domain architecture is found in a number of splicing factors (Lorkovic and Barta, 2002, *Nuc. Acids Res.*, 30:623-35).

(SEQ ID NO: 50)
MDGDAVSSSSNGDAATDDVWSAIHALQQHQQQQQKMQQSPTQIQSSSEDN

KTIWIGDLQQWMDESYLHSCFSQAGEVISVKIIRNKQTGQSERYGFVEEN

THAAAEKVLQSYNGIMMPNAEQPFRLNWAGFSTGEKRAETGSDFSIFVGD

LASDVTDTMLRDTFASRYPSLKGAKVVVDANIGHSKGYGEVREGDESERS

RAMTEMNGVYCSSRAMRIGVATPKKPSAQQQYSSQAVILSGGYASNGAAT

```
HGSQSDGDSSNTTIFVGGLDSDVTDEELRQSFNQFGEVVSVKIPAGKGCG

FVQFSDRSSAQEAIQKLSGAIIGKQAVRLSWGRSPANKQMRTDSGSQWNG

GYNGRQNYGGYGYGASQNQDSGMYATGAAYGASSNGYGNHQQPVS*
```

Example 5—RNAi Line Development, Plasmid Construction and Transformation

Figure 6:
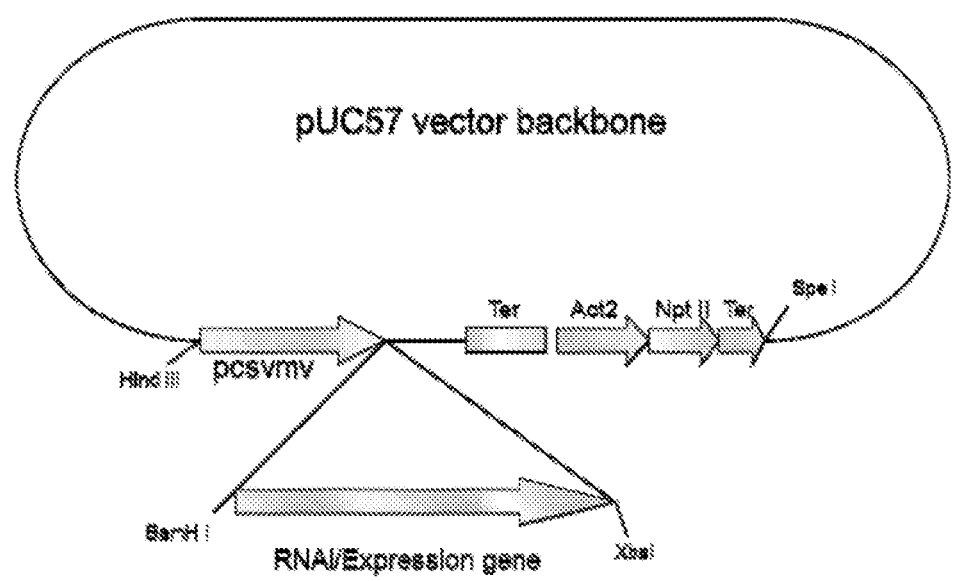
FIG. 6 is a schematic of the construct used to express RNAi molecules in transgenic plants as described herein.

In order to evaluate the function of the candidate genes, two sets of transgenic plants were generated, one using the full length coding sequence and one using an RNAi sequence (see FIG. 6). For expression of the full length coding sequence or the RNAi sequence, an expression vector (SEQ ID NO:21) was used that has a CsVMV promoter and a NOS terminator, as well as a cassette having a kanamycin selection marker (NPT II) under direction of the actin2 promoter and having the NOS terminator. The nucleic acid constructs carrying the transgenes of interest were introduced into tobacco leaf disc using DNA bombardment or a biolistic approach. See, for example, Sanford et al., 1993, Methods Enzymol., 217:483-510; and Okuzaki and Tabei, 2012, Plant Biotechnology, 29:307-310.

Briefly, the plasmid DNA containing the transformation cassette was coated on 1 μm gold particles (DNA/gold) as follows. The 1 μm gold particles were baked at 180° C. for 12 hours, and a stock solution (40 mg/ml) was prepared. To make a mixture for 10 shots, 100 μl of the stock solution was mixed with 40 μl of expression vector DNA (1 μg/μl), 100 μl of 2.5 M $CaCl_2$, and 40 μl of 0.1 M spermidine in a 1.5-ml tube. The mixture was centrifuged for 30 s at 13,000×g, and the pellet was washed with 500 μl 100% ethanol. The DNA/gold mixture was suspended in 100 μl of water, and 10 μl was applied onto a macrocarrier, dried, and then bombarded. Two shots were bombarded per plate using a 1,100 psi rupture disc under partial vacuum (711 mmHg) in a PDS-1000/He system (Bio-Rad Laboratories, Hercules, Calif., USA).

Narrow Leaf Madole (NLM) and Tennessee 90 (TN90) tobacco leaf discs were used for transformation with the RNAi constructs, and Nicotiana alata tobacco leaf discs were used for transformation with the full length candidate gene constructs. Whole tobacco leaf (about 45×30 mm in length) was placed on the MS medium overnight, and the leaf disc was bombarded with the construct on the second day. Leaves were then cut into small pieces (about 5×5 mm) and replaced on the TOM medium (MS medium with 20 g sucrose/L; 1 mg/L IAA and 2.5 mg/L BAP) to grow at 27° C. for 3-5 days, then transferred to TOM medium to grow, which contains 300 mg/l Kanamycin (TOM-Kan). Tissues were transferred to new TOM-Kan plates every 2-3 weeks for 4-6 weeks (27° C., 16 h light). Kanamycin-resistant primary shoots were regenerated at 4-6 weeks after bombardment. Shoots were transferred to MS-Kanamycin plates to grow root.

The leaves and/or roots from T1 plants (and subsequent generations) are evaluated to determine the amount of one or more alkaloids and/or one or more TSNAs.

Example 6—Sequences of RNAi Molecules and Expression Construct

RNAi molecule sequences are shown below. The double-underlined portion is the loop, which is from the tobacco QS gene sequence.

```
pALCS-TDNA-R1 RNAi sequence
                                    (22474; SEQ ID NO: 51)
GGATCCAAAG AGCAGGCCAG CGATATGGAA GCTGATCAAG AAGAAAGCAC GGGAAGCCCA  60

AGACTTAAAA TCAGCCAGTC GAAGAGAGAT GATCTCCCTC GATCCTTATC TGCAGCAGAT 120

GGAAATAAGA CAAGAGAAAT GGAAATCCGA CGAATGAGCA GTCATATCCA TTCTAGTGGC 180

CTCTACAGAA ATGAGGATGC AAATCTTGAG GCTGCAAATG GTGTCGCAGG TTCTTTACTT 240

GAACATTTTA GGAATTTAGG AAATGCTTGT TCGTCATTTG TTTTGTGTCC TAGCCTATTG 300

TTTATTGTTT GTTTTTATCT TCACTTTAGT GAGGATACAT ATTCTGAGCA CACTCTGAAA 360

ATATAGCTCA TTTATGTTTA TAGGGAAAGG AGAAAAGAGA GAGTCACATC ATGGCAACTG 420

CGACACCATT TGCAGCCTCA AGATTTGCAT CCTCATTTCT GTAGAGGCCA CTAGAATGGA 480

TATGACTGCT CATTCGTCGG ATTTCCATTT CTCTTGTCTT ATTTCCATCT GCTGCAGATA 540

AGGATCGAGG GAGATCATCT CTCTTCGACT GGCTGATTTT AAGTCTTGGG CTTCCCGTGC 600

TTTCTTCTTG ATCAGCTTCC ATATCGCTGG CCTGCTCTTT TCTAGA            646 pALCS-TDNA-R4 RNAi sequence
                                    (43677; SEQ ID NO: 52)
GGATCCGTTT TGGTCCTTTG CATAAAATTT GGGTAAGGAA AAGAATCAAT CCAAAGCCAC  60

CGAAATTCAA CAGTAGGACA AGTCTCAGTG TTTGCATCTG CAAAACCATT CCAAATTTCA 120

CAATCCACGA AACTGTGTAA CAATAACTAA AACATAACGA AATAAATACT AGGAGTATAA 180

TCTATAGGCA CAAAATTGAA GTTGTGCATG TTCTTTACTT GAACATTTTA GGAATTTAGG 240

AAATGCTTGT TCGTCATTTG TTTTGTGTCC TAGCCTATTG TTTATTGTTT GTTTTTATCT 300

TCACTTTAGT GAGGATACAT ATTCTGAGCA CACTCTGAAA ATATAGCTCA TTTATGTTTA 360
```

-continued

TAGGGAAAGG AGAAAAGAGA GAGTCACATC ATGGATGCAC AACTTCAATT TTGTGCCTAT 420

AGATTATACT CCTAGTATTT ATTTCGTTAT GTTTTAGTTA TTGTTACACA GTTTCGTGGA 480

TTGTGAAATT TGGAATGGTT TTGCAGATGC AAACACTGAG ACTTGTCCTA CTGTTGAATT 540

TCGGTGGCTT TGGATTGATT CTTTTCCTTA CCCAAATTTT ATGCAAAGGA CCAAAACGTC 600

TAGA                                                              604 pALCS-TDNA-R2 RNAi sequence
                                                (11099; SEQ ID NO: 53)
GGATCCAAAG ATTTCAAGGA CCTTATTTAT GCTCCCAAAC GAGGTCACAA TCCTATGATT  60

ATAAACAGCC TCCACAGCAG TTTGAGTGCT TTGATATTGT GCCTTGACGA ACTTAGCTGT 120

GATGGTGGAT AGCAAGACTT TTCGCGTGTA AAAGCATAGA ATTGTGAGAG GTTGGACAGC 180

AATCATAACT AGTGCAAGCT TCCAAGCGTT CTTTACTTGA ACATTTTAGG AATTTAGGAA 240

ATGCTTGTTC GTCATTTGTT TTGTGTCCTA GCCTATTGTT TATTGTTTGT TTTTATCTTC 300

ACTTTAGTGA GGATACATAT TCTGAGCACA CTCTGAAAAT ATAGCTCATT TATGTTTATA 360

GGGAAAGGAG AAAAGAGAGA GTCACATCAT GGCAAGCTTG GAAGCTTGCA CTAGTTATGA 420

TTGCTGTCCA ACCTCTCACA ATTCTATGCT TTTACACGCG AAAAGTCTTG CTATCCACCA 480

TCACAGCTAA GTTCGTCAAG GCACAATATC AAAGCACTCA AACTGCTGTG GAGGCTGTTT 540

ATAATCATAG GATTGTGACC TCGTTTGGGA GCATAAATAA GGTCCTTGAA ATCTTTGTCT 600

AGA                                                               603 pALCS-TDNA-R7 RNAi sequence
                                                (40974; SEQ ID NO: 54)
GGATCCGTGT CAACCTCTTC ACTTCTTCTT GCTGCTCAAC TTGCCTTCAC GGCAATAGGT  60

GCTTTCTTCA TAGTGAAGCT GAAATTCACA CCCTACTCTA TCAATGCAGT GGTTCTGTTG 120

ACAGTTGGTG CTGTTTTATT AGGTATTCGA TCAAATGGTG ATCGGCCAGA GGGTGTGACA 180

AGTAGAGCTT ATATTTACTC TTTGTTCTTT ACTTGAACAT TTTAGGAATT TAGGAAATGC 240

TTGTTCGTCA TTTGTTTTGT GTCCTAGCCT ATTGTTATT GTTTGTTTTT ATCTTCACTT 300

TAGTGAGGAT ACATATTCTG AGCACACTCT GAAAATATAG CTCATTTATG TTTATAGGGA 360

AAGGAGAAAA GAGAGAGTCA CATCATGGCA AGAAAGATA AACCTTTAGT ACTAGTGAGG 420

CTTGAACGTC TGTGACATTT AAAGTCCTAA GTTAGTTTCT ATTGTAATTG AATATAAGCT 480

CTACTTGTCA CACCCTCTGG CCGATCACCA TTTGATCGAA TACCTAATAA ACAGCACCA 540

ACTGTCAACA GAACCACTGC ATTGATAGAG TAGGGTGTGA ATTTCAGCTT CACTATGAAG 600

AAAGCACCTA TTGCCGTGAA GGCAAGTTGA GCAGCAAGAA GAAGTGAAGA GGTTGACACT 660

CTAGA                                                             665 pALCS-TDNA-R3 RNAi sequence
                                                (46276; SEQ ID NO: 55)
GGATCCACAC CATCTAAAAC AAACGCCAAT GAGTTGATTG GTTGTGTACC AGCGACAAAC  60

TGGCGAAGGA GCACAAGGTA AAAGAACAG TTAAAGATAG TGAAACAAAA GAAGAACAAA 120

TTGAAACAAA CATATAGTAC TACTATTTAT TGAATGTATA CCGGGATGGC AATGGTTATG 180

AGACGGATAA CATTTTTGTC CTTTGAGTTC TTTACTTGAA CATTTAGGA ATTTAGGAAA 240

TGCTTGTTCG TCATTTGTTT TGTGTCCTAG CCTATTGTTT ATTGTTGTT TTTATCTTCA 300

CTTTAGTGAG GATACATATT CTGAGCACAC TCTGAAAATA TAGCTCATTT ATGTTTATAG 360

GGAAAGGAGA AAAGAGAGAG TCACATCATG GCAATCAAAG GACAAAAATG TTATCCGTCT 420

CATAACCATT GCCATCCCGG TATACATTCA ATAAATAGTA GTACTATATG TTTGTTTCAA 480

TTTGTTCTTC TTTTGTTTCA CTATCTTTAA CTGTTCTTTT TACCTTGTGC TCCTTCGCCA 540

GTTTGTCGCT GGTACACAAC CAATCAACTC ATTGGCGTTT GTTTTAGATG GTGTTCTAGA 600

```
pALCS-TDNA-R5 RNAi sequence
                                               (39106; SEQ ID NO: 56)
GGATCCATGG GCTGATGTTC ATGGTTTCAA TGGGGTTCAA TGCTGCTGCT AGTGTAAGGG    60

TGAGCAATGA GTTAGGAGCA CCACACCCAA AGTCAGCAGC ATTCTTAGTG TTTGTGGTGA   120

CATTCATTTC ATTTCTCATA GCTGTGGTGG AAGCCATAAT TATGCTGTGT TTGCGCAATG   180

TGATCAGCTA TGCATTCACT AAGGGTTACT CTTTGTTCTT TACTTGAACA TTTTAGGAAT   240

TTAGGAAATG CTTGTTCGTC ATTTGTTTTG TGTCCTAGCC TATTGTTTAT TGTTTGTTTT   300

TATCTTCACT TTAGTGAGGA TACATATTCT GAGCACACTC TGAAAATATA GCTCATTTAT   360

GTTTATAGGG AAAGGAGAAA AGAGAGAGTC ACATCATGGC AAAGAAAGAT AAACCTTTAG   420

TACTAGTGAG GCTTGAACGT CTGTGACATT TAAAGTCCTA AGTTAGTTTC TATTGTAATT   480

GACCCTTAGT GAATGCATAG CTGATCACAT TGCGCAAACA CAGCATAATT ATGGCTTCCA   540

CCACAGCTAT GAGAAATGAA ATGAATGTCA CCACAAACAC TAAGAATGCT GCTGACTTTG   600

GGTGTGGTGC TCCTAACTCA TTGCTCACCC TTACACTAGC AGCAGCATTG AACCCCATTG   660

AAACCATGAA CATCAGCCCA TTCTAGA                                       687
```

The sequence of the expression cassette is shown in FIG. 10, with the relevant portions indicated in the left margin. See also FIG. 6.

Example 7—Random Mutagenesis and Characterization of Mutants

For EMS mutation, one gram (approximately 10,000 seeds) of Tennessee 90 tobacco (TN90) converter seed was washed in 0.1% Tween® for fifteen minutes and then soaked in 30 ml of ddH$_2$O for two hours. One hundred fifty (150) μl of 0.5% EMS (Sigma, Catalog No. M-0880) was then mixed into the seed/ddH$_2$O solution and incubated for 8-12 hours (rotating at 30 rpm) under a hood at room temperature (RT; approximately 20° C.). The liquid then was removed from the seeds and the liquid was mixed into 1 M NaOH overnight for decontamination and disposal. The seeds were then washed twice with 100 ml ddH$_2$O for 2-4 hours. The washed seeds were then suspended in 0.1% agar:water solution.

The EMS-treated seeds in the agar solution were evenly spread onto water-soaked Carolina's Choice Tobacco Mix3 (Carolina Soil Company, Kinston, N.C.) in flats at ~2000 seeds/flat. The flats were then covered with plastic wrap and placed in a growth chamber. Once the seedlings emerged from the soil, the plastic wrap was punctured to allow humidity to decline gradually. The plastic wrap was completely removed after two weeks. Flats were moved to a greenhouse and fertilized with NPK fertilizer. The seedlings were plugged into a float tray and grown until transplanting size. The plants were transplanted into a field. During growth, the plants were self-pollinated to form M$_1$ seeds. At the mature stage, five capsules were harvested from each plant and individual designations were given to the set of seeds from each plant. This formed the M$_1$ population.

A composite of M$_1$ seed from each M$_0$ plant was grown, and leaves from M$_1$ plants were collected and DNA extracted. Target genes were amplified and sequenced for mutation identification.

Example 8—Targeted Mutagenesis Using TALENs

Gene specific TALEN recognition sequences were found within either the specific gene targets or within the promoter sequence that allow for targeted deletions or promoter insertions in order to reduce expression of the gene or change the tissue-specific expression. The sequences of the regions of interest are shown below (SEQ ID NOs: 61-69). The specific target sequences for gene C22474 (Pdr5b) are underlined in the corresponding sequence of the region of interest. The locations of all of the TALEN regions of interest are shown schematically in FIG. 7. The yellow bar denotes the primary transcript including introns. The green denotes the upstream region which has been marked as the promoter region. These TALEN sites are specific for the single gene target based on known genomic sequence information. TALEN regions 1 and 2 for each gene are used to disrupt the promoter or 5' end of the coding region, while other regions are used to disrupt only the coding sequence.

```
C22474-TAL1
                                              (SEQ ID NO: 61)
AATTCAAACCTGTCAAAACCATAAAAAGATATTGGACAAATGCTTTTAAT

ATAATTGCCTTAGATTAATCTATATATATATATATATATATATAGGTAAA

TACTTACTTGTATCAGACATTTATCTTTATAAATATGTTATTCACTAAAT

CATAGTTAATTAATATATATTTTTACCTTAAGGGGCCGTTTGGTTGGGAA

A

C22474-TAL2
                                              (SEQ ID NO: 62)
TATCGCACTACTATTGAACCTATCGCCTTTTGAGTTTTGATATATAAATA

GCGACGAACGTTTCTTAGATAATGGACTCATAACCTCCCTCTTCACAACT

AGAAGAGCGTGAGACCTTTTCAATTAGAATTCGTAGGAAAAAATCAAACA

CAAATTCACAAAACAAAAATTTATTAAGATTTCAGCGACCAAGCCCGTGA

G

C22474-TAL3
                                              (SEQ ID NO: 63)
TCGTTTGAGAAAAACGGTCCTTAAATCGGTCATGGAAAGTGAGAATAATC

AGGGCAATAAAAAAGTTGTTCATAAGGAAGTTGATGTTCGGAATCTGGGA

TTGAATGAGCGACAAGAGTTCATTGATCGATTTTTCAGGGTTGCTGAGGA
```

```
-continued
AGATAATGAAAAGTTTCTGAGAAAGTTCAGAAATCGAATTGACAAGTAAG

TTTCCAGTATTACT

C22474-TAL4
                                              (SEQ ID NO: 64)
ACAAGCCACAAGCTACACTATCCAAAGAGCAGGCCAGCGATATGGAAGCT

GAGCAAGAAGAAAGCACGGGAACCCCTAGACTTCGAATCAGCCAGTCGAA

GAGAGATGATCTCCCTCGATCCTTATCTGCAGCAGATGGGAACAAGACAA

GTATGATCTTTAGCCCATCAATAACAGAATCTGCTTGGGGAATATAAGTA

ATGCTTACAGT

C11099-TAL1
                                              (SEQ ID NO: 65)
ATACGATAAGTCCTCTTAAAATTACCATACTTATAAAGTCATAAAAGTAG

AAAGAAAAAGGACCTCTTTGAAAATTTTTATATAAAAGGGGCTGAAAATA

TGCGATAATGTCAAGTAGCAGTTTGGCTTCATATATTGGTCCATGTTATC

GGAGTTGGTATTTATGTTAAATATTAAGTACTTTTTTATCATATCTATCA

C11099-TAL2
                                              (SEQ ID NO: 66)
ACTCAATTTCTGCCACTTTATTATAAATAGTAAGTTAGTATTCCATTCTT

GGTCAGAAAGGAGTATGGGAAATCAAGGTCTATTTTCTTAGTTACAGACC

TAACAATTTCCATTGTCACCTTTTTTCAGCTGTTGGCGTGTAGAAACGGA

CCTTTGAGCATTGTTGATGCGTTTGACTTGTTTTAGAAAAGAAAAAAGAA

TG

C11099-TAL3
                                              (SEQ ID NO: 67)
GGCTAGTTGTGGCTTGGAAGCTTGCACTAGTTATGATTGCTGTCCAACCT

CTCACAATTCTATGCTTTTACACGCGAAAAGTCTTGCTATCCACCATCAC

AGCTAAGTTCGTCAAGGCACAATATCAAAGCACTCAAACTGCTGTGGAGG

CTGTTTATAATCATAGGATTGTGACCTCGTTTGGGAGCATAAATAAGGTC

CTTGAAATCTTTGATGAGGCACAGGATGAGTCAA

C43677-TAL1
                                              (SEQ ID NO: 68)
TTTTTAACCACCTAGTGGATGCTAATATGGTGTCAGCATTAGAAGAAACT

AATTCATGATTTAAGTTTTATAGGTTCAATTTTTAGATTTTTAATATTAA

ATATATTATATTTTAAAGTTATGAGTTAATATTTGTTGAAGTATTTGTTA

AGTATAATTATAATAAATTTTAACACTAATATTTATATTTATGCTCTGCG

TCAACAG

C43677-TAL2
                                              (SEQ ID NO: 69)
TTTTTAACCACCTAGTGGATGCTAATATGGTGTCAGCATTAGAAGAAACT

AATTCATGATTTAAGTTTTATAGGTTCAATTTTTAGATTTTTAATATTAA

ATATATTATATTTTAAAGTTATGAGTTAATATTTGTTGAAGTATTTGTTA

AGTATAATTATAATAAATTTTAACACTAATATTTATATTTATGCTCTGCG

TCAACAG
```

The target sequences of the genes of interest are sent to Life Technology (Carlsbad, Calif.) to determine possible binding site sequences of the transcription activator like (TAL) effector proteins. The TALs are synthesized and cloned into the inventors' plant expression vector, pALCS1, by Life Technology to serve as entry vectors. Depending on the purpose, five different protocols can be used to generate mutagenic tobacco lines: 1) one or more entry vectors (pALCS1 containing the target TALs) are directly transformed into tobacco protoplasts to generate random sequence deletion or insertion mutagenic tobacco lines; 2) a donor sequence (e.g., a reporter gene, e.g., the GUS gene) flanked on the left and right side with sequences that are homologous with the target insertion sequence is co-transformed into tobacco protoplasts with one or more entry vectors (pALCS1 containing the target TALs) to generated mutagenic tobacco lines containing a reporter gene; 3) a donor sequence containing target TALs that have a point mutation is co-transformed into tobacco protoplasts with one or more entry vectors (pALCS1 containing the target TALs) to generated mutagenic tobacco lines having a point mutation; 4) a donor sequence containing a tissue specific promoter sequence to generate mutant tobacco lines that express the endogenous gene in a tissue specific manner; and 5) a donor sequence containing a combination of the aforementioned donor sequences with a reporter gene construct to facilitate mutant tobacco screening.

Tobacco protoplasts are isolated from TN90 tobacco leaves growing in Magenta boxes in a growth chamber. Well-expanded leaves (5 cm) from 3-4-week-old plants are cut into 0.5 to 1-mm leaf strips from the middle part of a leaf. Leaf strips are transferred into the prepared enzyme solution (1% cellulase R10, 0.25% macerozyme R10, 0.4 M mannitol, 20 mM KCl, 20 mM MES (pH 5.7), 10 mM $CaCl_2$, 0.1% BSA) by dipping both sides of the strips. Leaf strips are vacuum infiltrated for 30 min in the dark using a desiccator with continuing digestion in the dark for 4 hour to overnight at room temperature without shaking. Protoplasts are filtered in 100 μm nylon filter and purified with 3 ml Lymphoprep. Protoplasts are centrifuged and washed with W5n solution (154 mM NaCl, 125 mM $CaCl_2$, 5 mM KCl, 2 mM MES, 991 mg/l glucose pH 5.7) and suspended in W5n solution at the concentration of $5 \times 10^5$/ml. Protoplasts are kept on ice for 30 minutes to settle at the bottom of the tube by gravity. W5n solution was moved and protoplasts were re-suspended in P2 solution at room temperature. 50 μl DNA (10-20 μg of plasmid), 500 μl protoplasts ($2 \times 10^5$ protoplasts) and 550 μl of PEG solution (40%, v/v 10 ml 4 g PEG4000, 0.2 M mannitol, 0.1 M $CaCl_2$) are mixed gently in a 15 ml microfuge tube, and the mixture incubated at room temperature for 5 minutes.

Protoplasts are pelleted and re-suspended with 1 ml 2X 8EN1 (8EN1: MS salt without $NH_4NO_3$, MS vitamin, 0.2% myo-Inositol, 4 mM MES, 1 mg/l NAA, 1 mg/l IAA, 0.5 M mannitol, 0.5 mg/l BAP, 1.5% sucrose). Transformed protoplasts are jellified with equal amount of low-meting agarose (LMA), and 0.2 ml of protoplast-LAM is dropped to form a bead. 10 ml 8EN1 is added to the bead, and in 7 days, 5 ml 8EN1 is taken out and 5 ml 8EN2 (8EN1 with 0.25 M mannitol) is added; after another 7 days (14 day), 10 ml 8EN2 is taken out and 10 ml 8EN2 is added; in another 7 days (21 day), 5 ml 8EN2 is taken out and 5 ml 8EN3 (8EN1 with 3% sucrose and without mannitol) is added; after another 7 days (28 day), 10 ml 8EN3 is taken out and 10 ml 8EN3 is added. Protoplasts are kept for two weeks until micro-callus growth. Callus is transferred to NCM solid media until it reaches about 5 mm (usually about two weeks). Callus was transferred to TOM-Kan solid media to grow shoots, and transformed tobacco plants were regenerated using the methods described herein.

TABLE 10

TAL effector binding site sequences

| TALEN | Target sequence | SEQ ID NO: |
|---|---|---|
| TALEN site 1 | TATGTTATTCACTAAATCATAGTTAAT TA<u>ATATATATTTTTACCTTA</u> | 58 |
| TALEN site 2 | TTCACAACTAGAAGAGCGTGAGACCTT TTC<u>AATTAGAATTCGTAGGA</u> | 59 |
| TALEN site 3 | TCCTTAAATCGGTCATGGAAAGTGAGA ATA<u>ATCAGGGCAATAAAAAA</u> | 60 | underlining = TAL binding sites; non-underlining region between TAL binding sites = position where DNA cleavage is designed to occur Example 9—Screening Plants for Modulation of Alkaloid Content Transgenic and mutant tobacco plants identified in Examples 5, 6, 7 or 8 are grown in a greenhouse under field-like conditions in Carolina's Choice Tobacco Mix (Carolina Soil Co., Kinston, N.C.) in 10 inch pots. At flowering stage, the plants are topped and tissue samples are collected from expanded leaves and roots 2 weeks later.

The tissue is ground in a mortar and pestle. Alkaloid content is determined by gas chromatography coupled to mass spectroscopy using certified protocols from Arista Laboratories. The amount of nicotine, nornicotine, anabasine, and anatabine, as well as the total alkaloid content, are determined.

Example 10—Nicotine Feeding Assay

Figure 8A:
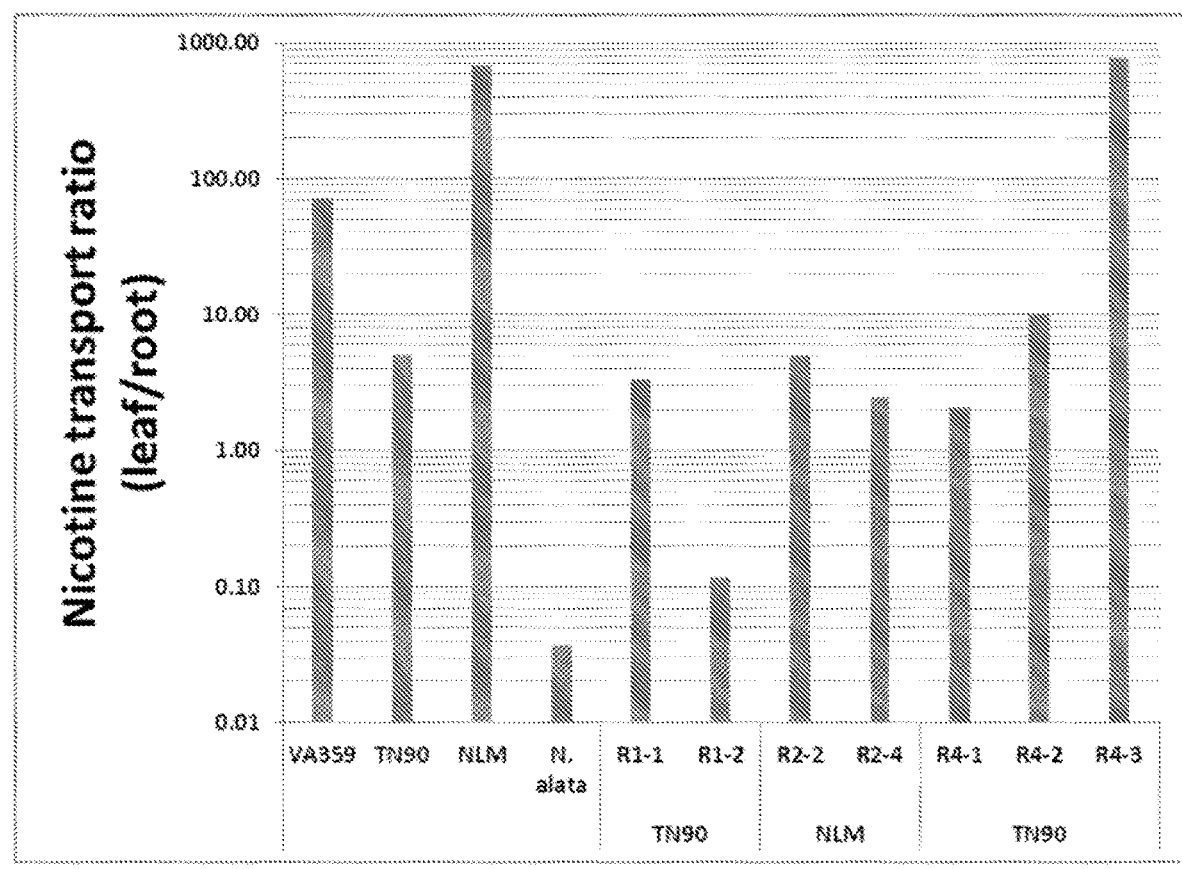
FIG. 8A is the leaf to root ratio of nicotine content after nicotine feeding using the float tray protocol and FIG. 8B is the root and leaf nicotine content of individual plants.
Figure 8B:
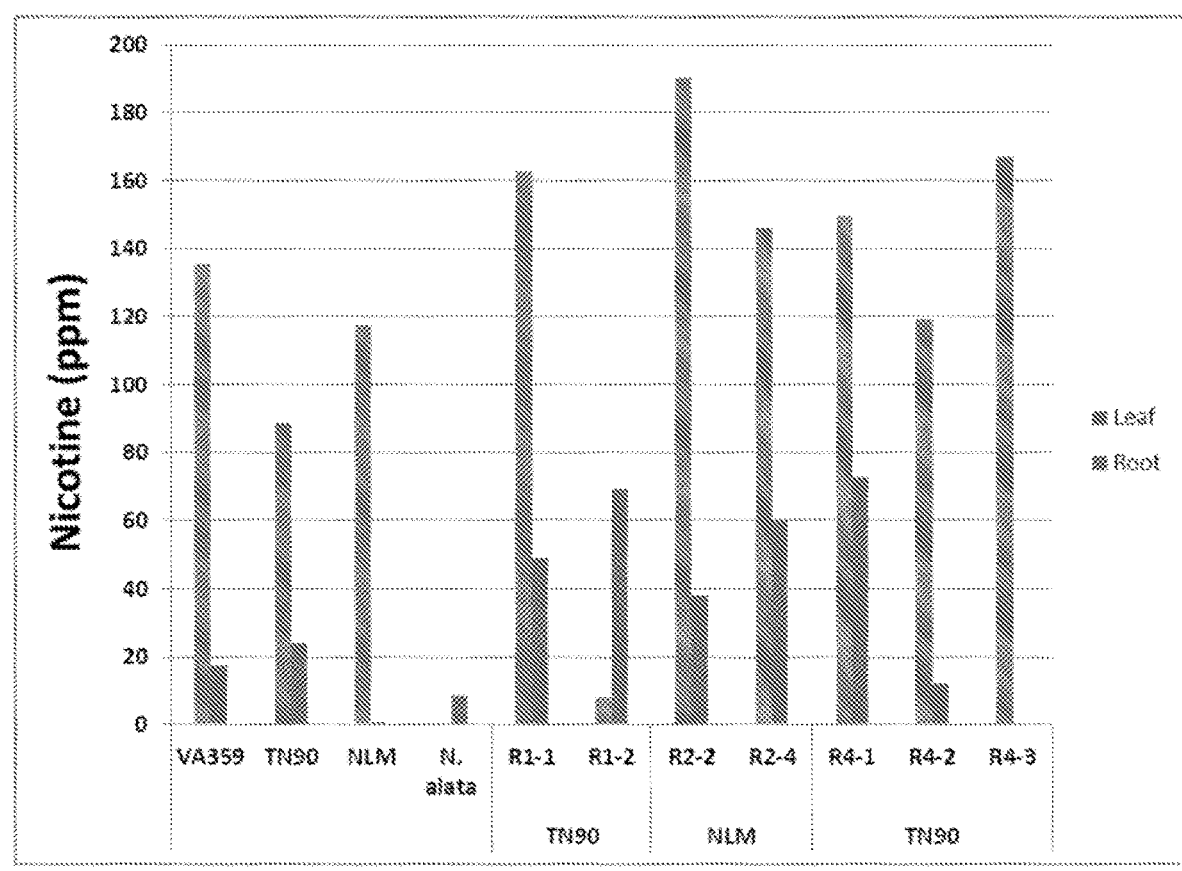
Figure 9A:
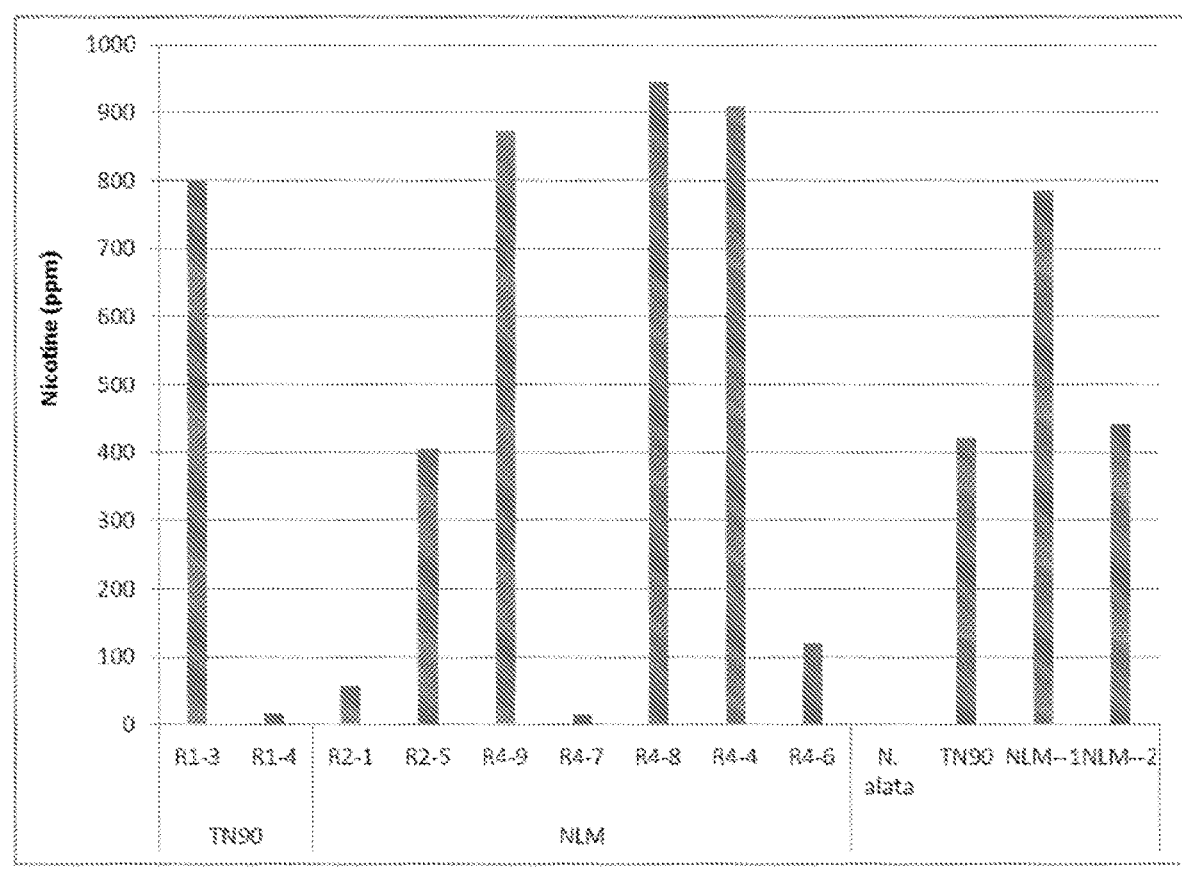
FIG. 9A is the nicotine content of leaves of individual plants after nicotine feeding using the bottomless pot feeding protocol and FIG. 9B is the nicotine content of leaves before and after feeding of the same plants.
Figure 9B:
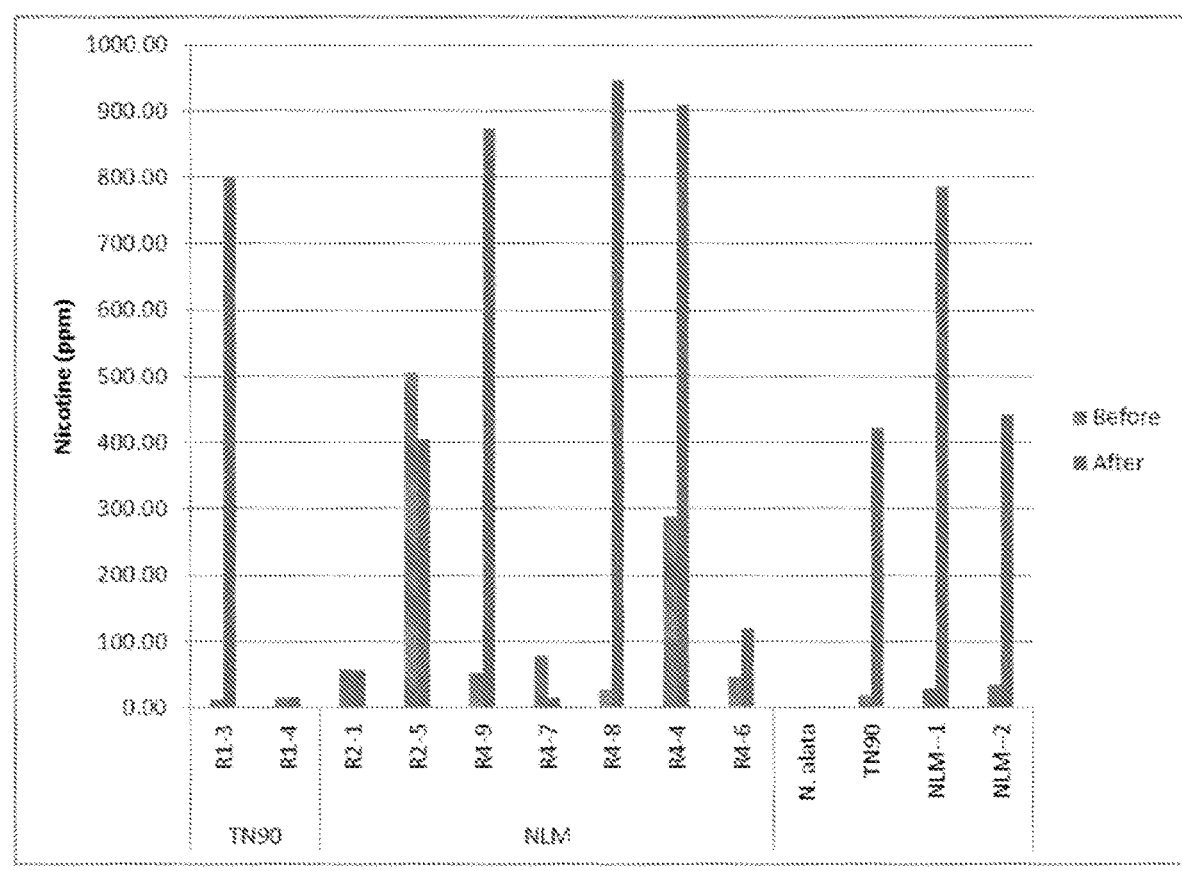

The transport of nicotine in young transgenic plants can be tested by feeding nicotine along with the fertilized water to boost the amount of nicotine and determine the phenotype much earlier than waiting for the endogenous alkaloids to be measurable. Feeding assays were conducted by two separate methods. In the first method, seedlings were transferred to a Styrofoam float tray. These plants were allowed to grow on 100 ppm fertilized water (Pete's Professional) until roots began to emerge from the bottom of the tray. The trays were then floated on fertilized nicotine solution (1 mM nicotine, 100 ppm fertilizer) for three days. Root and leaf tissue was harvested and alkaloids were extracted and analyzed as described above. Nicotine content of the roots and leaves were calculated as well as the ratio of leaf to root nicotine levels (FIG. 8). In the second method, plants were transferred to 4 inch pots. After the roots had grown enough to hold the soil together, these were transferred to 4 inch pots with the bottoms removed. After 2 weeks of growth, plants were treated twice a day with fertilized nicotine solution for 2 days. Leaves were harvested before and after nicotine feeding and alkaloids were extracted and analyzed as described above. The nicotine content of the leaves before and after feeding is shown in FIG. 9.

Figure 7:
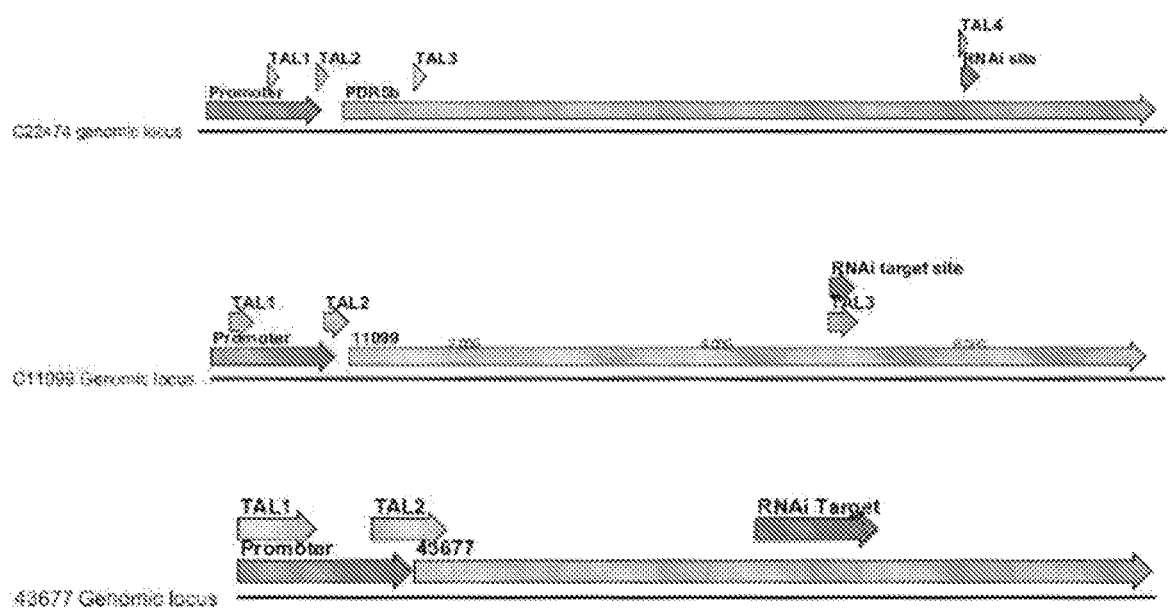
FIG. 7 is a schematic of the construct used for TALEN mutagenesis.

Reduced nicotine levels were found in two plants expressing RNAi constructs targeting the PDR family gene, C22474 (pALCS-TDNA-R1): one plant expressing the RNAi construct targeting the MDR family gene 11099 (pALCS-TDNA-R2) showed reduced nicotine levels after feeding; and one plant expressing the RNAi construct targeting the unclassified gene C43677 (pALCS-TDNA-R4) also showed reduced nicotine levels in the leaf. The locations of the RNAi targeted sites are shown in FIG. 7.

Example 11—Comparison of *N. tabacum* with *N. otophora*

*N. tabacum* originated from the hybridization of two distinct lineages of *Nicotiana*. *N. alata* represents a member of the *N. sylvestris* lineage that does not transport alkaloids (see Example 3 above). *N. otophora* is a non-transporting member of the other lineage (*N. tomentosiformis*). RNA sequencing was conducted to determine transport associated genes that are missing from *N. otophora* but are present at high levels in *N. tabacum*.

Briefly, root samples from *N. otophora* and *N. tabacum* TN90 were collected 10 days after topping. RNA was extracted and sequencing was done by Ambry Genetics (Aliso Viejo, Calif.). RNA sequencing generated 125 million sequence reads. Denovo contig sequences were generated for *N. otophora* and previously obtained genomic sequence from TN90 was used for comparison. Sequence reads were mapped to the denovo *N. otophora* contig sequences, and the remaining unmapped reads were then mapped to the TN90 genome to generate a list of genes that would be predicted to be missing from *N. otophora*. Genes related to secondary metabolite transport were chosen based on gene ontology terms. The expression levels of these genes at various time points are shown in Table 11.

TABLE 11

| | Gene Desig. | Gene expression in TN90 | | | | | | | SEQ ID NO (nt/prot) |
| | | Root (0 hr*) | Root (24 hr*) | Root (72 hr*) | BUD | SEM | Leaf | *N. otophora* | |
|---|---|---|---|---|---|---|---|---|---|
| MDR | g192339 | 173 | 316 | 209 | 101 | 69 | 121 | ND | 70/71 |
| | g192334 | 312 | 568 | 410 | 156 | 106 | 261 | ND | 72/73 |
| | g190446 | 852 | 1454 | 1391 | 464 | 416 | 386 | ND | 74/75 |
| | g124216 | 6564 | 4838 | 4545 | 10359 | 11259 | 5844 | ND | 76/77 |
| | g132727 | 114 | 88 | 48 | 161 | 137 | 105 | ND | 78/79 |
| | g84371 | 461 | 443 | 426 | 591 | 524 | 431 | ND | 80/81 |
| NUP | g144767 | 2313 | 2679 | 2202 | 370 | 190 | 404 | ND | 82/83 |
| Other | g195231 | 976 | 2472 | 1555 | 499 | 524 | 3382 | ND | 84/85 |
| MATE | g105138 | 953 | 1692 | 1356 | 524 | 485 | 1613 | ND | 86/87 |
| | g127664 | 499 | 605 | 451 | 160 | 192 | 134 | ND | 88/89 |
| | g173763 | 893 | 1521 | 1381 | 431 | 300 | 804 | ND | 90/91 |

*, hrs after topping;
ND = not detected

The nucleotide sequences and the predicted polypeptide sequences were compared with sequences deposited in public databases. The results of those comparisons are shown in Table 12.

TABLE 12

Sequence Alignments

| Gene | Nuc ID % | Prot ID % | Protein Accession | Description |
|---|---|---|---|---|
| g144767 | 100 | 100 | XP_009767545.1 | amino acid permease 3-like [*Nicotiana sylvesteris*] |
| g192339 | 99 | 95 | XP_009759241 | ABC transporter A family member 2 [*Nicotiana sylvesteris*] |
| g192334 | 99 | 99 | XP_009759239 | ABC transporter A family member 7-like isoform X1 [*Nicotiana sylvesteris*] |
| g124216 | 100 | 100 | XP_009788997 | ABC transporter F family member 1 [*Nicotiana sylvesteris*] |
| g132727 | 99 | 99 | XP_009760683 | ABC transporter G family member 11-like [*Nicotiana sylvesteris*] |
| g84371 | 86 | 69 | XP_006363174 | ABC transporter G family member 31-like [*Solanum tuberosum*] |

TABLE 12-continued

Sequence Alignments

| Gene | Nuc ID % | Prot ID % | Protein Accession | Description |
|---|---|---|---|---|
| g190446 | 99 | 92 | XP_009768405 | putative ABC transporter C family member 15 isoform X1 [*Nicotiana sylvesteris*] |
| g105138 | 95 | 88 | XP_009760570.1 | protein transparent testa 12-like [*Nicotiana sylvesteris*] |
| g173763 | 99 | 94 | XP_009760619.1 | protein transperant testa 12-like [*Nicotiana sylvesteris*] |
| g127664 | 99 | 99 | XP_009768477.1 | protein transperant testa 12-like [*Nicotiana sylvesteris*] |
| g195231 | 100 | 100 | XP_009800568.1 | polyol transporter 5-like [*Nicotiana sylvesteris*] |

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

What is claimed is:

1. A tobacco plant comprising an induced mutation in an endogenous gene, wherein a naturally occurring sequence of the endogenous gene has the sequence shown in SEQ ID NO: 35, wherein the mutation results in reduced expression of the endogenous gene relative to a corresponding tobacco plant lacking the mutation, and wherein the tobacco plant exhibits reduced transport of nicotine from root tissue to leaf tissue relative to the corresponding tobacco plant lacking the mutation.

2. Seed produced by the tobacco plant of claim 1, wherein the seed comprises the induced mutation.

3. A method of making a tobacco plant, comprising the steps of:
(a) inducing mutagenesis in tobacco cells to produce mutagenized cells;
(b) obtaining one or more tobacco plants from the mutagenized cells;
(c) identifying at least one tobacco plant obtained in step (b) that comprises a mutation in an endogenous gene, wherein a naturally occurring sequence of the endogenous gene has the sequence shown in SEQ ID NO: 35, wherein the mutation results in reduced expression of the endogenous gene relative to a corresponding tobacco plant lacking the mutation, and wherein the tobacco plant exhibits reduced transport of nicotine from root tissue to leaf tissue relative to leaf from the corresponding tobacco plant lacking the mutation.

4. The method of claim 3, wherein mutagenesis is induced using a chemical mutagen or ionizing radiation.

5. The method of claim 4, wherein the chemical mutagen is selected from the group consisting of nitrous acid, sodium azide, acridine orange, ethidium bromide, and ethyl methane sulfonate (EMS).

6. The method of claim 4, wherein the ionizing radiation is selected from the group consisting of x-rays, gamma rays, fast neutron irradiation, and UV irradiation.

7. The method of claim 3, wherein mutagenesis is induced using TALEN.

8. The method of claim 3, wherein mutagenesis is induced using zinc-finger technology.

9. A method for producing a tobacco plant, said method comprising the steps of:
(a) crossing at least one plant of a first tobacco line with at least one plant of a second tobacco line, wherein the at least one plant of the first tobacco line comprises an induced mutation in an endogenous gene, wherein a naturally occurring sequence of the endogenous gene has the sequence shown in SEQ ID NO: 35, wherein the induced mutation results in reduced expression of the endogenous gene relative to a corresponding plant lacking the mutation, and wherein the plant of the first tobacco line exhibits reduced transport of nicotine from root tissue to leaf tissue relative to the corresponding tobacco plant lacking the mutation;
(b) selecting for progeny tobacco plants that comprise the mutation and exhibit reduced expression of the endogenous gene relative to a corresponding tobacco plant lacking the induced mutation; and
(c) selecting for progeny tobacco plants from the progeny tobacco plants selected in step (b) that comprise leaf exhibiting reduced transport of nicotine from root tissue to leaf tissue relative to the corresponding tobacco plant lacking the induced mutation.

10. A tobacco product comprising cured leaf from a tobacco plant having a mutation in an endogenous gene, wherein said endogenous gene has the sequence shown in SEQ ID NO: 35, wherein the mutation results in reduced expression of the endogenous gene relative to a corresponding tobacco plant lacking the mutation, and wherein the the tobacco plant exhibits reduced transport of nicotine from root tissue to leaf tissue relative to the corresponding tobacco plant lacking the mutation.

11. The tobacco product of claim 10, wherein the tobacco product is selected from the group consisting of smokeless tobacco products, cigarillos, non-ventilated recess filter cigarettes, vented recess filter cigarettes, cigars, snuff, pipe tobacco, cigar tobacco, cigarette tobacco, chewing tobacco, leaf tobacco, shredded tobacco, and cut tobacco.

12. A method of producing a tobacco product, the method comprising:
(a) providing cured leaf from a tobacco plant having a mutation in an endogenous gene, wherein said endogenous gene has having the sequence shown in SEQ ID NO: 35, wherein the mutation results in reduced expression of the endogenous gene relative to a corresponding tobacco plant lacking the mutation, and wherein the the tobacco plant exhibits reduced transport of nicotine from root tissue to leaf tissue relative to the corresponding tobacco plant lacking the mutation; and
(b) manufacturing a tobacco product using the cured leaf.

13. The method of claim 12, wherein the mutation is selected from the group consisting of a point mutation, an insertion, a deletion, and a substitution.

* * * * *

SEQUENCE LISTING

```
<160> NUMBER OF SEQ ID NOS: 97

<210> SEQ ID NO 1
<211> LENGTH: 796
<212> TYPE: DNA
<213> ORGANISM: Nicotiana tabacum
<220> FEATURE:
<221> NAME/KEY: misc_feature
<222> LOCATION: 793, 794, 795, 796
<223> OTHER INFORMATION: n = A,T,C or G

<400> SEQUENCE: 1 atgaacatc aaggattaag caccaatatg aggagaatcc tcctgctgat taactgtcta      60
atactcgctg ttggtatctg tggtggtcct ctaatgatgc gtctatatta tagtagggtt     120
tggttacaaa ctgctggatg gccactcacc cttatacctc ttgccatcct atactttat      180
cgtcgaaaaa ccgaaggctc taatgccaag ttttacttta taacaccccg aattttcatt     240
gcatcattcg tcattggcgt tgtcactggt cttgatgatt ttctctattc gtggggcggg     300
tcaaaactcc ctgtgtcaac ctcttcactt cttcttgctg ctcaacttgc cttcacggca     360
ataggtgctt tcttcatagt gaagctgaag ttcacaccct actctatcaa tgcagtggtt     420
ctgttgacag ttggtgctgt tttattgggt attcgatcta atggtgatcg accagagggt     480
gtgacaagta aagcctatat tcttggtttt atgatgacac ttctggcagc agctttatat     540
ggagtcattt tgccttgtat tgagttgatt tacttgaagg caaaacaagc tattactgct     600
acgttggtat tggagattca aatggtcatg tattttgcct tgtattgagt tgatttactt     660
gaaggcaaaa caagctatta ctgctacgtt ggtgttggag attcagatgg tcatgtgttt     720
tgctgctact gcttttgca ccgtaggaat gatcgccaat aacgattttc aggtactttt     780
ttcttcccctt gtnnnn                                                   796
```

```
<210> SEQ ID NO 2
<211> LENGTH: 215
```

<212> TYPE: PRT
<213> ORGANISM: Nicotiana tabacum

<400> SEQUENCE: 2

```
Met Glu His Gln Gly Leu Ser Thr Asn Met Arg Arg Ile Leu Leu
1               5                   10                  15

Ile Asn Cys Leu Ile Leu Ala Val Gly Ile Cys Gly Gly Pro Leu Met
                20                  25                  30

Met Arg Leu Tyr Tyr Ser Arg Val Trp Leu Gln Thr Ala Gly Trp Pro
            35                  40                  45

Leu Thr Leu Ile Pro Leu Ala Ile Leu Tyr Phe Tyr Arg Arg Lys Thr
        50                  55                  60

Glu Gly Ser Asn Ala Lys Phe Tyr Phe Ile Thr Pro Arg Ile Phe Ile
65                  70                  75                  80

Ala Ser Phe Val Ile Gly Val Val Thr Gly Leu Asp Asp Phe Leu Tyr
                85                  90                  95

Ser Trp Gly Gly Ser Lys Leu Pro Val Ser Thr Ser Ser Leu Leu Leu
            100                 105                 110

Ala Ala Gln Leu Ala Phe Thr Ala Ile Gly Ala Phe Phe Ile Val Lys
        115                 120                 125

Leu Lys Phe Thr Pro Tyr Ser Ile Asn Ala Val Val Leu Leu Thr Val
        130                 135                 140

Gly Ala Val Leu Leu Gly Ile Arg Ser Asn Gly Asp Arg Pro Glu Gly
145                 150                 155                 160

Val Thr Ser Lys Ala Tyr Ile Leu Gly Phe Met Met Thr Leu Leu Ala
                165                 170                 175

Ala Ala Leu Tyr Gly Val Ile Leu Pro Cys Ile Glu Leu Ile Tyr Leu
            180                 185                 190

Lys Ala Lys Gln Ala Ile Thr Ala Thr Leu Val Leu Glu Ile Gln Met
        195                 200                 205

Val Met Tyr Phe Ala Leu Tyr
210                 215
```

<210> SEQ ID NO 3
<211> LENGTH: 975
<212> TYPE: DNA
<213> ORGANISM: Nicotiana tabacum

<400> SEQUENCE: 3

```
atggaacatc aaggattaag caccactatg aggagaatcc tcctgctcat taactgttta    60
atactcgctg ttggtatctg cggtggtcct ctaatgatgc gtctatatta tgtcgaggga   120
ggttcaagag tatggtttag cagttggtta caaactgctg gatggccatt caccctttta   180
cctcttgcca tcctatactt ctatcgtcga aaaaccgaag cgctaatgca caagtattac   240
ttgataacac cccgaatttt catcgcatca ttcatcattg gcgttgtcac tggtcttgat   300
gattttctct attcgtgggg cgggtcaaaa cttcctgtgt caacctcttc acttcttctt   360
gctgctcaac ttgccttcac ggcaataggt gctttcttca gtgaagct gaagttcaca   420
ccctactcta tcaatgcagt ggttctgttg acagttggtg ctgtttttat aggtgttcga   480
tctaatggta tcggccaga gggtgtgaca agtaaagcct atattcttgg ttttatgatg   540
acacttttgg cagcagcttt atatggagtc attttgcctt gtattgagtt gatttacttg   600
aaggcaaagc aagctattac tgctacatta gtattggaga ttcaaatggt catgtgtttt   660
gctgctactg cttttttgcac tgttggaatg atcgccaata acgactttca gtgcttcttt   720
```

```
gtgggtgtca ttggagtcat ttactgctct tcttctttga tgtctggggt tatgatcgca    780
gttctacttc ctgttactga ggtattagct gtagttttct ttagggaaaa ttttcaggt    840 gaaaagggcc ttgctctttt tctttctctt tggggtttcg tctcatactt ttacggagag    900
ttcagacaaa caaagaagca gaagaacaaa agtccaaaaa ctgagatgac aacaacgcat    960
accgagtctg tttaa                                                    975
```

<210> SEQ ID NO 4
<211> LENGTH: 324
<212> TYPE: PRT
<213> ORGANISM: Nicotiana tabacum

<400> SEQUENCE: 4

```
Met Glu His Gln Gly Leu Ser Thr Thr Met Arg Arg Ile Leu Leu Leu
 1               5                  10                  15

Ile Asn Cys Leu Ile Leu Ala Val Gly Ile Cys Gly Gly Pro Leu Met
                20                  25                  30

Met Arg Leu Tyr Tyr Val Glu Gly Gly Ser Arg Val Trp Phe Ser Ser
            35                  40                  45

Trp Leu Gln Thr Ala Gly Trp Pro Phe Thr Leu Ile Pro Leu Ala Ile
        50                  55                  60

Leu Tyr Phe Tyr Arg Arg Lys Thr Glu Gly Ala Asn Ala Lys Tyr Tyr
 65                  70                  75                  80

Leu Ile Thr Pro Arg Ile Phe Ile Ala Ser Phe Ile Ile Gly Val Val
                85                  90                  95

Thr Gly Leu Asp Asp Phe Leu Tyr Ser Trp Gly Gly Ser Lys Leu Pro
            100                 105                 110

Val Ser Thr Ser Ser Leu Leu Leu Ala Ala Gln Leu Ala Phe Thr Ala
        115                 120                 125

Ile Gly Ala Phe Phe Ile Val Lys Leu Lys Phe Thr Pro Tyr Ser Ile
    130                 135                 140

Asn Ala Val Val Leu Leu Thr Val Gly Ala Val Leu Leu Gly Val Arg
145                 150                 155                 160

Ser Asn Gly Asp Arg Pro Glu Gly Val Thr Ser Lys Ala Tyr Ile Leu
                165                 170                 175

Gly Phe Met Met Thr Leu Leu Ala Ala Ala Leu Tyr Gly Val Ile Leu
            180                 185                 190

Pro Cys Ile Glu Leu Ile Tyr Leu Lys Ala Lys Gln Ala Ile Thr Ala
        195                 200                 205

Thr Leu Val Leu Glu Ile Gln Met Val Met Cys Phe Ala Ala Thr Ala
    210                 215                 220

Phe Cys Thr Val Gly Met Ile Ala Asn Asn Asp Phe Gln Cys Phe Phe
225                 230                 235                 240

Val Gly Val Ile Gly Val Ile Tyr Cys Ser Ser Ser Leu Met Ser Gly
                245                 250                 255

Val Met Ile Ala Val Leu Leu Pro Val Thr Glu Val Leu Ala Val Val
            260                 265                 270

Phe Phe Arg Glu Asn Phe Ser Gly Glu Lys Gly Leu Ala Leu Phe Leu
        275                 280                 285

Ser Leu Trp Gly Phe Val Ser Tyr Phe Tyr Gly Glu Phe Arg Gln Thr
    290                 295                 300

Lys Lys Gln Lys Asn Lys Ser Pro Lys Thr Glu Met Thr Thr Thr His
305                 310                 315                 320

Thr Glu Ser Val
```

<210> SEQ ID NO 5
<211> LENGTH: 1160
<212> TYPE: DNA
<213> ORGANISM: Nicotiana tabacum

<400> SEQUENCE: 5

```
atggaagata aaggattaag caccaatatg aggagaatcc tcctactgat taactgtcta      60
atactcgctg ttggtatttg tggtggccct ctaatgatgc gtctatatta tgtcgaagga     120
ggtatggttg catgaggaga atactcctgt tggttaactg tctaatactc gctgttggtg     180
tttgtggtgg tcctcttatg atgcgcctat attatgtcga aggaggttca agagtatggt     240
tcagtagttg gttacaaact gctggatggc cactcaccct tatacctctt gccatcctat     300
acttctatcg tcgaaaaacc gaaggctcta atgccaagtt ttactttata caccccgaa      360
ttttcattgc atcattcatc attggcgttg tcactggtgt tgatgatttt ctctattcgt     420
ggggcgggtc aaaactccct gtgtcaacct cttcacttct tcttgctgct caacttgcct     480
tcacggcagt aggtgctttc ttcatagtaa agttaaagtt cacaccctac tccatcaatg     540
cagtgatttt gttgacagtt ggtgctgttt tattgggtgt tcgatctaat ggtgatcgac     600
cagaaggtgt gacaagtaaa gcctatattc ttggttttat gatgacactt ctggcagcag     660
ctttgtatgg agtcattttg ccttgtattg agttgattta cttgaaggca aaacaagcta     720
ttactgctac gttggtgttg agattcaga tggtcatgtg ttttgctgct actgcttttt      780
gcaccgtagg aatgatagca atatcaaggg aggcaaaaca atttaacctc ggagaagcta     840
gatattatac agtgatagta tggactgcca ttatttggca atgcttcttt gtgggtgtta     900
ttggagtcat ttactgctct tcttctttga tgtctggtgt tatgatcgca gttttactcc     960
ctgttactga ggtattagct gtagtttttt ttagggaaaa gttttcaggt gaaaagggcc    1020
ttgctttatt cctttctctt tggggtttcg tctcatactt ttacggagag ttcagacaaa    1080
caaagaagca gaagaataaa agtccagaaa ctgagatgac aatgatgcat accgagtctg    1140
tttgatttat tgagactgtt                                                1160
```

<210> SEQ ID NO 6
<211> LENGTH: 337
<212> TYPE: PRT
<213> ORGANISM: Nicotiana tabacum

<400> SEQUENCE: 6

Met Arg Arg Ile Leu Leu Val Asn Cys Leu Ile Leu Ala Val Gly
1               5                   10                  15

Val Cys Gly Gly Pro Leu Met Met Arg Leu Tyr Tyr Val Glu Gly
                20                  25                  30

Ser Arg Val Trp Phe Ser Ser Trp Leu Gln Thr Ala Gly Trp Pro Leu
        35                  40                  45

Thr Leu Ile Pro Leu Ala Ile Leu Tyr Phe Tyr Arg Arg Lys Thr Glu
            50                  55                  60

Gly Ser Asn Ala Lys Phe Tyr Phe Ile Thr Pro Arg Ile Phe Ile Ala
65                  70                  75                  80

Ser Phe Ile Ile Gly Val Val Thr Gly Val Asp Asp Phe Leu Tyr Ser
                85                  90                  95

Trp Gly Gly Ser Lys Leu Pro Val Ser Thr Ser Ser Leu Leu Leu Ala
            100                 105                 110

Ala Gln Leu Ala Phe Thr Ala Val Gly Ala Phe Phe Ile Val Lys Leu

```
              115                 120                 125
Lys Phe Thr Pro Tyr Ser Ile Asn Ala Val Ile Leu Leu Thr Val Gly
130                 135                 140

Ala Val Leu Leu Gly Val Arg Ser Asn Gly Asp Arg Pro Glu Gly Val
145                 150                 155                 160

Thr Ser Lys Ala Tyr Ile Leu Gly Phe Met Met Thr Leu Leu Ala Ala
                165                 170                 175

Ala Leu Tyr Gly Val Ile Leu Pro Cys Ile Glu Leu Ile Tyr Leu Lys
                180                 185                 190

Ala Lys Gln Ala Ile Thr Ala Thr Leu Val Leu Glu Ile Gln Met Val
                195                 200                 205

Met Cys Phe Ala Ala Thr Ala Phe Cys Thr Val Gly Met Ile Ala Ile
210                 215                 220

Ser Arg Glu Ala Lys Gln Phe Asn Leu Gly Glu Ala Arg Tyr Tyr Thr
225                 230                 235                 240

Val Ile Val Trp Thr Ala Ile Ile Trp Gln Cys Phe Phe Val Gly Val
                245                 250                 255

Ile Gly Val Ile Tyr Cys Ser Ser Leu Met Ser Gly Val Met Ile
                260                 265                 270

Ala Val Leu Leu Pro Val Thr Glu Val Leu Ala Val Val Phe Phe Arg
            275                 280                 285

Glu Lys Phe Ser Gly Lys Gly Leu Ala Leu Phe Leu Ser Leu Trp
290                 295                 300

Gly Phe Val Ser Tyr Phe Tyr Gly Glu Phe Arg Gln Thr Lys Lys Gln
305                 310                 315                 320

Lys Asn Lys Ser Pro Glu Thr Glu Met Thr Met Met His Thr Glu Ser
                325                 330                 335

Val

<210> SEQ ID NO 7
<211> LENGTH: 1223
<212> TYPE: DNA
<213> ORGANISM: Nicotiana tabacum

<400> SEQUENCE: 7
ccttcggaga agaaaagcat ttcagcctga gtaacagaat actccaattt agtatccaaa    60
tctctagaaa aaaatatgg aacatccagg attaagcacc aatatgagga gaatcctcct   120
gctgattagc tgcttaatac tcgctgttgg catatgtggt ggtcctctaa tgatgcgtct   180
atattatgtc gagggaggtt caagaatatg cttagcagt tggttacaaa ctggtggatg   240
gccactcacc cttatacctc ttgccatcct atactattat cgtcgaaaaa ccgaaggctc   300
aaacgccaag ttttacttga tgaccccccg aattttttatt gcatcatttg ttattggcgt   360
tgccactggt cttgatgatt ttctctattc gtggggcggg tcaaaactcc ccgtatcaac   420
ctcttcactt cttcttgctg ctcaacttgc cttcacggca gtaggtgggt caaaactccc   480
cgtatcaacc tcttcacttc ttcttgctgc tcaacttgcc ttcacggcag taggtgcttt   540
cttcatagtg aagttgaagt tatcacccct ctctatcaat gcagtggttt tactaacagt   600
tggtgctgtt ttattgggta ttcgatctaa tggtgatcga ccagagggcg tgacaagtaa   660
agaatatatt attggtttta tgatgacact tctagcagca gctttgtacg gagtcatttt   720
gccttgtatt gagttgattt acatgaaggc aaaacaagct attacttcta cgttagtatt   780
ggagattcag atgatcatgt gttttgctgc tactgctttt tgcactgtag gaatgatcgc   840
```

```
caataaggac tttcaggcaa tgtcaaggga ggcaaaacaa tttaacctcg agaagctag      900
atattataca gttatagtat gcactgccgc tatttggcag tgcttcttcg tgggtattat      960
tggagttatc tactgctctt cttctttgat gtctggggtt atgattgcag ttttgctccc     1020
cgttactgag gtattagctg taattttctt taaggaaaat ttttcaggtg aaaagggtct     1080
tgctctttc ctttctcttt ggggtttcgt ctcatacttc tatggagagt tcagacaaac     1140
aaagaagcag aagaataaaa gtccagaagc tgagatgaca aggacaacga cgcatactga     1200
atctgtttga tttactattc atg                                             1223
```

<210> SEQ ID NO 8
<211> LENGTH: 377
<212> TYPE: PRT
<213> ORGANISM: Nicotiana tabacum

<400> SEQUENCE: 8

```
Met Glu His Pro Gly Leu Ser Thr Asn Met Arg Arg Ile Leu Leu Leu
1               5                   10                  15

Ile Ser Cys Leu Ile Leu Ala Val Gly Ile Cys Gly Gly Pro Leu Met
            20                  25                  30

Met Arg Leu Tyr Tyr Val Glu Gly Gly Ser Arg Ile Trp Leu Ser Ser
        35                  40                  45

Trp Leu Gln Thr Gly Gly Trp Pro Leu Thr Leu Ile Pro Leu Ala Ile
    50                  55                  60

Leu Tyr Tyr Arg Arg Lys Thr Glu Gly Ser Asn Ala Lys Phe Tyr
65                  70                  75                  80

Leu Met Thr Pro Arg Ile Phe Ile Ala Ser Phe Val Ile Gly Val Ala
                85                  90                  95

Thr Gly Leu Asp Asp Phe Leu Tyr Ser Trp Gly Gly Ser Lys Leu Pro
            100                 105                 110

Val Ser Thr Ser Ser Leu Leu Leu Ala Ala Gln Leu Ala Phe Thr Ala
        115                 120                 125

Val Gly Gly Ser Lys Leu Pro Val Ser Thr Ser Ser Leu Leu Leu Ala
    130                 135                 140

Ala Gln Leu Ala Phe Thr Ala Val Gly Ala Phe Phe Ile Val Lys Leu
145                 150                 155                 160

Lys Leu Ser Pro Phe Ser Ile Asn Ala Val Val Leu Thr Val Gly
                165                 170                 175

Ala Val Leu Leu Gly Ile Arg Ser Asn Gly Asp Arg Pro Glu Gly Val
            180                 185                 190

Thr Ser Lys Glu Tyr Ile Ile Gly Phe Met Met Thr Leu Leu Ala Ala
        195                 200                 205

Ala Leu Tyr Gly Val Ile Leu Pro Cys Ile Glu Leu Ile Tyr Met Lys
    210                 215                 220

Ala Lys Gln Ala Ile Thr Ser Thr Leu Val Leu Glu Ile Gln Met Ile
225                 230                 235                 240

Met Cys Phe Ala Ala Thr Ala Phe Cys Thr Val Gly Met Ile Ala Asn
                245                 250                 255

Lys Asp Phe Gln Ala Met Ser Arg Glu Ala Lys Gln Phe Asn Leu Gly
            260                 265                 270

Glu Ala Arg Tyr Tyr Thr Val Ile Val Cys Thr Ala Ala Ile Trp Gln
        275                 280                 285

Cys Phe Phe Val Gly Ile Ile Gly Val Ile Tyr Cys Ser Ser Ser Leu
    290                 295                 300
```

```
Met Ser Gly Val Met Ile Ala Val Leu Leu Pro Val Thr Glu Val Leu
305                 310                 315                 320

Ala Val Ile Phe Phe Lys Glu Asn Phe Ser Gly Glu Lys Gly Leu Ala
                325                 330                 335

Leu Phe Leu Ser Leu Trp Gly Phe Val Ser Tyr Phe Tyr Gly Glu Phe
            340                 345                 350

Arg Gln Thr Lys Lys Gln Lys Asn Lys Ser Pro Glu Ala Glu Met Thr
        355                 360                 365

Arg Thr Thr His Thr Glu Ser Val
    370                 375

<210> SEQ ID NO 9
<211> LENGTH: 4761
<212> TYPE: DNA
<213> ORGANISM: Nicotiana tabacum

<400> SEQUENCE: 9
```

| | | | | | |
|---|---|---|---|---|---|
| atgtgctgct | tttgcgggaa | aatcttccct | ccattcattt | tcctctctcc | atgtccacaa | 60 |
| aggactcttc | tatcttccat | tgatgtgctg | cttttgctta | ctttcattgt | atttgcagta | 120 |
| caaaagttgt | actcaaagtt | gaggtccaat | gagcactcta | cttctagcat | tgataagcct | 180 |
| ctaattgcac | acaacaggac | ttctgttaga | accaatcttt | ggtttaagct | gtctctgatt | 240 |
| ttgtcagcta | ttttagcctt | atcttctata | gttttatgca | ttttggttat | tgtgggaaat | 300 |
| tcccagtcgc | cttggaaagt | catagatgga | ctgtattggt | tgtttcaggc | gattacacat | 360 |
| gttgtaatca | ctatactaat | agttcatgag | aaaagatttc | acgctatttc | ccatccactg | 420 |
| tccctgcgcg | tgttttggat | tgcaaacttt | gtagttatga | gtttgttctt | tggttgtgga | 480 |
| gtcacaaggc | ttgtgtcact | taaggaaatt | gatcctaatt | taagaatgga | tgatataagt | 540 |
| tcattagttt | catttcctat | ttctgttgtt | ctcttcattg | ttgccattaa | aggttcgacc | 600 |
| ggagttgctg | taattagtga | ttctgaatct | cacttaagtg | atgaaaccaa | tggttatgaa | 660 |
| ctcctggata | aatccagtgt | gagtggcttt | gcttcagctt | ctctaatatc | gaaagccttt | 720 |
| tggatttgga | tgaacccttt | actgcaaaaa | ggttacaagt | cacctctcaa | gattgatgaa | 780 |
| gttccttcac | tttccccact | gcatagagca | gagaaaatgt | ctcaacttt | cgaaagaaat | 840 |
| tggcctaaac | ctgaagaaat | atcaaagcat | cctgtccgaa | caacattgct | gcgttgcttt | 900 |
| tggaaggaag | ttatttttac | tgccattctt | gcagtaatta | gggtatgtgt | tatgtatgta | 960 |
| gggccaacac | tcatacaaag | atttgttgat | tacacagcag | gaaagaggac | atctccttat | 1020 |
| gaaggatact | accttatagg | aactctccta | atagccaaat | ttgtggaagt | caggacatct | 1080 |
| ccttatgaag | gatactacct | tataggaact | ctcctaatag | ccaaatttgt | ggaagttcta | 1140 |
| acctctcatc | agttcaactt | taactcccaa | aagcttggca | tgcttattcg | agcgacactt | 1200 |
| ctcacttctt | tgtataagaa | ggggttaagg | ttgtcatgct | cagctagaca | ggctcatggt | 1260 |
| gttggacaga | ttgtaaatta | tatggccgtc | gatgctcagc | agctgtccga | tatgatgcta | 1320 |
| cagctacatt | ccatttggct | catgccattg | caagtttctg | tggctttagg | catcctttat | 1380 |
| acttacctcg | gtgcttcaac | tgttgtaacg | ctagctggac | ttgcagcagt | gatggtattt | 1440 |
| gtggtgtttg | gaactaaaag | aaacaacagg | tttcaattta | acatcatgaa | gatcgtgat | 1500 |
| tctagaatga | aagcgacaaa | tgagatgctt | aattatatgc | gcgttataaa | gttccaggca | 1560 |
| tgggaagaac | attttaacaa | agaattgaa | tccttccgcg | aatccgagta | tggatggttg | 1620 |
| tccaagttct | tgtactcaat | cgctgggaat | atcattgtct | tgtggagcac | tcctcttcta | 1680 |

```
gtggctacac tcacttttgg aagtgcaatc ttgttgggaa tcccgcttgg tgcagggaca      1740
gtgttcactg caacatctct cttcaagatg ttgcaggaac cgatcagggc tttccctcaa      1800
tccatgatct cactttcaca agcaatgata tctcttgata gattggacaa atatatgatg      1860
agtaaggagt tagtggataa agctgtgaaa agactagaag gttgtggggg tacaattgct      1920
atgcaggtga agatggagc ttttgctgg gatgatgaaa acagtaaaga agaattgaaa        1980
aatgtaaact ttgagattag aaaaggagag cttgcagcag tagtggggac agttggggcg      2040
gggaagtctt ccctccttgc atctgtactt ggtgagatgc acaagttgtc gggtcaggtc      2100
acaatttgtg gttcaactgc ctatgttgca caaacatcgt ggattcagaa tggcacgata      2160
caagaaaata tcctgtttgg tatgccaatg aacagagaca gatacaagga agtgatccgg      2220
gtttgctgct tggagaagga cttggaaata atggagtttg agaccagac tgaaatagga       2280 gaacgtggca tcaacctcag tggtggtcag aagcagcgaa tccagcttgc aagagctgtt     2340
taccaggact gtgatattta tcttctagat gatgtattca gtgcagttga tgctcacact      2400
ggctctgaaa tcttcaagga atgtgtgagg ggaattctta aagataaaac cattttgctt      2460
gtcacacacc aagttgactt cttgcataat gttgacctga tccttgtcat gcgagatggg      2520
atgatcgtgc aatctggcaa atataatgag atattagaag ctggaatgga ttttaaagag      2580
ctagtagctg cacatgagac ctctttagaa cttgttgacg tggaaacaac caaagagagc      2640
aatgcctccc ttgaagaatc aaaatcttct cgaagattat ctaaggaaga aaacggagat      2700
gataaatctc aacagtctac atctgatagg ggggattcta aacttataaa ggaagaagaa      2760
agagaaactg gaaaagtcag tcctcgtgtg tacaagctat atattactga agcttttgga      2820
tggtggggtg tagtgctagt tatcttgttt tcgttcttgt ggcaaagttc tctaatggca      2880
agtgattatt ggctggcata tgaaacttca gcggatcgtg ccatgtcctt caatccttct      2940
ctgtttattg ggatatacgg tgttattgca gttgtttctt cgttgctgat agtgatcagg      3000 atgtatttt gacacttat ggggctcaag actgccccaaa tattttttcgg acagattctt      3060 tacagcatac tgcatgctcc tatgtcattt tttgacacaa caccttccgg aagaattctg      3120
agtcgggcat ctaatgatca gaccaacatt gatgtcttcc tcccgtttt tatgaatctc      3180 actttggcca tgtttatcac actgctcggc atcatcatca tcacatgcca atattcttgg    3240
cctaccgtac tactttttgat tcctctgggt tggcttaata tctggtaccg gggatattat    3300
cttgcaacat ctcgtgaatt gactcggctt gactcaatta caaaagcacc tgttattcat    3360
catttctctg aaagcatctc aggtgttatg actatacgtt gctttaggaa gcaggagatg    3420
ttttgtaacg agaatgtaaa ccgagtgaat tccaatctgc gaatggattt ccacaacaat    3480
ggatccaatg aatggttggg ctttcgactg gaattgatgg gaagcttact tcttttgtgtt    3540 tctgcaatgt tcatgattgt cttacctagc agcatcatca agccagaaaa tgttggtttg    3600
tcactatcat atggcttgtc tcttaatagt gtcctattct ggtccatctt tgtgagttgc     3660
tttgtggaaa ataaaatggt ttctgtcgaa agattaaaac agttctcaga ataccatca     3720 gaagcagagt ggagaaagat ggattttctc ccaccttcaa gttggccaag ccgtgggaat    3780
gttgagcttg aaaacgtgca ggttagatat cgtccgaaca ctcctctagt gcttaaagga    3840
gttactctca gcattagagg gggagagaag ataggtgttg ttggtcgtac aggggggtgga   3900 aaatcaacat taattcaagt tttctttcgt ttggtggagc ctgcagctgg aagaataatc    3960
attgatgacg tagatatatc cagacttggg cttcatgatc ttagatctcg cttcgggatc   4020
attccccaag agccagtcct ttttgaagga actgtgagaa gcaacattga ccccattgga   4080
```

```
caatattcag atgatgaaat ttggaagagc ctcgaacgct gccaactcaa agatgtggtg    4140
tctttaaaac ccgaaaaact tgattcacca ggtaccttt cctctctac tgcatctctt    4200 ctgagttata caatcaactt tttatgcttg gcaatatata tactgaatac tgtcattggt    4260
aaaatagttg ttgataacgg agataactgg agtgtcggac agaggcagct tctttgcttg    4320
ggaagagtga tgctaaaacg tagcagactt ctatttatgg atgaggcaac tgcctctgtt    4380
gattcacaga cagatgcagt gattcagaaa atcatccgcg aggactttgc ggcctgtact    4440
ataatcagca ttgcccacag aataccaaca gtcatggact gtgatagagt tcttgttata    4500
gatgcaggaa tagcaaaaga gtttgacaaa ccatctcgtt tgcttgaaag gccttcactt    4560
tttgggcttt tggttcaaga atatgccaac cgatcctctg agctctaacc acactaatca    4620
ggctttcatg cctttgctg taaattgcta tcttggacga tagtaggtga acaggaaaa    4680 ataatgttac atagatttcc aaatagtgtc atctcctcct tagtctgtcc agtagatttt    4740
cggaaatgta acaacattgg g                                             4761
```

<210> SEQ ID NO 10
<211> LENGTH: 1535
<212> TYPE: PRT
<213> ORGANISM: Nicotiana tabacum

<400> SEQUENCE: 10

```
Met Cys Cys Phe Cys Gly Lys Ile Phe Pro Phe Ile Phe Leu Ser
1               5                   10                  15

Pro Cys Pro Gln Arg Thr Leu Leu Ser Ser Ile Asp Val Leu Leu Leu
            20                  25                  30

Leu Thr Phe Ile Val Phe Ala Val Gln Lys Leu Tyr Ser Lys Leu Arg
        35                  40                  45

Ser Asn Glu His Ser Thr Ser Ser Ile Asp Lys Pro Leu Ile Ala His
    50                  55                  60

Asn Arg Thr Ser Val Arg Thr Asn Leu Trp Phe Lys Leu Ser Leu Ile
65                  70                  75                  80

Leu Ser Ala Ile Leu Ala Leu Ser Ser Ile Val Leu Cys Ile Leu Val
                85                  90                  95

Ile Val Gly Asn Ser Gln Ser Pro Trp Lys Val Ile Asp Gly Leu Tyr
            100                 105                 110

Trp Leu Phe Gln Ala Ile Thr His Val Val Ile Thr Ile Leu Ile Val
        115                 120                 125

His Glu Lys Arg Phe His Ala Ile Ser His Pro Leu Ser Leu Arg Val
    130                 135                 140

Phe Trp Ile Ala Asn Phe Val Val Met Ser Leu Phe Phe Gly Cys Gly
145                 150                 155                 160

Val Thr Arg Leu Val Ser Leu Lys Glu Ile Asp Pro Asn Leu Arg Met
                165                 170                 175

Asp Asp Ile Ser Ser Leu Val Ser Phe Pro Ile Ser Val Val Leu Phe
            180                 185                 190

Ile Val Ala Ile Lys Gly Ser Thr Gly Val Ala Val Ile Ser Asp Ser
        195                 200                 205

Glu Ser His Leu Ser Asp Glu Thr Asn Gly Tyr Glu Leu Leu Asp Lys
    210                 215                 220

Ser Ser Val Ser Gly Phe Ala Ser Ala Ser Leu Ile Ser Lys Ala Phe
225                 230                 235                 240

Trp Ile Trp Met Asn Pro Leu Leu Gln Lys Gly Tyr Lys Ser Pro Leu
```

```
            245                 250                 255
Lys Ile Asp Glu Val Pro Ser Leu Ser Pro Leu His Arg Ala Glu Lys
            260                 265                 270

Met Ser Gln Leu Phe Glu Arg Asn Trp Pro Lys Pro Glu Glu Ile Ser
            275                 280                 285

Lys His Pro Val Arg Thr Thr Leu Leu Arg Cys Phe Trp Lys Glu Val
            290                 295                 300

Ile Phe Thr Ala Ile Leu Ala Val Ile Arg Val Cys Val Met Tyr Val
305                 310                 315                 320

Gly Pro Thr Leu Ile Gln Arg Phe Val Asp Tyr Thr Ala Gly Lys Arg
                325                 330                 335

Thr Ser Pro Tyr Glu Gly Tyr Leu Ile Gly Thr Leu Leu Ile Ala
                340                 345             350

Lys Phe Val Glu Val Arg Thr Ser Pro Tyr Glu Gly Tyr Tyr Leu Ile
                355                 360                 365

Gly Thr Leu Leu Ile Ala Lys Phe Val Glu Val Leu Thr Ser His Gln
        370                 375                 380

Phe Asn Phe Asn Ser Gln Lys Leu Gly Met Leu Ile Arg Ala Thr Leu
385                 390                 395                 400

Leu Thr Ser Leu Tyr Lys Lys Gly Leu Arg Leu Ser Cys Ser Ala Arg
                405                 410                 415

Gln Ala His Gly Val Gly Gln Ile Val Asn Tyr Met Ala Val Asp Ala
                420                 425                 430

Gln Gln Leu Ser Asp Met Met Leu Gln Leu His Ser Ile Trp Leu Met
            435                 440                 445

Pro Leu Gln Val Ser Val Ala Leu Gly Ile Leu Tyr Thr Tyr Leu Gly
        450                 455                 460

Ala Ser Thr Val Val Thr Leu Ala Gly Leu Ala Ala Val Met Val Phe
465                 470                 475                 480

Val Val Phe Gly Thr Lys Arg Asn Asn Arg Phe Gln Phe Asn Ile Met
                485                 490                 495

Lys Asn Arg Asp Ser Arg Met Lys Ala Thr Asn Glu Met Leu Asn Tyr
            500                 505                 510

Met Arg Val Ile Lys Phe Gln Ala Trp Glu His Phe Asn Lys Arg
        515                 520                 525

Ile Glu Ser Phe Arg Glu Ser Glu Tyr Gly Trp Leu Ser Lys Phe Leu
            530                 535                 540

Tyr Ser Ile Ala Gly Asn Ile Ile Val Leu Trp Ser Thr Pro Leu Leu
545                 550                 555                 560

Val Ala Thr Leu Thr Phe Gly Ser Ala Ile Leu Leu Gly Ile Pro Leu
                565                 570                 575

Gly Ala Gly Thr Val Phe Thr Ala Thr Ser Leu Phe Lys Met Leu Gln
                580                 585                 590

Glu Pro Ile Arg Ala Phe Pro Gln Ser Met Ile Ser Leu Ser Gln Ala
                595                 600                 605

Met Ile Ser Leu Asp Arg Leu Asp Lys Tyr Met Met Ser Lys Glu Leu
        610                 615                 620

Val Asp Lys Ala Val Glu Arg Leu Glu Gly Cys Gly Gly Thr Ile Ala
625                 630                 635                 640

Met Gln Val Lys Asp Gly Ala Phe Cys Trp Asp Asp Glu Asn Ser Lys
                645                 650                 655

Glu Glu Leu Lys Asn Val Asn Phe Glu Ile Arg Lys Gly Glu Leu Ala
            660                 665                 670
```

```
Ala Val Val Gly Thr Val Gly Ala Gly Lys Ser Ser Leu Leu Ala Ser
            675                 680                 685

Val Leu Gly Glu Met His Lys Leu Ser Gly Gln Val Thr Ile Cys Gly
690                 695                 700

Ser Thr Ala Tyr Val Ala Gln Thr Ser Trp Ile Gln Asn Gly Thr Ile
705                 710                 715                 720

Gln Glu Asn Ile Leu Phe Gly Met Pro Met Asn Arg Asp Arg Tyr Lys
                725                 730                 735

Glu Val Ile Arg Val Cys Cys Leu Glu Lys Asp Leu Glu Ile Met Glu
                740                 745                 750

Phe Gly Asp Gln Thr Glu Ile Gly Glu Arg Gly Ile Asn Leu Ser Gly
                755                 760                 765

Gly Gln Lys Gln Arg Ile Gln Leu Ala Arg Ala Val Tyr Gln Asp Cys
            770                 775                 780

Asp Ile Tyr Leu Leu Asp Asp Val Phe Ser Ala Val Asp Ala His Thr
785                 790                 795                 800

Gly Ser Glu Ile Phe Lys Glu Cys Val Arg Gly Ile Leu Lys Asp Lys
                805                 810                 815

Thr Ile Leu Leu Val Thr His Gln Val Asp Phe Leu His Asn Val Asp
                820                 825                 830

Leu Ile Leu Val Met Arg Asp Gly Met Ile Val Gln Ser Gly Lys Tyr
            835                 840                 845

Asn Glu Ile Leu Glu Ala Gly Met Asp Phe Lys Glu Leu Val Ala Ala
850                 855                 860

His Glu Thr Ser Leu Glu Leu Val Asp Val Glu Thr Thr Lys Glu Ser
865                 870                 875                 880

Asn Ala Ser Leu Glu Glu Ser Lys Ser Arg Arg Leu Ser Lys Glu
                885                 890                 895

Glu Asn Gly Asp Asp Lys Ser Gln Gln Ser Thr Ser Asp Arg Gly Asp
                900                 905                 910

Ser Lys Leu Ile Lys Glu Glu Arg Glu Thr Gly Lys Val Ser Pro
            915                 920                 925

Arg Val Tyr Lys Leu Tyr Ile Thr Glu Ala Phe Gly Trp Trp Gly Val
            930                 935                 940

Val Leu Val Ile Leu Phe Ser Phe Leu Trp Gln Ser Ser Leu Met Ala
945                 950                 955                 960

Ser Asp Tyr Trp Leu Ala Tyr Glu Thr Ser Ala Asp Arg Ala Met Ser
                965                 970                 975

Phe Asn Pro Ser Leu Phe Ile Gly Ile Tyr Gly Val Ile Ala Val Val
                980                 985                 990

Ser Ser Leu Leu Ile Val Ile Arg Met Tyr Phe Val Thr Leu Met Gly
            995                 1000                1005

Leu Lys Thr Ala Gln Ile Phe Phe Gly Gln Ile Leu Tyr Ser Ile Leu
        1010                1015                1020

His Ala Pro Met Ser Phe Asp Thr Thr Pro Ser Gly Arg Ile Leu
    1025                1030                1035                1040

Ser Arg Ala Ser Asn Asp Gln Thr Asn Ile Asp Val Phe Leu Pro Phe
                1045                1050                1055

Phe Met Asn Leu Thr Leu Ala Met Phe Ile Thr Leu Leu Gly Ile Ile
            1060                1065                1070

Ile Ile Thr Cys Gln Tyr Ser Trp Pro Thr Val Leu Leu Leu Ile Pro
        1075                1080                1085
```

```
Leu Gly Trp Leu Asn Ile Trp Tyr Arg Gly Tyr Tyr Leu Ala Thr Ser
    1090                1095                1100

Arg Glu Leu Thr Arg Leu Asp Ser Ile Thr Lys Ala Pro Val Ile His
1105                1110                1115                1120

His Phe Ser Glu Ser Ile Ser Gly Val Met Thr Ile Arg Cys Phe Arg
                1125                1130                1135

Lys Gln Glu Met Phe Cys Asn Glu Asn Val Asn Arg Val Asn Ser Asn
        1140                1145                1150

Leu Arg Met Asp Phe His Asn Asn Gly Ser Asn Glu Trp Leu Gly Phe
            1155                1160                1165

Arg Leu Glu Leu Met Gly Ser Leu Leu Leu Cys Val Ser Ala Met Phe
1170                1175                1180

Met Ile Val Leu Pro Ser Ser Ile Ile Lys Pro Glu Asn Val Gly Leu
1185                1190                1195                1200

Ser Leu Ser Tyr Gly Leu Ser Leu Asn Ser Val Leu Phe Trp Ser Ile
                1205                1210                1215

Phe Val Ser Cys Phe Val Glu Asn Lys Met Val Ser Val Glu Arg Leu
            1220                1225                1230

Lys Gln Phe Ser Glu Ile Pro Ser Glu Ala Glu Trp Arg Lys Met Asp
        1235                1240                1245

Phe Leu Pro Pro Ser Ser Trp Pro Ser Arg Gly Asn Val Glu Leu Glu
1250                1255                1260

Asn Val Gln Val Arg Tyr Arg Pro Asn Thr Pro Leu Val Leu Lys Gly
1265                1270                1275                1280

Val Thr Leu Ser Ile Arg Gly Gly Glu Lys Ile Gly Val Val Gly Arg
                1285                1290                1295

Thr Gly Gly Gly Lys Ser Thr Leu Ile Gln Val Phe Phe Arg Leu Val
            1300                1305                1310

Glu Pro Ala Ala Gly Arg Ile Ile Ile Asp Asp Val Asp Ile Ser Arg
1315                1320                1325

Leu Gly Leu His Asp Leu Arg Ser Arg Phe Gly Ile Ile Pro Gln Glu
    1330                1335                1340

Pro Val Leu Phe Glu Gly Thr Val Arg Ser Asn Ile Asp Pro Ile Gly
1345                1350                1355                1360

Gln Tyr Ser Asp Asp Glu Ile Trp Lys Ser Leu Glu Arg Cys Gln Leu
                1365                1370                1375

Lys Asp Val Val Ser Leu Lys Pro Glu Lys Leu Asp Ser Pro Gly Thr
            1380                1385                1390

Phe Ser Phe Ser Thr Ala Ser Leu Leu Ser Tyr Thr Ile Asn Phe Leu
        1395                1400                1405

Cys Leu Ala Ile Tyr Ile Leu Asn Thr Val Ile Gly Lys Ile Val Val
    1410                1415                1420

Asp Asn Gly Asp Asn Trp Ser Val Gly Gln Arg Gln Leu Leu Cys Leu
1425                1430                1435                1440

Gly Arg Val Met Leu Lys Arg Ser Arg Leu Leu Phe Met Asp Glu Ala
                1445                1450                1455

Thr Ala Ser Val Asp Ser Gln Thr Asp Ala Val Ile Gln Lys Ile Ile
            1460                1465                1470

Arg Glu Asp Phe Ala Ala Cys Thr Ile Ser Ile Ala His Arg Ile
        1475                1480                1485

Pro Thr Val Met Asp Cys Asp Arg Val Leu Val Ile Asp Ala Gly Ile
    1490                1495                1500

Ala Lys Glu Phe Asp Lys Pro Ser Arg Leu Leu Glu Arg Pro Ser Leu
```

```
                1505                1510                1515                1520
         Phe Gly Ala Leu Val Gln Glu Tyr Ala Asn Arg Ser Ser Glu Leu
                     1525                1530                1535

<210> SEQ ID NO 11
<211> LENGTH: 3684
<212> TYPE: DNA
<213> ORGANISM: Nicotiana tabacum

<400> SEQUENCE: 11
atgagtacta ctacgaagag taaagcgatg atacaaaaga aaagctacgg ctcttttgtg      60
tcaattttca tgcatgccga tagagcagat atcttgttga tgattttagg ttttttttgga    120 gcagtttgcg acgggttttc catgccgata atgctcatag tcaccagcaa actcatgaac    180
aatcttggtg gtactgacac ttcaaacgcc gataatttca cgcaccacat caatgagaat    240
gctttggttc tggttttcct tgcatgtgga caatgggtcg cttgtttctt agagggattt    300
tgttggacaa gaacagcaga gaggcaagct tcaaggctac gaataagata cttgaaagca    360
gttctaaggc aagatgttgg ctactttgat ctacatgttg ctagcacagc cgacgttata    420
actagcgtct caagtgacag tcttgtcatt caagactgca ttagtgaaaa ggttccagtt    480
ttcttgatga acgtagcagc ttttattgga tcatacgtgg taggattctt gatgctatgg    540
aggctggcat tagtaggatt tccctttgtt attttcttag taataccagg tctcatgtac    600
gggcgggctc taatgggcat agtcagaaaa atcagggacg aatatggcaa agctggaaca    660
gttgtggagc aagcaatttc ttcggttaga acagtttatt cgtttgtagg agaaaacaaa    720
actatagcag agtactctgt tgcactacaa ggaactgtag aattgggact aaagcaaggt    780
ttagcaaaag gtttggctat tggaagtaat ggcatagtat ttgcaattttg gtccttcatg    840 tcttattatg gtagcagatt ggtcatgtat aatggagcac atggtggcac cgtctttgcc    900
gtcggcgctg caattgctat cggtggacta tcattgggtt ctggttttgtc caacgtgaag    960 tatttttccg aagcaagtgc agctggtgaa cgagtaatgg aagtgataaa aagggtacca   1020
aaaatagact cagataacat ggaaggaaaa acagtagcat tagtgggcgg aagtggatct   1080
gggaaatcaa cagtagtagc attgctacag agattttacg aaccacttgc aggagagata   1140
tttgtggatg gggtcgctat tgaaaagttg cagctcaagt ggctaaggtc tcaaatgggt   1200
ttagtgagtc aagagccagc acttttttgca actacaatta ggaaaatat acttttttggg   1260 aaagaggatg catctatgga acaagttatt gaggctgcaa aagcttctaa tgctcataac   1320
ttcatcagtc agttgcctca gggttatgat acccaggtgg gggagagagg tgtacaaatg   1380 tcagggggggc agaagcagag gatagccata gcaagagcca aatcaaatc gcccagaata   1440 ctcctcctag acgaggcaac cagtgcactt gactctgaat cagagcgcgt cgtgcaggaa   1500
gctctagaca tggccgctgt tggccgcacc acaatcatca tagcccatcg cctctccact   1560
attcgcaatg ctgaccttat agccgtggtc caagatggtc aagtcaagga aattggctca   1620
cacgacgacc tgattgaaga ggaaaatgga ctatacacct ccttagtccg tctccaacaa   1680
actgaaaaac caagtgatga attctacatt gcacctacca ataaaaacat tgtctttgcc   1740
ccatcaaatt taaatcctgg atccgcctct gactatgaca tacaaaatac aagtagccga   1800 aggcttttcaa ttgtgagccg gtcaagttca gcaaactcag ctgcgcaaag ccgtagagtg   1860
gatcaaaatg caacaatttc cagtactaca gaacaattat tccctgtacc ttcatttaaa   1920
aggctactgg ctatgaattt gccagaatgg aaggaagcaa cgctgggatg tataggagca   1980
```

| | |
|---|---|
| atattatttg gaggagttca accagtgtat gcttttgcaa tggggtcaat gatttctgtc | 2040 |
| tatttcttgc ctagtcatga tgagattaag gagaagacta agatatatgc tctgtgtttc | 2100 |
| ctcgggctgg cattctttc ccttattgtc aatgtacttc agcactataa ttttgcagcc | 2160 |
| atgggagagc aattgactaa aagggttagg gaaaggatgt tgtccaagat gcttactttt | 2220 |
| gaaattgggt ggtatgacaa ggacgagaat tccactggtg ctgtttgctc tagactagcc | 2280 |
| aaggatgcca atgtggtgag gtctttggtc ggggacagga tggcactact cattcaaaca | 2340 |
| gtctcggcag tgaccattgc ttgcaccatg ggcctagtta tcgcgtggaa acttgcattg | 2400 |
| gttatgatcg cggtccagcc tctcatcata gtgtgctact attgcaagag agtgctattg | 2460 |
| aaaagtatgt ctaagaaatc cataaagtca caagaagaaa gcagcaagtt ggcagctgaa | 2520 |
| gcagttttcca atctcagaac tgtaacagcc ttctcctccc aggcacgaat cctacaaatg | 2580 |
| ctcaagaaag cccaagaagg cccacaacga gaaagtatac gccaatcatg gttcgctgga | 2640 |
| attgggcttg gcacttccaa cagtctcatg acctgtactt gggctcttga tttctggtat | 2700 |
| ggcggcaaac tcatggcagc aggggaaatt ggagcaaagg cactcttcca gaccttcatg | 2760 |
| attttagtta gcactgggcg tgtcattgcg gatgctggaa caatgacgaa cgacctcgcc | 2820 |
| aaaggtgccg atgcagttgg gtcggtcttt tcagtgttgg atcgatattc cttaatcgag | 2880 |
| ccagaggatt cagaaggtta caagcccaag aagataacgg caatgtcga gctgtgtgat | 2940 |
| gtggatttcg cgtaccctgc taggcccaat gtgattatct tcaagggggtt ctcaataaaa | 3000 |
| atcgaagcag gaaaatcaac agcattggta ggacaaagtg gatcaggaaa atctactata | 3060 |
| ataggtctaa tagaaagatt ctatgatccc tcaagtggtg tagtgaaaat agacggccgt | 3120 |
| gacataagat cataccactt gagatcattg aggaaacaga ttgcacttgt aagccaagaa | 3180 |
| ccaacattat ttgcaggaac cataagggaa aacatagcct atggagcatc agaagaagtg | 3240 |
| gatgaatcag aaataattga ggctgcgaag gcagcaaacg cccatgattt catctcagca | 3300 |
| ttaaaagatg gatatgagac ttggtgtggg gacaggggac tgcagttgtc aggaggccaa | 3360 |
| aagcagagaa tcgcgatagc acgggcaata ttaaaaaatc caggagtgct attgttggac | 3420 |
| gaggcaacaa gtgcattgga cagtcaatct gagaaagtag tacaagatgc acttgagaga | 3480 |
| gtgatggttg ccgaacaag tgtggtggtg gctcacaggc taagtactat acagaattgt | 3540 |
| gacaccattg ctgtactgga caaaggcaaa attgtggaga aagggactca ctcttctttg | 3600 |
| ttagccaaag ggcctagtgg agtttactac tctcttgtta gccttcaaag aacaccaaac | 3660 |
| tctagcaaca cctacatcag ttaa | 3684 |

<210> SEQ ID NO 12
<211> LENGTH: 1227
<212> TYPE: PRT
<213> ORGANISM: Nicotiana tabacum

<400> SEQUENCE: 12

Met Ser Thr Thr Thr Lys Ser Lys Ala Met Ile Gln Lys Lys Ser Tyr
1               5                   10                  15

Gly Ser Phe Val Ser Ile Phe Met His Ala Asp Arg Ala Asp Ile Leu
            20                  25                  30

Leu Met Ile Leu Gly Phe Phe Gly Ala Val Cys Asp Gly Phe Ser Met
        35                  40                  45

Pro Ile Met Leu Ile Val Thr Ser Lys Leu Met Asn Asn Leu Gly Gly
    50                  55                  60

Thr Asp Thr Ser Asn Ala Asp Asn Phe Thr His His Ile Asn Glu Asn

```
                65                  70                  75                  80
Ala Leu Val Leu Val Phe Leu Ala Cys Gly Gln Trp Val Ala Cys Phe
                    85                  90                  95

Leu Glu Gly Phe Cys Trp Thr Arg Thr Ala Glu Arg Gln Ala Ser Arg
                    100                 105                 110

Leu Arg Ile Arg Tyr Leu Lys Ala Val Leu Arg Gln Asp Val Gly Tyr
                    115                 120                 125

Phe Asp Leu His Val Ala Ser Thr Ala Asp Val Ile Thr Ser Val Ser
                    130                 135                 140

Ser Asp Ser Leu Val Ile Gln Asp Cys Ile Ser Glu Lys Val Pro Val
145                 150                 155                 160

Phe Leu Met Asn Val Ala Ala Phe Ile Gly Ser Tyr Val Gly Phe
                    165                 170                 175

Leu Met Leu Trp Arg Leu Ala Leu Val Gly Phe Pro Phe Val Ile Phe
                    180                 185                 190

Leu Val Ile Pro Gly Leu Met Tyr Gly Arg Ala Leu Met Gly Ile Val
                    195                 200                 205

Arg Lys Ile Arg Asp Glu Tyr Gly Lys Ala Gly Thr Val Val Glu Gln
                    210                 215                 220

Ala Ile Ser Ser Val Arg Thr Val Tyr Ser Phe Val Gly Glu Asn Lys
225                 230                 235                 240

Thr Ile Ala Glu Tyr Ser Val Ala Leu Gln Gly Thr Val Glu Leu Gly
                    245                 250                 255

Leu Lys Gln Gly Leu Ala Lys Gly Leu Ala Ile Gly Ser Asn Gly Ile
                    260                 265                 270

Val Phe Ala Ile Trp Ser Phe Met Ser Tyr Tyr Gly Ser Arg Leu Val
                    275                 280                 285

Met Tyr Asn Gly Ala His Gly Gly Thr Val Phe Ala Val Gly Ala Ala
                    290                 295                 300

Ile Ala Ile Gly Gly Leu Ser Leu Gly Ser Gly Leu Ser Asn Val Lys
305                 310                 315                 320

Tyr Phe Ser Glu Ala Ser Ala Ala Gly Glu Arg Val Met Glu Val Ile
                    325                 330                 335

Lys Arg Val Pro Lys Ile Asp Ser Asp Asn Met Glu Gly Lys Thr Val
                    340                 345                 350

Ala Leu Val Gly Gly Ser Gly Ser Gly Lys Ser Thr Val Val Ala Leu
                    355                 360                 365

Leu Gln Arg Phe Tyr Glu Pro Leu Ala Gly Glu Ile Phe Val Asp Gly
                    370                 375                 380

Val Ala Ile Glu Lys Leu Gln Leu Lys Trp Leu Arg Ser Gln Met Gly
385                 390                 395                 400

Leu Val Ser Gln Glu Pro Ala Leu Phe Ala Thr Thr Ile Lys Glu Asn
                    405                 410                 415

Ile Leu Phe Gly Lys Glu Asp Ala Ser Met Glu Gln Val Ile Glu Ala
                    420                 425                 430

Ala Lys Ala Ser Asn Ala His Asn Phe Ile Ser Gln Leu Pro Gln Gly
                    435                 440                 445

Tyr Asp Thr Gln Val Gly Glu Arg Gly Val Gln Met Ser Gly Gly Gln
                    450                 455                 460

Lys Gln Arg Ile Ala Ile Ala Arg Ala Thr Ile Lys Ser Pro Arg Ile
465                 470                 475                 480

Leu Leu Leu Asp Glu Ala Thr Ser Ala Leu Asp Ser Glu Ser Glu Arg
                    485                 490                 495
```

-continued

```
Val Val Gln Glu Ala Leu Asp Met Ala Ala Val Gly Arg Thr Thr Ile
        500                 505                 510
Ile Ile Ala His Arg Leu Ser Thr Ile Arg Asn Ala Asp Leu Ile Ala
        515                 520                 525
Val Val Gln Asp Gly Gln Val Lys Glu Ile Gly Ser His Asp Asp Leu
        530                 535                 540
Ile Glu Glu Asn Gly Leu Tyr Thr Ser Leu Val Arg Leu Gln Gln
545                 550                 555                 560
Thr Glu Lys Pro Ser Asp Glu Phe Tyr Ile Ala Pro Thr Asn Lys Asn
                565                 570                 575
Ile Val Phe Ala Pro Ser Asn Leu Asn Pro Gly Ser Ala Ser Asp Tyr
                580                 585                 590
Asp Ile Gln Asn Thr Ser Ser Arg Arg Leu Ser Ile Val Ser Arg Ser
                595                 600                 605
Ser Ser Ala Asn Ser Ala Ala Gln Ser Arg Arg Val Asp Gln Asn Ala
        610                 615                 620
Thr Ile Ser Ser Thr Thr Glu Gln Leu Phe Pro Val Pro Ser Phe Lys
625                 630                 635                 640
Arg Leu Leu Ala Met Asn Leu Pro Glu Trp Lys Glu Ala Thr Leu Gly
                645                 650                 655
Cys Ile Gly Ala Ile Leu Phe Gly Gly Val Gln Pro Val Tyr Ala Phe
                660                 665                 670
Ala Met Gly Ser Met Ile Ser Val Tyr Phe Leu Pro Ser His Asp Glu
        675                 680                 685
Ile Lys Glu Lys Thr Lys Ile Tyr Ala Leu Cys Phe Leu Gly Leu Ala
        690                 695                 700
Phe Phe Ser Leu Ile Val Asn Val Leu Gln His Tyr Asn Phe Ala Ala
705                 710                 715                 720
Met Gly Glu Gln Leu Thr Lys Arg Val Arg Glu Arg Met Leu Ser Lys
                725                 730                 735
Met Leu Thr Phe Glu Ile Gly Trp Tyr Asp Lys Asp Glu Asn Ser Thr
                740                 745                 750
Gly Ala Val Cys Ser Arg Leu Ala Lys Asp Ala Asn Val Val Arg Ser
        755                 760                 765
Leu Val Gly Asp Arg Met Ala Leu Leu Ile Gln Thr Val Ser Ala Val
        770                 775                 780
Thr Ile Ala Cys Thr Met Gly Leu Val Ile Ala Trp Lys Leu Ala Leu
785                 790                 795                 800
Val Met Ile Ala Val Gln Pro Leu Ile Ile Val Cys Tyr Tyr Cys Lys
                805                 810                 815
Arg Val Leu Leu Lys Ser Met Ser Lys Lys Ser Ile Lys Ser Gln Glu
                820                 825                 830
Glu Ser Ser Lys Leu Ala Ala Glu Ala Val Ser Asn Leu Arg Thr Val
        835                 840                 845
Thr Ala Phe Ser Ser Gln Ala Arg Ile Leu Gln Met Leu Lys Lys Ala
        850                 855                 860
Gln Glu Gly Pro Gln Arg Glu Ser Ile Arg Gln Ser Trp Phe Ala Gly
865                 870                 875                 880
Ile Gly Leu Gly Thr Ser Asn Ser Leu Met Thr Cys Thr Trp Ala Leu
                885                 890                 895
Asp Phe Trp Tyr Gly Gly Lys Leu Met Ala Ala Gly Glu Ile Gly Ala
                900                 905                 910
```

-continued

```
Lys Ala Leu Phe Gln Thr Phe Met Ile Leu Val Ser Thr Gly Arg Val
            915                 920                 925
Ile Ala Asp Ala Gly Thr Met Thr Asn Asp Leu Ala Lys Gly Ala Asp
        930                 935                 940
Ala Val Gly Ser Val Phe Ser Val Leu Asp Arg Tyr Ser Leu Ile Glu
945                 950                 955                 960
Pro Glu Asp Ser Glu Gly Tyr Lys Pro Lys Ile Thr Gly Asn Val
                965                 970                 975
Glu Leu Cys Asp Val Asp Phe Ala Tyr Pro Ala Arg Pro Asn Val Ile
            980                 985                 990
Ile Phe Lys Gly Phe Ser Ile Lys Ile Glu Ala Gly Lys Ser Thr Ala
        995                 1000                1005
Leu Val Gly Gln Ser Gly Ser Gly Lys Ser Thr Ile Ile Gly Leu Ile
        1010                1015                1020
Glu Arg Phe Tyr Asp Pro Ser Ser Gly Val Val Lys Ile Asp Gly Arg
1025                1030                1035                1040
Asp Ile Arg Ser Tyr His Leu Arg Ser Leu Arg Lys Gln Ile Ala Leu
            1045                1050                1055
Val Ser Gln Glu Pro Thr Leu Phe Ala Gly Thr Ile Arg Glu Asn Ile
        1060                1065                1070
Ala Tyr Gly Ala Ser Glu Glu Val Asp Glu Ser Glu Ile Ile Glu Ala
        1075                1080                1085
Ala Lys Ala Ala Asn Ala His Asp Phe Ile Ser Ala Leu Lys Asp Gly
        1090                1095                1100
Tyr Glu Thr Trp Cys Gly Asp Arg Gly Leu Gln Leu Ser Gly Gly Gln
1105                1110                1115                1120
Lys Gln Arg Ile Ala Ile Ala Arg Ala Ile Leu Lys Asn Pro Gly Val
            1125                1130                1135
Leu Leu Leu Asp Glu Ala Thr Ser Ala Leu Asp Ser Gln Ser Glu Lys
        1140                1145                1150
Val Val Gln Asp Ala Leu Glu Arg Val Met Val Gly Arg Thr Ser Val
        1155                1160                1165
Val Val Ala His Arg Leu Ser Thr Ile Gln Asn Cys Asp Thr Ile Ala
        1170                1175                1180
Val Leu Asp Lys Gly Lys Ile Val Glu Lys Gly Thr His Ser Ser Leu
1185                1190                1195                1200
Leu Ala Lys Gly Pro Ser Gly Val Tyr Tyr Ser Leu Val Ser Leu Gln
            1205                1210                1215
Arg Thr Pro Asn Ser Ser Asn Thr Tyr Ile Ser
            1220                1225
```

<210> SEQ ID NO 13
<211> LENGTH: 4023
<212> TYPE: DNA
<213> ORGANISM: Nicotiana tabacum

<400> SEQUENCE: 13

| | | | | | |
|---|---|---|---|---|---|
| tttttcttcc | cgtgaccact | tttctaagga | atagctcctc | ttcttcttct | tgcctttgaa | 60 |
| gaatttatt | cttcaaagct | tactttctta | tctctccatt | ctgttatatc | tttaaagaat | 120 |
| cctacatata | gaagtgaaca | acaaagattt | attaaacaat | aagggatagc | gaaaaggaag | 180 |
| aaaaatcctt | tttctatatt | cccctcaaga | ttcaagaaaa | tggccgataa | tagtggagaa | 240 |
| aaaatagaaa | aagggtcgag | aaaaggagat | caagatcaaa | aagtgccatt | ttacaggtta | 300 |
| ttttcgtttg | cagataggct | ggatgttgcc | ctaatgatcg | ttggaacgat | aggagccatt | 360 |

-continued

```
ggcaatggat tatctcaacc tttaatgaca ctcattttg gccaacttgt taattctttt      420
ggttcttctt ctgatgatga tgttgttcac aaaatttcaa aggtttccat ttactatgtc      480
tacctcgcta ttgggtctgg cattgcatcc cttctacaaa tgtcatgttg atggttact       540 ggagagagac aagcaactcg aattcgggga ttgtacttga aaacaatttt aaggcaagac      600
attgccttct ttgacactga acaacaact  ggagaagtca ttggaagaat gtctggagat      660
actattctca ttcaagatgc cttaggtgaa aaggtcggga agttcatcca attcctgtca      720
acatttgttg gaggcttcat aattgccttc ataaagggat ggcttctctc aatagtattg      780
gtttcttgca tacctgctct tgtcattgct ggaggagcta tggcattgat catgtccaaa      840
atgtcaagtc gcggacaagt tgcctacgca caagctggaa atgtagtaga gcaaacaata      900
ggagcaatca gaacagttgc agcattcaca ggagagaagc tggcgataag taagtatgac      960
agcaaactaa aaattgcctg tgctgctact gttcaacaag gcttgtttc  aggcgttgga     1020 cttggcacag tcttactcgt agtcttctct acttatggac tagccgtttg gtatggttcc     1080
aaactgataa ttgagaaagg ttataatggt ggagatgtca tcagtgttat catggctata     1140
atgactggtg aatgtcact  aggccaaaca acaccatcat tgaatgcatt tgcagcagga     1200
caagctgcag cctacaaaat gtttgagaca atcaaccgga aacctctgat tgacacatct     1260
gacaccagcg ggattgtgtt ggaagacgtc aagggtgata ttgaattgaa agatgtgtac     1320
ttcagttacc cagccagacc tgatgagcaa atattcagtg gattctcact attcgtatca     1380
agtggcacaa ctgcagcttt ggttgggcaa agtggaagtg ggaagtcaac agtcataagt     1440
ctgatagaaa gattctatga tcctcaagct ggagaggtac tcatagatgg tgtcaatttg     1500
aagaaattcc aactcaaatg gctaaggcag cagatgggat tagtaagtca ggaacctatc     1560
ctgtttgcaa caaccataaa agagaatatc agttatggta agaaaatgc  tactgacgac     1620 gagattaaga cagctattga acttgctaat gctgctaagt tcctcaacaa acttccccag     1680
gggcttgaca ctatggtagg tgagcaagga atacaactat ctggtggaca aaagcaaaga     1740
attgcaatag caagggctat tctaaagaac ccaaaaatac tcctactcga tgaggctaca     1800
agtgcacttg atgctgaatc cgaatgtgtg ttacaagaag cactcgacaa agtcatggcg     1860
aatagaacaa ctgtggttgt tgctcatcgt ctaacaacca ttagaaatgc tgaccttata     1920
gcagtggtga atgctggaaa actactagaa caaggaacgc attctgagtt gatacaagat     1980
ccaaatgggg cgtattccca gcttgtgcga atgcaaggag gaaatataggga agaagagaac    2040 acaaaaaata tggaccttga taaggtggat ttaaccacgg atttggagaa taacttgagc      2100
aggtcatcaa gccagcgatt gtcagcagtg aaacgatcaa caagccacgg atcatctaga      2160
cattccttca cactcagcta tcctgttccg gggctaattg atattcatga atcagagata      2220
ggagatgagg gcaagaaaaa agaagataaa ggaagcttag agaaacgaaa gaaagtttcc      2280
attaggcggc ttgctgaact aaacaaacct gagcttcctt atttgctact tggatcgttg      2340
gctgcgatca tacatggtct gattttcccc ttatttggac tcttgctatc aacagctatt      2400
aaaatattct tttatccacc acataagttg cgaactgaat caagattctg gtcactcatg      2460
tacgttggcc ttggtgtggt aactttgcta gttgtaccttt tccagaacta cttatttgga    2520
gttgcaggtg ggaaattgat cgagagaatt cgttctttga cgtttaagaa agtagtccac     2580
caagaaatca gctggttcga tgaccctgca aattcaagcg gtgcagtggg tgcaaggtta     2640
tcaactgatg cttctacagt caggacgatt atgggtgatg cactggcact tattgtacag     2700
```

```
aacatagcaa ctgtagtagc tggtcttgtg atagccttca ctgctaattg gattttggca    2760
attataatcc ttctcgtatt gcctttaatt ggtttgcaag gattcctcca gaccaagttg    2820
tacaaaggat tcagtgcaga tgcaaagatg atgtatgagg aagcaagtca agttgcaaat    2880
gatgctgttg gaggtataag aactgttgcg tcattttgtg cagaagagaa ggtgatggaa    2940
atatacagaa gaaagtgtga aggcccaatg aagcaaggag taaagatagg aattgttagt    3000
ggagctagct ttggttttgg ttcttttata ctgtattgta caaatgcctt ctgtttctac    3060
ataggatctg tccttattca tcatggatta gcaacatttg gccaagtttt taaggttttc    3120
tttgcattga cactatcagc tgttggagtt actcaaagca ctggaatggc tccagatgct    3180
aacaaagcca aggattctat agcttctatt ttcgacattc ttgatagaaa acccaagatt    3240
gactcaaatt ctgatgttgg cactactcta gctgttattc gtggagatat tgaatttaaa    3300
catgtgagtt acagatatga aactcgcccg gatgtccaaa tcttcaagga cttatgccta    3360
accatccctt ctggaaagac tgttgctcta gtgggagaga gtggaagcgg gaaatcaact    3420
gtcattagcc taatagagag gttctacaat cctgaatcag gagagatata tttggatggt    3480
gtggagatca acaattcaa gctaagttgg ctaaggcaac aaatgggcct agtgagtcaa    3540
gaaccaatac tgtttaacga aacaattcgt gacaacattg cctacagcag acaagggaat    3600
gcaacagaag aagagatcat tcaagcagca aaatcagcaa atgcacacaa ctttgtatcc    3660
tcattgcctc aaggatatga tacatctgtt ggggaaagag gggtacaatt atccggtgga    3720
caaaagcaaa gaatagctat agcgagagca atactgaagg atccaaagat cctattgcta    3780
gatgaagcaa caagtgcact agatgcagaa tcagaaagta tagtacaaga agcattggat    3840
cgagtaatgg taaataggac aaccgtggta gtagctcatc gcttaaccac aatcaaaggg    3900
gctgatatca ttgctgttgt gaagaatgga gtaattgctg agaaaggaag gcatgaagtt    3960
cttatgaaca taaaagatgg agtttatgca tccttagtag cattgcatat gacttcaacc    4020
tga                                                                  4023
```

<210> SEQ ID NO 14
<211> LENGTH: 1267
<212> TYPE: PRT
<213> ORGANISM: Nicotiana tabacum

<400> SEQUENCE: 14

```
Met Ala Asp Asn Ser Gly Glu Lys Ile Glu Lys Gly Ser Arg Lys Gly
1               5                   10                  15

Asp Gln Asp Gln Lys Val Pro Phe Tyr Arg Leu Phe Ser Phe Ala Asp
            20                  25                  30

Arg Leu Asp Val Ala Leu Met Ile Val Gly Thr Ile Gly Ala Ile Gly
        35                  40                  45

Asn Gly Leu Ser Gln Pro Leu Met Thr Leu Ile Phe Gly Gln Leu Val
    50                  55                  60

Asn Ser Phe Gly Ser Ser Asp Asp Val His Lys Ile Ser
65                  70                  75                  80

Lys Val Ser Ile Tyr Tyr Val Tyr Leu Ala Ile Gly Ser Gly Ile Ala
                85                  90                  95

Ser Leu Leu Gln Met Ser Cys Trp Met Val Thr Gly Glu Arg Gln Ala
            100                 105                 110

Thr Arg Ile Arg Gly Leu Tyr Leu Lys Thr Ile Leu Arg Gln Asp Ile
        115                 120                 125

Ala Phe Phe Asp Thr Glu Thr Thr Thr Gly Glu Val Ile Gly Arg Met
```

```
              130                 135                 140
Ser Gly Asp Thr Ile Leu Ile Gln Asp Ala Leu Gly Glu Lys Val Gly
145                 150                 155                 160

Lys Phe Ile Gln Phe Leu Ser Thr Phe Val Gly Gly Phe Ile Ile Ala
                165                 170                 175

Phe Ile Lys Gly Trp Leu Leu Ser Ile Val Leu Val Ser Cys Ile Pro
                180                 185                 190

Ala Leu Val Ile Ala Gly Gly Ala Met Ala Leu Ile Met Ser Lys Met
                195                 200                 205

Ser Ser Arg Gly Gln Val Ala Tyr Ala Gln Ala Gly Asn Val Val Glu
210                 215                 220

Gln Thr Ile Gly Ala Ile Arg Thr Val Ala Ala Phe Thr Gly Glu Lys
225                 230                 235                 240

Leu Ala Ile Ser Lys Tyr Asp Ser Lys Leu Lys Ile Ala Cys Ala Ala
                245                 250                 255

Thr Val Gln Gln Gly Leu Val Ser Gly Val Gly Leu Gly Thr Val Leu
                260                 265                 270

Leu Val Val Phe Ser Thr Tyr Gly Leu Ala Val Trp Tyr Gly Ser Lys
                275                 280                 285

Leu Ile Ile Glu Lys Gly Tyr Asn Gly Gly Asp Val Ile Ser Val Ile
                290                 295                 300

Met Ala Ile Met Thr Gly Gly Met Ser Leu Gly Gln Thr Thr Pro Ser
305                 310                 315                 320

Leu Asn Ala Phe Ala Ala Gly Gln Ala Ala Ala Tyr Lys Met Phe Glu
                325                 330                 335

Thr Ile Asn Arg Lys Pro Leu Ile Asp Thr Ser Asp Thr Ser Gly Ile
                340                 345                 350

Val Leu Glu Asp Val Lys Gly Asp Ile Glu Leu Lys Asp Val Tyr Phe
                355                 360                 365

Ser Tyr Pro Ala Arg Pro Asp Glu Gln Ile Phe Ser Gly Phe Ser Leu
370                 375                 380

Phe Val Ser Ser Gly Thr Thr Ala Ala Leu Val Gly Gln Ser Gly Ser
385                 390                 395                 400

Gly Lys Ser Thr Val Ile Ser Leu Ile Glu Arg Phe Tyr Asp Pro Gln
                405                 410                 415

Ala Gly Glu Val Leu Ile Asp Gly Val Asn Leu Lys Lys Phe Gln Leu
                420                 425                 430

Lys Trp Leu Arg Gln Gln Met Gly Leu Val Ser Gln Glu Pro Ile Leu
                435                 440                 445

Phe Ala Thr Thr Ile Lys Glu Asn Ile Ser Tyr Gly Lys Glu Asn Ala
                450                 455                 460

Thr Asp Asp Glu Ile Lys Thr Ala Ile Glu Leu Ala Asn Ala Ala Lys
465                 470                 475                 480

Phe Leu Asn Lys Leu Pro Gln Gly Leu Asp Thr Met Val Gly Glu Gln
                485                 490                 495

Gly Ile Gln Leu Ser Gly Gly Gln Lys Gln Arg Ile Ala Ile Ala Arg
                500                 505                 510

Ala Ile Leu Lys Asn Pro Lys Ile Leu Leu Leu Asp Glu Ala Thr Ser
                515                 520                 525

Ala Leu Asp Ala Glu Ser Glu Cys Val Leu Gln Glu Ala Leu Asp Lys
530                 535                 540

Val Met Ala Asn Arg Thr Thr Val Val Val Ala His Arg Leu Thr Thr
545                 550                 555                 560
```

-continued

```
Ile Arg Asn Ala Asp Leu Ile Ala Val Val Asn Ala Gly Lys Leu Leu
                565                 570                 575
Glu Gln Gly Thr His Ser Glu Leu Ile Gln Asp Pro Asn Gly Ala Tyr
                580                 585                 590
Ser Gln Leu Val Arg Met Gln Gly Gly Asn Arg Glu Glu Glu Asn Thr
                595                 600                 605
Lys Asn Met Asp Leu Asp Lys Val Asp Leu Thr Thr Asp Leu Glu Asn
                610                 615                 620
Asn Leu Ser Arg Ser Ser Gln Arg Leu Ser Ala Val Lys Arg Ser
625                 630                 635                 640
Thr Ser His Gly Ser Ser Arg His Ser Phe Thr Leu Ser Tyr Pro Val
                645                 650                 655
Pro Gly Leu Ile Asp Ile His Glu Ser Glu Ile Gly Asp Glu Gly Lys
                660                 665                 670
Lys Lys Glu Asp Lys Gly Ser Leu Glu Lys Arg Lys Lys Val Ser Ile
                675                 680                 685
Arg Arg Leu Ala Glu Leu Asn Lys Pro Glu Leu Pro Tyr Leu Leu Leu
                690                 695                 700
Gly Ser Leu Ala Ala Ile Ile His Gly Leu Ile Phe Pro Leu Phe Gly
705                 710                 715                 720
Leu Leu Leu Ser Thr Ala Ile Lys Ile Phe Phe Tyr Pro Pro His Lys
                725                 730                 735
Leu Arg Thr Glu Ser Arg Phe Trp Ser Leu Met Tyr Val Gly Leu Gly
                740                 745                 750
Val Val Thr Leu Leu Val Val Pro Phe Gln Asn Tyr Leu Phe Gly Val
                755                 760                 765
Ala Gly Gly Lys Leu Ile Glu Arg Ile Arg Ser Leu Thr Phe Lys Lys
                770                 775                 780
Val Val His Gln Glu Ile Ser Trp Phe Asp Asp Pro Ala Asn Ser Ser
785                 790                 795                 800
Gly Ala Val Gly Ala Arg Leu Ser Thr Asp Ala Ser Thr Val Arg Thr
                805                 810                 815
Ile Met Gly Asp Ala Leu Ala Leu Ile Val Gln Asn Ile Ala Thr Val
                820                 825                 830
Val Ala Gly Leu Val Ile Ala Phe Thr Ala Asn Trp Ile Leu Ala Ile
                835                 840                 845
Ile Ile Leu Leu Val Leu Pro Leu Ile Gly Leu Gln Gly Phe Leu Gln
850                 855                 860
Thr Lys Leu Tyr Lys Gly Phe Ser Ala Asp Ala Lys Met Met Tyr Glu
865                 870                 875                 880
Glu Ala Ser Gln Val Ala Asn Asp Ala Val Gly Gly Ile Arg Thr Val
                885                 890                 895
Ala Ser Phe Cys Ala Glu Glu Lys Val Met Glu Ile Tyr Arg Arg Lys
                900                 905                 910
Cys Glu Gly Pro Met Lys Gln Gly Val Lys Ile Gly Ile Val Ser Gly
                915                 920                 925
Ala Ser Phe Gly Phe Gly Ser Phe Ile Leu Tyr Cys Thr Asn Ala Phe
                930                 935                 940
Cys Phe Tyr Ile Gly Ser Val Leu Ile His His Gly Leu Ala Thr Phe
945                 950                 955                 960
Gly Gln Val Phe Lys Val Phe Phe Ala Leu Thr Leu Ser Ala Val Gly
                965                 970                 975
```

Val Thr Gln Ser Thr Gly Met Ala Pro Asp Ala Asn Lys Ala Lys Asp
            980                 985                 990

Ser Ile Ala Ser Ile Phe Asp Ile Leu Asp Arg Lys Pro Lys Ile Asp
        995                 1000                1005

Ser Asn Ser Asp Val Gly Thr Thr Leu Ala Val Ile Arg Gly Asp Ile
    1010                1015                1020

Glu Phe Lys His Val Ser Tyr Arg Tyr Glu Thr Arg Pro Asp Val Gln
1025                1030                1035                1040

Ile Phe Lys Asp Leu Cys Leu Thr Ile Pro Ser Gly Lys Thr Val Ala
                1045                1050                1055

Leu Val Gly Glu Ser Gly Ser Gly Lys Ser Thr Val Ile Ser Leu Ile
            1060                1065                1070

Glu Arg Phe Tyr Asn Pro Glu Ser Gly Glu Ile Tyr Leu Asp Gly Val
        1075                1080                1085

Glu Ile Lys Gln Phe Lys Leu Ser Trp Leu Arg Gln Gln Met Gly Leu
    1090                1095                1100

Val Ser Gln Glu Pro Ile Leu Phe Asn Glu Thr Ile Arg Asp Asn Ile
1105                1110                1115                1120

Ala Tyr Ser Arg Gln Gly Asn Ala Thr Glu Glu Ile Ile Gln Ala
                1125                1130                1135

Ala Lys Ser Ala Asn Ala His Asn Phe Val Ser Ser Leu Pro Gln Gly
            1140                1145                1150

Tyr Asp Thr Ser Val Gly Glu Arg Gly Val Gln Leu Ser Gly Gly Gln
        1155                1160                1165

Lys Gln Arg Ile Ala Ile Ala Arg Ala Ile Leu Lys Asp Pro Lys Ile
    1170                1175                1180

Leu Leu Leu Asp Glu Ala Thr Ser Ala Leu Asp Ala Glu Ser Glu Ser
1185                1190                1195                1200

Ile Val Gln Glu Ala Leu Asp Arg Val Met Val Asn Arg Thr Thr Val
                1205                1210                1215

Val Val Ala His Arg Leu Thr Thr Ile Lys Gly Ala Asp Ile Ile Ala
            1220                1225                1230

Val Val Lys Asn Gly Val Ile Ala Glu Lys Gly Arg His Glu Val Leu
        1235                1240                1245

Met Asn Ile Lys Asp Gly Val Tyr Ala Ser Leu Val Ala Leu His Met
    1250                1255                1260

Thr Ser Thr
1265

<210> SEQ ID NO 15
<211> LENGTH: 3847
<212> TYPE: DNA
<213> ORGANISM: Nicotiana tabacum

<400> SEQUENCE: 15
tacgaaccta acaatttcca ttgtcacctt ttttcagctg ttggcgtgta gaaacggacc      60
tttgagcatt gttgaacttg ttttagaaaa gaaaagaat gacgacttca tctgaaaaag     120
cattagcgaa gaaagataga aattcagtag ctattatttt cagatatgct gatggaatag     180 acatttatt gatgtgtttg ggcactattg gagccattgg atgggcata tcaacaaact     240 gtttgctggt atatgttagc catcttttta atagcttggg ttatggtaag actcaacaga     300
acaatgagat tttatggaa gaaattgaga agtgcagctt gtattttgta ttattgggat     360
tggcagtcat ggttgtggcc tttatggaag gttactgctg gagtaaaaca agtgagcggc     420

```
aagtgctaaa aattcggtac aagtatttgg aagccattct taggcaagaa gttggtttct    480
ttgattctca agaagctacc acatcggaaa tcactaacag catttcgaaa gacacttgtc    540
tcatacagga agttcttagt gaaaaggtac ccatatttt tatgcataca acagttttca     600
tgtcaggaat tgcattttca gcctacttct cgtggaggtt ggctttagtt gccttaccaa    660
cacttattct cctcataatc ccaggtttga tctatgggaa atatctactc catttgtctg    720
aaaagtcgtt caaggaatat gggaaagcaa atgctattgt atggcaggct cttagctcca    780
ttaaaactat atattcattt actggtgaga agagcgtgat tgaaaggtat tcttcgattc    840
ttgatcgaac cataatgctg ggaatgaagc aaggaattgc aaaaggtctt gctgttggaa    900
gcactgggct ttcctttgca atatgggctt tactagcatg gtatgggagc catttgatta    960
tgcacaaagg agaaagtggt ggcagaattt atgcagctgg agtttctttt gtcttgggtg   1020
gactatcgct tgggatggca ctgcctgagg tgaaatactt gacagaagct tcagttgctg   1080
cctcaagaat atttgccagg attgatcgcg ttccagaaat tgatgggaa cacacaaggg    1140 gactcgttct agaaaatatt agaggagaag ttgaattcaa gaatgtaaac ttcacatatc   1200
cttgtcggcc agatagcgtt gtgctcaagg aattcaatct taaaattgaa gcaggaaaaa   1260
cagtggccct tgttggagca agtggtagtg gaaaatccac tgccattgcc atgattcaaa   1320
ggttttatga tactaacgtt ggagctatat gtattgatgg tgtagatata aagtcattgc   1380
agttgaaatg gttgagaggg cagatggggt tagtaagtca agaacatgca ttatttggaa   1440
catctattaa gaagaatatt atgttaggga aaattgacgc aagcatggat gaagttgtgg   1500
ctgcagcaat gactgcgaat gctcataatt tcattacgca acttccagaa ggatatgaga   1560
ccaagattgg tgaaagagga gcatttttat caggtgggca aaagcaacga gtggcaatag   1620
cgagggccat agtgaaaaat ccagcgatac ttctactaga tgaggccaca agtgcacttg   1680
attctgaatc agaaaaacta gttcaggagg ctctagatca agcctccatt ggaagaacta   1740
cactggttgt tgcccacaag ttatcaacag ttagaaatgc agacctcatt gcaatagtga   1800
gtagtggttg catcactgaa ctagggtcac acaatgagct tatcgagaaa gatggacact   1860
atggaagaat ggcaaaactt caaagacaat ttagctctgt tgatcaagaa caaagcgcca   1920
aatctcttat ttcttcagta ggaagaagca gtgcaggaag acaacgctca attattagat   1980
caagtccgac tgtattcgcc tcacctttac tcatcgaaga cagctcccaa gcttcacctc   2040
atcctccccc ttccttctct cggctccttt tactaaactt acctgaatgg aagcaaggaa   2100
taattggaag cttatctgcc atttcatttg gttcagtgca gcctgtatat gcactgacca   2160
taggtggcat gatttcagca ttttactcac caactcacga ggaaatgcaa tttagaattc   2220
agaaatactg tttgattttc agtatccttt gccttgtttc atttgttctc aatctatgcc   2280
aacattacaa ttttgcttac atgggagaac gcctgacaag aagaataaga atgcaaatgc   2340
ttgagaaaat cttgacgttt gaagcagcct ggtttgatga ggaacagaat tcaagtggag   2400
ccttatgttc tagattgagc aatgaagcag ctatggttaa atcccttgtt gctgatagag   2460
tctcactctt ggtccaaagc atttcagctg tcactgttgc catggtaatg gggctagttg   2520
tggcttggaa gcttgcacta gttatgattg ctgtccaacc tctcacaatt ctatgctttt   2580
acacgcgaaa agtcttgcta tccaccatca cagctaagtt cgtcaaggca caatatcaaa   2640
gcactcaaac tgctgtggag gctgtttata atcataggat tgtgacctcg tttgggagca   2700
taaataaggt ccttgaaatc tttgatgagg cacaggatga gtcaaggaag gaggctagga   2760
agaaatcgtg gttagctggt attggtatag gatcagcaca aggcctagct ttcatttgtt   2820
```

-continued

```
gggccctcga ttttggtat ggcggaaagc tagttaatgc tggagaaata tcagctgctg    2880
atgttttcaa gactttcttt atattagtca gcactggtaa ggtagtagct gaagctggaa    2940
gcatgacttc tgatctggcc aagggctcag cagcagttgc ttctatattt gccattcttg    3000
atcgaaactc actcatccat ggatcgtatg atgcgaagaa taacagtagc ggaaccaact    3060
tggagaagat gaccggtggg atagagatga aaaaggttga ttttgcatat ccaagccggc    3120
ctaatagcct agtgttgcgc gaattcagcc tggaagtgaa agcaggaact agcattggac    3180
ttgttggaaa gagtggctgc ggaaaatcaa cagtgattgc cttgattcaa agattttacg    3240
atgcagacag gggatcactg aaaattgatg gtatggacat tcgattactc gatataggat    3300
ggtatagaag gcaaatggcg cttgtgagcc aagaaccggc accatccatg aaaacatttt    3360
gtttggcaaa cttgatgcat cagaaaatga ggtcactgga taatggatac gatacggaat    3420
gtggggagag aggtgtgcag ctatcaggag gcaaaagca aagaattgcc attgcaagag    3480
caatattacg gaaaccaacc atactacttt tagacgaagc aacgagtgct ctagatgttc    3540
agtcggagca agttgtgcag gaagcattag atcgactaat ggttggaaga acgacagtgg    3600
ttgtggcaca caggcttaat accatcagga atttagactc cattgtattt gtttatgaag    3660
ggaaggtggt ggagaaagga acctattctc agctaaagga taagcgaggc gcattttca    3720 atcttgtcaa acttcaatcc acataatgtg aagagtgaat gtattcacgt atataagttt    3780
caaattttgg acatattgat aacttgtgta gtctcaaatg gataaaatca ttgctttgca    3840
tcttccc                                                             3847
```

```
<210> SEQ ID NO 16
<211> LENGTH: 1246
<212> TYPE: PRT
<213> ORGANISM: Nicotiana tabacum

<400> SEQUENCE: 16

Met Thr Thr Ser Ser Glu Lys Ala Leu Ala Lys Lys Asp Arg Asn Ser
1               5                   10                  15

Val Ala Ile Ile Phe Arg Tyr Ala Asp Gly Ile Asp Ile Leu Leu Met
            20                  25                  30

Cys Leu Gly Thr Ile Gly Ala Ile Gly Asp Gly Ile Ser Thr Asn Cys
        35                  40                  45

Leu Leu Val Tyr Val Ser His Leu Phe Asn Ser Leu Gly Tyr Gly Lys
    50                  55                  60

Thr Gln Gln Asn Asn Glu Ile Phe Met Glu Glu Ile Glu Lys Cys Ser
65                  70                  75                  80

Leu Tyr Phe Val Leu Leu Gly Leu Ala Val Met Val Ala Phe Met
                85                  90                  95

Glu Gly Tyr Cys Trp Ser Lys Thr Ser Glu Arg Gln Val Leu Lys Ile
            100                 105                 110

Arg Tyr Lys Tyr Leu Glu Ala Ile Leu Arg Gln Glu Val Gly Phe Phe
        115                 120                 125

Asp Ser Gln Glu Ala Thr Thr Ser Glu Ile Thr Asn Ser Ile Ser Lys
    130                 135                 140

Asp Thr Cys Leu Ile Gln Glu Val Leu Ser Glu Lys Val Pro Ile Phe
145                 150                 155                 160

Phe Met His Thr Thr Val Phe Met Ser Gly Ile Ala Phe Ser Ala Tyr
                165                 170                 175

Phe Ser Trp Arg Leu Ala Leu Val Ala Leu Pro Thr Leu Ile Leu Leu
```

```
                180                 185                 190
Ile Ile Pro Gly Leu Ile Tyr Gly Lys Tyr Leu Leu His Leu Ser Glu
            195                 200                 205
Lys Ser Phe Lys Glu Tyr Gly Lys Ala Asn Ala Ile Val Trp Gln Ala
            210                 215                 220
Leu Ser Ser Ile Lys Thr Ile Tyr Ser Phe Thr Gly Glu Lys Ser Val
225                 230                 235                 240
Ile Glu Arg Tyr Ser Ser Ile Leu Asp Arg Thr Ile Met Leu Gly Met
                245                 250                 255
Lys Gln Gly Ile Ala Lys Gly Leu Ala Val Gly Ser Thr Gly Leu Ser
            260                 265                 270
Phe Ala Ile Trp Ala Leu Leu Ala Trp Tyr Gly Ser His Leu Ile Met
            275                 280                 285
His Lys Gly Glu Ser Gly Gly Arg Ile Tyr Ala Ala Gly Val Ser Phe
            290                 295                 300
Val Leu Gly Gly Leu Ser Leu Gly Met Ala Leu Pro Glu Val Lys Tyr
305                 310                 315                 320
Leu Thr Glu Ala Ser Val Ala Ala Ser Arg Ile Phe Ala Arg Ile Asp
                325                 330                 335
Arg Val Pro Glu Ile Asp Gly Glu His Thr Arg Gly Leu Val Leu Glu
            340                 345                 350
Asn Ile Arg Gly Glu Val Glu Phe Lys Asn Val Asn Phe Thr Tyr Pro
            355                 360                 365
Cys Arg Pro Asp Ser Val Val Leu Lys Glu Phe Asn Leu Lys Ile Glu
            370                 375                 380
Ala Gly Lys Thr Val Ala Leu Val Gly Ala Ser Gly Ser Gly Lys Ser
385                 390                 395                 400
Thr Ala Ile Ala Met Ile Gln Arg Phe Tyr Asp Thr Asn Val Gly Ala
                405                 410                 415
Ile Cys Ile Asp Gly Val Asp Ile Lys Ser Leu Gln Leu Lys Trp Leu
            420                 425                 430
Arg Gly Gln Met Gly Leu Val Ser Gln Glu His Ala Leu Phe Gly Thr
            435                 440                 445
Ser Ile Lys Lys Asn Ile Met Leu Gly Lys Ile Asp Ala Ser Met Asp
            450                 455                 460
Glu Val Val Ala Ala Met Thr Ala Asn Ala His Asn Phe Ile Thr
465                 470                 475                 480
Gln Leu Pro Glu Gly Tyr Glu Thr Lys Ile Gly Glu Arg Gly Ala Phe
                485                 490                 495
Leu Ser Gly Gly Gln Lys Gln Arg Val Ala Ile Ala Arg Ala Ile Val
            500                 505                 510
Lys Asn Pro Ala Ile Leu Leu Leu Asp Glu Ala Thr Ser Ala Leu Asp
            515                 520                 525
Ser Glu Ser Glu Lys Leu Val Gln Glu Ala Leu Asp Gln Ala Ser Ile
            530                 535                 540
Gly Arg Thr Thr Leu Val Val Ala His Lys Leu Ser Thr Val Arg Asn
545                 550                 555                 560
Ala Asp Leu Ile Ala Ile Val Ser Ser Gly Cys Ile Thr Glu Leu Gly
                565                 570                 575
Ser His Asn Glu Leu Ile Glu Lys Asp Gly His Tyr Gly Arg Met Ala
            580                 585                 590
Lys Leu Gln Arg Gln Phe Ser Ser Val Asp Gln Glu Gln Ser Ala Lys
            595                 600                 605
```

```
Ser Leu Ile Ser Ser Val Gly Arg Ser Ser Ala Gly Arg Gln Arg Ser
        610                 615                 620

Ile Ile Arg Ser Ser Pro Thr Val Phe Ala Ser Pro Leu Leu Ile Glu
625                 630                 635                 640

Asp Ser Ser Gln Ala Ser Pro His Pro Pro Ser Phe Ser Arg Leu
                645                 650                 655

Leu Leu Leu Asn Leu Pro Glu Trp Lys Gln Gly Ile Ile Gly Ser Leu
                660                 665                 670

Ser Ala Ile Ser Phe Gly Ser Val Gln Pro Val Tyr Ala Leu Thr Ile
                675                 680                 685

Gly Gly Met Ile Ser Ala Phe Tyr Ser Pro Thr His Glu Glu Met Gln
690                 695                 700

Phe Arg Ile Gln Lys Tyr Cys Leu Ile Phe Ser Ile Leu Cys Leu Val
705                 710                 715                 720

Ser Phe Val Leu Asn Leu Cys Gln His Tyr Asn Phe Ala Tyr Met Gly
                725                 730                 735

Glu Arg Leu Thr Arg Arg Ile Arg Met Gln Met Leu Glu Lys Ile Leu
                740                 745                 750

Thr Phe Glu Ala Ala Trp Phe Asp Glu Glu Gln Asn Ser Ser Gly Ala
                755                 760                 765

Leu Cys Ser Arg Leu Ser Asn Glu Ala Ala Met Val Lys Ser Leu Val
770                 775                 780

Ala Asp Arg Val Ser Leu Leu Val Gln Ser Ile Ser Ala Val Thr Val
785                 790                 795                 800

Ala Met Val Met Gly Leu Val Val Ala Trp Lys Leu Ala Leu Val Met
                805                 810                 815

Ile Ala Val Gln Pro Leu Thr Ile Leu Cys Phe Tyr Thr Arg Lys Val
                820                 825                 830

Leu Leu Ser Thr Ile Thr Ala Lys Phe Val Lys Ala Gln Tyr Gln Ser
                835                 840                 845

Thr Gln Thr Ala Val Glu Ala Val Tyr Asn His Arg Ile Val Thr Ser
850                 855                 860

Phe Gly Ser Ile Asn Lys Val Leu Glu Ile Phe Asp Glu Ala Gln Asp
865                 870                 875                 880

Glu Ser Arg Lys Glu Ala Arg Lys Lys Ser Trp Leu Ala Gly Ile Gly
                885                 890                 895

Ile Gly Ser Ala Gln Gly Leu Ala Phe Ile Cys Trp Ala Leu Asp Phe
                900                 905                 910

Trp Tyr Gly Gly Lys Leu Val Asn Ala Gly Glu Ile Ser Ala Ala Asp
                915                 920                 925

Val Phe Lys Thr Phe Phe Ile Leu Val Ser Thr Gly Lys Val Val Ala
930                 935                 940

Glu Ala Gly Ser Met Thr Ser Asp Leu Ala Lys Gly Ser Ala Ala Val
945                 950                 955                 960

Ala Ser Ile Phe Ala Ile Leu Asp Arg Asn Ser Leu Ile His Gly Ser
                965                 970                 975

Tyr Asp Ala Lys Asn Asn Ser Ser Gly Thr Asn Leu Glu Lys Met Thr
                980                 985                 990

Gly Gly Ile Glu Met Lys Lys Val Asp Phe Ala Tyr Pro Ser Arg Pro
                995                 1000                1005

Asn Ser Leu Val Leu Arg Glu Phe Ser Leu Glu Val Lys Ala Gly Thr
                1010                1015                1020
```

Ser Ile Gly Leu Val Gly Lys Ser Gly Cys Gly Lys Ser Thr Val Ile
    1025                1030                1035                1040

Ala Leu Ile Gln Arg Phe Tyr Asp Ala Asp Arg Gly Ser Leu Lys Ile
            1045                1050                1055

Asp Gly Met Asp Ile Arg Leu Leu Asp Ile Gly Trp Tyr Arg Arg Gln
        1060                1065                1070

Met Ala Leu Val Ser Gln Glu Pro Ala Pro Ser Met Lys Thr Phe Cys
    1075                1080                1085

Leu Ala Asn Leu Met His Gln Lys Met Arg Ser Leu Asp Asn Gly Tyr
        1090                1095                1100

Asp Thr Glu Cys Gly Glu Arg Gly Val Gln Leu Ser Gly Gly Gln Lys
1105                1110                1115                1120

Gln Arg Ile Ala Ile Ala Arg Ala Ile Leu Arg Lys Pro Thr Ile Leu
            1125                1130                1135

Leu Leu Asp Glu Ala Thr Ser Ala Leu Asp Val Gln Ser Glu Gln Val
        1140                1145                1150

Val Gln Glu Ala Leu Asp Arg Leu Met Val Gly Arg Thr Thr Val Val
    1155                1160                1165

Val Ala His Arg Leu Asn Thr Ile Arg Asn Leu Asp Ser Ile Val Phe
    1170                1175                1180

Val Tyr Glu Gly Lys Val Val Glu Lys Gly Thr Tyr Ser Gln Leu Lys
1185                1190                1195                1200

Asp Lys Arg Gly Ala Phe Phe Asn Leu Val Lys Leu Gln Ser Thr Cys
            1205                1210                1215

Glu Glu Met Tyr Ser Arg Ile Val Ser Asn Phe Gly His Ile Asp Asn
        1220                1225                1230

Leu Cys Ser Leu Lys Trp Ile Lys Ser Leu Leu Cys Ile Phe
        1235                1240                1245

<210> SEQ ID NO 17
<211> LENGTH: 471
<212> TYPE: DNA
<213> ORGANISM: Nicotiana tabacum

<400> SEQUENCE: 17
atgggaagtg cagtggagac attgtgtgga caagcatatg gagcgcagag gtatgagatg    60
ctaggaatat acctacaaag atcaacagga attccactct tattcatcta catcttctcc   120
aagccaatct tgattctact cggtcagaaa ccagcgatcg cgtcagcagc tgcagttttc   180
gtctatggtc taattcccca aattttcgcg tacgcagcga acttctcaat tcaaaaattc   240
cttcaatcac agagcattat caagcctagt gcttatattg cagcagccac cctggttgtt   300
catagcttct ttacatggct tgttgtgtat aaaactcgtt ggggaatttt gggggcttca   360
ttgatgctga ttttcgtg gtggattata gttgtagcac agtttgtgta tattttgtca   420
agtaaaaagt gcaagaagac atggacaggt tggtatgtaa tcatggatta a   471

<210> SEQ ID NO 18
<211> LENGTH: 156
<212> TYPE: PRT
<213> ORGANISM: Nicotiana tabacum

<400> SEQUENCE: 18

Met Gly Ser Ala Val Glu Thr Leu Cys Gly Gln Ala Tyr Gly Ala Gln
1               5                   10                  15

Arg Tyr Glu Met Leu Gly Ile Tyr Leu Gln Arg Ser Thr Gly Ile Pro
            20                  25                  30

Leu Leu Phe Ile Tyr Ile Phe Ser Lys Pro Ile Leu Ile Leu Leu Gly
         35                  40                  45

Gln Lys Pro Ala Ile Ala Ser Ala Ala Ala Val Phe Val Tyr Gly Leu
     50                  55                  60

Ile Pro Gln Ile Phe Ala Tyr Ala Ala Asn Phe Ser Ile Gln Lys Phe
65                  70                  75                  80

Leu Gln Ser Gln Ser Ile Ile Lys Pro Ser Ala Tyr Ile Ala Ala Ala
             85                  90                  95

Thr Leu Val Val His Ser Phe Phe Thr Trp Leu Val Val Tyr Lys Thr
             100                 105                 110

Arg Trp Gly Ile Leu Gly Ala Ser Leu Met Leu Ser Phe Ser Trp Trp
             115                 120                 125

Ile Ile Val Val Ala Gln Phe Val Tyr Ile Leu Ser Ser Lys Lys Cys
             130                 135                 140

Lys Lys Thr Trp Thr Gly Trp Tyr Val Ile Met Asp
145                 150                 155

<210> SEQ ID NO 19
<211> LENGTH: 1304
<212> TYPE: DNA
<213> ORGANISM: Nicotiana tabacum

<400> SEQUENCE: 19

| | | |
|---|---|---|
| atgccacctt cacctgaata tgtaacacaa aaatggccag catcaagcct catgcaaaat | 60 |
| gccgtttcag agctaaaatt gcaaagagga atactacttc cttttgatgg catgaacttc | 120 |
| acatggtttg caaaaacagc catcacaact gcatttcttg gtaggcttgg agatctttat | 180 |
| ttagctggag gaacacttgg ttttactttt gcaaatgtaa ccggattttc agtactaaat | 240 |
| ggcctttgtg gtgcaatgga gcctatttgt ggacaagctt ttggagccaa gaattacaaa | 300 |
| cttcttcata agaccccttgt tatggctact ttattattac tactaatcag cttgcctatt | 360 |
| tcatttttgt ggctaaatat tgatacgatc ctcattcaat ttggccaaca agaagatatt | 420 |
| tcaaatatgg ccaaaaagta tctcccatgt tactttcaag aactaagggt ataataggag | 480 |
| tttctatggc atattggata acagattttt tgatcatgat atttttgtct atttatgtag | 540 |
| tgatagcaga gaataaaaag ggaggaaaat ggaagaagg aggatggtgg atcaaagaa | 600 |
| ttcgcgattg gatcagacta ctaaaattat gtggaccatg ttgtcttact acttgtcttg | 660 |
| aatggtggtg ttatgaaatc ttggttttgt taacaggaca tctcccaaat gctaaacaag | 720 |
| caattggagt tatagccatt gtgttaaatt ttgattattt gctgttttct gttatgcttt | 780 |
| cgttatcaac gtgtgcatct attcgtgtgt ctaatgagct tggtgcagat agtcctggtc | 840 |
| ctgcttatcg cgcagcctat gtatcgttag ctacgagcat tgtttcaggt tttcttggtg | 900 |
| gtgctgttat ggctggtgca agaggaattt gggggccatt gtttagtcat aataaaggga | 960 |
| ttataaatgg cgttaagaaa atgatgttgt taatggcatt acttgaagtg gttaattttc | 1020 |
| cattagcagt ttgtggtgga attgtacgtg aacggctag gccatggcta ggaatgtatg | 1080 |
| ctaatattag tggattttat ctgttagctt tgccattagg tgtggttttg gctttcaaga | 1140 |
| ttcatcttgg tcttactgga ttgttgacag ggttgtggt tggagttgct gtttgtttgg | 1200 |
| ccttgttgtt ggtgtttatt gctcggattg attgggttca agaagctaag aaagcacaag | 1260 |
| ttttttgcttg taatcttgaa gaaataggta atgatgataa ttga | 1304 |

<210> SEQ ID NO 20

<400> SEQUENCE: 20

000

<210> SEQ ID NO 21
<211> LENGTH: 2790
<212> TYPE: DNA
<213> ORGANISM: Nicotiana tabacum

<400> SEQUENCE: 21

| | | | | | |
|---|---|---|---|---|---|
| gatcagtctg | tacaatcatt | ggtttcaccc | ctcaggcgca | ttagctaacg | agttttgctc | 60 |
| gaaaagtgat | caaaaccagg | gagtcatggc | tgaaggtggc | aatgtagctt | gtactgagag | 120 |
| aaaatgcaag | ataccactct | ttgttttctt | tgaagatatt | aggcatgtgt | ttaaattcga | 180 |
| cgatcttgga | atggaaatcc | taagtatcgc | gttccctgca | gctctagcat | tagctgctga | 240 |
| tcccattgct | tctctcattg | atactgcatt | cattggtcat | ttaggttcgg | tggaaatcgc | 300 |
| tgcagtagga | gtatcaattg | ccatatttaa | tcaagcctct | aaagtcacaa | tattcccttt | 360 |
| agttaacata | acaacttctt | tcgttgctga | ggaagacact | gttagaagaa | ttaaagaaaa | 420 |
| agcagcaatt | gctgacttgg | agaaaggttc | agaggagaag | aatgatacaa | aactgccagt | 480 |
| aactgatgat | actgaccatg | agaagctgga | aaaatgtgca | tccacaaaag | ttgaaccaa | 540 |
| agagtctgca | ccagcaccag | cacctgcagc | agaattcaag | acaacagcat | gcaagtctcc | 600 |
| tgataatcaa | agtaaaggca | agtcaaacg | tgtgaagcga | catattccat | ctgcttcaac | 660 |
| tgcaattctt | atgggctgca | ttcttggcat | tttgcaaaca | atcttcctta | tatttctcgc | 720 |
| aaaaccaatt | ctaagcttaa | tgggtgtgaa | atctggatct | gctatgcttt | ccccagcaaa | 780 |
| gaagtattta | atactgagag | cacttggtgc | tcctgcagtc | ctccttctc | tggctatgca | 840 |
| aggcgttttc | cgtggtttta | aggatacaag | aactccttta | tatgctactg | ttgctggaga | 900 |
| tttgacaaat | atagttttgg | acccaatctt | tatctttgtt | ttccgttggg | gtgttagtgg | 960 |
| tgctgccatt | gctcatgtgc | tttctcagta | cttgatatca | attattctct | tatgcaaact | 1020 |
| gatgacagaa | gtcgaattat | tacctcctag | tgcaaaagat | ctgcagttca | gcaaatttct | 1080 |
| taaaaatgga | ttttggttac | tagcaagggt | gatagctgtc | acattttgtg | tgacgttggc | 1140 |
| tgcgtcattg | gctgcacgac | taggcacaac | accgatggct | gcatttcaag | tgtgcttaca | 1200 |
| gatctggtta | acatcatctc | tacttgctga | tggattggct | gtagcaggac | aggcaatcct | 1260 |
| tgctagttct | tttgctgaga | aagactacca | gaaggcaaag | gctgcaggag | tacgagtcct | 1320 |
| acagatggga | tttgtgttgg | gactaggact | tgctttggtt | gttggaattg | gtctatattt | 1380 |
| tggatcagga | gttttttcaa | aggacaaaaa | tgttatccgt | ctcataacca | ttgccatccc | 1440 |
| gtttgtcgct | ggtacacaac | caatcaactc | attggcgttt | gttttagatg | tgtcaacttt | 1500 |
| tggagcaaat | gattttgcat | actctgcata | ttccatggtt | ttggttggtg | cactaacagt | 1560 |
| aacctgtgag | tttgtccttt | ccaaaagcaa | tggttacatt | ggaatatgga | ttgctttaac | 1620 |
| catattcatg | gccctgcgta | ccattgccgg | tttatggagg | atggggacag | gaaccggacc | 1680 |
| ctggcgtttc | ctgcggattc | catcatcgtc | tccagaagcc | aagtcataga | gttcctagca | 1740 |
| cttctgtggc | tatttatatc | atacattttc | catctttctt | tcctttgtac | ttctcccttt | 1800 |
| tttcttttgc | ttttgttgtt | cttggtgatg | cgtacagggt | ggaaattgta | cacactttct | 1860 |
| actcatatgt | ttgtataata | gtctgacttc | agtgtcatta | tcataagatt | ttgtagctat | 1920 |
| atgcagatat | atacatcttt | gcatacgtaa | actttaattg | cttttatatt | agctagtgcc | 1980 |

```
atatcttcat gacataatgt tgtacgttta ggcatgcctg tccatcctga caacgttgca    2040
ggtaacatat tctccttcat ggtgtttatt tcgccagtac ctacattta tgggatcgtt    2100 aagaagaaat caacagaagg ctatcaatca attccgtacg tggttgcact ctttagttca    2160
atgctttgga tttactatgc atttctcaag acaaacacga cccttatcat caccataaac    2220
tcctttggct gcattgcgga gactatttat attgctattt attttgctta tgcgacaaaa    2280
aaaacaagga tgcaaacgtt gagacttgtt ctaatgttga atttcggtgg ctttgggttg    2340
attcttttcc tcacccaaat tttatgcaaa ggagcaaaac gagctgaagt tattggatgg    2400
atttgcatgg cgttttctat tagtgtgttt gtagcacctc taagcattat ggggcgggta    2460
atacggacca aaagtgtgga gttcatgcca tttaacttgt cgttaaccct tacacttagt    2520
gctgtgataa acgccaagcc aaataatcag gcagaagaga agaaactacc cactgttgtg    2580
aagctggagg agttgcctac aaaagttaat tctgaggttt atccagttag tttaccatcc    2640
atgggcagtg aaaacggaga ggctaaagat ggtaaacatt ttgaagatgc ccaaatcaaa    2700
tctcctatta tttacctgga aattaaccta actactgata caccgaattc cggtacaact    2760
tgcaagtcag taagtctagg gcaaaagtaa                                    2790
```

<210> SEQ ID NO 22
<211> LENGTH: 547
<212> TYPE: PRT
<213> ORGANISM: Nicotiana tabacum

<400> SEQUENCE: 22

```
Met Ala Glu Gly Gly Asn Val Ala Cys Thr Glu Arg Lys Cys Lys Ile
1               5                   10                  15

Pro Leu Phe Val Phe Glu Asp Ile Arg His Val Phe Lys Phe Asp
            20                  25                  30

Asp Leu Gly Met Glu Ile Leu Ser Ile Ala Phe Pro Ala Ala Leu Ala
        35                  40                  45

Leu Ala Ala Asp Pro Ile Ala Ser Leu Ile Asp Thr Ala Phe Ile Gly
    50                  55                  60

His Leu Gly Ser Val Glu Ile Ala Ala Val Gly Val Ser Ile Ala Ile
65                  70                  75                  80

Phe Asn Gln Ala Ser Lys Val Thr Ile Phe Pro Leu Val Asn Ile Thr
                85                  90                  95

Thr Ser Phe Val Ala Glu Glu Asp Thr Val Arg Arg Ile Lys Glu Lys
            100                 105                 110

Ala Ala Ile Ala Asp Leu Glu Lys Gly Ser Glu Glu Lys Asn Asp Thr
        115                 120                 125

Lys Leu Pro Val Thr Asp Asp Thr Asp His Glu Lys Leu Glu Lys Cys
    130                 135                 140

Ala Ser Thr Lys Val Glu Thr Lys Glu Ser Ala Pro Ala Pro Ala Pro
145                 150                 155                 160

Ala Ala Glu Phe Lys Thr Thr Ala Cys Lys Ser Pro Asp Asn Gln Ser
                165                 170                 175

Lys Gly Lys Val Lys Arg Val Lys Arg His Ile Pro Ser Ala Ser Thr
            180                 185                 190

Ala Ile Leu Met Gly Cys Ile Leu Gly Ile Leu Gln Thr Ile Phe Leu
        195                 200                 205

Ile Phe Leu Ala Lys Pro Ile Leu Ser Leu Met Gly Val Lys Ser Gly
    210                 215                 220

Ser Ala Met Leu Ser Pro Ala Lys Lys Tyr Leu Ile Leu Arg Ala Leu
```

```
              225                 230                 235                 240
Gly Ala Pro Ala Val Leu Leu Ser Leu Ala Met Gln Gly Val Phe Arg
                     245                 250                 255
Gly Phe Lys Asp Thr Arg Thr Pro Leu Tyr Ala Thr Val Ala Gly Asp
                 260                 265                 270
Leu Thr Asn Ile Val Leu Asp Pro Ile Phe Ile Phe Val Phe Arg Trp
             275                 280                 285
Gly Val Ser Gly Ala Ala Ile Ala His Val Leu Ser Gln Tyr Leu Ile
         290                 295                 300
Ser Ile Ile Leu Leu Cys Lys Leu Met Thr Glu Val Glu Leu Leu Pro
305                 310                 315                 320
Pro Ser Ala Lys Asp Leu Gln Phe Ser Lys Phe Leu Lys Asn Gly Phe
                 325                 330                 335
Trp Leu Leu Ala Arg Val Ile Ala Val Thr Phe Cys Val Thr Leu Ala
             340                 345                 350
Ala Ser Leu Ala Ala Arg Leu Gly Thr Thr Pro Met Ala Ala Phe Gln
         355                 360                 365
Val Cys Leu Gln Ile Trp Leu Thr Ser Ser Leu Leu Ala Asp Gly Leu
     370                 375                 380
Ala Val Ala Gly Gln Ala Ile Leu Ala Ser Ser Phe Ala Glu Lys Asp
385                 390                 395                 400
Tyr Gln Lys Ala Lys Ala Ala Gly Val Arg Val Leu Gln Met Gly Phe
                 405                 410                 415
Val Leu Gly Leu Gly Leu Ala Leu Val Val Gly Ile Gly Leu Tyr Phe
             420                 425                 430
Gly Ser Gly Val Phe Ser Lys Asp Lys Asn Val Ile Arg Leu Ile Thr
         435                 440                 445
Ile Ala Ile Pro Phe Val Ala Gly Thr Gln Pro Ile Asn Ser Leu Ala
     450                 455                 460
Phe Val Leu Asp Gly Val Asn Phe Gly Ala Asn Asp Phe Ala Tyr Ser
465                 470                 475                 480
Ala Tyr Ser Met Val Leu Val Gly Ala Leu Thr Val Thr Cys Glu Phe
                 485                 490                 495
Val Leu Ser Lys Ser Asn Gly Tyr Ile Gly Ile Trp Ile Ala Leu Thr
             500                 505                 510
Ile Phe Met Ala Leu Arg Thr Ile Ala Gly Leu Trp Arg Met Gly Thr
         515                 520                 525
Gly Thr Gly Pro Trp Arg Phe Leu Arg Ile Pro Ser Ser Ser Pro Glu
     530                 535                 540
Ala Lys Ser
545

<210> SEQ ID NO 23
<211> LENGTH: 2179
<212> TYPE: DNA
<213> ORGANISM: Nicotiana tabacum

<400> SEQUENCE: 23
ataaatatga aactatatca tctaaacaat tgtcagttgt gagtgaatgt tatgaatgag      60
aaaggtttgg ctatagtaat tgggaagaca tggtggacca aggagctgat gcggataata     120
gaggaaattg cagacttggt gactatgatg tgaaccatgg ttagaggata ggggtaaatt     180
agtggagcgg gggacaagga atctggtggt tatataattg cagtcttggg acgtatttgc     240
tatgctgctt taatttggag aacaaagcag caaaagatta gatatggcga tggaagaggc     300
```

```
actgctggat gtgaataata ataataataa taataataat aataaggtag tgtttgggaa    360
ggaggtgaag gaggtgagtc ggatagcaat gccgatgata gtggtgacgg tgtcacagta    420 cctttgcgc gtttcaccaa tgataatgtt gggtcatctt ggtgaacttc aactttctag    480
tgcttctatt gctacttcac tttccaatgt taccggcttc agtcttatgt tagggatggg    540
gagtgcagtg gagacactat gtgggcaggc atatggagct cacaagtatg gaaatcttgg    600
aacttttact tatggtgcaa ttatttgtct attccttgta tgcataccag tttctgttct    660
gtggatcttc acggataggc ttcttatatt gatgggccaa gatcctgaaa tcgcaactga    720
agctggaaaa tacacgattt ggctcattcc tacgctattt ccatatgcta ttcttcagtc    780
acttgtccgg tacctgcagg cacagagttt aatcctacca atgcttttga gtgctgttgt    840
atctttatgc ttccaagtgc cgatatgttg gttttttata ttcaaattgg atttggggaa    900
cgctggagca gcaatgtcaa ttggtttatc ctattggctg aatgtgatct tgcttatgct    960
ttatgtgaag tactcatcag cttgtgcaga aactcgggct tcattctcta gagatgtttt   1020
tctgactata ggggacttct tccgctttgc tatcccatct gctgtaatgg tttgcttgga   1080
atggtggtcg tttgaactaa tcattctcct ctctggtctg ttgccaaatc cagcgctaga   1140
gacttccgtt ctatccatat gctttacaac cacttcagtg cactaccata tacgttattc   1200
tttcggtgcc gctgcaagca ctcgtgtttc aaatgagctt ggagcgggga ggccacaggc   1260
cgcgaaagtt gctcttggcg ctgtgctaat tctttctgtc acagaggttg ttcttgcaag   1320
tatttctata ttcgtggtcc gccatgtatg gggctatgta tttacctatg agaaagaagt   1380
aatcacttat gtagcagaaa ttactcctgt tctttgcatc tcaatcatca tggatggcac   1440
ccaagccgta ttatcaggag ttgcaagagg aagtgggtgg cagcatattg gagcatatgt   1500
gaatcttgga gcatattatt tggttggaat tccaacggct ctattgctgg atttgttttt   1560
gcatctaaaa ggcaaaggcc tttggattgg attggtggct ggagcaactg tgcaatctat   1620
ttcgctttcc cttatcacag gcctcaccaa ttgggaaaaa caggccattg aagcaagaca   1680
tagaatcttt agtggaaggc ctgctgttga aaatcagaat taaagagcac atgcagatgc   1740
tataacatac atatcgaaat aaaccttcaa cttgctatga tttagcgaga atcaccactc   1800
atcatagtac caattggaca attttgaaag tgatcagcct cttagatgta aatgaacaac   1860
tttggcggat caattccaga tacgggatt ttccagtttc cttaagcatg ttgtttccaa   1920
gttgaatttg ttttgctttg ctaaatcgtt tagctgcggc ttcttgtaac ttgtaacgca   1980
aatttcttgt tcgaaaatat aaacagaaat tattgattct gatggtaagc aacccccact   2040
tccaaccaag aggttgtgag ttcgagtcac cccaagagca aggtggtagt gtgtacgcag   2100
accttacccc taccctgggg tagagaggct gtttccaata gaccctcggc ataaatcccc   2160
accttgctct tggggtgac                                                2179
```

<210> SEQ ID NO 24
<211> LENGTH: 479
<212> TYPE: PRT
<213> ORGANISM: Nicotiana tabacum

<400> SEQUENCE: 24

```
Met Ala Met Glu Glu Ala Leu Leu Asp Val Asn Asn Asn Asn Asn
1               5                   10                  15

Asn Asn Asn Asn Lys Val Val Phe Gly Lys Glu Val Lys Glu Val Ser
            20                  25                  30
```

-continued

```
Arg Ile Ala Met Pro Met Ile Val Thr Val Ser Gln Tyr Leu Leu
             35                  40                  45
Arg Val Ser Pro Met Ile Met Leu Gly His Leu Gly Glu Leu Gln Leu
 50                  55                  60
Ser Ser Ala Ser Ile Ala Thr Ser Leu Ser Asn Val Thr Gly Phe Ser
 65                  70                  75                  80
Leu Met Leu Gly Met Gly Ser Ala Val Glu Thr Leu Cys Gly Gln Ala
                 85                  90                  95
Tyr Gly Ala His Lys Tyr Gly Asn Leu Gly Thr Phe Thr Tyr Gly Ala
                100                 105                 110
Ile Ile Cys Leu Phe Leu Val Cys Ile Pro Val Ser Val Leu Trp Ile
            115                 120                 125
Phe Thr Asp Arg Leu Leu Ile Leu Met Gly Gln Asp Pro Glu Ile Ala
    130                 135                 140
Thr Glu Ala Gly Lys Tyr Thr Ile Trp Leu Ile Pro Thr Leu Phe Pro
145                 150                 155                 160
Tyr Ala Ile Leu Gln Ser Leu Val Arg Tyr Leu Gln Ala Gln Ser Leu
                165                 170                 175
Ile Leu Pro Met Leu Leu Ser Ala Val Val Ser Leu Cys Phe Gln Val
            180                 185                 190
Pro Ile Cys Trp Val Phe Ile Phe Lys Leu Asp Leu Gly Asn Ala Gly
        195                 200                 205
Ala Ala Met Ser Ile Gly Leu Ser Tyr Trp Leu Asn Val Ile Leu Leu
    210                 215                 220
Met Leu Tyr Val Lys Tyr Ser Ser Ala Cys Ala Glu Thr Arg Ala Ser
225                 230                 235                 240
Phe Ser Arg Asp Val Phe Leu Thr Ile Gly Asp Phe Phe Arg Phe Ala
                245                 250                 255
Ile Pro Ser Ala Val Met Val Cys Leu Glu Trp Trp Ser Phe Glu Leu
            260                 265                 270
Ile Ile Leu Leu Ser Gly Leu Leu Pro Asn Pro Ala Leu Glu Thr Ser
        275                 280                 285
Val Leu Ser Ile Cys Phe Thr Thr Thr Ser Val His Tyr His Ile Pro
    290                 295                 300
Tyr Ser Phe Gly Ala Ala Ala Ser Thr Arg Val Ser Asn Glu Leu Gly
305                 310                 315                 320
Ala Gly Arg Pro Gln Ala Ala Lys Val Ala Leu Gly Ala Val Leu Ile
                325                 330                 335
Leu Ser Val Thr Glu Val Val Leu Ala Ser Ile Ser Ile Phe Val Val
            340                 345                 350
Arg His Val Trp Gly Tyr Val Phe Thr Tyr Glu Lys Glu Val Ile Thr
        355                 360                 365
Tyr Val Ala Glu Ile Thr Pro Val Leu Cys Ile Ser Ile Met Asp
    370                 375                 380
Gly Thr Gln Ala Val Leu Ser Gly Val Ala Arg Gly Ser Gly Trp Gln
385                 390                 395                 400
His Ile Gly Ala Tyr Val Asn Leu Gly Ala Tyr Tyr Leu Val Gly Ile
                405                 410                 415
Pro Thr Ala Leu Leu Gly Phe Val Leu His Leu Lys Gly Lys Gly
            420                 425                 430
Leu Trp Ile Gly Leu Val Ala Gly Ala Thr Val Gln Ser Ile Ser Leu
        435                 440                 445
Ser Leu Ile Thr Gly Leu Thr Asn Trp Glu Lys Gln Ala Ile Glu Ala
```

```
             450                 455                 460
Arg His Arg Ile Phe Ser Gly Arg Pro Ala Val Glu Asn Gln Asn
465                 470                 475
```

<210> SEQ ID NO 25
<211> LENGTH: 1868
<212> TYPE: DNA
<213> ORGANISM: Nicotiana tabacum
<220> FEATURE:
<221> NAME/KEY: misc_feature
<222> LOCATION: 1427, 1428, 1429, 1430, 1431, 1432, 1433, 1434, 1435,
      1436, 1437, 1438, 1439, 1440, 1441, 1442, 1443, 1444, 1445, 1446,
      1447, 1448, 1449, 1450, 1451, 1452, 1453, 1454, 1455, 1456,
      1457, 1458, 1459, 1460, 1461, 1462, 1463, 1464, 1582
<223> OTHER INFORMATION: n = A,T,C or G
<220> FEATURE:
<221> NAME/KEY: misc_feature
<222> LOCATION: 1583, 1584, 1585, 1586, 1587, 1588, 1589, 1590, 1591,
      1592, 1593, 1594, 1595, 1596, 1597, 1598, 1599, 1600, 1601, 1602,
      1603, 1604, 1605, 1606, 1607, 1608, 1609, 1610, 1611, 1612,
      1613, 1614, 1615, 1616, 1617, 1618, 1619, 1620, 1621
<223> OTHER INFORMATION: n = A,T,C or G
<220> FEATURE:
<221> NAME/KEY: misc_feature
<222> LOCATION: 1622, 1623, 1624, 1625, 1626, 1627, 1711, 1712, 1713,
      1714, 1715, 1716, 1717, 1718, 1719, 1720, 1721
<223> OTHER INFORMATION: n = A,T,C or G

<400> SEQUENCE: 25

```
ggaagaggca ctgctggatg tgaataataa taataataat ataaggtagt      60
gtttgggaag gaggtgaagg aggtgagtcg gatagcaatg ccgatgatag tggtgacggt     120
gtcacagtac cttttgcgcg tttcaccaat gataatgttg ggtcatcttg gtgaacttca    180
actttctagt gcttctattg ctacttcact ttccaatgtt accggcttca gtcttatgtt    240
agggatgggg agtgcagtgg agacactatg tgggcaggca tatggagctc acaagtatgg    300
aaatcttgga acttttactt atggtgcaat tatttgtcta ttccttgtat gcataccagt    360
ttctgttctg tggatcttca cggataggct tcttatattg atgggccaag atcctgaaat    420
cgcaactgaa gctggaaaat acacgatttg gctcattcct acgctatttc catatgctat    480
tcttcagtca cttgtccggt acctgcaggc acagagttta atcctaccaa tgcttttgag    540
tgctgttgta tctttatgct ccaagtgcc gatatgttgg gttttatat tcaaattgga      600 tttggggaac gctggagcag caatgtcaat tggtttatcc tattgctga atgtgatctt     660 gcttatgctt tatgtgaagt actcatcagc ttgtgcagaa actcgggctt cattctctag    720
agatgttttt ctgactatag ggacttctt ccgctttgct atcccatctg ctgtaatggt     780
ttgcttggaa tggtggtcgt ttgaactaat cattctcctc tctggtctgt tgccaaatcc    840
agcgctagag acttccgttc tatccatatg ctttacaacc acttcagtgc actaccatat    900
accttattct ttcggtgccg ctgcaagcac tcgtgtttca aatgagcttg gagcggggag    960
gccacaggcc gcgaaagttg ctcttggcgc tgtgctaatt cttttctgtca cagaggttgt    1020 tcttgcaagt atttctatat tcgtggtccg ccatgtatgg ggctatgtat ttacctatga    1080
gaaagaagta atcacttatg tagcagaaat tactcctgtt ctttgcatct caatcatcat    1140
ggatggcacc caagccgtat tatcaggagt tgcaagagga agtgggtggc agcatattgg    1200
agcatatgtg aatcttggag catattattt ggttggaatt ccaacggctc tattgctggg    1260
atttgttttg catctaaaag gcaaaggcct ttggattgga ttggtggctg gagcaactgt    1320
gcaatctatt tcgcttttcc ttatcacagg cctcaccaat tgggaaaaac aggccattga    1380
agcaagacat agaatcttta gtggaaggcc tgctgttgaa aatcagnnnn nnnnnnnnn    1440
```

```
nnnnnnnnnn nnnnnnnnnn nnnngaaata aaccttcaac ttgctatgat ttagcgagaa    1500
tcaccactca tcatagtacc aattggacaa ttttgaaagt gatcagcctc ttagatgtaa    1560
atgaacaact ttggcggatc annnnnnnnn nnnnnnnnnn nnnnnnnnnn nnnnnnnnnn    1620
nnnnnnnaag ttgaatttgt tttgctttgc taaatcgttt agctgcggct tcttgtaact    1680
tgtaacgcaa atttcttgtt cgaaaatata nnnnnnnnnn nttgattctg atggtaagca    1740 accccccactt ccaaccaaga ggttgtgagt tcgagtcacc ccaagagcaa ggtggtagtg   1800
tgtacgcaga ccttacccct accctggggt agagaggctg tttccaatag accctcggca    1860
taaatccc                                                             1868
```

<210> SEQ ID NO 26

<400> SEQUENCE: 26

000

<210> SEQ ID NO 27
<211> LENGTH: 1869
<212> TYPE: DNA
<213> ORGANISM: Nicotiana tabacum

<400> SEQUENCE: 27

```
ttaaccttttt attatctcaa atgaaacctc gagatgacaa cttcatctag tatttatatg     60
cctagctaga agttactttc attgcattct acatattcat tgtcatggga aaaagcatga    120
agtctgaagt tgagcagccc ttgttggctg ctgctcatgg gggtagctcc gagctagagg    180
aggtgctctc cgactcccaa ttaccctact ttcgacgcct taggtatgcc tcttggatcg    240
aattccagct actttatcga cttgctgccc cttcagttgc cgtctacatg atcaacaatg    300
ccatgtccat gtctactcgg atcttttctg gccaactcgg gaacctacag cttgcagcag    360
cctctcttgg caatcaaggc atccaattat ttgcttatgg ccttatgcta ggaatgggca    420
gtgcagtgga aacgctttgt ggccaagcat atggagctca cagatatgaa atgctaggag    480
tctacctgca aagagcaaca gtagtacttt ccttaacagg cattccacta gctgtggttt    540
atttattttc caagaatata ctgctcgctc ttggtgaatc aaaactagtg gcatcagcag    600
cagcagtatt tgtttatggt ttgattccac aaattttgc ttatgcggtg aacttcccaa     660
tacagaagtt cttgcaatcc cagagtattg ttgctcccag tgcctttatt tccctgggga    720
ctctgtttgt acacatattg ctcagttggg ttgttgtata caaaattgga ctgggattgc    780
taggggcgtc gttggtgctg agcttttctt ggtggataat tgtggtggct cagtttatat    840
atatactaaa aagtgaaagg tgtaaagcta cctgggcagg ttttcgatgg gaggccttta    900
gtggattatg ccaatttgtc aagttgtctg ctggttcggc tgttatgttg tgcttggaga    960
cttggtattt ccagattcta gtgttgctct cgggattact caagaatcct gagattgcct   1020
tggcttcaat ctctgtttgc ttggcagtga atggactgat gttcatggtt gcagtggggt   1080
tcaatgctgc tgctagtgtg agagtgagca atgagctagg agcagcacac ccaaagtcag   1140
cagcattctc agtgttcatg gtgacattca tttcatttct cattgctgtg gtggaagcca   1200
taattgtgct cagtttgcgc aatgttatca gctatgcatt caccgaaggt gaagttgtgg   1260
ccaaagaagt atctagtttg tgtccatatt tagctgtcac cctcattctc aatggcattc   1320
aaccagtctt atcgggtgtt gctgttggct gtggatggca ggcgtttgtt gcctacgtga   1380
atgtagggtg ttattatggt gtaggaattc cattgggatg tcttctcggc ttcaagtttg   1440
```

-continued

```
actttggtgc taagggaata tggactggga tgattggagg gactgtgatg caaaccatca    1500
ttctgctttg ggttacattc cgtaccgact ggaataaaga ggtggagtgc gccagaaaac    1560
gtctggacaa atgggaaaac ctaaaaggac ctctaaacaa ggaatgaagg tggtgaagat    1620
cattatgact tggaataata atacggggac atgaaattca aagttattca tgcagtactt    1680
gcaagggcaa agaagtcatc aacagtttac atcaatcaaa ggttttagca tatctgcgaa    1740
attagagagt cacttatcat tactttaaat caattaatca tttcaattct gtcaattcct    1800
ttgtctgtat ctgcacattt attgattgta ttacaaagag cttgaaatca actacagttc    1860
tccaattaa                                                           1869

<210> SEQ ID NO 28
<211> LENGTH: 500
<212> TYPE: PRT
<213> ORGANISM: Nicotiana tabacum

<400> SEQUENCE: 28

Met Gly Lys Ser Met Lys Ser Glu Val Glu Gln Pro Leu Leu Ala
1               5                   10                  15

Ala His Gly Gly Ser Ser Glu Leu Glu Glu Val Leu Ser Asp Ser Gln
            20                  25                  30

Leu Pro Tyr Phe Arg Arg Leu Arg Tyr Ala Ser Trp Ile Glu Phe Gln
        35                  40                  45

Leu Leu Tyr Arg Leu Ala Ala Pro Ser Val Ala Val Tyr Met Ile Asn
    50                  55                  60

Asn Ala Met Ser Met Ser Thr Arg Ile Phe Ser Gly Gln Leu Gly Asn
65                  70                  75                  80

Leu Gln Leu Ala Ala Ala Ser Leu Gly Asn Gln Gly Ile Gln Leu Phe
                85                  90                  95

Ala Tyr Gly Leu Met Leu Gly Met Gly Ser Ala Val Glu Thr Leu Cys
            100                 105                 110

Gly Gln Ala Tyr Gly Ala His Arg Tyr Glu Met Leu Gly Val Tyr Leu
        115                 120                 125

Gln Arg Ala Thr Val Val Leu Ser Leu Thr Gly Ile Pro Leu Ala Val
    130                 135                 140

Val Tyr Leu Phe Ser Lys Asn Ile Leu Leu Ala Leu Gly Glu Ser Lys
145                 150                 155                 160

Leu Val Ala Ser Ala Ala Ala Val Phe Val Tyr Gly Leu Ile Pro Gln
                165                 170                 175

Ile Phe Ala Tyr Ala Val Asn Phe Pro Ile Gln Lys Phe Leu Gln Ser
            180                 185                 190

Gln Ser Ile Val Ala Pro Ser Ala Phe Ile Ser Leu Gly Thr Leu Phe
        195                 200                 205

Val His Ile Leu Leu Ser Trp Val Val Tyr Lys Ile Gly Leu Gly
    210                 215                 220

Leu Leu Gly Ala Ser Leu Val Leu Ser Phe Ser Trp Trp Ile Ile Val
225                 230                 235                 240

Val Ala Gln Phe Ile Tyr Ile Leu Lys Ser Glu Arg Cys Lys Ala Thr
                245                 250                 255

Trp Ala Gly Phe Arg Trp Glu Ala Phe Ser Gly Leu Cys Gln Phe Val
            260                 265                 270

Lys Leu Ser Ala Gly Ser Ala Val Met Leu Cys Leu Glu Thr Trp Tyr
        275                 280                 285
```

```
Phe Gln Ile Leu Val Leu Leu Ser Gly Leu Leu Lys Asn Pro Glu Ile
            290                 295                 300

Ala Leu Ala Ser Ile Ser Val Cys Leu Ala Val Asn Gly Leu Met Phe
305                 310                 315                 320

Met Val Ala Val Gly Phe Asn Ala Ala Ala Ser Val Arg Val Ser Asn
                325                 330                 335

Glu Leu Gly Ala Ala His Pro Lys Ser Ala Ala Phe Ser Val Phe Met
            340                 345                 350

Val Thr Phe Ile Ser Phe Leu Ile Ala Val Val Glu Ala Ile Ile Val
            355                 360                 365

Leu Ser Leu Arg Asn Val Ile Ser Tyr Ala Phe Thr Glu Gly Glu Val
370                 375                 380

Val Ala Lys Glu Val Ser Ser Leu Cys Pro Tyr Leu Ala Val Thr Leu
385                 390                 395                 400

Ile Leu Asn Gly Ile Gln Pro Val Leu Ser Gly Val Ala Val Gly Cys
                405                 410                 415

Gly Trp Gln Ala Phe Val Ala Tyr Val Asn Val Gly Cys Tyr Tyr Gly
                420                 425                 430

Val Gly Ile Pro Leu Gly Cys Leu Leu Gly Phe Lys Phe Asp Phe Gly
                435                 440                 445

Ala Lys Gly Ile Trp Thr Gly Met Ile Gly Gly Thr Val Met Gln Thr
450                 455                 460

Ile Ile Leu Leu Trp Val Thr Phe Arg Thr Asp Trp Asn Lys Glu Val
465                 470                 475                 480

Glu Cys Ala Arg Lys Arg Leu Asp Lys Trp Glu Asn Leu Lys Gly Pro
                485                 490                 495

Leu Asn Lys Glu
            500

<210> SEQ ID NO 29
<211> LENGTH: 1870
<212> TYPE: DNA
<213> ORGANISM: Nicotiana tabacum

<400> SEQUENCE: 29
aacaacctcc acgagtccga agcaccgaat tctcttttgt cctccaatgg agggctcctc      60
taagcaaccc cttctttcgc ctaaagaccc tcaaatcacc gaccaagcta gtgataatta     120
tcttatcaga ttatcacata cttcttttgc ttcttccttt gttgctgatt ccgatgatat     180
tcccccgatt actggattcc gagatttctt cagagagttt tctgttgaat ctaagaaatt     240
atggtacctt gcgggtccag caatatttac ttcccttttgt caatactctc ttggtgctgt     300
cactcaaact tttgctggac atgtcgggac tcttgagctt gctgccgttt ctgttgaaaa     360
ctcggtcatc gccggtttct cttttggtgt catgttggga atgggaagtg cgttagaaac     420
actatgtgga caagcatttg agcaggaca aattgatatg ctaggagtat acatgcaaag     480
atcatgggtt attctcaata caacagcagt aattctaatg ttactttaca ttttcgcggc     540
accatttctg agattaattg gacaaacaga ggacatatca cgggaagcag ggaaaatggc     600
tttatatatg attcctcaac tttatgcata tgccatgaat tttccaatcg ccaagttctt     660
gcagtcacag agcaaaatta tggtcatggc gtggattgca gcaatagcgt tggtattgca     720
tacttttttc agctggttat ttatgctaaa acttgggtgg gggctcgtcg gcgctgcggt     780
ggtgctgaac tcatcgtggt ggttcatagt ggtggcgcag ctgctatata tatttagtgg     840
gacttgtgga caagcttggt caggtttctc atggaaggct ttccataatc tatgggcc tt     900
```

```
tgttagatta tctcttgcgt cagctgtcat gctatgcctg gaaacttggt actttatggc    960
gttggtcctc ttcgctggtt atttaaagaa cgcagaagtc gctgttgatg ccctgtccat   1020
ttgtatgaac atattgggat gggcggtgat ggcagctatt ggatgcaatg cagctataag   1080
cgtgagagtg tcaaatgaac tcggggcagc tcatccaaga acggctaaat tttcagtggt   1140
ggtggtggta gtatcctcat tcttgattgg ccttcttcta tcggtctttt tacttgtctt   1200
tcgaaggcaa tatcctacct tattcgcgga gagtgaatca gtcaagcgtc ttgtctatga   1260
gctaacacca ttacttgcat tctgcatagt ggttaacaac attcagccag ctctatctgg   1320
tgtggcaatt ggagcaggat ggcaagcttt ggttgcttat gtcaatattg cttgttacta   1380
tttgtttggt attccactgg gtttactatt agggtataag ctcaatatgg gtgtccaagg   1440
tatttggtat ggaatggtta gcggaactct gattcaaact ttcgccttat tttgatagt    1500 ttacaaaacc agctggaaca agaggcttc tattgcagca gagaggataa aaatgtgggg   1560 agggaatca aatggaaagg ccgatgatgc agagaaatga actgcgattt ggagtcattg    1620
cattaagctc atcaagtgta tatgaagaaa ttttgaaaat ttaagttgct tattgttcaa   1680
tgtaacagct cagtagtact agtgttaatc attgtaagga actttgccaa aattattctc   1740
aacttgaaag tggacaagac ccttgataag ttagctttta gctaattttt ctagtgtttt   1800
gatatagctt tatgccccat ttgtcggaat taattgatta attatgcttt gaatgatgaa   1860
gtttcaggat                                                          1870

<210> SEQ ID NO 30
<211> LENGTH: 517
<212> TYPE: PRT
<213> ORGANISM: Nicotiana tabacum

<400> SEQUENCE: 30

Met Glu Gly Ser Ser Lys Gln Pro Leu Leu Ser Pro Lys Asp Pro Gln
1               5                   10                  15

Ile Thr Asp Gln Ala Ser Asp Asn Tyr Leu Ile Arg Leu Ser His Thr
            20                  25                  30

Ser Phe Ala Ser Ser Phe Val Ala Asp Ser Asp Ile Pro Pro Ile
        35                  40                  45

Thr Gly Phe Arg Asp Phe Phe Arg Glu Phe Ser Val Glu Ser Lys Lys
    50                  55                  60

Leu Trp Tyr Leu Ala Gly Pro Ala Ile Phe Thr Ser Leu Cys Gln Tyr
65                  70                  75                  80

Ser Leu Gly Ala Val Thr Gln Thr Phe Ala Gly His Val Gly Thr Leu
                85                  90                  95

Glu Leu Ala Ala Val Ser Val Glu Asn Ser Val Ile Ala Gly Phe Ser
            100                 105                 110

Phe Gly Val Met Leu Gly Met Gly Ser Ala Leu Glu Thr Leu Cys Gly
        115                 120                 125

Gln Ala Phe Gly Ala Gly Gln Ile Asp Met Leu Gly Val Tyr Met Gln
    130                 135                 140

Arg Ser Trp Val Ile Leu Asn Thr Thr Ala Val Ile Leu Met Leu Leu
145                 150                 155                 160

Tyr Ile Phe Ala Ala Pro Phe Leu Arg Leu Ile Gly Gln Thr Glu Asp
                165                 170                 175

Ile Ser Arg Glu Ala Gly Lys Met Ala Leu Tyr Met Ile Pro Gln Leu
            180                 185                 190
```

Tyr Ala Tyr Ala Met Asn Phe Pro Ile Ala Lys Phe Leu Gln Ser Gln
            195                 200                 205

Ser Lys Ile Met Val Met Ala Trp Ile Ala Ile Ala Leu Val Leu
    210                 215                 220

His Thr Phe Phe Ser Trp Leu Phe Met Leu Lys Leu Gly Trp Gly Leu
225                 230                 235                 240

Val Gly Ala Ala Val Leu Asn Ser Ser Trp Trp Phe Ile Val Val
                245                 250                 255

Ala Gln Leu Leu Tyr Ile Phe Ser Gly Thr Cys Gly Gln Ala Trp Ser
                260                 265                 270

Gly Phe Ser Trp Lys Ala Phe His Asn Leu Trp Gly Phe Val Arg Leu
                275                 280                 285

Ser Leu Ala Ser Ala Val Met Leu Cys Leu Glu Thr Trp Tyr Phe Met
            290                 295                 300

Ala Leu Val Leu Phe Ala Gly Tyr Leu Lys Asn Ala Glu Val Ala Val
305                 310                 315                 320

Asp Ala Leu Ser Ile Cys Met Asn Ile Leu Gly Trp Ala Val Met Ala
                325                 330                 335

Ala Ile Gly Cys Asn Ala Ala Ile Ser Val Arg Val Ser Asn Glu Leu
                340                 345                 350

Gly Ala Ala His Pro Arg Thr Ala Lys Phe Ser Val Val Val Val
            355                 360                 365

Val Ser Ser Phe Leu Ile Gly Leu Leu Leu Ser Val Phe Leu Leu Val
    370                 375                 380

Phe Arg Arg Gln Tyr Pro Thr Leu Phe Ala Glu Ser Glu Ser Val Lys
385                 390                 395                 400

Arg Leu Val Tyr Glu Leu Thr Pro Leu Ala Phe Cys Ile Val Val
                405                 410                 415

Asn Asn Ile Gln Pro Ala Leu Ser Gly Val Ala Ile Gly Ala Gly Trp
                420                 425                 430

Gln Ala Leu Val Ala Tyr Val Asn Ile Ala Cys Tyr Tyr Leu Phe Gly
            435                 440                 445

Ile Pro Leu Gly Leu Leu Leu Gly Tyr Lys Leu Asn Met Gly Val Gln
450                 455                 460

Gly Ile Trp Tyr Gly Met Val Ser Gly Thr Leu Ile Gln Thr Phe Ala
465                 470                 475                 480

Leu Phe Trp Ile Val Tyr Lys Thr Ser Trp Asn Lys Glu Ala Ser Ile
                485                 490                 495

Ala Ala Glu Arg Ile Lys Met Trp Gly Gly Glu Ser Asn Gly Lys Ala
            500                 505                 510

Asp Asp Ala Glu Lys
        515

<210> SEQ ID NO 31
<211> LENGTH: 398
<212> TYPE: DNA
<213> ORGANISM: Nicotiana tabacum

<400> SEQUENCE: 31
atggttttgc catatctgtc ccatcattga atgaagttct acagatattc atgattgcag      60
cccctgtgtt tctaacaatg atgtcaaagg ttgcattcta ctctctactt gtctattttg     120
ctacctcaat gggcacacag acaattgctg cgcatcaggt catggtacaa ctgttcatga     180
tatgtgcagt atggggtgag cctctctctc aaacagcaca gtcgtttatg cccgaattgt     240

```
tatatggagt caaccgaaat tgtcaaagg ctcggatgct gctgaagtcc cttttaatca    300
ttggagcatc aaatggatta ttactgggat ctgtcggagt atcagttaca tggttttttcc   360 ccaaaatatt ttcacctgat cctctggtca tacaagag                           398
```

<210> SEQ ID NO 32

<400> SEQUENCE: 32

000

<210> SEQ ID NO 33
<211> LENGTH: 3411
<212> TYPE: DNA
<213> ORGANISM: Nicotiana tabacum

<400> SEQUENCE: 33

```
gaaatatcaa ctggattgga cagttccact acttactcca ttgtgaattc cttaaggcaa    60
tctgttcgaa tcttgaaggg aacagctgtg atttctctgt tgcaacctgc ccccgagacc   120
tacaacctgt tcgatgatat tattctgtta tccgatgggt atattgttta tcagggtccg   180
cgagatgatg tgctcgagtt cttgaatcc atgggattca aatgccctga gagaaaaggc    240
gtggccgact tcttgcaaga agtgacatca aagaaggatc aacagcaata ttggtcaaag   300
aggaatgagc cttataggtt tatcacatcg aaagaatttg ctgaggcata tcagtctttt   360
catgttggaa ggaaactagg cgacgagctt gctactccat tgacaagac caaatgtcac   420 cctgctgctt tgactaatga aagtatggt ataggaaaga aagagctgtt gaaggtttgc    480
actgaaagag aacttctact aatgaagagg aactcgtttg tttacatgtt caagttctct   540
cagcttacga taatggctct tataacaatg acactcttct tccgtactga gatgccacga   600
gatactacag atgatggagg aatatatgct ggtgctctct ttttcgtggt gattatgatt   660
atgttcaacg ggatgtctga gcttgccatg acaattttca gcttcccgt cttttacaag    720 caaagagacc ttctctttt ccccttcatg gcttatgcaa ttccctcatg gatcctcaaa    780
atccctgtaa cacttgttga agtcggtctt tgggtgatct taacatatta tgtcattgga   840
tttgatccta atatttcaag attttgaaa caattcttgc tgctcatagt tgtaaaccag    900
atggcatcag gattgtttag attcattggg gcagtaggaa ggaccatggg agttgctagc   960
acatttggag catttgctct tcttttacaa tttgcattgg gcggttttgt cctttcacga   1020
gatgatgtga aaagctggtg gatttggggt tactggactt cgccgatgat gtattcagtg   1080
aattcaattc ttgtgaacga atttgatggg aaaaaatgga atcatattgt gccaggtgga   1140
aacgagaccc ttggatctac agttgtgaag tctcgaggat tctttcccga ggcatactgg   1200
tactggattg tgttggggc acttgtcgga tttacagttg tgtttaactt ctgctacagt   1260
cttgcactcg cttatctcaa cccatttgat aagccacaag cagtgctacc agaagacggt   1320
gagaatgctg aaaatgttga gtttcatcc cagataacta gcacagatgg aggagattct   1380
atcactgaga gccaaaataa taataagaag ggaatggttc ttccatttga accccattct   1440
atcaccttcg atgatgttgt atactccgtt gacatgcctc aggaaatgaa agaacaaggt   1500
gctggtgaaa atagattggt acttctaaag ggtgtgagtg gagctttcag accaggtgtt   1560
ctcaccgctt tgatgggtgt tagtggggct ggtaaaacaa cattaatgga tgttttggct   1620
ggaagaaaaa caggaggata cattgacggc gacatcaaga tttctggcta tcccaagaag   1680
caagaaacct ttgctcgtat ttctggatac tgtgagcaga acgacatcca ttcaccttat   1740
```

```
gttacagttt acgagtcctt ggtttactca gcatggcttc gtttacccca agatgttgat    1800
gaaaaaacta gaaagatgtt tgttgatgaa gttatggaac ttgttgagct tagacccta    1860
agatcagcct tagtcgggtt gccaggagtc aacggtctct caactgagca acgcaaaagg    1920
ttgaccattg cagttgaatt ggtagcaaac ccctctatca tttttatgga tgaaccaact    1980
tcagggctag atgcaagagc tgctgccatt gtgatgagag ctgttaggaa cactgtcgat    2040
acaggaagaa ccgttgtttg taccattcat cagcctagca tcgacatttt tgaagccttt    2100
gatgagctat ttctaatgaa acgaggagga caagagatat acgttggtcc attgggtcgc    2160
cattcttgcc atttgatcaa atactttgag tcaaatcctg gggtagcaaa atcaaggag    2220
ggttacaacc cagcaacttg gatgttagaa gtcacagcct cagctcaaga aatgatgtta    2280
ggcgttgatt tcaccgacgt atacaagaac tcagacctgt acaggaggaa caaagcattg    2340
attagtgaat taggcgtccc tcgccctggt tcaaaggact tgcattttga aactcaatac    2400
tcacaatcat tctggacgca atgtatggct tgcctatgga agcaacactg gtcatactgg    2460
cgtaatccag cttacaccgc agtcagattc atcttcacga cattcatagc actaatcttc    2520
gggacaatgt tctgggatct tggtaccaaa gtgagtaaga gccaagatct tttaaacgct    2580
atgggatcta tgtatgctgc tgttctcttc cttggtgtac aaaattcatc atcagttcag    2640
cccgttgtag ccgttgagcg tactgtattt tacagagaaa gagctgctgg aatgtactct    2700
gccatcccct atgcctttgg acaggtttcc attgaaatcc cttacatatt tgtacaatct    2760
gtgtttatg gtatcatcgt ctatgctatg attggattcg aatgggatgt tggcaagttc    2820
ttttggtact tgttcatcat gttttttcacc cttttgtact ttacattcta tggtatgatg    2880
agtgtggctg tcacaccaaa tcaaaacgtg gcttcaattg ttgctgcctt cttctatggt    2940
gtatggaatc tcttctcagg attcatcgtt ccacgacctc gtatgcctgt atggtggaga    3000
tggtactact gggctaaccc tgttgcatgg accttgtatg gtttggttgc atcacaattc    3060
ggagacatcc aaacgacact atctgataat gaaactgtgg aacaattctt gagacgttac    3120
tttggattta agcatgattt tcttggagtt gttgcagctg tgctcactgc atatgtcttt    3180
gtgtttgcct ttacattttgc tttttgccatc aaggcgttca atttccagag aagataagtg    3240
agtttaatcg actgaagaac tttgaggaag cattggttac aaaattagta tgtataggtt    3300
actacttgag aaagtctttt cttttcaact tttgaatact aggtgtatgt tgttgtaata    3360
ttcattggaa atccaaactt tatttgttaa tataaaaaaa aaaaaaaaaa a              3411
```

<210> SEQ ID NO 34
<211> LENGTH: 1008
<212> TYPE: PRT
<213> ORGANISM: Nicotiana tabacum

<400> SEQUENCE: 34

Met Gly Phe Lys Cys Pro Glu Arg Lys Gly Val Ala Asp Phe Leu Gln
1               5                   10                  15

Glu Val Thr Ser Lys Lys Asp Gln Gln Gln Tyr Trp Ser Lys Arg Asn
            20                  25                  30

Glu Pro Tyr Arg Phe Ile Thr Ser Lys Glu Phe Ala Glu Ala Tyr Gln
        35                  40                  45

Ser Phe His Val Gly Arg Lys Leu Gly Asp Glu Leu Ala Thr Pro Phe
    50                  55                  60

Asp Lys Thr Lys Cys His Pro Ala Ala Leu Thr Asn Glu Lys Tyr Gly
65                  70                  75                  80

-continued

```
Ile Gly Lys Lys Glu Leu Leu Lys Val Cys Thr Glu Arg Glu Leu Leu
                85                  90                  95

Leu Met Lys Arg Asn Ser Phe Val Tyr Met Phe Lys Phe Ser Gln Leu
            100                 105                 110

Thr Ile Met Ala Leu Ile Thr Met Thr Leu Phe Phe Arg Thr Glu Met
        115                 120                 125

Pro Arg Asp Thr Thr Asp Asp Gly Gly Ile Tyr Ala Gly Ala Leu Phe
    130                 135                 140

Phe Val Val Ile Met Ile Met Phe Asn Gly Met Ser Glu Leu Ala Met
145                 150                 155                 160

Thr Ile Phe Lys Leu Pro Val Phe Tyr Lys Gln Arg Asp Leu Leu Phe
                165                 170                 175

Phe Pro Ser Trp Ala Tyr Ala Ile Pro Ser Trp Ile Leu Lys Ile Pro
            180                 185                 190

Val Thr Leu Val Glu Val Gly Leu Trp Val Ile Leu Thr Tyr Tyr Val
        195                 200                 205

Ile Gly Phe Asp Pro Asn Ile Ser Arg Phe Leu Lys Gln Phe Leu Leu
    210                 215                 220

Leu Ile Val Val Asn Gln Met Ala Ser Gly Leu Phe Arg Phe Ile Gly
225                 230                 235                 240

Ala Val Gly Arg Thr Met Gly Val Ala Ser Thr Phe Gly Ala Phe Ala
                245                 250                 255

Leu Leu Leu Gln Phe Ala Leu Gly Gly Phe Val Leu Ser Arg Asp Asp
            260                 265                 270

Val Lys Ser Trp Trp Ile Trp Gly Tyr Trp Thr Ser Pro Met Met Tyr
        275                 280                 285

Ser Val Asn Ser Ile Leu Val Asn Glu Phe Asp Gly Lys Lys Trp Asn
    290                 295                 300

His Ile Val Pro Gly Gly Asn Glu Thr Leu Gly Ser Thr Val Val Lys
305                 310                 315                 320

Ser Arg Gly Phe Phe Pro Glu Ala Tyr Trp Tyr Trp Ile Gly Val Gly
                325                 330                 335

Ala Leu Val Gly Phe Thr Val Val Phe Asn Phe Cys Tyr Ser Leu Ala
            340                 345                 350

Leu Ala Tyr Leu Asn Pro Phe Asp Lys Pro Gln Ala Val Leu Pro Glu
        355                 360                 365

Asp Gly Glu Asn Ala Glu Asn Val Glu Val Ser Ser Gln Ile Thr Ser
    370                 375                 380

Thr Asp Gly Gly Asp Ser Ile Thr Glu Ser Gln Asn Asn Asn Lys Lys
385                 390                 395                 400

Gly Met Val Leu Pro Phe Glu Pro His Ser Ile Thr Phe Asp Asp Val
                405                 410                 415

Val Tyr Ser Val Asp Met Pro Gln Glu Met Lys Glu Gln Gly Ala Gly
            420                 425                 430

Glu Asp Arg Leu Val Leu Leu Lys Gly Val Ser Gly Ala Phe Arg Pro
        435                 440                 445

Gly Val Leu Thr Ala Leu Met Gly Val Ser Gly Ala Gly Lys Thr Thr
    450                 455                 460

Leu Met Asp Val Leu Ala Gly Arg Lys Thr Gly Gly Tyr Ile Asp Gly
465                 470                 475                 480

Asp Ile Lys Ile Ser Gly Tyr Pro Lys Lys Gln Glu Thr Phe Ala Arg
                485                 490                 495

Ile Ser Gly Tyr Cys Glu Gln Asn Asp Ile His Ser Pro Tyr Val Thr
```

```
              500                 505                 510
Val Tyr Glu Ser Leu Val Tyr Ser Ala Trp Leu Arg Leu Pro Gln Asp
            515                 520                 525

Val Asp Glu Lys Thr Arg Lys Met Phe Val Asp Val Met Glu Leu
530                 535                 540

Val Glu Leu Arg Pro Leu Arg Ser Ala Leu Val Gly Leu Pro Gly Val
545                 550                 555                 560

Asn Gly Leu Ser Thr Glu Gln Arg Lys Arg Leu Thr Ile Ala Val Glu
                565                 570                 575

Leu Val Ala Asn Pro Ser Ile Ile Phe Met Asp Glu Pro Thr Ser Gly
                580                 585                 590

Leu Asp Ala Arg Ala Ala Ile Val Met Arg Ala Val Arg Asn Thr
            595                 600                 605

Val Asp Thr Gly Arg Thr Val Val Cys Thr Ile His Gln Pro Ser Ile
            610                 615                 620

Asp Ile Phe Glu Ala Phe Asp Glu Leu Phe Leu Met Lys Arg Gly Gly
625                 630                 635                 640

Gln Glu Ile Tyr Val Gly Pro Leu Gly Arg His Ser Cys His Leu Ile
                645                 650                 655

Lys Tyr Phe Glu Ser Asn Pro Gly Val Ala Lys Ile Lys Glu Gly Tyr
                660                 665                 670

Asn Pro Ala Thr Trp Met Leu Glu Val Thr Ala Ser Ala Gln Glu Met
            675                 680                 685

Met Leu Gly Val Asp Phe Thr Asp Val Tyr Lys Asn Ser Asp Leu Tyr
            690                 695                 700

Arg Arg Asn Lys Ala Leu Ile Ser Glu Leu Gly Val Pro Arg Pro Gly
705                 710                 715                 720

Ser Lys Asp Leu His Phe Glu Thr Gln Tyr Ser Gln Ser Phe Trp Thr
                725                 730                 735

Gln Cys Met Ala Cys Leu Trp Lys Gln His Trp Ser Tyr Trp Arg Asn
                740                 745                 750

Pro Ala Tyr Thr Ala Val Arg Phe Ile Phe Thr Thr Phe Ile Ala Leu
            755                 760                 765

Ile Phe Gly Thr Met Phe Trp Asp Leu Gly Thr Lys Val Ser Lys Ser
770                 775                 780

Gln Asp Leu Leu Asn Ala Met Gly Ser Met Tyr Ala Ala Val Leu Phe
785                 790                 795                 800

Leu Gly Val Gln Asn Ser Ser Ser Val Gln Pro Val Val Ala Val Glu
                805                 810                 815

Arg Thr Val Phe Tyr Arg Glu Arg Ala Ala Gly Met Tyr Ser Ala Ile
                820                 825                 830

Pro Tyr Ala Phe Gly Gln Val Ser Ile Glu Ile Pro Tyr Ile Phe Val
            835                 840                 845

Gln Ser Val Phe Tyr Gly Ile Ile Val Tyr Ala Met Ile Gly Phe Glu
            850                 855                 860

Trp Asp Val Gly Lys Phe Phe Trp Tyr Leu Phe Ile Met Phe Phe Thr
865                 870                 875                 880

Leu Leu Tyr Phe Thr Tyr Gly Met Met Ser Val Ala Val Thr Pro
            885                 890                 895

Asn Gln Asn Val Ala Ser Ile Val Ala Ala Phe Phe Tyr Gly Val Trp
            900                 905                 910

Asn Leu Phe Ser Gly Phe Ile Val Pro Arg Pro Arg Met Pro Val Trp
            915                 920                 925
```

Trp Arg Trp Tyr Tyr Trp Ala Asn Pro Val Ala Trp Thr Leu Tyr Gly
        930                 935                 940

Leu Val Ala Ser Gln Phe Gly Asp Ile Gln Thr Thr Leu Ser Asp Asn
945                 950                 955                 960

Glu Thr Val Glu Gln Phe Leu Arg Arg Tyr Phe Gly Phe Lys His Asp
            965                 970                 975

Phe Leu Gly Val Val Ala Ala Val Leu Thr Ala Tyr Val Phe Val Phe
            980                 985                 990

Ala Phe Thr Phe Ala Phe Ala Ile Lys Ala Phe Asn Phe Gln Arg Arg
        995                 1000                1005

<210> SEQ ID NO 35
<211> LENGTH: 4497
<212> TYPE: DNA
<213> ORGANISM: Nicotiana tabacum

<400> SEQUENCE: 35

```
atggagggaa atgggggacc gagaaggctg gggagtagta ggagtagtat gagcagaacg        60
atgagtcgaa gcagaagcag agcaaattgg aatgtagaag acgtgttcaa tccaatgccg       120
agcagaagaa gcactcgtgg cgaagaagat gaagaagctc ttacgtgggc tgcgttagag       180
aaattgccta cttacgatcg tttgagaaaa acggtcctta atcggtcat ggaaagtgag        240
aataatcagg gcaataaaaa agttgttcat aaggaagtcg atgttcggaa tctgggaatg       300
aatgagcgac aagagttcat tgatcgattt ttcaggggttg ctgaggaaga taatgaaaag       360
ttcctgagaa agttcagaaa tcgaattgac aaagttggga ttacccttcc tacggtagaa       420
gttcggtacg agcatttaac tatagaggca gattgctata tcggcgacag agctcttcct       480
acgctgccta atgctgctag aaatatagct gaatcagctt tgagttgcgt tggaattaat       540
ttggcagaga aaacaaaact aaccatcctt aaagatgctt ctggaataat caagccctct       600
aggatgaccc ttttattagg tccaccatct tctgggaaaa cgacccttct gttggctttg       660
gctggaaaat tagaccctac cttaaaggtt agaggagaaa tcacttacaa tgggcacggg       720
ttaaaggaat ttgtaccaca gaaaacatcg gcatacatta gtcaaaatga tgttcatgtt       780
gctgaaatga ctgttaaaga aacccttgat ttctctgcta gatgccaagg agtcggctct       840
cgatatgaat tgctgacgga gcttgcaagg agagaaaggg atgctggaat cttcccggag       900
gctgaaatcg atcttttcat gaaggcaaca gctatggagg gagttgaaag cagccttatt       960
actgattaca cgctcaggat tttgggactt gatgtgtgtc gggacaccat tgttggggat      1020
gaaatgatac gaggcatttc tggtggccag aagaagcgtg tcactacagg tgagatgatc      1080
gttgggccaa caaaaacact attcatggac gagatatcta ctggactgga cagctccacc      1140
acatttcaga tagtgaaatg cttgcagcag attgtacatc tcactgaggc cactgttttg      1200
atgtctctcc tccagcctgc tcctgagaca tttgatctct tgacgatat cattctttta       1260
tctgaaggcc agattgttta ccagggccca cgtgaacatg tcctcgagtt ctttgaaact      1320
tgtggttttta atgtccgga agaaagggt actgctgatt tcttgcaaga ggttacatca       1380
agaaaggacc aagagcagta ctgggcaaat agacatagac cataccagta catttcagta      1440
actgaatttg caaagagatt caagcgcttc cacgtcggct acgtatagaa aatgagctc       1500
tctgttccct atgacaaaac aagaagtcac ccagcagctc taatattcaa gaagtacaca      1560
gtccctacac tagagcttct aaagacaaac ttcgacaagg aatggctttt gatcaagaga      1620
aactcttttg tttacgtctt caagaccgtt caaatcatca ttgttgcatt cattggatca      1680
```

```
actgtgttct tgaggaccaa aatgcacact aatactgtag atgatggcgc tacctatgtt   1740
ggtgcactcc tatttggaat ggtcatcaat atgtttaacg gtttctctga actctcaatg   1800
atcatacaga ggcttcccgt tttctacaag catagggacc ttctcttcca tccaccttgg   1860
gctttcactt taccaactgt gctcctaaag gtaccaattt ctgtgttcga gactattgtg   1920
tggatggtca tgacatacta taccattggt tatgcccctg aagctagcag gttcttcaag   1980
caatcactgc tgacttttct gatccaacaa atggctgctg gattatttag gctcactgca   2040
ggagtttgta ggactatgat tattgcaaat actggtggag cactcatgct ccttcttgtg   2100
ttcctattgg gtggtttcat cctgcctaga ggctcaattc cagactggtg gcgatggggc   2160
tattggattt caccctcttt ctatgggttc aatgccttca ctgtaaacga aatgtttgct   2220
ccaaggtgga tgaacaaatt tgccccagat ggcacaacta gattgggtct gcaagtgatg   2280
aaaaattttg acgtctttac tgaaagacga tggttctgga ttggtgctgc tgctcttcta   2340
gggttcacaa ttctcttcaa cgttcttttc accttagtcc ttatgtatct cagcccttta   2400
aacaagccac aagctacact atccaaagag caggccagcg atatggaagc tgatcaagaa   2460
gaaagcacgg gaagcccaag acttaaaatc agccagtcga agagagatga tctccctcga   2520
tccttatctg cagcagatgg aaataagaca agagaaatgg aaatccgacg aatgagcagt   2580
catatccatt ctagtggcct ctacagaaat gaggatgcaa atcttgaggc tgcaaatggt   2640
gtcgcagcaa agaaaggaat gatactgcca tttaccccctc tggcaatgtc cttcgaggat   2700
gtgagctatt tgttgacat gccacctgag atgaaggacc aaggagtgac agaggacaaa   2760
cttcaattgc ttcgcgaagt gactggtgca tttaggccag gagtattgac agcattgatg   2820
ggagtcagtg gagcagggaa gactacactc atggatgttc tagcaggacg taagactgga   2880
ggctacatcg aaggtgacgt tagaatatct ggatttccaa aaaatcaaga aacatttgcc   2940
agggtttcgg atattgtga acaaactgat atacactcac ctcaagtaac tatccatgag   3000
tctctgatat tttcggcttt cctccggctc cctaaagaag tcagcaaaga agataagatg   3060
atttttgtgg atgaagtaat ggatctggtt gagctagaca atctcaagga tgcaattgta   3120
gggcttccag gagttactgg tttgtcaacg gaacaaagaa aaagattgac cattgcagta   3180
gagcttgtcg caaatccttc aattatattc atggatgaac cgacttctgg tctggatgca   3240
agagcagcag ctattgttat gagaactgta agaaacacag tagacaccgg gagaactgtt   3300
gtctgcacaa tacatcaacc aagtattgat atatttgaag catttgatga gctgcttctt   3360
atgaaaagag gaggacaagt aatttacgca ggtccattgg gtcgacattc tcagaaaatt   3420
attgaatatt tcgaggcaat tccaggagtt caaaaaatta agagaaata caatccagca   3480 acctggatgc tagaagcgag ttcaattggc acagaagccc gacttggaat ggattttgct   3540
gaatactaca gatcatcagc tttacatcaa cgaaataagg ctcttgtcaa agagttgagt   3600
gcacctcctc ctggagccaa agacctctat tttaccacac aatttcccca gccaacatgg   3660
ggtcagttta atcctgctt atggaagcaa tggtggactt actggagaag tccagactat   3720
aaccttgtca gattcttctt tagtctggct gcagcactat tgattgggac aattttctgg   3780
aatgttggca gtaaaagaca aagtagtggt gatctaatga cagtcatcgg ggcaatgtat   3840
gcagctgtgc tgtttgttgg aatcaataat tgttcgaccg tacagccaat tgtagccgtc   3900
gaaagaaccg tcttttatag agaaagggct gctgggatgt attcagcttt accatatgct   3960
atggcacagg tatttgcaga aataccatac atactcgtcc aaactacata ctatactctt   4020
```

-continued

```
atagtgtatg ctatggtggc ctttgagtgg acggcagcta aattcttctg gttctatttt    4080
gtaaccttct tctccttcct atactggacg tactatggaa tgatgaccgt ttccatcaca    4140
cccaaccacc aagtagccgc gatctttgct gcagctttct atgcactttt caatcttttc    4200
tccggtttct tcatccccag accgagaatt cccaagtggt ggatatggta ttactggatc    4260
tgtccagtgg catggactgt ttatggtagc attgtgtcac agtatggtga tgtggaggat    4320
actatccaag taccgggagt gtttccaaac ccaaggatta aggactacat taaagatcat    4380
ttcggataca attcggactt catggcgcca gttgctgtgg ttttggttgg ttttgcagcc    4440
tttttcgcct ttatgtacgc ttacgctatt aagacattga acttccaaac tagatag      4497
```

<210> SEQ ID NO 36
<211> LENGTH: 1498
<212> TYPE: PRT
<213> ORGANISM: Nicotiana tabacum

<400> SEQUENCE: 36

```
Met Glu Gly Asn Gly Gly Pro Arg Arg Leu Gly Ser Ser Arg Ser Ser
1               5                   10                  15

Met Ser Arg Thr Met Ser Arg Ser Arg Ser Arg Ala Asn Trp Asn Val
            20                  25                  30

Glu Asp Val Phe Asn Pro Met Pro Ser Arg Arg Ser Thr Arg Gly Glu
        35                  40                  45

Glu Asp Glu Glu Ala Leu Thr Trp Ala Ala Leu Glu Lys Leu Pro Thr
    50                  55                  60

Tyr Asp Arg Leu Arg Lys Thr Val Leu Lys Ser Val Met Glu Ser Glu
65                  70                  75                  80

Asn Asn Gln Gly Asn Lys Lys Val Val His Lys Glu Val Asp Val Arg
                85                  90                  95

Asn Leu Gly Met Asn Glu Arg Gln Glu Phe Ile Asp Arg Phe Phe Arg
            100                 105                 110

Val Ala Glu Glu Asp Asn Glu Lys Phe Leu Arg Lys Phe Arg Asn Arg
        115                 120                 125

Ile Asp Lys Val Gly Ile Thr Leu Pro Thr Val Glu Val Arg Tyr Glu
    130                 135                 140

His Leu Thr Ile Glu Ala Asp Cys Tyr Ile Gly Asp Arg Ala Leu Pro
145                 150                 155                 160

Thr Leu Pro Asn Ala Ala Arg Asn Ile Ala Glu Ser Ala Leu Ser Cys
                165                 170                 175

Val Gly Ile Asn Leu Ala Glu Lys Thr Lys Leu Thr Ile Leu Lys Asp
            180                 185                 190

Ala Ser Gly Ile Ile Lys Pro Ser Arg Met Thr Leu Leu Gly Pro
        195                 200                 205

Pro Ser Ser Gly Lys Thr Thr Leu Leu Ala Leu Ala Gly Lys Leu
    210                 215                 220

Asp Pro Thr Leu Lys Val Arg Gly Glu Ile Thr Tyr Asn Gly His Gly
225                 230                 235                 240

Leu Lys Glu Phe Val Pro Gln Lys Thr Ser Ala Tyr Ile Ser Gln Asn
                245                 250                 255

Asp Val His Val Ala Glu Met Thr Val Lys Glu Thr Leu Asp Phe Ser
            260                 265                 270

Ala Arg Cys Gln Gly Val Gly Ser Arg Tyr Glu Leu Leu Thr Glu Leu
        275                 280                 285

Ala Arg Arg Glu Arg Asp Ala Gly Ile Phe Pro Glu Ala Glu Ile Asp
```

-continued

```
              290                 295                 300
Leu Phe Met Lys Ala Thr Ala Met Glu Gly Val Glu Ser Ser Leu Ile
305                 310                 315                 320

Thr Asp Tyr Thr Leu Arg Ile Leu Gly Leu Asp Val Cys Arg Asp Thr
                325                 330                 335

Ile Val Gly Asp Glu Met Ile Arg Ile Ser Gly Gly Gln Lys Lys
                340                 345                 350

Arg Val Thr Thr Gly Glu Met Ile Val Gly Pro Thr Lys Thr Leu Phe
                355                 360                 365

Met Asp Glu Ile Ser Thr Gly Leu Asp Ser Ser Thr Thr Phe Gln Ile
            370                 375                 380

Val Lys Cys Leu Gln Gln Ile Val His Leu Thr Glu Ala Thr Val Leu
385                 390                 395                 400

Met Ser Leu Leu Gln Pro Ala Pro Glu Thr Phe Asp Leu Phe Asp Asp
                405                 410                 415

Ile Ile Leu Leu Ser Glu Gly Gln Ile Val Tyr Gln Gly Pro Arg Glu
                420                 425                 430

His Val Leu Glu Phe Phe Glu Thr Cys Gly Phe Lys Cys Pro Glu Arg
            435                 440                 445

Lys Gly Thr Ala Asp Phe Leu Gln Glu Val Thr Ser Arg Lys Asp Gln
            450                 455                 460

Glu Gln Tyr Trp Ala Asn Arg His Arg Pro Tyr Gln Tyr Ile Ser Val
465                 470                 475                 480

Thr Glu Phe Ala Lys Arg Phe Lys Arg Phe His Val Gly Leu Arg Ile
                485                 490                 495

Glu Asn Glu Leu Ser Val Pro Tyr Asp Lys Thr Arg Ser His Pro Ala
                500                 505                 510

Ala Leu Ile Phe Lys Lys Tyr Thr Val Pro Thr Leu Glu Leu Leu Lys
            515                 520                 525

Thr Asn Phe Asp Lys Glu Trp Leu Leu Ile Lys Arg Asn Ser Phe Val
            530                 535                 540

Tyr Val Phe Lys Thr Val Gln Ile Ile Val Ala Phe Ile Gly Ser
545                 550                 555                 560

Thr Val Phe Leu Arg Thr Lys Met His Thr Asn Thr Val Asp Asp Gly
                565                 570                 575

Ala Thr Tyr Val Gly Ala Leu Leu Phe Gly Met Val Ile Asn Met Phe
                580                 585                 590

Asn Gly Phe Ser Glu Leu Ser Met Ile Ile Gln Arg Leu Pro Val Phe
                595                 600                 605

Tyr Lys His Arg Asp Leu Leu Phe His Pro Pro Trp Ala Phe Thr Leu
            610                 615                 620

Pro Thr Val Leu Leu Lys Val Pro Ile Ser Val Phe Glu Thr Ile Val
625                 630                 635                 640

Trp Met Val Met Thr Tyr Tyr Thr Ile Gly Tyr Ala Pro Glu Ala Ser
                645                 650                 655

Arg Phe Phe Lys Gln Ser Leu Leu Thr Phe Leu Ile Gln Gln Met Ala
                660                 665                 670

Ala Gly Leu Phe Arg Leu Thr Ala Gly Val Cys Arg Thr Met Ile Ile
            675                 680                 685

Ala Asn Thr Gly Gly Ala Leu Met Leu Leu Val Phe Leu Leu Gly
            690                 695                 700

Gly Phe Ile Leu Pro Arg Gly Ser Ile Pro Asp Trp Trp Arg Trp Gly
705                 710                 715                 720
```

-continued

Tyr Trp Ile Ser Pro Leu Ser Tyr Gly Phe Asn Ala Phe Thr Val Asn
            725                 730                 735
Glu Met Phe Ala Pro Arg Trp Met Asn Lys Phe Ala Pro Asp Gly Thr
            740                 745                 750
Thr Arg Leu Gly Leu Gln Val Met Lys Asn Phe Asp Val Phe Thr Glu
            755                 760                 765
Arg Arg Trp Phe Trp Ile Gly Ala Ala Leu Leu Gly Phe Thr Ile
770                 775                 780
Leu Phe Asn Val Leu Phe Thr Leu Val Leu Met Tyr Leu Ser Pro Leu
785                 790                 795                 800
Asn Lys Pro Gln Ala Thr Leu Ser Lys Glu Gln Ala Ser Asp Met Glu
            805                 810                 815
Ala Asp Gln Glu Glu Ser Thr Gly Ser Pro Arg Leu Lys Ile Ser Gln
            820                 825                 830
Ser Lys Arg Asp Asp Leu Pro Arg Ser Leu Ser Ala Ala Asp Gly Asn
            835                 840                 845
Lys Thr Arg Glu Met Glu Ile Arg Arg Met Ser Ser His Ile His Ser
            850                 855                 860
Ser Gly Leu Tyr Arg Asn Glu Asp Ala Asn Leu Glu Ala Ala Asn Gly
865                 870                 875                 880
Val Ala Ala Lys Lys Gly Met Ile Leu Pro Phe Thr Pro Leu Ala Met
            885                 890                 895
Ser Phe Glu Asp Val Ser Tyr Phe Val Asp Met Pro Pro Glu Met Lys
            900                 905                 910
Asp Gln Gly Val Thr Glu Asp Lys Leu Gln Leu Leu Arg Glu Val Thr
            915                 920                 925
Gly Ala Phe Arg Pro Gly Val Leu Thr Ala Leu Met Gly Val Ser Gly
            930                 935                 940
Ala Gly Lys Thr Thr Leu Met Asp Val Leu Ala Gly Arg Lys Thr Gly
945                 950                 955                 960
Gly Tyr Ile Glu Gly Asp Val Arg Ile Ser Gly Phe Pro Lys Asn Gln
            965                 970                 975
Glu Thr Phe Ala Arg Val Ser Gly Tyr Cys Glu Gln Thr Asp Ile His
            980                 985                 990
Ser Pro Gln Val Thr Ile His Glu Ser Leu Ile Phe Ser Ala Phe Leu
            995                 1000                1005
Arg Leu Pro Lys Glu Val Ser Lys Glu Asp Lys Met Ile Phe Val Asp
    1010                1015                1020
Glu Val Met Asp Leu Val Glu Leu Asp Asn Leu Lys Asp Ala Ile Val
1025                1030                1035                1040
Gly Leu Pro Gly Val Thr Gly Leu Ser Thr Glu Gln Arg Lys Arg Leu
            1045                1050                1055
Thr Ile Ala Val Glu Leu Val Ala Asn Pro Ser Ile Ile Phe Met Asp
            1060                1065                1070
Glu Pro Thr Ser Gly Leu Asp Ala Arg Ala Ala Ala Ile Val Met Arg
            1075                1080                1085
Thr Val Arg Asn Thr Val Asp Thr Gly Arg Thr Val Val Cys Thr Ile
            1090                1095                1100
His Gln Pro Ser Ile Asp Ile Phe Glu Ala Phe Asp Glu Leu Leu Leu
1105                1110                1115                1120
Met Lys Arg Gly Gly Gln Val Ile Tyr Ala Gly Pro Leu Gly Arg His
            1125                1130                1135

Ser Gln Lys Ile Ile Glu Tyr Phe Glu Ala Ile Pro Gly Val Gln Lys
        1140                1145                1150

Ile Lys Glu Lys Tyr Asn Pro Ala Thr Trp Met Leu Glu Ala Ser Ser
    1155                1160                1165

Ile Gly Thr Glu Ala Arg Leu Gly Met Asp Phe Ala Glu Tyr Tyr Arg
    1170                1175                1180

Ser Ser Ala Leu His Gln Arg Asn Lys Ala Leu Val Lys Glu Leu Ser
1185                1190                1195                1200

Ala Pro Pro Gly Ala Lys Asp Leu Tyr Phe Thr Thr Gln Phe Ser
            1205                1210                1215

Gln Pro Thr Trp Gly Gln Phe Lys Ser Cys Leu Trp Lys Gln Trp Trp
        1220                1225                1230

Thr Tyr Trp Arg Ser Pro Asp Tyr Asn Leu Val Arg Phe Phe Ser
        1235                1240                1245

Leu Ala Ala Ala Leu Leu Ile Gly Thr Ile Phe Trp Asn Val Gly Ser
        1250                1255                1260

Lys Arg Gln Ser Ser Gly Asp Leu Met Thr Val Ile Gly Ala Met Tyr
1265                1270                1275                1280

Ala Ala Val Leu Phe Val Gly Ile Asn Asn Cys Ser Thr Val Gln Pro
            1285                1290                1295

Ile Val Ala Val Glu Arg Thr Val Phe Tyr Arg Glu Arg Ala Ala Gly
        1300                1305                1310

Met Tyr Ser Ala Leu Pro Tyr Ala Met Ala Gln Val Phe Ala Glu Ile
        1315                1320                1325

Pro Tyr Ile Leu Val Gln Thr Thr Tyr Thr Leu Ile Val Tyr Ala
        1330                1335                1340

Met Val Ala Phe Glu Trp Thr Ala Ala Lys Phe Phe Trp Phe Tyr Phe
1345                1350                1355                1360

Val Thr Phe Phe Ser Phe Leu Tyr Trp Thr Tyr Tyr Gly Met Met Thr
            1365                1370                1375

Val Ser Ile Thr Pro Asn His Gln Val Ala Ala Ile Phe Ala Ala Ala
        1380                1385                1390

Phe Tyr Ala Leu Phe Asn Leu Phe Ser Gly Phe Phe Ile Pro Arg Pro
        1395                1400                1405

Arg Ile Pro Lys Trp Trp Ile Trp Tyr Tyr Trp Ile Cys Pro Val Ala
    1410                1415                1420

Trp Thr Val Tyr Gly Ser Ile Val Ser Gln Tyr Gly Asp Val Glu Asp
1425                1430                1435                1440

Thr Ile Gln Val Pro Gly Val Phe Pro Asn Pro Arg Ile Lys Asp Tyr
            1445                1450                1455

Ile Lys Asp His Phe Gly Tyr Asn Ser Asp Phe Met Ala Pro Val Ala
            1460                1465                1470

Val Val Leu Val Gly Phe Ala Ala Phe Phe Ala Phe Met Tyr Ala Tyr
        1475                1480                1485

Ala Ile Lys Thr Leu Asn Phe Gln Thr Arg
    1490                1495

<210> SEQ ID NO 37
<211> LENGTH: 1566
<212> TYPE: DNA
<213> ORGANISM: Nicotiana tabacum

<400> SEQUENCE: 37
atggagatga aagtaaacga agcaatttca aagagtaaaa ttggcaaata cttcaagtta      60

```
gaagctagaa aaagctcttt tactaaagaa tttcgtgctg gtacggcgac gtttcttaca    120
atggcttaca tcatcaccgt caacgccagc gttttatcgg actccggcgg cacttgctcc    180
gtttccgact gcactttttcc ggcgaaccaa acacgtgcaa ctccagagtg catgttgaaa    240
ccaaatgaag gttatgaaaa gtgtgttttcc aaaatgagga gtgatcttat tgttgctact    300
gctttagctt ctatgattgg gtcatttgct atgggtttat tagctaatct tccttttgggc    360 ttggccccag gtatgggccc aaatgcttat ttagcttata atttagtggg atttcatggg    420
tctggaaaaa tgtcatatca aactgttatg gcaattttct tagttgaagg ttgtgctttt    480
cttgctatag ctgtatttgg gcttcgtggg agaatagccc ggtttattcc tcagcctgta    540
agattggctt gtgcggctgg tattgggctt tttattgcat ttgtgggcct acaagcccat    600
caaggagtga gcctagtcgg cccagatcca tctactctat tgaccctcac tgcttgctct    660
agtacaaatc cggtgaccgg agaatgcacc ggcgggaaaa tgcaaagccc aactttttgg    720
ttaagttcag ttggatttat aattatgtgt tatggactaa tgaaggaaat taaaggtagt    780
atgatatatg gtattttatt tgtgacatta gtttcttgga ttaggaatac tgctgttaca    840 attttttccta acacaacatc aggtaattca agttatgagt acttcaaaaa agtggtagat    900
tttcataaaa ttgagtccac agctggagct attaattttta gccattttaa taatggtgaa    960
gtatgggtgg cattattaac attgttatac atagatgtac tagctacaac aggtacatta   1020
tatacaatgg ctgaaattgg tggatttgtt aatgaagaag gagaatttga aggtgaatat   1080
atagcatata tggtagatgc aggatcaaca atagttgcat caactctagg agtttcacct   1140
atagccacat ttgtagaatc atcagctggg attaaagaag gtggtaggac gggactaacg   1200
gcgattatcg ttggattttta ttttctattg tctttgtttt ttacacccttt gattgctagt   1260 gtaccacctt gggctatagg tccatctttg gtaatggttg gtgtgttgat gatgaaagtt   1320
gttaaagata ttgattggaa taatattaag catgcagtgc ctgcatttgt gactatggtt   1380 ctaatgccctt tgcatactc aatttccaat ggtattattg gtgggattgg agtgtatatt   1440
gctctaagtt tgtatgatag tatggattgt tgggtgaagt ggttgatgag aatgagaaag   1500
atggtggtga aggagcaaaa tcaagtgtca gctgccacta cagatcagaa cattgaaatt   1560
gtttga                                                              1566
```

<210> SEQ ID NO 38
<211> LENGTH: 521
<212> TYPE: PRT
<213> ORGANISM: Nicotiana tabacum

<400> SEQUENCE: 38

```
Met Glu Met Lys Val Asn Glu Ala Ile Ser Lys Ser Lys Ile Gly Lys
1               5                   10                  15

Tyr Phe Lys Leu Glu Ala Arg Lys Ser Ser Phe Thr Lys Glu Phe Arg
            20                  25                  30

Ala Gly Thr Ala Thr Phe Leu Thr Met Ala Tyr Ile Ile Thr Val Asn
        35                  40                  45

Ala Ser Val Leu Ser Asp Ser Gly Gly Thr Cys Ser Val Ser Asp Cys
    50                  55                  60

Thr Phe Pro Ala Asn Gln Thr Arg Ala Thr Pro Glu Cys Met Leu Lys
65                  70                  75                  80

Pro Asn Glu Gly Tyr Glu Lys Cys Val Ser Lys Met Arg Ser Asp Leu
                85                  90                  95

Ile Val Ala Thr Ala Leu Ala Ser Met Ile Gly Ser Phe Ala Met Gly
```

```
                    100                 105                 110
Leu Leu Ala Asn Leu Pro Leu Gly Leu Ala Pro Gly Met Gly Pro Asn
            115                 120                 125
Ala Tyr Leu Ala Tyr Asn Leu Val Gly Phe His Gly Ser Gly Lys Met
            130                 135                 140
Ser Tyr Gln Thr Val Met Ala Ile Phe Leu Val Glu Gly Cys Ala Phe
145                 150                 155                 160
Leu Ala Ile Ala Val Phe Gly Leu Arg Gly Arg Ile Ala Arg Phe Ile
                165                 170                 175
Pro Gln Pro Val Arg Leu Ala Cys Ala Ala Gly Ile Gly Leu Phe Ile
            180                 185                 190
Ala Phe Val Gly Leu Gln Ala His Gln Gly Val Ser Leu Val Gly Pro
            195                 200                 205
Asp Pro Ser Thr Leu Leu Thr Leu Thr Ala Cys Ser Ser Thr Asn Pro
210                 215                 220
Val Thr Gly Glu Cys Thr Gly Gly Lys Met Gln Ser Pro Thr Phe Trp
225                 230                 235                 240
Leu Ser Ser Val Gly Phe Ile Ile Met Cys Tyr Gly Leu Met Lys Glu
                245                 250                 255
Ile Lys Gly Ser Met Ile Tyr Gly Ile Leu Phe Val Thr Leu Val Ser
            260                 265                 270
Trp Ile Arg Asn Thr Ala Val Thr Ile Phe Pro Asn Thr Thr Ser Gly
            275                 280                 285
Asn Ser Ser Tyr Glu Tyr Phe Lys Lys Val Val Asp Phe His Lys Ile
            290                 295                 300
Glu Ser Thr Ala Gly Ala Ile Asn Phe Ser His Phe Asn Asn Gly Glu
305                 310                 315                 320
Val Trp Val Ala Leu Leu Thr Leu Leu Tyr Ile Asp Val Leu Ala Thr
                325                 330                 335
Thr Gly Thr Leu Tyr Thr Met Ala Glu Ile Gly Gly Phe Val Asn Glu
            340                 345                 350
Glu Gly Glu Phe Glu Gly Glu Tyr Ile Ala Tyr Met Val Asp Ala Gly
            355                 360                 365
Ser Thr Ile Val Ala Ser Thr Leu Gly Val Ser Pro Ile Ala Thr Phe
            370                 375                 380
Val Glu Ser Ser Ala Gly Ile Lys Glu Gly Gly Arg Thr Gly Leu Thr
385                 390                 395                 400
Ala Ile Ile Val Gly Phe Tyr Phe Leu Leu Ser Leu Phe Phe Thr Pro
                405                 410                 415
Leu Ile Ala Ser Val Pro Pro Trp Ala Ile Gly Pro Ser Leu Val Met
            420                 425                 430
Val Gly Val Leu Met Met Lys Val Lys Asp Ile Asp Trp Asn Asn
            435                 440                 445
Ile Lys His Ala Val Pro Ala Phe Val Thr Met Val Leu Met Pro Leu
            450                 455                 460
Thr Tyr Ser Ile Ser Asn Gly Ile Ile Gly Gly Ile Gly Val Tyr Ile
465                 470                 475                 480
Ala Leu Ser Leu Tyr Asp Ser Met Asp Cys Trp Val Lys Trp Leu Met
                485                 490                 495
Arg Met Arg Lys Met Val Val Lys Glu Gln Asn Gln Val Ser Ala Ala
            500                 505                 510
Thr Thr Asp Gln Asn Ile Glu Ile Val
            515                 520
```

<210> SEQ ID NO 39
<211> LENGTH: 665
<212> TYPE: DNA
<213> ORGANISM: Nicotiana tabacum

<400> SEQUENCE: 39

| | | | | | |
|---|---|---|---|---|---|
| ggtaacatat | tctccttcat | ggtgtttatt | tcgccagtac | ctacatttta | tgggatcgtt | 60 |
| aagaagaaat | caacagaagg | ctatcaatca | attccgtacg | tggttgcact | ctttagttca | 120 |
| atgctttgga | tttactatgc | atttctcaag | acaaacacga | cccttatcat | caccataaac | 180 |
| tcctttggct | gcattgcgga | gactatttat | attgctattt | attttgctta | tgcgacaaaa | 240 |
| aaaacaagga | tgcaaacgtt | gagacttgtt | ctaatgttga | atttcggtgg | ctttgggttg | 300 |
| attcttttcc | tcacccaaat | tttatgcaaa | ggagcaaaac | gagctgaagt | tattggatgg | 360 |
| atttgcatgg | cgttttctat | tagtgtgttt | gtagcacctc | taagcattat | ggggcgggta | 420 |
| atacggacca | aaagtgtgga | gttcatgcca | tttaacttgt | cgttaaccct | tacacttagt | 480 |
| gctgtgataa | acgccaagcc | aaataatcag | gcagaagaga | agaaactacc | cactgttgtg | 540 |
| aagctggagg | agttgcctac | aaaagttaat | tctgaggttt | atccagttag | tttaccatcc | 600 |
| atgggcagtg | aaaacggaga | ggctaaagat | ggtaaacatt | ttgaagatgc | ccaaatcaaa | 660 |
| tctcc | | | | | | 665 |

<210> SEQ ID NO 40

<400> SEQUENCE: 40

000

<210> SEQ ID NO 41
<211> LENGTH: 4212
<212> TYPE: DNA
<213> ORGANISM: Nicotiana tabacum

<400> SEQUENCE: 41

| | | | | | |
|---|---|---|---|---|---|
| atgttttat | aagagaaact | aatcacctct | ttccaaaaca | aaagtatatc | caatttatct | 60 |
| cagagccaaa | agtcccttttt | tcatttatta | tcttctcctc | ttccttagag | taggggaaaa | 120 |
| atagaaagaa | gagaatggtg | gaaagtgaga | aaatgaatga | cacaaagaat | ctgagcaaga | 180 |
| gctatttttga | tgttttggga | atttgctgta | cttcagaagt | tgttcttgtt | gaaaaaattc | 240 |
| tcaagaatct | tgaaggggtt | aaagaggttt | cagtaattgt | cacaacaaag | actgtcattg | 300 |
| ttattcatga | ttctctcctc | atttctcagc | aacaaattgt | taaagcattg | aatcaagcaa | 360 |
| gattagaagc | aagtataaga | gtgaaaggag | agaaaaacta | ccaaaagaaa | tggccaagtc | 420 |
| catttgcaat | tggcagtgga | atattgcttg | gactctcatt | tttgaagtac | ttttttgcac | 480 |
| ctttccaatg | gttagcactt | gcagctgttg | cagttgggat | tcctccaatt | attttaggg | 540 |
| gtgtggctgc | cgtgcgaaac | ctcactcttg | acatcaacat | tcttgtttta | atagcagtga | 600 |
| cgggatcaat | tgttttacac | gattattggg | aagctggtac | tattgtcttc | ttattcacca | 660 |
| ttgcagaatg | gctagagtca | agggcaagtc | acaaggctac | tgctgctatg | tcatcactgg | 720 |
| tcaatatagt | ccctccaaca | gcagtttttag | ctgaaagtgg | agaagtcgta | aatgttgatg | 780 |
| aagtcaagtt | gaatagcatt | cttgctgtta | aagctggtga | aactataccct | attgatggag | 840 |
| ttgtaatgga | aggggaatgt | gacgtggacg | agaaaacact | gacaggcgag | tcgtttccag | 900 |
| tttctaagca | aatagattca | acggtctggg | ctggcactac | aaatctaaat | gcaattgtgg | 960 |

```
ctatatcagc ttctttggca atagttccta ctgcattaag agttcacaat cgaaatgaat    1020
ggtatcgctt ggctttggtc acattggtga gtgcatgtcc gtgtgcactt gttctatcta    1080
caccagttgc catgtgttgc gcactttcaa aagcagcaac gtccggtctt ctgtttaaag    1140
gagcagagta ccttgagact cttgctaaaa tcaaaatcat ggcttttgac aaaacaggga    1200
ctataactag aggagaattt atggtgaccg agttcaaggt ttcaagtatt gagagcaagt    1260
caggtcatcc gatggcagcc gctctggtgg actatgcaca atcaaattcc gttgagccaa    1320
agcctgatag agttgagcag tttcaaaatt ttcctggtga agggatattt ggaagaattg    1380
atggaatgga aatctatgtc gggaatagga aaatttcttc aagagctgga tgtaccacag    1440
taccagaaat agagggtgat agtttccaag gaaagtctgt tggatacata ttttgggat    1500 catctcccgc tggaattttc ggtctttccg atgtttgtcg aattggtgta aaagaagcaa    1560
tgagagaact gaagcagatg ggtatcaaaa ccgcgatgct tactggtgat tgttatgcag    1620
ctgccaacca tgtgcaggat cagaaggaag ctccaacagc gatgataggc gacggcctta    1680
atgatgctcc tgcattagca acagctgaca ttggcatctc aatgggcatc tctgggtcag    1740
ctctcgcgaa agaaacaggc catgttatac taatgacaaa tgacatcgga agaataccaa    1800
aagctgcacg tcttgctaga agagttcgaa ggaagattgt tgagaatatg attatatcag    1860
tcgttacaaa ggccgccata gttgcattgg caatagcagg ttatccattg gtttgggctg    1920
ctgtcctcgc agatactggg acatgcttgc tagtgatttt gaacagcatg ctacttctac    1980
gaggaggcac acgcagacat gggaaaaaat gttggagatc ttctactcct tcgcatgctc    2040
cccaccacaa agacaaagct tcatgttgca agtcggaaaa tgctccccag ctgtgttgct    2100
ctgatattga gtcacaaaag aaatgtacga gtcaatcatg ctcgtccgag gtgtgtgttc    2160
caagatgtca acctgtctcc tcaggatcaa agtcatgtgg aaataatcag tgcccagact    2220
ccgttgaaaa tagtggtttt cattctcatc cccgtcctca atgctgctcg tcgaagatgg    2280
ctgctaaagc atgccaatct gcagtttcag aatcaaagtc atgtggaaat aatcagtgcc    2340
cagactccgt tgaaaatagt gaatcaaagt catgtggaaa taacaattgc tcggagtcca    2400
tttacaagag tagttgtcat tctttaacaa actctctagt atgttcttcc aagatgtctg    2460
ctccacaatg tcattctgcc acttcaagca acaaatcatg tggaagtacc aagtgctccg    2520
acttcagtga caaaaaatgt tgccaatatg acaaaattcc tcaaacgtgc tctaccaaga    2580
agtctgctcc aggatgtcaa tctgcagttt ctgggtctaa atcatgtgga gatagcaagt    2640
gttcagactc gaaagacaat agtagccatc cttcacatcc cgatcatcaa acatgcacgt    2700
ctaagttgtg tgctccacaa agccaatctg caacttcaag ctccaggaca tgtggaaata    2760
tgaagtgctc ggacaccaat agcaagaatt cttgttattc acataccaac tctgaatcat    2820
gctcttcaaa gatgtctggt ccatcatgca aaactgctaa ttcaggttca aggtcatgca    2880
gaaataagaa gtgcctagac tctgcaaccg agaacagttt tcattcacca cttactaatc    2940
cactcagtgg ggaaaagctt ttggagaaga aaagcttgga tttagtccga aaagataagg    3000
aatcaaatca tgatcttagt catggttgct ctgacgagga acatgatcat ctaaattag    3060 acaaggcaca tgcagttgt gccttacaag aatgttgtta ttctgttcaa ggcaataaaa    3120
ctgatgtatc agaaactgga atccaggaag ctgctcattg tgacagcatc aatcaaacat    3180
gccaaactgc aatttcagga tcaatgacat gcggaaataa taagagtctg gactctctaa    3240
gcatccatgg ttgtcattcg catgataatc cactccacaa ggagaacaac ttggagcaga    3300
```

```
aaagcttgga tgttgttgga gaaggtataa aatcacctca tgctgtcggt catggctgtt    3360
cggacaagga acacgatcac tcgcatccag aaaaggcgta tgacagttgt gcaacagacg    3420
attgttgttt ttcagttcaa gtccatggca ttgacgacgt atcaagaagt gaaattcaag    3480
aaactgctca ttgtgacagc acaaaacaga gcacggtcat ccccagcagc tgcaaacatg    3540
aaccaaaaga tcaggtaaat cactgtggat ctcactctaa aagtattcca actgatgaag    3600
aactagccaa gctggttaga agatgctgca aatacaaacc atgccacgac gtccgttctg    3660
gctgcaggaa gcatgctgca gaatgtggtc caaccgttcg atcaaccatc aatatcttac    3720
gggacaacca tcatcatcat ctagactgca gtggtcgtaa ggtttgttcg ctgttggaga    3780
agagacacat tggtggatgc tgtgacagct tcagaaaaga atgttgtgcc aagaacaatc    3840
accttggagc aagttttgga ggaggtttat cagaaattga ttgggcatcg cttgggctaa    3900
tgccagttgt tagtgtacgt aacgaaggta agaagaaact tgttatcata gatatatgaa    3960
aaatcaactc atggataata aaggcgtagc accaaatatg tcggagtagc cccacccagt    4020
agatggaaaa gccagtagta ccaatcaagg aagccttgaa cggagcaggt tgcggtgaat    4080
tataatgtgc agaattgtgg ggtataaatt agatgattac aattgtggta aagtgtaatt    4140
atttattgta ctaattctat gtagctatct cccccgaata atggatccac tatgagaatt    4200
tatttagacc cg                                                       4212
```

<210> SEQ ID NO 42
<211> LENGTH: 1274
<212> TYPE: PRT
<213> ORGANISM: Nicotiana tabacum

<400> SEQUENCE: 42

```
Met Val Glu Ser Glu Lys Met Asn Asp Thr Lys Asn Leu Ser Lys Ser
1               5                   10                  15

Tyr Phe Asp Val Leu Gly Ile Cys Cys Thr Ser Glu Val Val Leu Val
            20                  25                  30

Glu Lys Ile Leu Lys Asn Leu Glu Gly Val Lys Glu Val Ser Val Ile
        35                  40                  45

Val Thr Thr Lys Thr Val Ile Val Ile His Asp Ser Leu Leu Ile Ser
    50                  55                  60

Gln Gln Gln Ile Val Lys Ala Leu Asn Gln Ala Arg Leu Glu Ala Ser
65                  70                  75                  80

Ile Arg Val Lys Gly Glu Lys Asn Tyr Gln Lys Lys Trp Pro Ser Pro
                85                  90                  95

Phe Ala Ile Gly Ser Gly Ile Leu Leu Gly Leu Ser Phe Leu Lys Tyr
            100                 105                 110

Phe Phe Ala Pro Phe Gln Trp Leu Ala Leu Ala Ala Val Ala Val Gly
        115                 120                 125

Ile Pro Pro Ile Ile Phe Arg Gly Val Ala Ala Val Arg Asn Leu Thr
    130                 135                 140

Leu Asp Ile Asn Ile Leu Val Leu Ile Ala Val Thr Gly Ser Ile Val
145                 150                 155                 160

Leu His Asp Tyr Trp Glu Ala Gly Thr Ile Val Phe Leu Phe Thr Ile
                165                 170                 175

Ala Glu Trp Leu Glu Ser Arg Ala Ser His Lys Ala Thr Ala Ala Met
            180                 185                 190

Ser Ser Leu Val Asn Ile Val Pro Pro Thr Ala Val Leu Ala Glu Ser
        195                 200                 205
```

```
Gly Glu Val Val Asn Val Asp Glu Val Lys Leu Asn Ser Ile Leu Ala
210                 215                 220
Val Lys Ala Gly Glu Thr Ile Pro Ile Asp Gly Val Val Met Glu Gly
225                 230                 235                 240
Glu Cys Asp Val Asp Glu Lys Thr Leu Thr Gly Glu Ser Phe Pro Val
                245                 250                 255
Ser Lys Gln Ile Asp Ser Thr Val Trp Ala Gly Thr Thr Asn Leu Asn
                260                 265                 270
Ala Ile Val Ala Ile Ser Ala Leu Ala Ile Val Pro Thr Ala Leu
275                 280                 285
Arg Val His Asn Arg Asn Glu Trp Tyr Arg Leu Ala Leu Val Thr Leu
290                 295                 300
Val Ser Ala Cys Pro Cys Ala Leu Val Leu Ser Thr Pro Val Ala Met
305                 310                 315                 320
Cys Cys Ala Leu Ser Lys Ala Ala Thr Ser Gly Leu Leu Phe Lys Gly
                325                 330                 335
Ala Glu Tyr Leu Glu Thr Leu Ala Lys Ile Lys Ile Met Ala Phe Asp
                340                 345                 350
Lys Thr Gly Thr Ile Thr Arg Gly Glu Phe Met Val Thr Glu Phe Lys
                355                 360                 365
Val Ser Ser Ile Glu Ser Lys Ser Gly His Pro Met Ala Ala Ala Leu
370                 375                 380
Val Asp Tyr Ala Gln Ser Asn Ser Val Glu Pro Lys Pro Asp Arg Val
385                 390                 395                 400
Glu Gln Phe Gln Asn Phe Pro Gly Glu Gly Ile Phe Gly Arg Ile Asp
                405                 410                 415
Gly Met Glu Ile Tyr Val Gly Asn Arg Lys Ile Ser Ser Arg Ala Gly
                420                 425                 430
Cys Thr Thr Val Pro Glu Ile Glu Gly Asp Ser Phe Gln Gly Lys Ser
                435                 440                 445
Val Gly Tyr Ile Phe Leu Gly Ser Ser Pro Ala Gly Ile Phe Gly Leu
450                 455                 460
Ser Asp Val Cys Arg Ile Gly Val Lys Glu Ala Met Arg Glu Leu Lys
465                 470                 475                 480
Gln Met Gly Ile Lys Thr Ala Met Leu Thr Gly Asp Cys Tyr Ala Ala
                485                 490                 495
Ala Asn His Val Gln Asp Gln Lys Glu Ala Pro Thr Ala Met Ile Gly
                500                 505                 510
Asp Gly Leu Asn Asp Ala Pro Ala Leu Ala Thr Ala Asp Ile Gly Ile
                515                 520                 525
Ser Met Gly Ile Ser Gly Ser Ala Leu Ala Lys Glu Thr Gly His Val
530                 535                 540
Ile Leu Met Thr Asn Asp Ile Gly Arg Ile Pro Lys Ala Ala Arg Leu
545                 550                 555                 560
Ala Arg Arg Val Arg Arg Lys Ile Val Glu Asn Met Ile Ile Ser Val
                565                 570                 575
Val Thr Lys Ala Ala Ile Val Ala Leu Ala Ile Ala Gly Tyr Pro Leu
                580                 585                 590
Val Trp Ala Ala Val Leu Ala Asp Thr Gly Thr Cys Leu Leu Val Ile
                595                 600                 605
Leu Asn Ser Met Leu Leu Leu Arg Gly Gly Thr Arg Arg His Gly Lys
610                 615                 620
Lys Cys Trp Arg Ser Ser Thr Pro Ser His Ala Pro His His Lys Asp
```

-continued

```
            625                 630                 635                 640
Lys Ala Ser Cys Cys Lys Ser Glu Asn Ala Pro Gln Leu Cys Cys Ser
                645                 650                 655
Asp Ile Glu Ser Gln Lys Lys Cys Thr Ser Gln Ser Cys Ser Ser Glu
                660                 665                 670
Val Cys Val Pro Arg Cys Gln Pro Val Ser Ser Gly Ser Lys Ser Cys
                675                 680                 685
Gly Asn Asn Gln Cys Pro Asp Ser Val Glu Asn Ser Gly Phe His Ser
                690                 695                 700
His Pro Arg Pro Gln Cys Cys Ser Ser Lys Met Ala Ala Lys Ala Cys
705                 710                 715                 720
Gln Ser Ala Val Ser Glu Ser Lys Ser Cys Gly Asn Asn Gln Cys Pro
                725                 730                 735
Asp Ser Val Glu Asn Ser Glu Ser Lys Ser Cys Gly Asn Asn Asn Cys
                740                 745                 750
Ser Glu Ser Ile Tyr Lys Ser Ser Cys His Ser Leu Thr Asn Ser Leu
                755                 760                 765
Val Cys Ser Ser Lys Met Ser Ala Pro Gln Cys His Ser Ala Thr Ser
                770                 775                 780
Ser Asn Lys Ser Cys Gly Ser Thr Lys Cys Ser Asp Phe Ser Asp Lys
785                 790                 795                 800
Lys Cys Cys Gln Tyr Asp Lys Ile Pro Gln Thr Cys Ser Thr Lys Lys
                805                 810                 815
Ser Ala Pro Gly Cys Gln Ser Ala Val Ser Gly Ser Lys Ser Cys Gly
                820                 825                 830
Asp Ser Lys Cys Ser Asp Ser Lys Asp Asn Ser Ser His Pro Ser His
                835                 840                 845
Pro Asp His Gln Thr Cys Thr Ser Lys Leu Cys Ala Pro Gln Ser Gln
                850                 855                 860
Ser Ala Thr Ser Ser Ser Arg Thr Cys Gly Asn Met Lys Cys Ser Asp
865                 870                 875                 880
Thr Asn Ser Lys Asn Ser Cys Tyr Ser His Thr Asn Ser Glu Ser Cys
                885                 890                 895
Ser Ser Lys Met Ser Gly Pro Ser Cys Lys Thr Ala Asn Ser Gly Ser
                900                 905                 910
Arg Ser Cys Arg Asn Lys Lys Cys Leu Asp Ser Ala Thr Glu Asn Ser
                915                 920                 925
Phe His Ser Pro Leu Thr Asn Pro Leu Ser Gly Glu Lys Leu Leu Glu
                930                 935                 940
Lys Lys Ser Leu Asp Leu Val Arg Lys Asp Lys Glu Ser Asn His Asp
945                 950                 955                 960
Leu Ser His Gly Cys Ser Asp Glu Glu His Asp His Leu Asn Leu Asp
                965                 970                 975
Lys Ala His Asp Ser Cys Ala Leu Gln Glu Cys Cys Tyr Ser Val Gln
                980                 985                 990
Gly Asn Lys Thr Asp Val Ser Glu Thr Gly Ile Gln Glu Ala Ala His
                995                 1000                1005
Cys Asp Ser Ile Asn Gln Thr Cys Gln Thr Ala Ile Ser Gly Ser Met
                1010                1015                1020
Thr Cys Gly Asn Asn Lys Ser Leu Asp Ser Leu Ser Ile His Gly Cys
1025                1030                1035                1040
His Ser His Asp Asn Pro Leu His Lys Glu Asn Asn Leu Glu Gln Lys
                1045                1050                1055
```

```
Ser Leu Asp Val Val Gly Glu Gly Ile Lys Ser Pro His Ala Val Gly
            1060                1065                1070

His Gly Cys Ser Asp Lys Glu His Asp His Ser His Pro Glu Lys Ala
        1075                1080                1085

Tyr Asp Ser Cys Ala Thr Asp Asp Cys Cys Phe Ser Val Gln Val His
    1090                1095                1100

Gly Ile Asp Asp Val Ser Arg Ser Glu Ile Gln Glu Thr Ala His Cys
1105                1110                1115                1120

Asp Ser Thr Lys Gln Ser Thr Val Ile Pro Ser Ser Cys Lys His Glu
                1125                1130                1135

Pro Lys Asp Gln Val Asn His Cys Gly Ser His Ser Lys Ser Ile Pro
            1140                1145                1150

Thr Asp Glu Glu Leu Ala Lys Leu Val Arg Arg Cys Cys Lys Tyr Lys
        1155                1160                1165

Pro Cys His Asp Val Arg Ser Gly Cys Arg Lys His Ala Ala Glu Cys
    1170                1175                1180

Gly Pro Thr Val Arg Ser Thr Ile Asn Ile Leu Arg Asp Asn His His
1185                1190                1195                1200

His His Leu Asp Cys Ser Gly Arg Lys Val Cys Ser Leu Leu Glu Lys
                1205                1210                1215

Arg His Ile Gly Gly Cys Cys Asp Ser Phe Arg Lys Glu Cys Cys Ala
            1220                1225                1230

Lys Asn Asn His Leu Gly Ala Ser Phe Gly Gly Leu Ser Glu Ile
        1235                1240                1245

Asp Trp Ala Ser Leu Gly Leu Met Pro Val Val Ser Val Arg Asn Glu
    1250                1255                1260

Gly Lys Lys Lys Leu Val Ile Ile Asp Ile
1265                1270

<210> SEQ ID NO 43
<211> LENGTH: 1296
<212> TYPE: DNA
<213> ORGANISM: Nicotiana tabacum

<400> SEQUENCE: 43
atgggaagtg aagctttgga gttttttgct tgtgataata cttttcgata tgaaccaaaa      60
cgcataacaa tggaggagag tgatgatctt cccattaatg atggttcttg gtttgaagaa     120
gagattgatg ttgatctcaa atggtctttt gctttgaaca gtgtgctgca caaggaaca     180 agcgagtacc aagatatcgc cctttttggac accaagcatt tcgggaaggt attggtgata    240
gatgggaaga tgcagagtgc agaagtggat gaatttatat atcatgaatg cttaattcat    300
ccagctctct tgtgtcaccc taacccaaaa aatgttttta atgggaggg tggtgaagga    360 tctgcagcaa gggaagctct cagacacaaa tctatggaga agttgtcat gtgtgacatt     420 gatcaggagg ttgtggattt ctgcaggaag catctaacag caaaccatga ggcttttcgt    480
aacaagaagc ttaacttgat cattaacgat gccaaagctg agctagagca gaggcaagaa    540
aaatttgata ttatagttgg agatttagct gatccagttg aaggaggacc ttgttaccaa    600
ctctacacca aatctttcta cgaaaatatc cttaaaccta agctcaacga caatggcatc    660
ttcgttactc aggctggacc agcaggggtt ttcacacaca aggaagtttt ctcatccatt    720
tacaacacaa tcaagcaggt cttcaaatat gtgctggcat atacagctca tgtaccctct    780
tttgctgata catgggggatg ggttatggct tctgaccaac cattctgtct tgatgctgga    840
```

```
aaactggaca agaaaatagc tgaaagaatt gaaggggaac tcttatatct taatggtgct    900
tctttcttct cttccaccat cttgaataag accgttgcca aaacgctgaa gaatgagact    960
catgtgtaca ctgaagatga tgcaaggttc attcatggac atggagtggc attcagaaat   1020
tgaggcaaca aattggtggg ggaactgtac agtcaagtgt ttggaaacaa agaaatatga   1080 agtaggggg tgttgaaagt tgaaacattg agagttctct caaagaaagt tgttagtagc    1140
ttttggtttg gttcagcaaa ataggcttag gcttcttctg gttgtcctat gactatacat   1200
ttactatttt atgtactgct cagaaatgaa aaacaaaaaa agaccttttt ccaatcatat   1260
gtcatatttt acatgtttgg taaatattat tcttat                             1296
```

<210> SEQ ID NO 44
<211> LENGTH: 340
<212> TYPE: PRT
<213> ORGANISM: Nicotiana tabacum

<400> SEQUENCE: 44

```
Met Gly Ser Glu Ala Leu Glu Phe Phe Ala Cys Asp Asn Thr Phe Arg
1               5                   10                  15

Tyr Glu Pro Lys Arg Ile Thr Met Glu Glu Ser Asp Asp Leu Pro Ile
            20                  25                  30

Asn Asp Gly Ser Trp Phe Glu Glu Ile Asp Val Asp Leu Lys Trp
        35                  40                  45

Ser Phe Ala Leu Asn Ser Val Leu His Lys Gly Thr Ser Glu Tyr Gln
    50                  55                  60

Asp Ile Ala Leu Leu Asp Thr Lys His Phe Gly Lys Val Leu Val Ile
65                  70                  75                  80

Asp Gly Lys Met Gln Ser Ala Glu Val Asp Glu Phe Ile Tyr His Glu
                85                  90                  95

Cys Leu Ile His Pro Ala Leu Leu Cys His Pro Asn Pro Lys Asn Val
            100                 105                 110

Phe Ile Met Gly Gly Gly Glu Gly Ser Ala Ala Arg Glu Ala Leu Arg
        115                 120                 125

His Lys Ser Met Glu Lys Val Val Met Cys Asp Ile Asp Gln Glu Val
    130                 135                 140

Val Asp Phe Cys Arg Lys His Leu Thr Ala Asn His Glu Ala Phe Arg
145                 150                 155                 160

Asn Lys Lys Leu Asn Leu Ile Ile Asn Asp Ala Lys Ala Glu Leu Glu
                165                 170                 175

Gln Arg Gln Glu Lys Phe Asp Ile Ile Val Gly Asp Leu Ala Asp Pro
            180                 185                 190

Val Glu Gly Gly Pro Cys Tyr Gln Leu Tyr Thr Lys Ser Phe Tyr Glu
        195                 200                 205

Asn Ile Leu Lys Pro Lys Leu Asn Asp Asn Gly Ile Phe Val Thr Gln
    210                 215                 220

Ala Gly Pro Ala Gly Val Phe Thr His Lys Glu Val Phe Ser Ser Ile
225                 230                 235                 240

Tyr Asn Thr Ile Lys Gln Val Phe Lys Tyr Val Leu Ala Tyr Thr Ala
                245                 250                 255

His Val Pro Ser Phe Ala Asp Thr Trp Gly Trp Val Met Ala Ser Asp
            260                 265                 270

Gln Pro Phe Cys Leu Asp Ala Gly Lys Leu Asp Lys Lys Ile Ala Glu
        275                 280                 285

Arg Ile Glu Gly Glu Leu Leu Tyr Leu Asn Gly Ala Ser Phe Phe Ser
```

```
                  290                 295                 300

Ser Thr Ile Leu Asn Lys Thr Val Ala Lys Thr Leu Lys Asn Glu Thr
305                 310                 315                 320

His Val Tyr Thr Glu Asp Asp Ala Arg Phe Ile His Gly His Gly Val
                325                 330                 335

Ala Phe Arg Asn
            340

<210> SEQ ID NO 45
<211> LENGTH: 1122
<212> TYPE: DNA
<213> ORGANISM: Nicotiana tabacum

<400> SEQUENCE: 45
atggatcatc atcctgctaa ctatgatctt gatgagaaat ctgatctcaa atatgttgat      60
tgggtcactt tcaagagcca ttcctccaaa aaagttgaga gcttgattct agccaggttt     120
cctaggtggg agtattggaa actttgcctc gtaaacaaga gatgttcgat gcttctaaag     180
agcggtgaga tatttgagat tcgtaaagag attggattta agaaccttca gtattcatg      240
ttggcaagtg gggagactaa ctggtgggcg tttgatcgag agttcaagta ccggaggaaa     300
ttgcccgatt taccatcaga tgagtgcttc ccatttagtg ataaggaatc actttgtgta     360
ggcacacatt tgcttgtttc gggcagggaa atcgatggtc tcgttatttg gaggttcgaa     420
ttagcaacaa atagttggca caaggccccc tctatggtta atccgaggtg tttatttgca     480
tcagcaactt gtggtaccac tgcttttgtt gctggtggtg ttggtattat gccgaataac     540
gaggtctatg acacagctga gatacaaccc cgatagta gattgtggga gccactaccg      600
aggatgaaga ggaatagaaa actttgttca ggatgctaca tggacaacag attctacgtg     660
atcgggggaa ggaataagaa cggtgagtta acgtgtggag aattcttcga cgaggctaag     720
aacaaatggg agctgattcc ggacatgttg aaggatgatc cggtacagga ctaccattca     780
ccgcccctcc ttgctgtcgt gaataacgag ctatactcgc tcgaggcttc ttcgaatcag     840
cttaaggttt acttgaaaaa aaccaacact tggaaacagt tagggccagt tccagtacga     900
gctgattcaa acaggggatg gggcattgca ttcaagtcac tggggaatga acttctagta     960
ataggagctg cttcgtcgtc agtgtcttat tctggtaatt ccatggctat atatacttgc    1020
tgtcctgatc ctgaggcaat ggagttgcag tggaaaccac ttgacagtgg tcgaaatcga    1080
cttagtagtt ttatcttaaa ctgttcagtc atggtagctt ga                       1122

<210> SEQ ID NO 46
<211> LENGTH: 373
<212> TYPE: PRT
<213> ORGANISM: Nicotiana tabacum

<400> SEQUENCE: 46

Met Asp His His Pro Ala Asn Tyr Asp Leu Asp Glu Lys Ser Asp Leu
1               5                   10                  15

Lys Tyr Val Asp Trp Val Thr Phe Lys Ser His Ser Ser Lys Lys Val
            20                  25                  30

Glu Ser Leu Ile Leu Ala Arg Phe Pro Arg Trp Glu Tyr Trp Lys Leu
        35                  40                  45

Cys Leu Val Asn Lys Arg Cys Ser Met Leu Leu Lys Ser Gly Glu Ile
    50                  55                  60

Phe Glu Ile Arg Lys Glu Ile Gly Phe Lys Glu Pro Ser Val Phe Met
65                  70                  75                  80
```

```
Leu Ala Ser Gly Glu Thr Asn Trp Trp Ala Phe Asp Arg Glu Phe Lys
                 85                  90                  95
Tyr Arg Arg Lys Leu Pro Asp Leu Pro Ser Asp Glu Cys Phe Pro Phe
            100                 105                 110
Ser Asp Lys Glu Ser Leu Cys Val Gly Thr His Leu Leu Val Ser Gly
        115                 120                 125
Arg Glu Ile Asp Gly Leu Val Ile Trp Arg Phe Glu Leu Ala Thr Asn
    130                 135                 140
Ser Trp His Lys Gly Pro Ser Met Val Asn Pro Arg Cys Leu Phe Ala
145                 150                 155                 160
Ser Ala Thr Cys Gly Thr Thr Ala Phe Val Ala Gly Gly Val Gly Ile
                165                 170                 175
Met Pro Asn Asn Glu Val Tyr Asp Thr Ala Glu Arg Tyr Asn Pro Asp
            180                 185                 190
Ser Arg Leu Trp Glu Pro Leu Pro Arg Met Lys Arg Asn Arg Lys Leu
        195                 200                 205
Cys Ser Gly Cys Tyr Met Asp Asn Arg Phe Tyr Val Ile Gly Gly Arg
    210                 215                 220
Asn Lys Asn Gly Glu Leu Thr Cys Gly Glu Phe Phe Asp Glu Ala Lys
225                 230                 235                 240
Asn Lys Trp Glu Leu Ile Pro Asp Met Leu Lys Asp Asp Pro Val Gln
                245                 250                 255
Asp Tyr His Ser Pro Pro Leu Leu Ala Val Val Asn Asn Glu Leu Tyr
            260                 265                 270
Ser Leu Glu Ala Ser Ser Asn Gln Leu Lys Val Tyr Leu Lys Lys Thr
        275                 280                 285
Asn Thr Trp Lys Gln Leu Gly Pro Val Pro Val Arg Ala Asp Ser Asn
    290                 295                 300
Arg Gly Trp Gly Ile Ala Phe Lys Ser Leu Gly Asn Glu Leu Leu Val
305                 310                 315                 320
Ile Gly Ala Ala Ser Ser Ser Val Ser Tyr Ser Gly Asn Ser Met Ala
                325                 330                 335
Ile Tyr Thr Cys Cys Pro Asp Pro Glu Ala Met Glu Leu Gln Trp Lys
            340                 345                 350
Pro Leu Asp Ser Gly Arg Asn Arg Leu Ser Ser Phe Ile Leu Asn Cys
        355                 360                 365
Ser Val Met Val Ala
        370

<210> SEQ ID NO 47
<211> LENGTH: 1101
<212> TYPE: DNA
<213> ORGANISM: Nicotiana tabacum

<400> SEQUENCE: 47
actcatggtt tcaggtggga gttgttctga gcatgggtgt caacagcgcc tatgctctag    60
gatatgcagg cacaattatg gttcctttgg gttggactgg tggtgtaatt ggtcttgttt   120
tatcaactgt tatatcatta tatgcaagta ctcttatagc caagattcat gaatatgtat   180
gcaaatcttt tcttgataaa tattggattc atcatttagg gggacaagcc ttaaaggctt   240
tctatattct ctttagggat gaccatcaga tgaagctacc atacttcatc gcgattgctg   300
gattagcatg cgtcttattt gccattgctg ttcccacctt gtcatcacta aggatttggc   360
tggtgatttc atcagtgttc agtctaattt atctcagtat agcatttgcg ttgtctctta   420
```

```
aagatggtat gaaggctcct cctagggact atagcattcc aggatcaaag ataaacagaa      480 ttttacaac tgctggtgca gctgcaaata ttgctacagt aagagcacct gttgttgaca       540
acagtttagg agctgtgcct gttcatgctg ttacttacat tggatattgg gcttatggat     600
ccagttcatc ttcctatttg ctcaacaatg tcagcggtcc ggtttgggtt aaggcactgg     660
ctaacatcag tgcattcttg caagctatca tcactttgca tatatttgca agtccaacat     720
atgagtttct ggatacaaaa tatggaatta aaggaagtgc agttgctgtt cgaaacctgg     780
cgtttagaac tctagttaga ggtggttata tagccattac aacttttccta tctgctttgt    840 tacctttcct gggagatttc atgagtctta ctggtgctat cagctcaatt ccgctcacgt     900
ttatacttcc aaatcacatg taccttgttg ccatgaaaaa gcaactgtcg tcgttacaaa     960
ggagttggca tttgcttaat gttgtcttgt ttagtgtcat atctgctgct gcattagtag    1020
ctgcattcag gcttatagca gtggactcga aaacttacaa cgcatttgct gatttgtagt    1080 tttagagtc attatttgga g                                               1101
```

<210> SEQ ID NO 48
<211> LENGTH: 348
<212> TYPE: PRT
<213> ORGANISM: Nicotiana tabacum

<400> SEQUENCE: 48

```
Met Gly Val Asn Ser Ala Tyr Ala Leu Gly Tyr Ala Gly Thr Ile Met
1               5                   10                  15

Val Pro Leu Gly Trp Thr Gly Gly Val Ile Gly Leu Val Leu Ser Thr
            20                  25                  30

Val Ile Ser Leu Tyr Ala Ser Thr Leu Ile Ala Lys Ile His Glu Tyr
        35                  40                  45

Val Cys Lys Ser Phe Leu Asp Lys Tyr Trp Ile His Leu Gly Gly
    50                  55                  60

Gln Ala Leu Lys Ala Phe Tyr Ile Leu Phe Arg Asp Asp His Gln Met
65                  70                  75                  80

Lys Leu Pro Tyr Phe Ile Ala Ile Ala Gly Leu Ala Cys Val Leu Phe
                85                  90                  95

Ala Ile Ala Val Pro Thr Leu Ser Ser Leu Arg Ile Trp Leu Val Ile
            100                 105                 110

Ser Ser Val Phe Ser Leu Ile Tyr Leu Ser Ile Ala Phe Ala Leu Ser
        115                 120                 125

Leu Lys Asp Gly Met Lys Ala Pro Pro Arg Asp Tyr Ser Ile Pro Gly
    130                 135                 140

Ser Lys Ile Asn Arg Ile Phe Thr Thr Ala Gly Ala Ala Ala Asn Ile
145                 150                 155                 160

Ala Thr Val Arg Ala Pro Val Val Asp Asn Ser Leu Gly Ala Val Pro
                165                 170                 175

Val His Ala Val Thr Tyr Ile Gly Tyr Trp Ala Tyr Gly Ser Ser
            180                 185                 190

Ser Ser Tyr Leu Leu Asn Asn Val Ser Gly Pro Val Trp Val Lys Ala
        195                 200                 205

Leu Ala Asn Ile Ser Ala Phe Leu Gln Ala Ile Ile Thr Leu His Ile
    210                 215                 220

Phe Ala Ser Pro Thr Tyr Glu Phe Leu Asp Thr Lys Tyr Gly Ile Lys
225                 230                 235                 240

Gly Ser Ala Val Ala Val Arg Asn Leu Ala Phe Arg Thr Leu Val Arg
```

```
                    245                 250                 255
Gly Gly Tyr Ile Ala Ile Thr Thr Phe Leu Ser Ala Leu Leu Pro Phe
            260                 265                 270

Leu Gly Asp Phe Met Ser Leu Thr Gly Ala Ile Ser Ser Ile Pro Leu
        275                 280                 285

Thr Phe Ile Leu Pro Asn His Met Tyr Leu Val Ala Met Lys Lys Gln
    290                 295                 300

Leu Ser Ser Leu Gln Arg Ser Trp His Leu Leu Asn Val Val Leu Phe
305                 310                 315                 320

Ser Val Ile Ser Ala Ala Ala Leu Val Ala Ala Phe Arg Leu Ile Ala
                325                 330                 335

Val Asp Ser Lys Thr Tyr Asn Ala Phe Ala Asp Leu
            340                 345

<210> SEQ ID NO 49
<211> LENGTH: 1562
<212> TYPE: DNA
<213> ORGANISM: Nicotiana tabacum

<400> SEQUENCE: 49
gaagaagtgg taaaattgat aagtgaaatt ggagggaaaa atgaacggag gagatatgaa      60
tcagcaacag caacagcagc agcaacaaca acagcagcaa caacaacaac agtggatggc     120
gatgcagcag tatcagcagc aatggatggc gatgcagtat ccagcagcag caatggcgat     180
gcagcaacag atgatgtatg gtcagcaata catgccttac agcaacatca acaacagcag     240
cagaagatgc agcagtcccc tactcagatt cagagctcat ctgaagataa taaaacgatc     300
tggattggtg atcttcagca gtggatggat gaaagttatc ttcattcttg ctttctcaa      360
gctggcgagg ttatttctgt gaaaattatt cgaaacaagc agactggtca atcagagcgt     420
tatggatttg ttgagttcaa tactcacgca gcagcggaga agtgctacga gctacaat      480
ggcactatga tgccaaatgc agagcaaccc ttccgtttaa actgggcagg ctttagcact     540
ggtgaaaagc gtgcagaaac tggttctgat ttctcgattt ttgtaggaga tttggcttct     600
gatgttactg atacaatgtt gcgtgacaca tttgctagta gatatccatc tcttaaaggt     660
gcaaaagtag tagtagatgc aaacacaggc cactcaaaag gctatggctt tgtaaggttt     720
ggtgatgaaa gcgagaggtc tcgggccatg actgagatga atggtgtata ttgttccagc     780
agggccatgc gtattggtgt tgctaccccca agaaaccat cagcacagca acaatattct     840
tcacaagctg tgatattatc tggtggatat gcatcaaatg gtgctgcaac ccatggatcc     900
cagtctgatg gtgattcatc aaacactaca atttttgttg gaggacttga ttctgatgtc     960
actgacgagg aacttaggca atcctttaat cagtttggag aagtggtctc tgtgaaaata    1020
cctgctggaa aaggatgtgg ttttgtacaa ttttctgaca ggagctctgc acaggaagcg    1080
atacagaaat taagtggagc aataattggc aagcaggcag ttcgtctttc ctggggcga     1140
agtccagcaa acaagcagat gagaactgat tctggtagtc aatggaatgg gggttataat    1200
ggaaggcaaa attatggagg atatggatat ggcgcatcgc aaaatcagga ttctggcatg    1260
tatgctactg gagcagctta cggagcatcc tctaatggat acgggaatca ccagcagcct    1320
gttagctgat ctctagtgga ctctgctgct aaatgagaga ttgccatagc tctgctctct    1380
cttccacttt ggggatcag atttatattt gacttataag cttaaagcat agtgtttgat     1440
gagaattttg tagctggatt tattttatgc ttagtgagtc caagatatgt taaacctaaa    1500
cttagaatga ttggtgaact tcgattttc tactgctttt ttccaaaaaa aaaaaaaaa      1560
``` aa                                                                    1562

<210> SEQ ID NO 50
<211> LENGTH: 395
<212> TYPE: PRT
<213> ORGANISM: Nicotiana tabacum

<400> SEQUENCE: 50

Met Asp Gly Asp Ala Val Ser Ser Ser Asn Gly Asp Ala Ala Thr
1               5                   10                  15

Asp Asp Val Trp Ser Ala Ile His Ala Leu Gln Gln His Gln Gln Gln
            20                  25                  30

Gln Gln Lys Met Gln Gln Ser Pro Thr Gln Ile Gln Ser Ser Ser Glu
        35                  40                  45

Asp Asn Lys Thr Ile Trp Ile Gly Asp Leu Gln Gln Trp Met Asp Glu
50                  55                  60

Ser Tyr Leu His Ser Cys Phe Ser Gln Ala Gly Glu Val Ile Ser Val
65                  70                  75                  80

Lys Ile Ile Arg Asn Lys Gln Thr Gly Gln Ser Glu Arg Tyr Gly Phe
                85                  90                  95

Val Glu Phe Asn Thr His Ala Ala Ala Glu Lys Val Leu Gln Ser Tyr
            100                 105                 110

Asn Gly Thr Met Met Pro Asn Ala Glu Gln Pro Phe Arg Leu Asn Trp
        115                 120                 125

Ala Gly Phe Ser Thr Gly Glu Lys Arg Ala Glu Thr Gly Ser Asp Phe
    130                 135                 140

Ser Ile Phe Val Gly Asp Leu Ala Ser Asp Val Thr Asp Thr Met Leu
145                 150                 155                 160

Arg Asp Thr Phe Ala Ser Arg Tyr Pro Ser Leu Lys Gly Ala Lys Val
                165                 170                 175

Val Val Asp Ala Asn Thr Gly His Ser Lys Gly Tyr Gly Phe Val Arg
            180                 185                 190

Phe Gly Asp Glu Ser Glu Arg Ser Arg Ala Met Thr Glu Met Asn Gly
        195                 200                 205

Val Tyr Cys Ser Ser Arg Ala Met Arg Ile Gly Val Ala Thr Pro Lys
    210                 215                 220

Lys Pro Ser Ala Gln Gln Gln Tyr Ser Ser Gln Ala Val Ile Leu Ser
225                 230                 235                 240

Gly Gly Tyr Ala Ser Asn Gly Ala Ala Thr His Gly Ser Gln Ser Asp
                245                 250                 255

Gly Asp Ser Ser Asn Thr Thr Ile Phe Val Gly Gly Leu Asp Ser Asp
            260                 265                 270

Val Thr Asp Glu Glu Leu Arg Gln Ser Phe Asn Gln Phe Gly Glu Val
        275                 280                 285

Val Ser Val Lys Ile Pro Ala Gly Lys Gly Cys Gly Phe Val Gln Phe
    290                 295                 300

Ser Asp Arg Ser Ser Ala Gln Glu Ala Ile Gln Lys Leu Ser Gly Ala
305                 310                 315                 320

Ile Ile Gly Lys Gln Ala Val Arg Leu Ser Trp Gly Arg Ser Pro Ala
                325                 330                 335

Asn Lys Gln Met Arg Thr Asp Ser Gly Ser Gln Trp Asn Gly Gly Tyr
            340                 345                 350

Asn Gly Arg Gln Asn Tyr Gly Gly Tyr Gly Tyr Gly Ala Ser Gln Asn
        355                 360                 365

Gln Asp Ser Gly Met Tyr Ala Thr Gly Ala Ala Tyr Gly Ala Ser Ser
    370                 375                 380

Asn Gly Tyr Gly Asn His Gln Gln Pro Val Ser
385                 390                 395

<210> SEQ ID NO 51
<211> LENGTH: 646
<212> TYPE: DNA
<213> ORGANISM: Artificial Sequence
<220> FEATURE:
<223> OTHER INFORMATION: synthetic oligonucleotide

<400> SEQUENCE: 51
ggatccaaag agcaggccag cgatatggaa gctgatcaag aagaaagcac gggaagccca      60
agacttaaaa tcagccagtc gaagagagat gatctccctc gatccttatc tgcagcagat     120
ggaaataaga caagagaaat ggaaatccga cgaatgagca gtcatatcca ttctagtggc     180
ctctacagaa atgaggatgc aaatcttgag gctgcaaatg gtgtcgcagg ttctttactt     240
gaacatttta ggaatttagg aaatgcttgt tcgtcatttg ttttgtgtcc tagcctattg     300
tttattgttt gttttatct tcactttagt gaggatacat attctgagca cactctgaaa      360
atatagctca tttatgttta tagggaaagg agaaaagaga gagtcacatc atggcaactg     420
cgacaccatt tgcagcctca agatttgcat cctcatttct gtagaggcca ctagaatgga     480
tatgactgct cattcgtcgg atttccattt ctcttgtctt atttccatct gctgcagata     540
aggatcgagg gagatcatct ctcttcgact ggctgatttt aagtcttggg cttcccgtgc     600
tttcttcttg atcagcttcc atatcgctgg cctgctcttt tctaga                   646

<210> SEQ ID NO 52
<211> LENGTH: 604
<212> TYPE: DNA
<213> ORGANISM: Artificial Sequence
<220> FEATURE:
<223> OTHER INFORMATION: synthetic oligonucleotide

<400> SEQUENCE: 52
ggatccgttt tggtcctttg cataaaattt gggtaaggaa aagaatcaat ccaaagccac      60
cgaaattcaa cagtaggaca agtctcagtg tttgcatctg caaaaccatt ccaaatttca     120
caatccacga aactgtgtaa caataactaa acataacga aataaatact aggagtataa      180
tctataggca caaattgaa gttgtgcatg ttctttactt gaacatttta ggaatttagg      240
aaatgcttgt tcgtcatttg ttttgtgtcc tagcctattg tttattgttt gttttatct     300 tcactttagt gaggatacat attctgagca cactctgaaa atatagctca tttatgttta     360
tagggaaagg agaaaagaga gagtcacatc atggatgcac aacttcaatt ttgtgcctat     420
agattatact cctagtattt atttcgttat gttttagtta ttgttacaca gtttcgtgga     480
ttgtgaaatt tggaatggtt ttgcagatgc aaacactgag acttgtccta ctgttgaatt     540
tcggtggctt tggattgatt cttttcctta cccaaatttt atgcaaagga ccaaaacgtc     600
taga                                                                  604

<210> SEQ ID NO 53
<211> LENGTH: 603
<212> TYPE: DNA
<213> ORGANISM: Artificial Sequence
<220> FEATURE:
<223> OTHER INFORMATION: synthetic oligonucleotide

<400> SEQUENCE: 53

```
ggatccaaag atttcaagga ccttatttat gctcccaaac gaggtcacaa tcctatgatt      60
ataaacagcc tccacagcag tttgagtgct ttgatattgt gccttgacga acttagctgt     120
gatggtggat agcaagactt ttcgcgtgta aaagcataga attgtgagag gttggacagc     180
aatcataact agtgcaagct tccaagcgtt ctttacttga acattttagg aatttaggaa     240
atgcttgttc gtcatttgtt ttgtgtccta gccattgtt tattgtttgt ttttatcttc      300
actttagtga ggatacatat tctgagcaca ctctgaaaat atagctcatt tatgtttata     360
gggaaaggag aaaagagaga gtcacatcat ggcaagcttg gaagcttgca ctagttatga     420
ttgctgtcca acctctcaca attctatgct tttacacgcg aaaagtcttg ctatccacca     480
tcacagctaa gttcgtcaag gcacaatatc aaagcactca aactgctgtg gaggctgttt     540
ataatcatag gattgtgacc tcgtttggga gcataaaataa ggtccttgaa atctttgtct     600
aga                                                                   603
```

<210> SEQ ID NO 54
<211> LENGTH: 665
<212> TYPE: DNA
<213> ORGANISM: Artificial Sequence
<220> FEATURE:
<223> OTHER INFORMATION: synthetic oligonucleotide

<400> SEQUENCE: 54

```
ggatccgtgt caacctcttc acttcttctt gctgctcaac ttgccttcac ggcaataggt      60
gctttcttca tagtgaagct gaaattcaca ccctactcta tcaatgcagt ggttctgttg     120
acagttggtg ctgttttatt aggtattcga tcaaatggtg atcggccaga gggtgtgaca     180
agtagagctt atatttactc tttgttcttt acttgaacat tttaggaatt taggaaatgc     240
ttgttcgtca tttgttttgt gtcctagcct attgtttatt gtttgttttt atcttcactt     300
tagtgaggat acatattctg agcacactct gaaaatatag ctcatttatg tttataggga     360
aaggagaaaa gagagagtca catcatggca agaaagata aacctttagt actagtgagg     420
cttgaacgtc tgtgacattt aaagtcctaa gttagtttct attgtaattg aatataagct     480
ctacttgtca caccctctgg ccgatcacca tttgatcgaa tacctaataa aacagcacca     540
actgtcaaca gaaccactgc attgatagag tagggtgtga atttcagctt cactatgaag     600
aaagcaccta ttgccgtgaa ggcaagttga gcagcaagaa gaagtgaaga ggttgacact     660
ctaga                                                                 665
```

<210> SEQ ID NO 55
<211> LENGTH: 600
<212> TYPE: DNA
<213> ORGANISM: Artificial Sequence
<220> FEATURE:
<223> OTHER INFORMATION: synthetic oligonucleotide

<400> SEQUENCE: 55

```
ggatccacac catctaaaac aaacgccaat gagttgattg gttgtgtacc agcgacaaac      60
tggcgaagga gcacaaggta aaagaacag ttaaagatag tgaaacaaaa gaagaacaaa     120
ttgaaacaaa catatagtac tactatttat tgaatgtata ccgggatggc aatggttatg     180
agacggataa cattttttgtc ctttgagttc tttacttgaa cattttagga atttaggaaa     240
tgcttgttcg tcatttgttt tgtgtccta g cctattgttt attgtttgtt tttatcttca     300
ctttagtgag gatacatatt ctgagcacac tctgaaaata tagctcattt atgtttatag     360
```

```
ggaaaggaga aaagagagag tcacatcatg gcaatcaaag gacaaaaatg ttatccgtct      420
cataaccatt gccatcccgg tatacattca ataaatagta gtactatatg tttgtttcaa      480
tttgttcttc ttttgtttca ctatctttaa ctgttctttt taccttgtgc tccttcgcca      540
gtttgtcgct ggtacacaac caatcaactc attggcgttt gttttagatg gtgttctaga      600
```

<210> SEQ ID NO 56
<211> LENGTH: 687
<212> TYPE: DNA
<213> ORGANISM: Artificial Sequence
<220> FEATURE:
<223> OTHER INFORMATION: synthetic oligonucleotide

<400> SEQUENCE: 56

```
ggatccatgg gctgatgttc atggtttcaa tggggttcaa tgctgctgct agtgtaaggg       60
tgagcaatga gttaggagca ccacacccaa agtcagcagc attcttagtg tttgtggtga      120
cattcatttc atttctcata gctgtggtgg aagccataat tatgctgtgt ttgcgcaatg      180
tgatcagcta tgcattcact aagggttact ctttgttctt tacttgaaca ttttaggaat      240
ttaggaaatg cttgttcgtc atttgttttg tgtcctagcc tattgtttat tgtttgtttt      300
tatcttcact ttagtgagga tacatattct gagcacactc tgaaaatata gctcatttat      360
gtttataggg aaaggagaaa agagagagtc acatcatggc aaagaaagat aaacctttag      420
tactagtgag gcttgaacgt ctgtgacatt taaagtccta agttagtttc tattgtaatt      480
gacccttagt gaatgcatag ctgatcacat tgcgcaaaca cagcataatt atggcttcca      540
ccacagctat gagaaatgaa atgaatgtca ccacaaacac taagaatgct gctgactttg      600
ggtgtggtgc tcctaactca ttgctcaccc ttacactagc agcagcattg aaccccattg      660
aaaccatgaa catcagccca ttctaga                                          687
```

<210> SEQ ID NO 57
<211> LENGTH: 3155
<212> TYPE: DNA
<213> ORGANISM: Artificial Sequence
<220> FEATURE:
<223> OTHER INFORMATION: synthetic nucleic acid construct

<400> SEQUENCE: 57

```
aagcttccag aaggtaatta tccaagatgt agcatcaaga atccaatgtt tacgggaaaa       60
actatggaag tattatgtga gctcagcaag aagcagatca atatgcggca catatgcaac      120
ctatgttcaa aaatgaagaa tgtacagata caagatccta tactgccaga atacgaagaa      180
gaatacgtag aaattgaaaa agaagaacca ggcgaagaaa agaatcttga agacgtaagc      240
actgacgaca caatgaaaaa gaagaagata aggtcggtga ttgtgaaaga gacatagagg      300
acacatgtaa ggtggaaaat gtaagggcgg aaagtaacct tatcacaaag gaatcttatc      360
ccccactact tatcctttta tatttttccg tgtcattttt gcccttgagt tttcctatat      420
aaggaaccaa gttcggcatt tgtgaaaaca agaaaaaatt tggtgtaagc tatttttcttt     480 gaagtactga ggatacaact tcagagaaat ttgtaagttt gtggatcctg caggctagcg      540
tgcactctag actcgacgaa ctgacagct cgaattcccc cgatcgttca acatttggc        600 aataaagttt cttaagattg aatcctgttg ccggtcttgc gatgattatc atataatttc      660
tgttgaatta cgttaagcat gtaataatta acatgtaatg catgacgtta tttatgagat      720
gggtttttat gattagagtc ccgcaattat acatttaata cgcgatagaa aacaaaatat      780
```

```
agcgcgcaaa ctatgataaa ttatcgcgcg cggtgtcatc tatgttacta gatcgggaat      840
tcctcgagca actatttta tgtatgcaag agtcagcata tgtataattg attcagaatc       900
gttttgacga gttcggatgt agtagtagcc attatttaat gtacatacta atcgtgaata      960
gtgaatatga tgaaacattg tatcttattg tataaatatc cataaacaca tcatgaaaga     1020
cactttcttt cacggtctga attaattatg atacaattct aatagaaaac gaattaaatt     1080
acgttgaatt gtatgaaatc taattgaaca agccaaccac gacgacgact aacgttgcct     1140
ggattgactc ggtttaagtt aaccactaaa aaacggagc tgtcatgtaa cacgcggatc      1200
gagcaggtca cagtcatgaa gccatcaaag caaagaact aatccaaggg ctgagatgat      1260
taattagttt aaaaattagt taacacgagg gaaaaggctg tctgacagcc aggtcacgtt     1320
atctttacct gtggtcgaaa tgattcgtgt ctgtcgattt taattatttt tttgaaaggc     1380
cgaaaataaa gttgtaagag ataaacccgc ctatataaat tcatatattt tcctctccgc     1440
tttgaattgt ctcgttgtcc tcctcacttt catcagccgt tttgaatctc cggcgacttg     1500
acagagaaga acaaggaaga agactaagag agaaagtaag agataatcca ggagattcat     1560
tctccgtttt gaatcttcct caatctcatc ttcttccgct cttttctttcc aaggtaatag    1620 gaactttctg gatctacttt atttgctgga tctcgatctt gttttctcaa tttccttgag     1680
atctggaatt cgtttaattt ggatctgtga acctccacta aatcttttgg ttttactaga     1740
atcgatctaa gttgaccgat cagttagctc gattatagct accagaattt ggcttgacct     1800
tgatggagag atccatgttc atgttacctg ggaaatgatt tgtatatgtg aattgaaatc     1860
tgaactgttg aagttagatt gaatctgaac actgtcaatg ttagattgaa tctgaacact     1920
gtttaaggtt agatgaagtt tgtgtataga ttcttcgaaa ctttaggatt tgtagtgtcg     1980
tacgttgaac agaaagctat ttctgattca atcagggttt atttgactgt attgaactct     2040
ttttgtgtgt ttgcagctca taaaaggtac caaacaatga ttgaacaaga tggattgcac     2100
gcaggttctc cggccgcttg ggtggagagg ctattcggct atgactgggc acaacagaca     2160
atcggctgct ctgatgccgc cgtgttccgg ctgtcagcgc agggcgcc ggttctttttt      2220 gtcaagaccg acctgtccgg tgccctgaat gaactgcagg acgaggcagc gcggctatcg     2280
tggctggcca cgacgggcgt tccttgcgca gctgtgctcg acgttgtcac tgaagcggga     2340
agggactggc tgctattggg cgaagtgccg gggcaggatc tcctgtcatc tcaccttgct     2400
cctgccgaga aagtatccat catggctgat gcaatgcggc ggctgcatac gcttgatccg     2460
gctacctgcc cattcgacca ccaagcgaaa catcgcatcg agcgagcacg tactcggatg     2520
gaagccggtc ttgtcgatca ggatgatctg gacgaagagc atcaggggct cgcgccagcc     2580
gaactgttcg ccaggctcaa ggcgcgcatg cccgacggcg aggatctcgt cgtgacccat     2640
ggcgatgcct gcttgccgaa tatcatggtg gaaaatggcc gcttttctgg attcatcgac     2700
tgtggccggc tgggtgtggc ggaccgctat caggacatag cgttggctac ccgtgatatt     2760
gctgaagagc ttggcggcga atgggctgac cgcttcctcg tgctttacgg tatcgccgct     2820
cccgattcgc agcgcatcgc cttctatcgc cttcttgacg agttcttttg agcgggactc     2880
tggcgatcgc cccgatcgtt caaacatttg gcaataaagt ttcttaagat tgaatcctgt     2940
tgccggtctt gcgatgatta tcatataatt tctgttgaat tacgttaagc atgtaataat     3000
taacatgtaa tgcatgacgt tatttatgag atgggttttt atgattagag tcccgcaatt     3060
atacatttaa tacgcgatag aaaacaaaat atagcgcgca aactaggata aattatcgcg     3120
cgcggtgtca tctatgttac tagatcggga ctagt                               3155
```

<210> SEQ ID NO 58
<211> LENGTH: 47
<212> TYPE: DNA
<213> ORGANISM: Artificial Sequence
<220> FEATURE:
<223> OTHER INFORMATION: synthetic oligonucleotide

<400> SEQUENCE: 58
tatgttattc actaaatcat agttaattaa tatatatttt tacctta    47

<210> SEQ ID NO 59
<211> LENGTH: 47
<212> TYPE: DNA
<213> ORGANISM: Artificial Sequence
<220> FEATURE:
<223> OTHER INFORMATION: synthetic oligonucleotide

<400> SEQUENCE: 59
ttcacaacta gaagagcgtg agacctttc aattagaatt cgtagga    47

<210> SEQ ID NO 60
<211> LENGTH: 47
<212> TYPE: DNA
<213> ORGANISM: Artificial Sequence
<220> FEATURE:
<223> OTHER INFORMATION: synthetic oligonucleotide

<400> SEQUENCE: 60
tccttaaatc ggtcatggaa agtgagaata atcagggcaa taaaaaa    47

<210> SEQ ID NO 61
<211> LENGTH: 201
<212> TYPE: DNA
<213> ORGANISM: Artificial Sequence
<220> FEATURE:
<223> OTHER INFORMATION: synthetic oligonucleotide

<400> SEQUENCE: 61
aattcaaacc tgtcaaaacc ataaaaagat attggacaaa tgcttttaat ataattgcct    60
tagattaatc tatatatata tatatatata taggtaaa tacttacttg tatcagacat    120
ttatctttat aaatatgtta ttcactaaat catagttaat taatatatat ttttaccttaa    180 aggggccgtt tggttgggaa a    201

<210> SEQ ID NO 62
<211> LENGTH: 201
<212> TYPE: DNA
<213> ORGANISM: Artificial Sequence
<220> FEATURE:
<223> OTHER INFORMATION: synthetic oligonucleotide

<400> SEQUENCE: 62
tatcgcacta ctattgaacc tatcgccttt tgagttttga tatataaata gcgacgaacg    60
tttcttagat aatggactca taacctccct cttcacaact agaagagcgt gagaccttt    120 caattagaat tcgtaggaaa aaatcaaaca caaattcaca aaacaaaaat ttattaagat    180
ttcagcgacc aagcccgtga g    201

<210> SEQ ID NO 63
<211> LENGTH: 214
<212> TYPE: DNA
<213> ORGANISM: Artificial Sequence
<220> FEATURE:

<223> OTHER INFORMATION: synthetic oligonucleotide

<400> SEQUENCE: 63

| | | |
|---|---|---|
| tcgtttgaga aaaacggtcc ttaaatcggt catggaaagt gagaataatc agggcaataa | 60 |
| aaaagttgtt cataaggaag ttgatgttcg gaatctggga ttgaatgagc gacaagagtt | 120 |
| cattgatcga tttttcaggg ttgctgagga agataatgaa aagtttctga gaaagttcag | 180 |
| aaatcgaatt gacaagtaag tttccagtat tact | 214 |

<210> SEQ ID NO 64
<211> LENGTH: 211
<212> TYPE: DNA
<213> ORGANISM: Artificial Sequence
<220> FEATURE:
<223> OTHER INFORMATION: synthetic oligonucleotide

<400> SEQUENCE: 64

| | | |
|---|---|---|
| acaagccaca agctacacta tccaaagagc aggccagcga tatggaagct gagcaagaag | 60 |
| aaagcacggg aacccctaga cttcgaatca gccagtcgaa gagagatgat ctccctcgat | 120 |
| ccttatctgc agcagatggg aacaagacaa gtatgatctt tagcccatca ataacagaat | 180 |
| ctgcttgggg aatataagta atgcttacag t | 211 |

<210> SEQ ID NO 65
<211> LENGTH: 200
<212> TYPE: DNA
<213> ORGANISM: Artificial Sequence
<220> FEATURE:
<223> OTHER INFORMATION: synthetic oligonucleotide

<400> SEQUENCE: 65

| | | |
|---|---|---|
| atacgataag tcctcttaaa attaccatac ttataaagtc ataaagtag aagaaaaag | 60 |
| gacctctttg aaaattttta tataaaggg gctgaaaata tgcgataatg tcaagtagca | 120 |
| gtttggcttc atatattggt ccatgttatc ggagttggta tttatgttaa atattaagta | 180 |
| cttttttatc atatctatca | 200 |

<210> SEQ ID NO 66
<211> LENGTH: 202
<212> TYPE: DNA
<213> ORGANISM: Artificial Sequence
<220> FEATURE:
<223> OTHER INFORMATION: synthetic oligonucleotide

<400> SEQUENCE: 66

| | | |
|---|---|---|
| actcaatttc tgccactttta ttataaatag taagttagta ttccattctt ggtcagaaag | 60 |
| gagtatggga aatcaaggtc tattttctta gttacagacc taacaatttc cattgtcacc | 120 |
| ttttttcagc tgttggcgtg tagaaacgga cctttgagca ttgttgatgc gtttgacttg | 180 |
| ttttagaaaa gaaaaaagaa tg | 202 |

<210> SEQ ID NO 67
<211> LENGTH: 234
<212> TYPE: DNA
<213> ORGANISM: Artificial Sequence
<220> FEATURE:
<223> OTHER INFORMATION: synthetic oligonucleotide

<400> SEQUENCE: 67

| | | |
|---|---|---|
| ggctagttgt ggcttggaag cttgcactag ttatgattgc tgtccaacct ctcacaattc | 60 |
| tatgctttta cacgcgaaaa gtcttgctat ccaccatcac agctaagttc gtcaaggcac | 120 |

```
aatatcaaag cactcaaact gctgtggagg ctgtttataa tcataggatt gtgacctcgt    180
ttgggagcat aaataaggtc cttgaaatct ttgatgaggc acaggatgag tcaa          234

<210> SEQ ID NO 68
<211> LENGTH: 207
<212> TYPE: DNA
<213> ORGANISM: Artificial Sequence
<220> FEATURE:
<223> OTHER INFORMATION: synthetic oligonucleotide

<400> SEQUENCE: 68
tttttaacca cctagtggat gctaatatgg tgtcagcatt agaagaaact aattcatgat     60
ttaagtttta taggttcaat ttttagattt ttaatattaa atatattata ttttaaagtt    120
atgagttaat atttgttgaa gtatttgtta agtataatta taataaattt taacactaat   180
atttatattt atgctctgcg tcaacag                                       207

<210> SEQ ID NO 69
<211> LENGTH: 207
<212> TYPE: DNA
<213> ORGANISM: Artificial Sequence
<220> FEATURE:
<223> OTHER INFORMATION: synthetic oligonucleotide

<400> SEQUENCE: 69
tttttaacca cctagtggat gctaatatgg tgtcagcatt agaagaaact aattcatgat     60
ttaagtttta taggttcaat ttttagattt ttaatattaa atatattata ttttaaagtt    120
atgagttaat atttgttgaa gtatttgtta agtataatta taataaattt taacactaat   180
atttatattt atgctctgcg tcaacag                                       207

<210> SEQ ID NO 70
<211> LENGTH: 2544
<212> TYPE: DNA
<213> ORGANISM: Nicotiana tabacum

<400> SEQUENCE: 70
atggaattgg agaggggatt tccattgcta aacagcagt acaaagctttt attaagaag     60 aattttatag tggcatggag gaacaagaga gccacattcc ttcagttatt ctcatccctc   120
ttcttgatat tccttctttt tataatccaa aaagcaatag aagctcgctt tcttcttcc    180 tcctcttacg agaacgtgcg ggacccacaa ccgttagtgt cgccgccaat cccgccctgt   240
gaacaaaaga acttcatccg tctcccctgc tatgattttg tttggagtgg ttctcagagt   300
ccaaaaatcg ggcagattgc gagcagaatt atggctaata atcctggccg gtctattcct   360
acctctaagg ttctgtcatt tagaacacga gatgaagtgg atgaatggct ttcaaaaac    420 cctatgcgtt gtcctggagc tctgcacttt gttgaaagga atgctagcat aatcagttat   480
ggcatacaga caaactccac tcctgttgtc aaacgaggag tctttgaaga tccaactttt   540
aaattccaaa tcccacttca actggcagca gaacgtgaaa ttgcaagatc tctgattgga   600
gatccaaact tcagtggggt tgtcagtttc aaagaatttg cacatcctgc ttttgaagtt   660
ttctcagcct tgggtgctgt tgggcctacc ttttcttgg ctgttgctat gtttggcttt   720
gtcttccaaa tcaatgtttt gatcattgaa aaggaactca aacttcggca ggcaatgact   780
atgatgggtc tctatgatac tgcctactgg ttgtcatggt tcacatggga gggattcatc   840
acacttatct cctctcttct catagttctc tttgggatga tgtttcaatt tgagtttttc   900
```

```
ttgaacaaca gttttgccgt cgtgtttctc cttttttcc ttttccagct taatatgatt    960
ggttttgcat tcatgctgtc tgcttttatt agcaagtcat cttcaacaac aactgtgggt   1020
ttcttcacat ttattgtcga tcttcttgct caaggtcttc agttacttgc tgatgcaact   1080
gccactcctg aagatcctgg tgtcagctgg agtggtagga caaaatgtgc ttttaatgat   1140
accgagtgtg taataactat gaatgagatt tacgtatggc tcgtgtcaac attctttctg   1200
tggtttgttc ttgctattta cttggacaac ataattccga atgttctgg tgtgagaaaa    1260
tcaatgttct acttcttgaa tcctggatac tggacaggca aaggtggaaa taaggtgaaa   1320
gaggggggta tttgtagctg cacaggttca gtgccgtccc tggatagtat tataccagat   1380
gatgaagatg ttcttgaaga agagaacatt gttaaacgcc aagctacgca aggtgaagtt   1440
gattctgata ttgcagttca actacatggc cttgtaaaga tatttccagg aacagcaaag   1500
atgggctgct gtaagtgcca aaggaaatct ccttatcatg ccctcaaggg cttatgggtg   1560
aatcttgcaa aggatcagct attttgtctt cttgggccga acggagctgg aaaaactact   1620
gctattaatt gtttgactgg gattacacct gttactgcag agatgcact agtatatggt    1680
cagtctataa gaagctctac gggcatgtca acattcgaa ggatgatagg ggtttgtccc    1740
cagtttgata ttctttggga tgcattgtcc ggtcaagaac acctgcatct ttttgccagc   1800
attaaaggtc tacccactgc tttagtaaaa gaggtcgtag agaagtcact agccgaggta   1860
aaactcacag acgcagccag aatgagagct ggtagttaca gtggaggaat gaaacgacgc   1920
ctcagtgttg ctatagcact tattggtgaa ccgaaattgc tcatttttgga tgaaccgact   1980
actggtatgg atccaataac tagaagacat gtctgggata taattgagga tgcaaaaaaa   2040
gggcgtgcta ttatactgac cactcattca atggaagaag ctgacatctt aagtgaccgt   2100
gttggtatca tggcaaaggg tagacttcgt tgcattggaa cttcaataag attgaaatca   2160
aggtttggaa ctggtttcat tgctaatgta agcttttctg gtgggacaaa cgggactcct   2220
gaaacaggag atactttgag tacatctcaa cctgaagctg tgaaacagtt ctttaaagt    2280
cgcttggacg tggtacctaa agaggaaaac aagtccttct taacctttat tattccccat   2340
gacaaggaga agttgttgac ggacttcttt gctgagcttc aagatagaga gaaggaattt   2400
ggcattacag atatccagct tggtcttaca actcttgaag aagttttct aaacattgct    2460
agacaggcag aactggaaga tgttgctgaa ggaagcttcg cgactcttac tttaaattcc   2520
gggctctcac ttcaagtaag ttga                                          2544
```

<210> SEQ ID NO 71
<211> LENGTH: 847
<212> TYPE: PRT
<213> ORGANISM: Nicotiana tabacum

<400> SEQUENCE: 71

```
Met Glu Leu Glu Arg Gly Phe Pro Leu Leu Lys Gln Gln Tyr Lys Ala
1               5                   10                  15

Leu Leu Lys Lys Asn Phe Ile Val Ala Trp Arg Asn Lys Arg Ala Thr
            20                  25                  30

Phe Leu Gln Leu Phe Ser Ser Leu Phe Leu Ile Phe Leu Leu Phe Ile
        35                  40                  45

Ile Gln Lys Ala Ile Glu Ala Arg Phe Ser Ser Ser Ser Tyr Glu
    50                  55                  60

Asn Val Arg Asp Pro Gln Pro Leu Val Ser Pro Pro Ile Pro Pro Cys
65                  70                  75                  80
```

-continued

```
Glu Gln Lys Asn Phe Ile Arg Leu Pro Cys Tyr Asp Phe Val Trp Ser
                85                  90                  95
Gly Ser Gln Ser Pro Lys Ile Gly Gln Ile Ala Ser Arg Ile Met Ala
            100                 105                 110
Asn Asn Pro Gly Arg Ser Ile Pro Thr Ser Lys Val Leu Ser Phe Arg
            115                 120                 125
Thr Arg Asp Glu Val Asp Glu Trp Leu Phe Lys Asn Pro Met Arg Cys
            130                 135                 140
Pro Gly Ala Leu His Phe Val Glu Arg Asn Ala Ser Ile Ile Ser Tyr
145                 150                 155                 160
Gly Ile Gln Thr Asn Ser Thr Pro Val Val Lys Arg Gly Val Phe Glu
                165                 170                 175
Asp Pro Thr Phe Lys Phe Gln Ile Pro Leu Gln Leu Ala Ala Glu Arg
            180                 185                 190
Glu Ile Ala Arg Ser Leu Ile Gly Asp Pro Asn Phe Ser Trp Val Val
            195                 200                 205
Ser Phe Lys Glu Phe Ala His Pro Ala Phe Glu Val Phe Ser Ala Leu
    210                 215                 220
Gly Ala Val Gly Pro Thr Phe Leu Ala Val Ala Met Phe Gly Phe
225                 230                 235                 240
Val Phe Gln Ile Asn Val Leu Ile Ile Glu Lys Glu Leu Lys Leu Arg
                245                 250                 255
Gln Ala Met Thr Met Met Gly Leu Tyr Asp Thr Ala Tyr Trp Leu Ser
            260                 265                 270
Trp Phe Thr Trp Glu Gly Phe Ile Thr Leu Ile Ser Ser Leu Leu Ile
            275                 280                 285
Val Leu Phe Gly Met Met Phe Gln Phe Glu Phe Phe Leu Asn Asn Ser
    290                 295                 300
Phe Ala Val Val Phe Leu Leu Phe Leu Phe Gln Leu Asn Met Ile
305                 310                 315                 320
Gly Phe Ala Phe Met Leu Ser Ala Phe Ile Ser Lys Ser Ser Thr
                325                 330                 335
Thr Thr Val Gly Phe Phe Thr Phe Ile Val Asp Leu Leu Ala Gln Gly
            340                 345                 350
Leu Gln Leu Leu Ala Asp Ala Thr Ala Thr Pro Glu Asp Pro Gly Val
    355                 360                 365
Ser Trp Ser Gly Arg Thr Lys Cys Ala Phe Asn Asp Thr Glu Cys Val
    370                 375                 380
Ile Thr Met Asn Glu Ile Tyr Val Trp Leu Val Ser Thr Phe Leu
385                 390                 395                 400
Trp Phe Val Leu Ala Ile Tyr Leu Asp Asn Ile Ile Pro Asn Val Ser
                405                 410                 415
Gly Val Arg Lys Ser Met Phe Tyr Phe Leu Asn Pro Gly Tyr Trp Thr
            420                 425                 430
Gly Lys Gly Gly Asn Lys Val Lys Glu Gly Ile Cys Ser Cys Thr
            435                 440                 445
Gly Ser Val Pro Ser Leu Asp Ser Ile Ile Pro Asp Glu Asp Val
    450                 455                 460
Leu Glu Glu Glu Asn Ile Val Lys Arg Gln Thr Gln Gly Glu Val
465                 470                 475                 480
Asp Ser Asp Ile Ala Val Gln Leu His Gly Leu Val Lys Ile Phe Pro
                485                 490                 495
Gly Thr Ala Lys Met Gly Cys Cys Lys Cys Gln Arg Lys Ser Pro Tyr
```

```
                500             505             510
His Ala Leu Lys Gly Leu Trp Val Asn Leu Ala Lys Asp Gln Leu Phe
            515                 520                 525
Cys Leu Leu Gly Pro Asn Gly Ala Gly Lys Thr Thr Ala Ile Asn Cys
        530                 535                 540
Leu Thr Gly Ile Thr Pro Val Thr Ala Gly Asp Ala Leu Val Tyr Gly
545                 550                 555                 560
Gln Ser Ile Arg Ser Ser Thr Gly Met Ser Asn Ile Arg Arg Met Ile
                565                 570                 575
Gly Val Cys Pro Gln Phe Asp Ile Leu Trp Asp Ala Leu Ser Gly Gln
            580                 585                 590
Glu His Leu His Leu Phe Ala Ser Ile Lys Gly Leu Pro Thr Ala Leu
        595                 600                 605
Val Lys Glu Val Val Glu Lys Ser Leu Ala Glu Val Lys Leu Thr Asp
610                 615                 620
Ala Ala Arg Met Arg Ala Gly Ser Tyr Ser Gly Gly Met Lys Arg Arg
625                 630                 635                 640
Leu Ser Val Ala Ile Ala Leu Ile Gly Glu Pro Lys Leu Leu Ile Leu
                645                 650                 655
Asp Glu Pro Thr Thr Gly Met Asp Pro Ile Thr Arg Arg His Val Trp
            660                 665                 670
Asp Ile Ile Glu Asp Ala Lys Lys Gly Arg Ala Ile Ile Leu Thr Thr
        675                 680                 685
His Ser Met Glu Glu Ala Asp Ile Leu Ser Asp Arg Val Gly Ile Met
        690                 695                 700
Ala Lys Gly Arg Leu Arg Cys Ile Gly Thr Ser Ile Arg Leu Lys Ser
705                 710                 715                 720
Arg Phe Gly Thr Gly Phe Ile Ala Asn Val Ser Phe Ser Gly Gly Thr
                725                 730                 735
Asn Gly Thr Pro Glu Thr Gly Asp Thr Leu Ser Thr Ser Gln Pro Glu
            740                 745                 750
Ala Val Lys Gln Phe Phe Lys Ser Arg Leu Asp Val Val Pro Lys Glu
        755                 760                 765
Glu Asn Lys Ser Phe Leu Thr Phe Ile Ile Pro His Asp Lys Glu Lys
        770                 775                 780
Leu Leu Thr Asp Phe Phe Ala Glu Leu Gln Asp Arg Glu Lys Glu Phe
785                 790                 795                 800
Gly Ile Thr Asp Ile Gln Leu Gly Leu Thr Thr Leu Glu Glu Val Phe
                805                 810                 815
Leu Asn Ile Ala Arg Gln Ala Glu Leu Glu Asp Val Ala Glu Gly Ser
            820                 825                 830
Phe Ala Thr Leu Thr Leu Asn Ser Gly Leu Ser Leu Gln Val Ser
        835                 840                 845

<210> SEQ ID NO 72
<211> LENGTH: 3054
<212> TYPE: DNA
<213> ORGANISM: Nicotiana tabacum

<400> SEQUENCE: 72
atggcggatg gtccagcgag cttctggact caagccaatg ctttgctcag aaagaatttg      60
acttttcaga tgggtagaaa cttttttcagc agtggatcaa ctctaaattc ctctgacatt     120
ttctatagct tagcctataa tatcttgggt tccgagtcgc agactgagct tatgaatttt     180
```

```
ctcgaggcag ctttcttctc caacttgcca gtctacaatc ttcgacctca atgtcctcca    240
aactctacat tttcttttcc attggaattt ggttctgtag ctgttcagca agagataagc    300
tgtgtgaaag gtatacactt gtggcgtaat agttcttatg agatcaatga tgagctttat    360
aaaggttaca ggaaaggaaa tccagaggga aagataaacg agataatagc agcatatgat    420
ttctttaatt caaacagaaa tggtttcaat gtgaatattt ggtataactc tacgtataag    480
gatgacacag gcaatcgacc tatgtcattg acaagggttc ctcgttcagt gaatttggca    540
tcaaatgcct accttcagtc tttgcttgga tcttctgcaa gaatgctctt tgagtttgtc    600
aaagaaatgc ccaaagcaga aacaaaactc aagctggact ttgcttctct cctgggacca    660
ctattcttta catgggttgt tttgatagct ctagtttatg agaagcagca gaaactaaga    720
atcatgatga aaatgcatgg acttgcggat ggtccctatt ggatgatttc ttattcttat    780
tttttggtcg tatcttctat atacatgtta tgttttgtgg ttttcggctc attagtaggc    840
ttgaagttct ttttgcttaa tgattacagc atccagttcg tgttttactt catttacata    900
aacttgcaaa tgtcccttgc ttttctggtt gctgcgtttt tctcgaatgt taagacagct    960
acagtcatcg gctatatgat ggtgtttgca acggactct tggcagcatt ccttttccag   1020
ttctttctcc aggatgaatc atttcccaga ggctggatta tagttatgga gatatatcct   1080
ggattttctc ttttttcgtgg attatatgag ttttcccaat atgctttcaa tgctaattat   1140
atgggaacag atggtatgag atggaaagat ttgagtgacg aaaaaatgg gatgaaggat    1200 gtcctaataa taatgatagt gcagtggttg gtctttctct ttcttgctta ttacattgat   1260
cagattgcat catcagggaa agatccccta tttttcttgt ggaactcccg aaagaagcct   1320
tcaccttcct tcaggaaaca tagtttacga aggcagggtt ctaaagtttt cgtccaaatg   1380
gagaaacctg atgttgctca ggagagggag agagttgaac agttactcga atcaagtaca   1440
actcatgcca tcatttgtga caatttgaaa aaggtttatc cagggaaaga cggaaaccct   1500
gagaaatttg cagtgagagg attgtcactt gctttgcctc aagggaatg ttttggtatg    1560 cttggtccca acggtgctgg caaaactact tttattaata tgatgattgg gctcgtaaaa   1620
ccaagctccg gtactgcata tgctcagggt atggatatac gaaaagacat ggatatgata   1680
tacaccaaca tgggtgtatg tccgcagcat gacttacttt gggaaaagtt aacaggaagg   1740
gagcacctac ttttctatgg aaggcttaaa aatcttaaag gagcagtcct gacacaagca   1800
gttgaagaat ctcttaagaa tgtcaactta tttcatgggg gtgttgctga caagcaagct   1860
gggaaataca gtggaggtat gaagaggagg ctaagtgttg caatttcact gatcggagat   1920
cctaaggttg tctacatgga tgagcccagt actggactgg atccagcttc gcgacataac   1980
ttatggaatg ttgtcaagcg tgcaaagcaa gatagagcaa ttattctcac aacccattcc   2040
atggaagaag cagagcatct atgtgatcga ctaggaatat tcgttgatgg cagcttgcag   2100
tgcataggaa atcccaaaga ggcactttgg gtttgcaaat atcccatatc caattcagca   2160
tcagtagctc gatccattca taattttctc tcaaaattga atcactactc ttctcttcac   2220
atctgttctt cagcgatgat aggaacagaa gtagcaccta ctctctctgt cactagatct   2280
atcaacagtg ggagcaacct tgattccaat caccccttatt atcgacattc ttctgatgct   2340
ccagggatga ctctagttag cacaccattt gacggaagag aatactcaca atggagcaag   2400
tgcaacgaca tggtgacctc ttggttgctg aattcactca ccaaggagat aggagacaat   2460
ataatttatt ctagaactgc aaaggatctc tgcaacagcc ttgagcacat gtttggccaa   2520
tcgagtggag caaagctcta tcatctacag aaggagatct cagagttagc tcaaggaagt   2580
```

```
agtagcatag catgggcata ctgctacagg ctcaataagt ttcttgatga cttccaattt    2640
accaaatcac tcatttctca aggagcagtg aaggccaatg cattggtttc tgcaacaaaa    2700
actgatggac aaacaaatgg atacactgaa ggaaattcaa gcaatcaaaa tcatttcttc    2760
agcaaggaac acgtctctga gctagtgaac ataatcaagc aagtacagat tggaaatgga    2820
ggaaatgcag gaacagagat caatgctaat gcagtagctg gtgcctctga gcacatgtgt    2880
tttgactcaa aatcattctt agaagtccgt ccattgcata tacctttgca cataagtttg    2940
cctaactcat ttcaattgtt tgttacacat ataggaaggg tccctttaat gaggagagga    3000
caagcttttg gtgaagtggg ggatggtcta tacctgccca gcctagtagt ttaa          3054
```

<210> SEQ ID NO 73
<211> LENGTH: 1017
<212> TYPE: PRT
<213> ORGANISM: Nicotiana tabacum

<400> SEQUENCE: 73

```
Met Ala Asp Gly Pro Ala Ser Phe Trp Thr Gln Ala Asn Ala Leu Leu
1               5                   10                  15

Arg Lys Asn Leu Thr Phe Gln Met Gly Arg Asn Phe Phe Ser Ser Gly
            20                  25                  30

Ser Thr Leu Asn Ser Ser Asp Ile Phe Tyr Ser Leu Ala Tyr Asn Ile
        35                  40                  45

Leu Gly Ser Glu Ser Gln Thr Glu Leu Met Asn Phe Leu Glu Ala Ala
    50                  55                  60

Phe Phe Ser Asn Leu Pro Val Tyr Asn Leu Arg Pro Gln Cys Pro Pro
65                  70                  75                  80

Asn Ser Thr Phe Ser Phe Pro Leu Glu Phe Gly Ser Val Ala Val Gln
                85                  90                  95

Gln Glu Ile Ser Cys Val Lys Gly Ile His Leu Trp Arg Asn Ser Ser
            100                 105                 110

Tyr Glu Ile Asn Asp Glu Leu Tyr Lys Gly Tyr Arg Lys Gly Asn Pro
        115                 120                 125

Glu Gly Lys Ile Asn Glu Ile Ile Ala Ala Tyr Asp Phe Phe Asn Ser
    130                 135                 140

Asn Arg Asn Gly Phe Asn Val Asn Ile Trp Tyr Asn Ser Thr Tyr Lys
145                 150                 155                 160

Asp Asp Thr Gly Asn Arg Pro Met Ser Leu Thr Arg Val Pro Arg Ser
                165                 170                 175

Val Asn Leu Ala Ser Asn Ala Tyr Leu Gln Ser Leu Leu Gly Ser Ser
            180                 185                 190

Ala Arg Met Leu Phe Glu Phe Val Lys Glu Met Pro Lys Ala Glu Thr
        195                 200                 205

Lys Leu Lys Leu Asp Phe Ala Ser Leu Leu Gly Pro Leu Phe Phe Thr
    210                 215                 220

Trp Val Val Leu Ile Ala Leu Val Tyr Glu Lys Gln Gln Lys Leu Arg
225                 230                 235                 240

Ile Met Met Lys Met His Gly Leu Ala Asp Gly Pro Tyr Trp Met Ile
                245                 250                 255

Ser Tyr Ser Tyr Phe Leu Val Val Ser Ser Ile Tyr Met Leu Cys Phe
            260                 265                 270

Val Val Phe Gly Ser Leu Val Gly Leu Lys Phe Phe Leu Leu Asn Asp
        275                 280                 285
```

```
Tyr Ser Ile Gln Phe Val Phe Tyr Phe Ile Tyr Ile Asn Leu Gln Met
    290             295             300
Ser Leu Ala Phe Leu Val Ala Ala Phe Phe Ser Asn Val Lys Thr Ala
305             310             315             320
Thr Val Ile Gly Tyr Met Met Val Phe Ala Asn Gly Leu Leu Ala Ala
            325             330             335
Phe Leu Phe Gln Phe Phe Leu Gln Asp Glu Ser Phe Pro Arg Gly Trp
        340             345             350
Ile Ile Val Met Glu Ile Tyr Pro Gly Phe Ser Leu Phe Arg Gly Leu
        355             360             365
Tyr Glu Phe Ser Gln Tyr Ala Phe Asn Ala Asn Tyr Met Gly Thr Asp
    370             375             380
Gly Met Arg Trp Lys Asp Leu Ser Asp Gly Lys Asn Gly Met Lys Asp
385             390             395             400
Val Leu Ile Ile Met Ile Val Gln Trp Leu Val Phe Leu Phe Leu Ala
            405             410             415
Tyr Tyr Ile Asp Gln Ile Ala Ser Ser Gly Lys Asp Pro Leu Phe Phe
        420             425             430
Leu Trp Asn Ser Arg Lys Lys Pro Ser Pro Ser Phe Arg Lys His Ser
        435             440             445
Leu Arg Arg Gln Gly Ser Lys Val Phe Val Gln Met Glu Lys Pro Asp
    450             455             460
Val Ala Gln Glu Arg Glu Arg Val Glu Gln Leu Leu Glu Ser Ser Thr
465             470             475             480
Thr His Ala Ile Ile Cys Asp Asn Leu Lys Lys Val Tyr Pro Gly Lys
            485             490             495
Asp Gly Asn Pro Glu Lys Phe Ala Val Arg Gly Leu Ser Leu Ala Leu
        500             505             510
Pro Gln Gly Glu Cys Phe Gly Met Leu Gly Pro Asn Gly Ala Gly Lys
        515             520             525
Thr Thr Phe Ile Asn Met Met Ile Gly Leu Val Lys Pro Ser Ser Gly
    530             535             540
Thr Ala Tyr Ala Gln Gly Met Asp Ile Arg Lys Asp Met Asp Met Ile
545             550             555             560
Tyr Thr Asn Met Gly Val Cys Pro Gln His Asp Leu Leu Trp Glu Lys
            565             570             575
Leu Thr Gly Arg Glu His Leu Leu Phe Tyr Gly Arg Leu Lys Asn Leu
        580             585             590
Lys Gly Ala Val Leu Thr Gln Ala Val Glu Glu Ser Leu Lys Asn Val
        595             600             605
Asn Leu Phe His Gly Gly Val Ala Asp Lys Gln Ala Gly Lys Tyr Ser
    610             615             620
Gly Gly Met Lys Arg Arg Leu Ser Val Ala Ile Ser Leu Ile Gly Asp
625             630             635             640
Pro Lys Val Val Tyr Met Asp Glu Pro Ser Thr Gly Leu Asp Pro Ala
            645             650             655
Ser Arg His Asn Leu Trp Asn Val Val Lys Arg Ala Lys Gln Asp Arg
        660             665             670
Ala Ile Ile Leu Thr Thr His Ser Met Glu Glu Ala Glu His Leu Cys
        675             680             685
Asp Arg Leu Gly Ile Phe Val Asp Gly Ser Leu Gln Cys Ile Gly Asn
    690             695             700
Pro Lys Glu Ala Leu Trp Val Cys Lys Tyr Pro Ile Ser Asn Ser Ala
```

|       |       |     | 705 |     |     |     |     | 710 |     |     |     |     | 715 |     |     |     |     | 720 |
|-------|-------|-----|-----|-----|-----|-----|-----|-----|-----|-----|-----|-----|-----|-----|-----|-----|-----|-----|

Ser Val Ala Arg Ser Ile His Asn Phe Leu Ser Lys Leu Asn His Tyr
            725                 730                 735

Ser Ser Leu His Ile Cys Ser Ser Ala Met Ile Gly Thr Glu Val Ala
            740                 745                 750

Pro Thr Leu Ser Val Thr Arg Ser Ile Asn Ser Gly Ser Asn Leu Asp
            755                 760                 765

Ser Asn His Pro Tyr Tyr Arg His Ser Ser Asp Ala Pro Gly Met Thr
            770                 775                 780

Leu Val Ser Thr Pro Phe Asp Gly Arg Glu Tyr Ser Gln Trp Ser Lys
785                 790                 795                 800

Cys Asn Asp Met Val Thr Ser Trp Leu Leu Asn Ser Leu Thr Lys Glu
                805                 810                 815

Ile Gly Asp Asn Ile Ile Tyr Ser Arg Thr Ala Lys Asp Leu Cys Asn
                820                 825                 830

Ser Leu Glu His Met Phe Gly Gln Ser Ser Gly Ala Lys Leu Tyr His
                835                 840                 845

Leu Gln Lys Glu Ile Ser Glu Leu Ala Gln Gly Ser Ser Ser Ile Ala
850                 855                 860

Trp Ala Tyr Cys Tyr Arg Leu Asn Lys Phe Leu Asp Asp Phe Gln Phe
865                 870                 875                 880

Thr Lys Ser Leu Ile Ser Gln Gly Ala Val Lys Ala Asn Ala Leu Val
                885                 890                 895

Ser Ala Thr Lys Thr Asp Gly Gln Thr Asn Gly Tyr Thr Glu Gly Asn
                900                 905                 910

Ser Ser Asn Gln Asn His Phe Phe Ser Lys Glu His Val Ser Glu Leu
                915                 920                 925

Val Asn Ile Ile Lys Gln Val Gln Ile Gly Asn Gly Asn Ala Gly
                930                 935                 940

Thr Glu Ile Asn Ala Asn Ala Val Ala Gly Ala Ser Glu His Met Cys
945                 950                 955                 960

Phe Asp Ser Lys Ser Phe Leu Glu Val Arg Pro Leu His Ile Pro Leu
                965                 970                 975

His Ile Ser Leu Pro Asn Ser Phe Gln Leu Phe Val Thr His Ile Gly
                980                 985                 990

Arg Val Pro Leu Met Arg Arg Gly Gln Ala Phe Gly Glu Val Gly Asp
                995                 1000                1005

Gly Leu Tyr Leu Pro Ser Leu Val Val
    1010                1015

<210> SEQ ID NO 74
<211> LENGTH: 3315
<212> TYPE: DNA
<213> ORGANISM: Nicotiana tabacum

<400> SEQUENCE: 74

| | |
|---|---|
| atgtcgcgct gtttttggga ggatgccagc atcattgtct ttcttggatt cctcggaatc | 60 |
| ttactgctgg attcactgtt atgcaaatgc agaaagaagg ttatgacagt tgatcagaag | 120 |
| tacactgttg aacagaagt ccgtgtttcc tactcctaca tattgagcat catttgcacg | 180 |
| actatattat cgtgcactca tctcataatg ctcttgatat tgcaaaagag aaatggtgct | 240 |
| cactgccaat tcagatttcc agttctctcc tctgagattc tgcaatcaac ttcatgggca | 300 |
| gtctcatttt tcgtgctcta cagaaccagg agtaggaaat acatcaagtt tccttgggtt | 360 |

```
ctgagaatct ggtggatttc cagcttctt  ctgtctattg ctcgtgcgac tcttgatgcc    420
cattttgtca tcacaagcga tgaacatcta ggactagcag actatgtgga catcattggt    480
cttatttcat ctgcctgtct tctcggtatc tcaatccgag ggaagacagg cataattctt    540
gacatctcgg acagtacaac tgagccactt ttaaatggga agaatgaaaa ggatccagaa    600
gacaaaaggg acagtccata tggaaaagct agtcttctcc aactgatcac cttctcttgg    660
ctcaatccac tatttgaagt tggaaacaag aagcccttg  accaggatga agtcccgat     720
gttgacttca gggactccgc aaaatttcta tctggttcct ttgatgaaag cctgaagtac    780
gtaaagggaa ggaatggagc caaaaaccca tctatctata aggccatta  tgtatttgca    840
gggaagaaag cagcaatcaa cgctgtcttt gcagttatta gtgcaggatc atcttatgtt    900
ggtccatacc ttatggatga ctttgtaaat ttcctcaacg aaaagaaact tcggggtta     960
caaactcgtg cagcttacca agatgctgat atatatcttc ttgatgaccc tttcagtgcc   1020
gttgatgctc acacaggcac gcacctcttt caggagtgct tgaggggggt tctcaaggac   1080
aagaccatac tttatgttac acaccaagtt gagtttcttc ctgcagcaga tctcattctg   1140
gtgatgcaaa atggaagaat tgcacaagct ggaacttttg aagaactact gaaacaaaat   1200
attggatttg aagttctagt tggagcacac aaccaggctt tagaatcaat tttaacagtt   1260
gaaagctcaa gtagagtatc tgaagaagca attactggta gtgagatgga tacagatagt   1320
aacataaata cagaaactaa gcaggattca gaacacagtc tctgtgtaga gataacagaa   1380
aaagatggaa gacttgtgca ggatgaggag agagtaaaag gaagcattgg aaaggaagtt   1440
tactattctt acttgaccac catgaaaggt ggtgcctttg ttccaataat tcttatagcg   1500
caatcatcat ttcaagtgct tcagattgcc agcaactact ggatggcatc ggcattcccc   1560
acaggtgatg atgcagcacc aatagctgag aagatgaact tcatacttgt tgttttttgtg  1620
cttctcgctg ttggaagttc cctttgcgtg ctagtgcggg catcatttgt ggctataata   1680
ggccttcaaa cagcagaaaa gctctttagc aacatgctgc acagcatcct tcgtgctcct   1740
atgtcattct ttgactctac tcctactgga cgaatcttaa accgcgcatc cacagatcaa   1800
agtgttgtgg acttgaaat  tgcactcaaa ttgggttggt gtgctctctc cattattcag   1860
cttcttggga caattgctgt catgtcgcag gttgcatggg aagtatttgt cctctttatt   1920
ccaataacag cagtttacgt ctggtaccag caatactaca taccaaccgc aagggaactt   1980
gctcgtttat ctggagttca agagctccg  atcctccatc actttgcaga atcactggca   2040
ggagcagcaa caattcgcgc tttcaaccaa aaagatcgct ttgctcatgc aaaccttagc   2100
ctcatagatg gcattgcagg attagcagta acatatggca tctatttgaa ctattcacaa   2160
gctgcagtaa tatggaatat ttgcggtact gaaaacaaaa tgatatcagt tgaaaggatt   2220
ctccagtatt cagaccttgc cagtgaagca ccctcgtga  ttgaaaactg caggctatcg   2280
agcacctggc cagaaactgg aacaatttcc ttccaaaatt tacagatacg ttatgctgaa   2340
cacctcccct ctgttttgaa aaacattaca tgcacatttc cgggaagtaa gaaagttggt   2400
gttgtgggaa ggacaggaag tggtaaatca accctcactc aagcccttt  ccggatcgta   2460
gaacccaaag aaggaagcat tatcattgac aatatagata tttgcaagat aggtcttcat   2520
gatttgaggt caaggtttag tattattcct caagatccaa caatgttcga tggaacagtt   2580
agaggaaacc tagatccaat agcacagcac tctgatactg aaatctggga ggctctggac   2640
aaatgccaac ttggtgatat aatacgtgca aagccagaaa agctagaatc tacagtggtt   2700
gaaaacggag aaaactggag tgtgggtcaa aggcagcttt tctgtcttgg aagagctttg   2760
```

```
ctaaagaaaa gtagcattct cgttttggat gaagcaacag catcagttga tgctgcaact   2820
gatgcagtgt tacaaaagat tatcagtcaa gagttcagaa atcgaacagt tatcacaata   2880
gctcacagga tccatacagt cattaatagc gatcttgtct tagtcttgaa tgaaggaaga   2940
atagccgaat atgattcacc agcaaagcta ttggaaagag aggattcttt cttctcaaaa   3000
ctgataaagg agtattcgat gagatccaaa ggtgcaaagg tgattgagaa gcatgcagca   3060
cagctttgtg tgttagcaga ggactgcgac cagccagatt atgtcaaatt ggtcaaagca   3120
ctctgtgctg atcacaatgt cagcttgatc acagttccga atgcaaaaac tcttggcgaa   3180
tgggctggtt tgtgtaagat tgactctgaa gggaaagcaa ggaaagtggt tggctgcggc   3240
tgtgttgttg tgaaggatta tggggaagag actgagggtc tgcatattgt ccaggagtac   3300
gtaaagtccc attaa                                                    3315
```

<210> SEQ ID NO 75
<211> LENGTH: 1104
<212> TYPE: PRT
<213> ORGANISM: Nicotiana tabacum

<400> SEQUENCE: 75

```
Met Ser Arg Cys Phe Trp Glu Asp Ala Ser Ile Ile Val Phe Leu Gly
1               5                   10                  15

Phe Leu Gly Ile Leu Leu Asp Ser Leu Leu Cys Lys Cys Arg Lys
            20                  25                  30

Lys Val Met Thr Val Asp Gln Lys Tyr Thr Gly Thr Glu Val Arg
        35                  40                  45

Val Ser Tyr Ser Tyr Ile Leu Ser Ile Ile Cys Thr Thr Ile Leu Ser
 50                  55                  60

Cys Thr His Leu Ile Met Leu Leu Ile Leu Gln Lys Arg Asn Gly Ala
 65                  70                  75                  80

His Cys Gln Phe Arg Phe Pro Val Leu Ser Glu Ile Leu Gln Ser
            85                  90                  95

Thr Ser Trp Ala Val Ser Phe Val Leu Tyr Arg Thr Arg Ser Arg
        100                 105                 110

Lys Tyr Ile Lys Phe Pro Trp Val Leu Arg Ile Trp Ile Ser Ser
        115                 120                 125

Phe Phe Leu Ser Ile Ala Arg Ala Thr Leu Asp Ala His Phe Val Ile
        130                 135                 140

Thr Ser Asp Glu His Leu Gly Leu Ala Asp Tyr Val Asp Ile Ile Gly
145                 150                 155                 160

Leu Ile Ser Ser Ala Cys Leu Leu Gly Ile Ser Ile Arg Gly Lys Thr
                165                 170                 175

Gly Ile Ile Leu Asp Ile Ser Asp Ser Thr Thr Glu Pro Leu Leu Asn
                180                 185                 190

Gly Lys Asn Glu Lys Asp Pro Glu Asp Lys Arg Asp Ser Pro Tyr Gly
            195                 200                 205

Lys Ala Ser Leu Leu Gln Leu Ile Thr Phe Ser Trp Leu Asn Pro Leu
    210                 215                 220

Phe Glu Val Gly Asn Lys Lys Pro Leu Asp Gln Asp Glu Val Pro Asp
225                 230                 235                 240

Val Asp Phe Arg Asp Ser Ala Lys Phe Leu Ser Gly Ser Phe Asp Glu
                245                 250                 255

Ser Leu Lys Tyr Val Lys Gly Arg Asn Gly Ala Lys Asn Pro Ser Ile
                260                 265                 270
```

```
Tyr Lys Ala Ile Tyr Val Phe Ala Gly Lys Ala Ala Ile Asn Ala
            275                 280                 285
Val Phe Ala Val Ile Ser Ala Gly Ser Ser Tyr Val Gly Pro Tyr Leu
        290                 295                 300
Met Asp Asp Phe Val Asn Phe Leu Asn Glu Lys Lys Leu Arg Gly Leu
305                 310                 315                 320
Gln Thr Arg Ala Ala Tyr Gln Asp Ala Asp Ile Tyr Leu Leu Asp Asp
                325                 330                 335
Pro Phe Ser Ala Val Asp Ala His Thr Gly Thr His Leu Phe Gln Glu
                340                 345                 350
Cys Leu Arg Gly Val Leu Lys Asp Lys Thr Ile Leu Tyr Val Thr His
                355                 360                 365
Gln Val Glu Phe Leu Pro Ala Ala Asp Leu Ile Leu Val Met Gln Asn
        370                 375                 380
Gly Arg Ile Ala Gln Ala Gly Thr Phe Glu Glu Leu Leu Lys Gln Asn
385                 390                 395                 400
Ile Gly Phe Glu Val Leu Val Gly Ala His Asn Gln Ala Leu Glu Ser
                405                 410                 415
Ile Leu Thr Val Glu Ser Ser Arg Val Ser Glu Glu Ala Ile Thr
                420                 425                 430
Gly Ser Glu Met Asp Thr Asp Ser Asn Ile Asn Thr Glu Thr Lys Gln
        435                 440                 445
Asp Ser Glu His Ser Leu Cys Val Glu Ile Thr Glu Lys Asp Gly Arg
        450                 455                 460
Leu Val Gln Asp Glu Glu Arg Val Lys Gly Ser Ile Gly Lys Glu Val
465                 470                 475                 480
Tyr Tyr Ser Tyr Leu Thr Thr Met Lys Gly Gly Ala Phe Val Pro Ile
                485                 490                 495
Ile Leu Ile Ala Gln Ser Ser Phe Gln Val Leu Gln Ile Ala Ser Asn
                500                 505                 510
Tyr Trp Met Ala Ser Ala Phe Pro Thr Gly Asp Asp Ala Ala Pro Ile
        515                 520                 525
Ala Glu Lys Met Asn Phe Ile Leu Val Val Phe Val Leu Leu Ala Val
        530                 535                 540
Gly Ser Ser Leu Cys Val Leu Val Arg Ala Ser Phe Val Ala Ile Ile
545                 550                 555                 560
Gly Leu Gln Thr Ala Glu Lys Leu Phe Ser Asn Met Leu His Ser Ile
                565                 570                 575
Leu Arg Ala Pro Met Ser Phe Phe Asp Ser Thr Pro Thr Gly Arg Ile
                580                 585                 590
Leu Asn Arg Ala Ser Thr Asp Gln Ser Val Val Asp Leu Glu Ile Ala
                595                 600                 605
Leu Lys Leu Gly Trp Cys Ala Leu Ser Ile Ile Gln Leu Leu Gly Thr
        610                 615                 620
Ile Ala Val Met Ser Gln Val Ala Trp Glu Val Phe Val Leu Phe Ile
625                 630                 635                 640
Pro Ile Thr Ala Val Tyr Val Trp Tyr Gln Gln Tyr Tyr Ile Pro Thr
                645                 650                 655
Ala Arg Glu Leu Ala Arg Leu Ser Gly Val Gln Arg Ala Pro Ile Leu
                660                 665                 670
His His Phe Ala Glu Ser Leu Ala Gly Ala Ala Thr Ile Arg Ala Phe
                675                 680                 685
```

```
Asn Gln Lys Asp Arg Phe Ala His Ala Asn Leu Ser Leu Ile Asp Gly
690                 695                 700

Ile Ala Gly Leu Ala Val Thr Tyr Gly Ile Tyr Leu Asn Tyr Ser Gln
705                 710                 715                 720

Ala Ala Val Ile Trp Asn Ile Cys Gly Thr Glu Asn Lys Met Ile Ser
                725                 730                 735

Val Glu Arg Ile Leu Gln Tyr Ser Asp Leu Ala Ser Glu Ala Pro Leu
                740                 745                 750

Val Ile Glu Asn Cys Arg Leu Ser Ser Thr Trp Pro Glu Thr Gly Thr
                755                 760                 765

Ile Ser Phe Gln Asn Leu Gln Ile Arg Tyr Ala Glu His Leu Pro Ser
770                 775                 780

Val Leu Lys Asn Ile Thr Cys Thr Phe Pro Gly Ser Lys Lys Val Gly
785                 790                 795                 800

Val Val Gly Arg Thr Gly Ser Gly Lys Ser Thr Leu Thr Gln Ala Leu
                805                 810                 815

Phe Arg Ile Val Glu Pro Lys Glu Gly Ser Ile Ile Ile Asp Asn Ile
                820                 825                 830

Asp Ile Cys Lys Ile Gly Leu His Asp Leu Arg Ser Arg Phe Ser Ile
                835                 840                 845

Ile Pro Gln Asp Pro Thr Met Phe Asp Gly Thr Val Arg Gly Asn Leu
850                 855                 860

Asp Pro Ile Ala Gln His Ser Asp Thr Glu Ile Trp Glu Ala Leu Asp
865                 870                 875                 880

Lys Cys Gln Leu Gly Asp Ile Ile Arg Ala Lys Pro Glu Lys Leu Glu
                885                 890                 895

Ser Thr Val Val Glu Asn Gly Glu Asn Trp Ser Val Gly Gln Arg Gln
                900                 905                 910

Leu Phe Cys Leu Gly Arg Ala Leu Leu Lys Lys Ser Ser Ile Leu Val
                915                 920                 925

Leu Asp Glu Ala Thr Ala Ser Val Asp Ala Ala Thr Asp Ala Val Leu
                930                 935                 940

Gln Lys Ile Ile Ser Gln Glu Phe Arg Asn Arg Thr Val Ile Thr Ile
945                 950                 955                 960

Ala His Arg Ile His Thr Val Ile Asn Ser Asp Leu Val Leu Val Leu
                965                 970                 975

Asn Glu Gly Arg Ile Ala Glu Tyr Asp Ser Pro Ala Lys Leu Leu Glu
                980                 985                 990

Arg Glu Asp Ser Phe Phe Ser Lys Leu Ile Lys Glu Tyr Ser Met Arg
                995                 1000                1005

Ser Lys Gly Ala Lys Val Ile Glu Lys His Ala Ala Gln Leu Cys Val
1010                1015                1020

Leu Ala Glu Asp Cys Asp Gln Pro Asp Tyr Val Lys Leu Val Lys Ala
1025                1030                1035                1040

Leu Cys Ala Asp His Asn Val Ser Leu Ile Thr Val Pro Asn Ala Lys
                1045                1050                1055

Thr Leu Gly Glu Trp Ala Gly Leu Cys Lys Ile Asp Ser Glu Gly Lys
                1060                1065                1070

Ala Arg Lys Val Val Gly Cys Gly Cys Val Val Lys Asp Tyr Gly
                1075                1080                1085

Glu Glu Thr Glu Gly Leu His Ile Val Gln Glu Tyr Val Lys Ser His
                1090                1095                1100
```

```
<210> SEQ ID NO 76
<211> LENGTH: 930
<212> TYPE: DNA
<213> ORGANISM: Nicotiana tabacum

<400> SEQUENCE: 76
atggtgtcgg atgcggcgaa gaagagagat gcacaaaaga aggcggcggc agctgctagg      60
agaggaggaa aagtgcagc cgcgtcatcc aagacggtgg cgacggcgtc caaagcggca     120
ccggagacca acggggttga taatttgacg aacggagtgg gggatcttca catatctgat     180
cgaaattgca ctggtgtttt gtgttcgcat ccccttttcaa gggatattcg gatacaatct     240
ttatcagtca ccttccacgg acatgatctc attgttgatt ctgaactgga gctcaactat     300
ggaagacgtt atgggttgct gggactgaat ggctgcggga atctactctt cttactgct      360 atagggcttc gggaacttcc catcccagag acatggata ttttttcatct ttcacgggag     420 attgatgcct ctgacatgtc tgctcttgag gccgtcatta attgtgatga agagaggttg     480
aaattggaga agaagctga agctttggct ggacaggatg atggtggtgg agagcaactt     540
gaacgaatct acgagcgttt agaagctatg gatgcagcca ctgctgagaa acgtgctgct     600
gagatcttgt ttggtctcgg atttgataag aaaatgcaag gaagaaaac atgtgatttc     660 tccggtggct ggagaatgag gatttctctt gcgcgagccc tatttatgaa tccaacaatt     720
ttacttagag gcctgtgtgt ggttagaaga atccttgaag aatttcgagc gcattctggt     780
tgtcatttca cactcccagg attttctcaa tggtgtttgt accaatatca tccacatgca     840
aaacaagaaa ttgaagctct atacaggaaa ctacgaccag tatgttcaaa cccggtcaga     900
gctagaagag aaccagatga aacagtataa                                       930

<210> SEQ ID NO 77
<211> LENGTH: 309
<212> TYPE: PRT
<213> ORGANISM: Nicotiana tabacum

<400> SEQUENCE: 77

Met Val Ser Asp Ala Ala Lys Lys Arg Asp Ala Gln Lys Lys Ala Ala
1               5                   10                  15

Ala Ala Ala Arg Arg Gly Gly Lys Gly Ala Ala Ala Ser Ser Lys Thr
            20                  25                  30

Val Ala Thr Ala Ser Lys Ala Ala Pro Glu Thr Asn Gly Val Asp Asn
        35                  40                  45

Leu Thr Asn Gly Val Gly Asp Leu His Ile Ser Asp Arg Asn Cys Thr
    50                  55                  60

Gly Val Leu Cys Ser His Pro Leu Ser Arg Asp Ile Arg Ile Gln Ser
65                  70                  75                  80

Leu Ser Val Thr Phe His Gly His Asp Leu Ile Val Asp Ser Glu Leu
                85                  90                  95

Glu Leu Asn Tyr Gly Arg Arg Tyr Gly Leu Leu Gly Leu Asn Gly Cys
            100                 105                 110

Gly Lys Ser Thr Leu Leu Thr Ala Ile Gly Leu Arg Glu Leu Pro Ile
        115                 120                 125

Pro Glu His Met Asp Ile Phe His Leu Ser Arg Glu Ile Asp Ala Ser
    130                 135                 140

Asp Met Ser Ala Leu Glu Ala Val Ile Asn Cys Asp Glu Glu Arg Leu
145                 150                 155                 160

Lys Leu Glu Lys Glu Ala Glu Ala Leu Ala Gly Gln Asp Asp Gly Gly
                165                 170                 175
```

```
Gly Glu Gln Leu Glu Arg Ile Tyr Glu Arg Leu Glu Ala Met Asp Ala
            180                 185                 190

Ala Thr Ala Glu Lys Arg Ala Ala Glu Ile Leu Phe Gly Leu Gly Phe
        195                 200                 205

Asp Lys Lys Met Gln Gly Lys Lys Thr Cys Asp Phe Ser Gly Gly Trp
    210                 215                 220

Arg Met Arg Ile Ser Leu Ala Arg Ala Leu Phe Met Asn Pro Thr Ile
225                 230                 235                 240

Leu Leu Arg Gly Leu Cys Val Val Arg Arg Ile Leu Glu Glu Phe Arg
                245                 250                 255

Ala His Ser Gly Cys His Phe Thr Leu Pro Gly Phe Ser Gln Trp Cys
            260                 265                 270

Leu Tyr Gln Tyr His Pro His Ala Lys Gln Glu Ile Glu Ala Leu Tyr
        275                 280                 285

Arg Lys Leu Arg Pro Val Cys Ser Asn Pro Val Arg Ala Arg Arg Glu
    290                 295                 300

Pro Asp Glu Thr Val
305
```

<210> SEQ ID NO 78
<211> LENGTH: 1296
<212> TYPE: DNA
<213> ORGANISM: Nicotiana tabacum

<400> SEQUENCE: 78

```
atggagttac aggttaatgt tccaagatgg acacctagtc caaacagatc accacataga      60
cgccaagaat ctgagacaga taatgaaagt gttacttatt ctcaagatga tattccttt      120
aacaacaaaa acccaaccaa aaatttccca tttagtaata gtccaccacc tcatattgct     180
gctattgaag caccatctct tagggttgat tctgaaataa aagggaaga gattaaggga      240
aataataata ctactggttt tgcatatgag gaagttgtac tccctttaa taatgaagga     300
atttacttga catggaaaga tttgtgggtg acagtgccag acaagaaaac agggaggaga    360
gcaatattac aagggctaac tggttatgta caacctggtc aagttttggc cattatgggt    420
ccttctggtt gtggcaaatc cactcttctt gatactttag cagggagatt ggattcgaac    480
acgagacaaa ctgagaaaat cctcatcaat ggtcggaggc aagctcttgc ttttggcact    540
tcggcttatg tgacacaaga tgatacattg atgacaacac tgacagtgaa agaagcaata    600
tactattcag cacaactcca attaccagat tcaataatag ttcaattggc taaacaagat    660
ggaagaactg tggttgcttc tatacatcag ccaagtagtg aagttttga gcttttccac     720
aatctttgcc ttctctcctc tggtaggact gtctactttg gttccattc tgctgcaaat     780
gagtttttg cactgaatgg cttcccatgt ccaactatga ggaatccttc tgaccactac     840
ttaaggacaa tcaacaagga ctttgatgct gatatcgaga aaggagttgg tggaaaagcc    900
acggcgacag aagcaatcaa tattctggtt aagtcataca agacctcaca gggttgccaa    960
caagttcaac gtcgagttct ggagatttgc aacagaatg gtggacaaga agcaaagaaa    1020
ggaaaccaag caagtttcat tactcagtgc acggttctaa ccaggagatc tttgtgaac     1080
atgtatcgtg atcttggtta ttactggctt cgttttgcaa tatatattgc tttgtgcttg    1140
tgtgttggca ctatatttca tgacattggc cacgactatg ctccattca gttccggagt    1200
tatgatgaaa atcgtgttct atcgtatatt ggcatgttgg gtgcagtgag tagtatggaa    1260
tttgaagtga ggatcaatgt tgcagttcgg tgttga                              1296
```

```
<210> SEQ ID NO 79
<211> LENGTH: 431
<212> TYPE: PRT
<213> ORGANISM: Nicotiana tabacum

<400> SEQUENCE: 79

Met Glu Leu Gln Val Asn Val Pro Arg Trp Thr Pro Ser Pro Asn Arg
1               5                   10                  15

Ser Pro His Arg Arg Gln Glu Ser Thr Asp Asn Glu Ser Val Thr
            20                  25                  30

Tyr Ser Gln Asp Asp Ile Pro Phe Asn Asn Lys Asn Pro Thr Lys Asn
            35                  40                  45

Phe Pro Phe Ser Asn Ser Pro Pro His Ile Ala Ala Ile Glu Ala
    50                  55                  60

Pro Ser Leu Arg Val Asp Ser Glu Ile Lys Arg Glu Glu Ile Lys Gly
65                  70                  75                  80

Asn Asn Asn Thr Thr Gly Phe Ala Tyr Glu Glu Val Val Leu Pro Phe
                85                  90                  95

Asn Asn Glu Gly Ile Tyr Leu Thr Trp Lys Asp Leu Trp Val Thr Val
            100                 105                 110

Pro Asp Lys Lys Thr Gly Arg Arg Ala Ile Leu Gln Gly Leu Thr Gly
        115                 120                 125

Tyr Val Gln Pro Gly Gln Val Leu Ala Ile Met Gly Pro Ser Gly Cys
        130                 135                 140

Gly Lys Ser Thr Leu Leu Asp Thr Leu Ala Gly Arg Leu Asp Ser Asn
145                 150                 155                 160

Thr Arg Gln Thr Gly Glu Ile Leu Ile Asn Gly Arg Arg Gln Ala Leu
                165                 170                 175

Ala Phe Gly Thr Ser Ala Tyr Val Thr Gln Asp Asp Thr Leu Met Thr
            180                 185                 190

Thr Leu Thr Val Lys Glu Ala Ile Tyr Tyr Ser Ala Gln Leu Gln Leu
        195                 200                 205

Pro Asp Ser Ile Ile Val Gln Leu Ala Lys Gln Asp Gly Arg Thr Val
210                 215                 220

Val Ala Ser Ile His Gln Pro Ser Ser Glu Val Phe Glu Leu Phe His
225                 230                 235                 240

Asn Leu Cys Leu Leu Ser Ser Gly Arg Thr Val Tyr Phe Gly Ser Ile
                245                 250                 255

Ser Ala Ala Asn Glu Phe Phe Ala Leu Asn Gly Phe Pro Cys Pro Thr
            260                 265                 270

Met Arg Asn Pro Ser Asp His Tyr Leu Arg Thr Ile Asn Lys Asp Phe
        275                 280                 285

Asp Ala Asp Ile Glu Lys Gly Val Gly Gly Lys Ala Thr Ala Thr Glu
290                 295                 300

Ala Ile Asn Ile Leu Val Lys Ser Tyr Lys Thr Ser Gln Gly Cys Gln
305                 310                 315                 320

Gln Val Gln Arg Arg Val Leu Glu Ile Cys Gln Gln Asn Gly Gly Gln
                325                 330                 335

Glu Ala Lys Lys Gly Asn Gln Ala Ser Phe Ile Thr Gln Cys Thr Val
            340                 345                 350

Leu Thr Arg Arg Ser Phe Val Asn Met Tyr Arg Asp Leu Gly Tyr Tyr
        355                 360                 365

Trp Leu Arg Phe Ala Ile Tyr Ile Ala Leu Cys Leu Cys Val Gly Thr
```

```
                370                 375                 380
Ile Phe His Asp Ile Gly His Asp Tyr Gly Ser Ile Gln Phe Arg Ser
385                 390                 395                 400

Tyr Asp Glu Asn Arg Val Leu Ser Tyr Ile Gly Met Leu Gly Ala Val
                405                 410                 415

Ser Ser Met Glu Phe Glu Val Arg Ile Asn Val Ala Val Arg Cys
                420                 425                 430

<210> SEQ ID NO 80
<211> LENGTH: 3855
<212> TYPE: DNA
<213> ORGANISM: Nicotiana tabacum

<400> SEQUENCE: 80
atgaagacat attcaacagc agggacttca gtttacatta ttcagacaga taatcatatt      60
ccagagctta tcgtaagaga aacagtagat ttcgcagcta gatgccaagg tgaaaatcac    120
aattttgaag actatgtctt gaatgttctt cgacttgata tatgttcaga cacattagtt    180
ggtaatgacg cgataagagg agtttcaggt gaacaaagga agataggaga aatgattgtt    240
ggtcccagga aaacactgtt catggatgag atttctaccg acatgacaga tagtacaagt    300
tccaaaatag tcaagtgcat acaaaatttt gttcatataa tggaaggaac tgtgatgatg    360
gctctttgtc gtccttcaca agagactttc gaattgttcg atgatcttgt attactatct    420
gaaggatatg tcctgtacca tggccctcga gaagatgtta ttccattttt tgagtggtta    480
ggatttcaat tgccagatcg taaggatgtc gttgatttta ttcaagaggt gcatttgtc    540 ggatccgtca caggcacaat gtttctaaga acaaggttac atcccacaga tctggtgaac    600
gggaacttgt atctttcctg cttgtttttc ggtctggttc atatgatgct cgacggattc    660
tcagaactgt ctctctttat atatcggctc ccagtattct ataagcaaag agataaattc    720
ttctatcctg cgtgggtgtg gtcattgtgt agttggatct tgtcgttacc ttactctgtt    780
attgaagctc ttgtatggtc ttatgttgta tactggactg taggatttgc acctggtgct    840
gggagatttt tcagctacat gttttactc ttctcggtac accaaatggc gatgggtctc    900
tttcggttaa tagcttcttt gtcacagagat ataattattg caaatacttt tggatcagct    960
gtgctaatca tattttact gggtggtttt atcttgccaa agaaatgat caagccatgg    1020 ttcgtatggg cattttgggt gtcaccattg tcgtatggac agcgagcaat ttctgttaat    1080
gaattcactg cgacaagatg gattgagaag acaaccagcg gaaatgtcac gcttggttac    1140
agtgttctgc aatcgcacag cctaccgaca tctggttact ggtactggtt gggattggga    1200
gttctgttgc tctctgtgtt gcttctcaac attattctga ctgtagcctt gactttctc    1260 aacccactaa gaaaatctag gcaattatt ccaacagatg ccagtggtgt aaattcagtt    1320
cctggtggaa atagcaaccg tggccagggg gggactagac agtcagaatt gcgcctacct    1380
ttcaaacaag aaatgggaat accgcagaaa aggttcagc tactgtccaa tgttagtaga    1440
gtattatcac ctggcgttct tattggattg gttggtgcaa gtggagcggg gaaaaccaca    1500
ttgatggatt gcctagctgg taggaagact actggatatg tagagggtga tattaggata    1560
tcaggctacc caaaaaaaca agagactttt gcgagaattt caggatatgt tgaacagaat    1620
gatatacatt ctcctcaagt gacagttttt gaatccctat gttttacgtc ttatctccgg    1680
ctctccaaaa aagtgaatga aaacaaaga ctggagtttg ttgaagaaat aatggcatta    1740
ctggaacttg actctctaag gcatgcttta gttggcttgc ctggcatttc tggcttatca    1800
```

| | | | |
|---|---|---|---|
| accgaccaaa | gaagacgctt | gacaattgca gtagaacttg tagcaaatcc tgcgatactt | 1860 |
| tttatggatg | atcctacatc | tggtcttgat gcacgagctg cttctattgt catgcgaact | 1920 |
| gttagtgatg | tagcacatgg | cggaagaatt gtggtctgct ctattcgcca tccaagtttt | 1980 |
| gatatttttg | aaacatttga | cgagcttctt ctaatgaaac acgggggaca actgatatat | 2040 |
| ggaggacagc | gtgggaacaa | ttcacaaact atgattaact atttccaggg tattgatggg | 2100 |
| ataccccaa | ttcctaatgg | ttgcaatcct gcaacgtgga tgcttcagat aagtacacca | 2160 |
| gctgctgaag | caagaatagg | acgagatttt gctgaaatat acagaagttc tgcactctac | 2220 |
| agggaagttg | aagccagaac | tatgcttcca ccagcagaaa actcaaaacc tctgaggttc | 2280 |
| acttccaaat | ataacacatc | tgtactttat cagcttaaaa tgtgcctgtg aagcaaagt | 2340 |
| cttgtatact | ggagaaatcc | agcacattat aattgtgaga ttcttctcca caactttta | 2400 |
| tttcttgggg | tccagaattc | ttcctccata cagcccattg tttcaatggg aagacccgtt | 2460 |
| ttccgtaggg | agagagatgc | agggatgtac tcctgcgtag tatatgcagc atctcagggg | 2520 |
| ctgattgagg | ttatttatgt | cctggcccag actgtactat ttggagccat tacctattct | 2580 |
| atgtgggct | tagtgagggc | agcaggcacg attttcattt acatcatgtt cttgcttctg | 2640 |
| accacctatt | ttacctttta | cggtatgatg gtggggtatg acttggttct atgtatcagc | 2700 |
| ttaagaattt | ctggaatttg | gcggattgaa ttgctgtcca ttgctatcga gttgctctcg | 2760 |
| tttggtcatc | ggtttgttgc | tgttatgttg ccggatctcc tcgcctattt cagaagcttg | 2820 |
| cttgttgttt | tcttcagtt | aatttcggct gctagttact ttcggtgcta caccagtggt | 2880 |
| agcggtgata | gccttttttg | gtctttgggt cgtggtgttt tctgtgtttt cagggaaagt | 2940 |
| ctcaaagtgg | ttggagacaa | gttgggtgca cgagcactag caaaggagag caacctggac | 3000 |
| gagcgtcaac | aaagggcggt | gggaagcagt gtagtggtgg cagtctggga tgatagatta | 3060 |
| aaggcatgtc | ctcagaggtc | agtacgaggc cgcccgagga ttaggtgggg ctccttgact | 3120 |
| aaggttaaag | cccaggagtt | ggaaggaagg ttgtcggcaa tgggagcttg agaagtagt | 3180 |
| gaggacgcaa | acactatgtg | gtcaacgacg gcagactata taggaaggc ggcgagagag | 3240 |
| gtgttagggg | tatcttcagg | ccgcacctgt ggccacaaag gagactggtg gtggaatgca | 3300 |
| gttgtacaag | gtaaagtgga | agcgaagaag gtggcttacc tgcggttagt ggggagcact | 3360 |
| ggagaggag | agaagagagc | gaacattgcg agatataagg tagctaggaa ggaggcaaag | 3420 |
| atggcagtga | cggaggcaaa | gacgacagct tttgctcgtt tgtatgagga actagggaac | 3480 |
| aaaggcgggg | agaagaagtt | actccgactc gctaaggtga gagagaggac ggctcgggat | 3540 |
| ctggacctag | tgaggtgcat | aaaagatgag gacgacaaag ttttttttggg ggatgaccag | 3600 |
| ataaagagga | gatggcagac | ctactttcat aaacttctaa atgaggaagg ggatcaggat | 3660 |
| attgtattag | gtgaattgag | gaacgacgac aaccccatg aactaagtga ttgtcgggac | 3720 |
| attgaggtcg | atgaggtcat | ggaggcaatg caaggagatg aaaattgtcg gagaaagttt | 3780 |
| ttcggtggta | ttaattgggt | gaaggcagaa attcatgagt tttgtcaagt gaaattggtg | 3840 |
| gtgaaaatag | agtag | | 3855 |

<210> SEQ ID NO 81
<211> LENGTH: 1284
<212> TYPE: PRT
<213> ORGANISM: Nicotiana tabacum

<400> SEQUENCE: 81

Met Lys Thr Tyr Ser Thr Ala Gly Thr Ser Val Tyr Ile Ile Gln Thr

-continued

```
  1               5                  10                 15
Asp Asn His Ile Pro Glu Leu Ile Val Arg Glu Thr Val Asp Phe Ala
             20                 25                 30

Ala Arg Cys Gln Gly Glu Asn His Asn Phe Glu Asp Tyr Val Leu Asn
             35                 40                 45

Val Leu Arg Leu Asp Ile Cys Ser Asp Thr Leu Val Gly Asn Asp Ala
 50                 55                 60

Ile Arg Gly Val Ser Gly Glu Gln Arg Lys Ile Gly Glu Met Ile Val
 65                 70                 75                 80

Gly Pro Arg Lys Thr Leu Phe Met Asp Glu Ile Ser Thr Gly His Asp
             85                 90                 95

Ser Ser Thr Ser Ser Lys Ile Val Lys Cys Ile Gln Asn Phe Val His
            100                105                110

Ile Met Glu Gly Thr Val Met Met Ala Leu Cys Arg Pro Ser Gln Glu
            115                120                125

Thr Phe Glu Leu Phe Asp Asp Leu Val Leu Leu Ser Glu Gly Tyr Val
            130                135                140

Leu Tyr His Gly Pro Arg Glu Asp Val Ile Pro Phe Phe Glu Trp Leu
145                150                155                160

Gly Phe Gln Leu Pro Asp Arg Lys Asp Val Asp Phe Ile Gln Glu
            165                170                175

Val Ala Phe Val Gly Ser Val Thr Gly Thr Met Phe Leu Arg Thr Arg
            180                185                190

Leu His Pro Thr Asp Leu Val Asn Gly Asn Leu Tyr Leu Ser Cys Leu
            195                200                205

Phe Phe Gly Leu Val His Met Met Leu Asp Gly Phe Ser Glu Leu Ser
            210                215                220

Leu Phe Ile Tyr Arg Leu Pro Val Phe Tyr Lys Gln Arg Asp Asn Phe
225                230                235                240

Phe Tyr Pro Ala Trp Val Trp Ser Leu Cys Ser Trp Ile Leu Ser Leu
            245                250                255

Pro Tyr Ser Val Ile Glu Ala Leu Val Trp Ser Tyr Val Val Tyr Trp
            260                265                270

Thr Val Gly Phe Ala Pro Gly Ala Gly Arg Phe Phe Ser Tyr Met Phe
            275                280                285

Leu Leu Phe Ser Val His Gln Met Ala Met Gly Leu Phe Arg Leu Ile
290                295                300

Ala Ser Leu Ser Arg Asp Ile Ile Ala Asn Thr Phe Gly Ser Ala
305                310                315                320

Val Leu Ile Ile Phe Leu Leu Gly Gly Phe Ile Leu Pro Lys Glu Met
            325                330                335

Ile Lys Pro Trp Phe Val Trp Ala Phe Trp Val Ser Pro Leu Ser Tyr
            340                345                350

Gly Gln Arg Ala Ile Ser Val Asn Glu Phe Thr Ala Thr Arg Trp Ile
            355                360                365

Glu Lys Thr Thr Ser Gly Asn Val Thr Leu Gly Tyr Ser Val Leu Gln
            370                375                380

Ser His Ser Leu Pro Thr Ser Gly Tyr Trp Tyr Trp Leu Gly Leu Gly
385                390                395                400

Val Leu Leu Leu Ser Val Leu Leu Asn Ile Ile Leu Thr Val Ala
            405                410                415

Leu Thr Phe Leu Asn Pro Leu Arg Lys Ser Arg Ala Ile Ile Pro Thr
            420                425                430
```

```
Asp Ala Ser Gly Val Asn Ser Pro Gly Gly Asn Ser Asn Arg Gly
        435                 440                 445

Gln Gly Gly Thr Arg Gln Ser Glu Leu Arg Leu Pro Phe Lys Gln Glu
    450                 455                 460

Met Gly Ile Pro Gln Lys Arg Leu Gln Leu Leu Ser Asn Val Ser Arg
465                 470                 475                 480

Val Leu Ser Pro Gly Val Leu Ile Gly Leu Val Gly Ala Ser Gly Ala
                485                 490                 495

Gly Lys Thr Thr Leu Met Asp Cys Leu Ala Gly Arg Lys Thr Thr Gly
                500                 505                 510

Tyr Val Glu Gly Asp Ile Arg Ile Ser Gly Tyr Pro Lys Lys Gln Glu
            515                 520                 525

Thr Phe Ala Arg Ile Ser Gly Tyr Val Glu Gln Asn Asp Ile His Ser
            530                 535                 540

Pro Gln Val Thr Val Phe Glu Ser Leu Cys Phe Thr Ser Tyr Leu Arg
545                 550                 555                 560

Leu Ser Lys Lys Val Asn Glu Lys Gln Arg Leu Glu Phe Val Glu Glu
                565                 570                 575

Ile Met Ala Leu Leu Glu Leu Asp Ser Leu Arg His Ala Leu Val Gly
                580                 585                 590

Leu Pro Gly Ile Ser Gly Leu Ser Thr Asp Gln Arg Arg Arg Leu Thr
            595                 600                 605

Ile Ala Val Glu Leu Val Ala Asn Pro Ala Ile Leu Phe Met Asp Asp
            610                 615                 620

Pro Thr Ser Gly Leu Asp Ala Arg Ala Ala Ser Ile Val Met Arg Thr
625                 630                 635                 640

Val Ser Asp Val Ala His Gly Gly Arg Ile Val Val Cys Ser Ile Arg
                645                 650                 655

His Pro Ser Phe Asp Ile Phe Glu Thr Phe Asp Glu Leu Leu Leu Met
                660                 665                 670

Lys His Gly Gly Gln Leu Ile Tyr Gly Gly Gln Arg Gly Asn Asn Ser
            675                 680                 685

Gln Thr Met Ile Asn Tyr Phe Gln Gly Ile Asp Gly Ile Pro Pro Ile
            690                 695                 700

Pro Asn Gly Cys Asn Pro Ala Thr Trp Met Leu Gln Ile Ser Thr Pro
705                 710                 715                 720

Ala Ala Glu Ala Arg Ile Gly Arg Asp Phe Ala Glu Ile Tyr Arg Ser
                725                 730                 735

Ser Ala Leu Tyr Arg Glu Val Glu Ala Arg Thr Met Leu Pro Pro Ala
            740                 745                 750

Glu Asn Ser Lys Pro Leu Arg Phe Thr Ser Lys Tyr Asn Thr Ser Val
            755                 760                 765

Leu Tyr Gln Leu Lys Met Cys Leu Trp Lys Gln Ser Leu Val Tyr Trp
770                 775                 780

Arg Asn Pro Ala His Tyr Asn Cys Glu Ile Leu His Asn Phe Leu
785                 790                 795                 800

Phe Leu Gly Val Gln Asn Ser Ser Ile Gln Pro Ile Val Ser Met
                805                 810                 815

Gly Arg Pro Val Phe Arg Arg Glu Arg Asp Ala Gly Met Tyr Ser Cys
                820                 825                 830

Val Val Tyr Ala Ala Ser Gln Gly Leu Ile Glu Val Ile Tyr Val Leu
                835                 840                 845
```

Ala Gln Thr Val Leu Phe Gly Ala Ile Thr Tyr Ser Met Leu Gly Leu
850                     855                 860

Val Arg Ala Ala Gly Thr Ile Phe Ile Tyr Ile Met Phe Leu Leu Leu
865                 870                 875                 880

Thr Thr Tyr Phe Thr Phe Tyr Gly Met Met Val Gly Tyr Asp Leu Val
            885                 890                 895

Leu Cys Ile Ser Leu Arg Ile Ser Gly Ile Trp Arg Ile Glu Leu Leu
            900                 905                 910

Ser Ile Ala Ile Glu Leu Leu Ser Phe Gly His Arg Phe Val Ala Val
            915                 920                 925

Met Leu Pro Asp Leu Leu Ala Tyr Phe Arg Ser Leu Leu Val Val Phe
930                 935                 940

Leu Gln Leu Ile Ser Ala Ala Ser Tyr Phe Arg Cys Tyr Thr Ser Gly
945                 950                 955                 960

Ser Gly Asp Ser Pro Phe Trp Ser Leu Gly Arg Gly Val Phe Cys Val
            965                 970                 975

Phe Arg Glu Ser Leu Lys Val Val Gly Asp Lys Leu Gly Ala Arg Ala
            980                 985                 990

Leu Ala Lys Glu Ser Asn Leu Asp Glu Arg Gln Gln Arg Ala Val Gly
            995                 1000                1005

Ser Ser Val Val Val Ala Val Trp Asp Asp Arg Leu Lys Ala Cys Pro
            1010                1015                1020

Gln Arg Ser Val Arg Gly Arg Pro Arg Ile Arg Trp Gly Ser Leu Thr
1025                1030                1035                1040

Lys Val Lys Ala Gln Glu Leu Glu Gly Arg Leu Ser Ala Met Gly Ala
                1045                1050                1055

Trp Arg Ser Ser Glu Asp Ala Asn Thr Met Trp Ser Thr Thr Ala Asp
                1060                1065                1070

Tyr Ile Arg Lys Ala Ala Arg Glu Val Leu Gly Val Ser Ser Gly Arg
            1075                1080                1085

Thr Cys Gly His Lys Gly Asp Trp Trp Asn Ala Val Val Gln Gly
            1090                1095                1100

Lys Val Glu Ala Lys Lys Val Ala Tyr Leu Arg Leu Val Gly Ser Thr
1105                1110                1115                1120

Gly Glu Glu Glu Lys Arg Ala Asn Ile Ala Arg Tyr Lys Val Ala Arg
                1125                1130                1135

Lys Glu Ala Lys Met Ala Val Thr Glu Ala Lys Thr Thr Ala Phe Ala
                1140                1145                1150

Arg Leu Tyr Glu Glu Leu Gly Asn Lys Gly Gly Glu Lys Lys Leu Leu
            1155                1160                1165

Arg Leu Ala Lys Val Arg Glu Arg Thr Ala Arg Asp Leu Asp Leu Val
            1170                1175                1180

Arg Cys Ile Lys Asp Glu Asp Asp Lys Val Phe Leu Gly Asp Asp Gln
1185                1190                1195                1200

Ile Lys Arg Arg Trp Gln Thr Tyr Phe His Lys Leu Leu Asn Glu Glu
            1205                1210                1215

Gly Asp Gln Asp Ile Val Leu Gly Glu Leu Arg Asn Asp Asp Asn Pro
            1220                1225                1230

His Glu Leu Ser Asp Cys Arg Asp Ile Glu Val Asp Glu Val Met Glu
            1235                1240                1245

Ala Met Gln Gly Asp Glu Asn Cys Arg Arg Lys Phe Phe Gly Gly Ile
            1250                1255                1260

Asn Trp Val Lys Ala Glu Ile His Glu Phe Cys Gln Val Lys Leu Val

Val Lys Ile Glu

<210> SEQ ID NO 82
<211> LENGTH: 861
<212> TYPE: DNA
<213> ORGANISM: Nicotiana tabacum

<400> SEQUENCE: 82

```
atgggagata acaaccatca ccaagtgttt gatgtatccg ccaatggcta cggtgaatcc      60
aagtgttttg acgatgatgg tcgtcttaaa agaagtggta gtgtttggac tgcaagtgct     120
catataatca cagcagttat tggttctgga gttttgtcat tagcttgggc cactgctcag     180
cttggttggg ttgctggtcc agctgttttg cttctcttct cctttgttac ttactacact     240
tctgcgctcc tcgctgattg ttaccgttct ggagatcaag tttctggcaa agaaactat      300
acttatatgg atgctgtccg agccaatctt ggtgggcttc aggtgaagat ttgtggggta     360
attcagtatg tgaatctttt tggagttgca gttggctata ctattgcatc ttctattagc     420
atgatggctg tgaaaaggtc tgattgtttc cataagcatg gacacagagc agcttgcaat     480
gtttcaagca ctccatacat gattatgttt ggagtaatgg aaatcctctt ctcacaaatc     540
ccagattttg atcagatttg gtggctttct attgtggctg ctgttatgtc tttcacatac     600
tctaccattg gtcttggttt aggagttgcc caagttgcag aaacaggaaa atccaagga      660
agtctcactg ggattagtat tggaacagaa gtaactgaaa tgcagaagat tggagaagc     720
tttcaagctc ttggagctat tgcttttgct tattcttact ccctcatcct tattgagatt     780
cagtctttga ctgtgtttga tcatgtagat attgccttga gtggtttgga tcacgttgaa     840
agtgttttgg cttttggttg a                                              861
```

<210> SEQ ID NO 83
<211> LENGTH: 286
<212> TYPE: PRT
<213> ORGANISM: Nicotiana tabacum

<400> SEQUENCE: 83

```
Met Gly Asp Asn Asn His His Gln Val Phe Asp Val Ser Ala Asn Gly
1               5                   10                  15

Tyr Gly Glu Ser Lys Cys Phe Asp Asp Asp Gly Arg Leu Lys Arg Ser
            20                  25                  30

Gly Ser Val Trp Thr Ala Ser Ala His Ile Ile Thr Ala Val Ile Gly
        35                  40                  45

Ser Gly Val Leu Ser Leu Ala Trp Ala Thr Ala Gln Leu Gly Trp Val
    50                  55                  60

Ala Gly Pro Ala Val Leu Leu Leu Phe Ser Phe Val Thr Tyr Tyr Thr
65                  70                  75                  80

Ser Ala Leu Leu Ala Asp Cys Tyr Arg Ser Gly Asp Gln Val Ser Gly
                85                  90                  95

Lys Arg Asn Tyr Thr Tyr Met Asp Ala Val Arg Ala Asn Leu Gly Gly
            100                 105                 110

Leu Gln Val Lys Ile Cys Gly Val Ile Gln Tyr Val Asn Leu Phe Gly
        115                 120                 125

Val Ala Val Gly Tyr Thr Ile Ala Ser Ser Ile Ser Met Met Ala Val
    130                 135                 140

Lys Arg Ser Asp Cys Phe His Lys His Gly His Arg Ala Ala Cys Asn
145                 150                 155                 160
```

```
Val Ser Ser Thr Pro Tyr Met Ile Met Phe Gly Val Met Glu Ile Leu
            165                 170                 175

Phe Ser Gln Ile Pro Asp Phe Asp Gln Ile Trp Trp Leu Ser Ile Val
            180                 185                 190

Ala Ala Val Met Ser Phe Thr Tyr Ser Thr Ile Gly Leu Gly Leu Gly
            195                 200                 205

Val Ala Gln Val Ala Glu Thr Gly Lys Ile Gln Gly Ser Leu Thr Gly
            210                 215                 220

Ile Ser Ile Gly Thr Glu Val Thr Glu Met Gln Lys Ile Trp Arg Ser
225                 230                 235                 240

Phe Gln Ala Leu Gly Ala Ile Ala Phe Ala Tyr Ser Tyr Ser Leu Ile
                245                 250                 255

Leu Ile Glu Ile Gln Ser Leu Thr Val Phe Asp His Val Asp Ile Ala
            260                 265                 270

Leu Ser Gly Leu Asp His Val Glu Ser Val Leu Ala Phe Gly
            275                 280                 285

<210> SEQ ID NO 84
<211> LENGTH: 1524
<212> TYPE: DNA
<213> ORGANISM: Nicotiana tabacum

<400> SEQUENCE: 84
```

| | | | |
|---|---|---|---|
| atggcagaag aaaaactagc cagtaataat ggccaacctc agatagttac aagtattcag | 60 |
| gattttgatc ctccaaagaa accaaaaaga aacaaatatg caatagcttg ttctttctta | 120 |
| gcttctttgg cttcaatctt gcttggttat gatattggag taatgagtgg agccataatc | 180 |
| tacattaaga aagacctcca tatcaccgat acccaagtag agattctagt aggaatcctc | 240 |
| aatatctact ctctctttgg ttctgccgcc gccggccgta catccgactg gattggccgc | 300 |
| cggtacacta tggtggttgc tgccgcaatc ttctttgccg gagctcttct gatgggtttt | 360 |
| gctaccacat atgcatttct catggtgggt cgtttcgttg ccggagtcgg agtcgggtac | 420 |
| gcactcatgg ttgctccagt ttacacagcc gaagtctcgc cggcgtcttc tcgcggattt | 480 |
| ctaacctcct tcccggaagt tttcattaat ggaggtatat tgctgggtta cgtgtctaac | 540 |
| ttcgcgtttt caagacttcc aactaacttg agttggcgat tcatgcttgg aatcggagca | 600 |
| gtcccatcag tattcttagc cgtaagtgta ctcgccatgc tgagtcacc tcgttggctc | 660 |
| gtgatgcagg tcgactcgg cgatgcaagg cgagttctga acaaaaacctc cgattcctta | 720 |
| gaagaagctc agttaagact cgccgatatt aaagcagccg ccggcatacc ggaacactgc | 780 |
| aacgacgaca tcgtcgaggt acccaaacgc cctaaaggcg acaacgtatg gcgcgaattg | 840 |
| atcttctcac caacgccggc cgtccgtcac atactactca ccggcgtcgg aattcatttc | 900 |
| tttcagcaag caagtggaat cgacgccgtc gttttgtaca gcccgaggat ttttgaaaaa | 960 |
| gcagggatta atccgatca cgacaagttg ctcgccaccg tagccgtcgg attcgtcaaa | 1020 |
| acaattttca tactcgtagc cacattcatg ctcgacaaat ccggccggcg gccattgctg | 1080 |
| ttaaccagtg tcgccggaat ggttataaca atggtgttgg cttacgtggc actttttctca | 1140 |
| atcgggatgg gtccaataac gtgggtttac agttcggaga ttttccgtt gaggctacgg | 1200 |
| gcaactggat gcagtatagg tgtggcggta acagggtaa caagtggagt agtgtcaatg | 1260 |
| acgtttttgt ccctggtaaa gtcgataaca attggcggtg cgttcttttt gtacttcgga | 1320 |
| ttggcggcgg tggcgtttgt gtttttcttt acgttgatgc cggaaacaca agggaagact | 1380 |

```
ctagaagaaa tggaggcatt gtttggatct ttctgggact ggagaaaaac ggctagagag   1440
ctgaaagaag ccaagataac ggagaagaac agcaacgata acggccaaat tcagatgggt   1500
actgcaccgg ctattagcag ttaa                                         1524
```

<210> SEQ ID NO 85
<211> LENGTH: 507
<212> TYPE: PRT
<213> ORGANISM: Nicotiana tabacum

<400> SEQUENCE: 85

| | | | | | | | | | | | | | | |
|---|---|---|---|---|---|---|---|---|---|---|---|---|---|---|
| Met | Ala | Glu | Glu | Lys | Leu | Ala | Ser | Asn | Asn | Gly | Gln | Pro | Gln | Ile | Val |
| 1 | | | | 5 | | | | | 10 | | | | | 15 | |
| Thr | Ser | Ile | Gln | Asp | Phe | Asp | Pro | Lys | Lys | Pro | Lys | Arg | Asn | Lys | |
| | | | 20 | | | | | 25 | | | | | 30 | | |
| Tyr | Ala | Ile | Ala | Cys | Ser | Phe | Leu | Ala | Ser | Leu | Ala | Ser | Ile | Leu | Leu |
| | | | 35 | | | | | 40 | | | | | 45 | | |
| Gly | Tyr | Asp | Ile | Gly | Val | Met | Ser | Gly | Ala | Ile | Ile | Tyr | Ile | Lys | Lys |
| | 50 | | | | | 55 | | | | | 60 | | | | |
| Asp | Leu | His | Ile | Thr | Asp | Thr | Gln | Val | Glu | Ile | Leu | Val | Gly | Ile | Leu |
| 65 | | | | | 70 | | | | | 75 | | | | | 80 |
| Asn | Ile | Tyr | Ser | Leu | Phe | Gly | Ser | Ala | Ala | Ala | Gly | Arg | Thr | Ser | Asp |
| | | | | 85 | | | | | 90 | | | | | 95 | |
| Trp | Ile | Gly | Arg | Arg | Tyr | Thr | Met | Val | Val | Ala | Ala | Ile | Phe | Phe | |
| | | | 100 | | | | | 105 | | | | | 110 | | |
| Ala | Gly | Ala | Leu | Leu | Met | Gly | Phe | Ala | Thr | Thr | Tyr | Ala | Phe | Leu | Met |
| | | | 115 | | | | | 120 | | | | | 125 | | |
| Val | Gly | Arg | Phe | Val | Ala | Gly | Val | Gly | Val | Gly | Tyr | Ala | Leu | Met | Val |
| | 130 | | | | | 135 | | | | | 140 | | | | |
| Ala | Pro | Val | Tyr | Thr | Ala | Glu | Val | Ser | Pro | Ala | Ser | Ser | Arg | Gly | Phe |
| 145 | | | | | 150 | | | | | 155 | | | | | 160 |
| Leu | Thr | Ser | Phe | Pro | Glu | Val | Phe | Ile | Asn | Gly | Gly | Ile | Leu | Leu | Gly |
| | | | | 165 | | | | | 170 | | | | | 175 | |
| Tyr | Val | Ser | Asn | Phe | Ala | Phe | Ser | Arg | Leu | Pro | Thr | Asn | Leu | Ser | Trp |
| | | | 180 | | | | | 185 | | | | | 190 | | |
| Arg | Phe | Met | Leu | Gly | Ile | Gly | Ala | Val | Pro | Ser | Val | Phe | Leu | Ala | Val |
| | | 195 | | | | | 200 | | | | | 205 | | | |
| Ser | Val | Leu | Ala | Met | Pro | Glu | Ser | Pro | Arg | Trp | Leu | Val | Met | Gln | Gly |
| 210 | | | | | 215 | | | | | 220 | | | | | |
| Arg | Leu | Gly | Asp | Ala | Arg | Arg | Val | Leu | Asn | Lys | Thr | Ser | Asp | Ser | Leu |
| 225 | | | | 230 | | | | | 235 | | | | | 240 | |
| Glu | Glu | Ala | Gln | Leu | Arg | Leu | Ala | Asp | Ile | Lys | Ala | Ala | Gly | Ile | |
| | | | 245 | | | | | 250 | | | | | 255 | | |
| Pro | Glu | His | Cys | Asn | Asp | Asp | Ile | Val | Glu | Val | Pro | Lys | Arg | Pro | Lys |
| | | | 260 | | | | | 265 | | | | | 270 | | |
| Gly | Asp | Asn | Val | Trp | Arg | Glu | Leu | Ile | Phe | Ser | Pro | Thr | Pro | Ala | Val |
| | | | 275 | | | | | 280 | | | | | 285 | | |
| Arg | His | Ile | Leu | Leu | Thr | Gly | Val | Gly | Ile | His | Phe | Phe | Gln | Gln | Ala |
| | | | 290 | | | | | 295 | | | | | 300 | | |
| Ser | Gly | Ile | Asp | Ala | Val | Val | Leu | Tyr | Ser | Pro | Arg | Ile | Phe | Glu | Lys |
| 305 | | | | | 310 | | | | | 315 | | | | | 320 |
| Ala | Gly | Ile | Lys | Ser | Asp | His | Asp | Lys | Leu | Leu | Ala | Thr | Val | Ala | Val |
| | | | | 325 | | | | | 330 | | | | | 335 | |
| Gly | Phe | Val | Lys | Thr | Ile | Phe | Ile | Leu | Val | Ala | Thr | Phe | Met | Leu | Asp |
| | | | 340 | | | | | 345 | | | | | 350 | | |

```
Lys Ser Gly Arg Arg Pro Leu Leu Leu Thr Ser Val Ala Gly Met Val
            355                 360                 365

Ile Thr Met Val Leu Ala Tyr Val Ala Leu Phe Ser Ile Gly Met Gly
        370                 375                 380

Pro Ile Thr Trp Val Tyr Ser Ser Glu Ile Phe Pro Leu Arg Leu Arg
385                 390                 395                 400

Ala Thr Gly Cys Ser Ile Gly Val Ala Val Asn Arg Val Thr Ser Gly
            405                 410                 415

Val Val Ser Met Thr Phe Leu Ser Leu Val Lys Ser Ile Thr Ile Gly
            420                 425                 430

Gly Ala Phe Phe Leu Tyr Phe Gly Leu Ala Ala Val Ala Phe Val Phe
            435                 440                 445

Phe Phe Thr Leu Met Pro Glu Thr Gln Gly Lys Thr Leu Glu Glu Met
        450                 455                 460

Glu Ala Leu Phe Gly Ser Phe Trp Asp Trp Arg Lys Thr Ala Arg Glu
465                 470                 475                 480

Leu Lys Glu Ala Lys Ile Thr Glu Lys Asn Ser Asn Asp Asn Gly Gln
            485                 490                 495

Ile Gln Met Gly Thr Ala Pro Ala Ile Ser Ser
            500                 505
```

<210> SEQ ID NO 86
<211> LENGTH: 1191
<212> TYPE: DNA
<213> ORGANISM: Nicotiana tabacum

<400> SEQUENCE: 86

```
atgtctagca atggaaaaat agaggaaaat aaggttccat tattagatta tgcatcctct      60
aatatccaca agagttatat attagaacaa aaccaagatg aacaaagttt tgcaaataga     120
ttttggattg aaacaaagaa gctatggcat atagttggcc ctgctatttt tagtagaata     180
gtttcttact ccatgtttgt catcactcaa gcttttgctg gtcatcttgg tgatcttgaa     240
cttgctgcta tgtccattgc tagtaatgtt gttcttggct tcgatttcgg cctcatgggt     300
tacagtacta atatatcagc attttctaaa atatacatac atatgttcat ggatatttta     360
ttgaactttg cgggtactag tgaaccctcg cttggtaaca tggtttcgcc tccgtttgct     420
actatacaaa gcttccgtt atgtcaaaaa gattcaacaa tttatccaat ttgcatagta     480
cgaagcttgg agaactggta ctacagggtg ctaattgtga tgactggtaa tttggaaaat     540
gctaaaattg ctgtggacgc attgtctata tgcatgaata tcaatggttg gaactaatg     600
attcctcttg gattcttcgc tggaactgga agacaaaacc atagggccaa taaatcaata     660
attgtcaacc agttagtagc agttacacaa tcaatgtga ttggtttatt tttctggatt      720
ttgatcatat ttttccacaa tgaacttgct cttatttct caactagcca acctgttctt      780
gaagctgttc ataaactctc tatcctctta gccttcactg ttctcctcaa cagcgttcag     840
cccattctct cgggggttgc tgttggatct ggatggcaag catatgttgc atatataaat     900
ttgggttgct attatttact ggagtacct cttggtttca taatgggatg gggtttccac      960
tatggtgtca tgggcatctg ggctggaatg atctttggtg aactgcaat tcagactttg     1020
attttggcta taatcacaat aagatgtgat tggaataaag agcaccaaca tcagcaaaag    1080
aaagaagaag aagaagaaga agaagaagaa gaagaagaag aagaagaagg aggaggagga    1140
agagaagaag aagaaggagg aggaggagga ggaggaggag aaagagactg a             1191
```

<210> SEQ ID NO 87
<211> LENGTH: 396
<212> TYPE: PRT
<213> ORGANISM: Nicotiana tabacum

<400> SEQUENCE: 87

Met Ser Ser Asn Gly Lys Ile Glu Glu Asn Lys Val Pro Leu Leu Asp
1               5                   10                  15

Tyr Ala Ser Ser Asn Ile His Lys Ser Tyr Ile Leu Glu Gln Asn Gln
            20                  25                  30

Asp Glu Gln Ser Phe Ala Asn Arg Phe Trp Ile Glu Thr Lys Lys Leu
        35                  40                  45

Trp His Ile Val Gly Pro Ala Ile Phe Ser Arg Ile Val Ser Tyr Ser
    50                  55                  60

Met Phe Val Ile Thr Gln Ala Phe Ala Gly His Leu Gly Asp Leu Glu
65                  70                  75                  80

Leu Ala Ala Met Ser Ile Ala Ser Asn Val Val Leu Gly Phe Asp Phe
                85                  90                  95

Gly Leu Met Gly Tyr Ser Thr Asn Ile Ser Ala Phe Ser Lys Ile Tyr
            100                 105                 110

Ile His Met Phe Met Asp Ile Leu Leu Asn Phe Ala Gly Thr Ser Glu
        115                 120                 125

Pro Ser Leu Gly Asn Met Val Ser Pro Phe Ala Thr Ile Gln Lys
    130                 135                 140

Leu Pro Leu Cys Gln Lys Asp Ser Thr Ile Tyr Pro Ile Cys Ile Val
145                 150                 155                 160

Arg Ser Leu Glu Asn Trp Tyr Tyr Arg Val Leu Ile Val Met Thr Gly
                165                 170                 175

Asn Leu Glu Asn Ala Lys Ile Ala Val Asp Ala Leu Ser Ile Cys Met
            180                 185                 190

Asn Ile Asn Gly Trp Glu Leu Met Ile Pro Leu Gly Phe Phe Ala Gly
        195                 200                 205

Thr Gly Arg Gln Asn His Arg Ala Asn Lys Ser Ile Ile Val Asn Gln
    210                 215                 220

Leu Val Ala Val Thr Gln Ser Ile Val Ile Gly Leu Phe Phe Trp Ile
225                 230                 235                 240

Leu Ile Ile Phe Phe His Asn Glu Leu Ala Leu Ile Phe Ser Thr Ser
                245                 250                 255

Gln Pro Val Leu Glu Ala Val His Lys Leu Ser Ile Leu Leu Ala Phe
            260                 265                 270

Thr Val Leu Leu Asn Ser Val Gln Pro Ile Leu Ser Gly Val Ala Val
        275                 280                 285

Gly Ser Gly Trp Gln Ala Tyr Val Ala Tyr Ile Asn Leu Gly Cys Tyr
    290                 295                 300

Tyr Leu Leu Gly Val Pro Leu Gly Phe Ile Met Gly Trp Gly Phe His
305                 310                 315                 320

Tyr Gly Val Met Gly Ile Trp Ala Gly Met Ile Phe Gly Thr Ala
                325                 330                 335

Ile Gln Thr Leu Ile Leu Ala Ile Ile Thr Ile Arg Cys Asp Trp Asn
            340                 345                 350

Lys Glu His Gln His Gln Gln Lys Lys Glu Glu Glu Glu Glu Glu
        355                 360                 365

Glu Glu Glu Glu Glu Glu Glu Gly Gly Gly Arg Glu Glu
    370                 375                 380

Glu Gly Gly Gly Gly Gly Gly Gly Glu Arg Asp
385                 390                 395

<210> SEQ ID NO 88
<211> LENGTH: 2223
<212> TYPE: DNA
<213> ORGANISM: Nicotiana tabacum

<400> SEQUENCE: 88

| | | | | | |
|---|---|---|---|---|---|
| atggattctt | ctaaaaacaa | catttaccag | ccattttag | ataacaatgg | aaattctagt | 60 |
| ttgtcacctc | agttttctga | acccataat | tttgaatcaa | gcaatgagtt | agaaactgta | 120 |
| cttttagaca | ctgaaatacc | actatggaat | aaactccgtt | tagctacatg | gattgaaatg | 180 |
| aagctccttt | tcaccttgc | tgcacctgct | gttatggttt | atatgattaa | ttatattatg | 240 |
| tctatgtcaa | ctcaaatatt | ttctggtcat | ttgggtaatc | ttgagctggc | tgctgcttca | 300 |
| cttggaaata | ctggaattca | agttttgct | tatggtctta | tgttgggaat | gggaagtgca | 360 |
| gttgaaacac | tatgtgggca | agcatttgga | gcaaagaaat | atgatatgtt | aggagtttat | 420 |
| ctgcaaagat | caacaattct | cctaactcta | acaggaattt | tactcgcttt | cgtgtacatt | 480 |
| ttctgcaagc | caattctaat | atttctaggc | gaatcggaaa | gaattgcttc | agcagctgcc | 540 |
| ttattcgtgt | acggtctaat | tccccaaatt | ttcgcctacg | cgttaaattt | cccaattcag | 600 |
| aagtttctac | aagctcagag | tattgtagcg | ccaagtgcat | acatttcagc | tgcgacttta | 660 |
| gtgttgcatt | tagtgatgag | ttgggttgtg | atttacaaga | ttgggcttgg | tctactcggg | 720 |
| gcgtctttga | tactgagttt | gtcatggtgg | ataatcgtaa | taggccaatt | tgtgtatatt | 780 |
| gtgaaaagtg | agaggtgtaa | gcaaacatgg | aatgggttca | gtttgcaggc | gttttccggc | 840 |
| ttgccggtgt | ttttcaagtt | atcagcagcg | tctgcggtga | tgttgtgctt | ggagacatgg | 900 |
| tactttcaaa | ttgtggtttt | gctcgctgga | ttgcttgaaa | tcctgaatt | gtctttggat | 960 |
| gctctttcta | tttgcatgac | aatttctggt | tgggtattca | tgatatcagt | tggattcaat | 1020 |
| gcagcagcaa | gtgtgagagt | gagcaatgaa | ctaggagcaa | ggcatccaaa | atcagcagct | 1080 |
| ttttctgttg | ttgtggttac | gtcgtggtct | ttcattctct | cggtgattgc | tgcagtcatc | 1140 |
| gttcttgcat | tgcgtaatct | catcagttat | gccttcactg | gtggtgaagt | tgttgctcaa | 1200 |
| gctgtctccg | atctttgtcc | attgctcgcg | atttccctta | tactcaatgg | aattcaaccc | 1260 |
| gtcttgtcag | gtgtggctgt | tggctgtgga | tggcaaactt | ttgtggccta | tgtaaatgtt | 1320 |
| ggctgctatt | acattgtcgg | agttccattg | ggtgctctcc | tcggcttcca | tttcaaactt | 1380 |
| ggagctaagg | gtatatggtc | aggaatgctg | ggaggtacgg | tgatgcagac | aatcattttg | 1440 |
| atatggatca | ctgctcgaac | cgattggaat | aaagaggcca | aggggttgga | attcactctc | 1500 |
| agccacctca | tccggttata | tcgacctcga | ctttttcgag | gattaatcaa | gctccaacac | 1560 |
| cgatcaacga | agtcctttt | tgcaagcatt | gatgaggaca | agaccgagg | ttggatgagc | 1620 |
| cggttcgtgc | gggtaaggac | ctgcgacctc | atccctgagg | agaaactgct | gttccccgag | 1680 |
| aagtggaacc | tgatccggt | tgcatggatg | cctcacgtgg | tccccgacct | cgaagactgg | 1740 |
| ttcgaaagct | ggctgcaact | tcctcccatg | ccgagcgctg | ctggcgtgac | atggcaaggg | 1800 |
| gcagatagga | ggctaagaat | catagtgagc | tcatcttgcc | tcggggatgt | tgctgaaata | 1860 |
| aggcctacct | cgcctgggga | agaggtggat | cccaaaccgg | ttaaggacaa | gaaaaggaga | 1920 |
| agggcctcac | cctctgatac | cccaaagtcc | aagaagatta | aggcccgtaa | attgaaggac | 1980 |
| gattctgcca | ctctatctgc | cgacgtagtc | caacagctac | gagatgaaga | agaggagggg | 2040 |

```
gaagatgctg gttgtgatct ggtgcctcga aagaggggga gcgtcgaagc tccaaaaata    2100
gttgggccgg tgatggtcga ggagactcat ccttggaccg aggagatctc ggaaggtact    2160
ccgagcagag ttcccgagtc atcgggggcc caagatattc ccgtcgtgat gaaaaatcgg    2220
tga                                                                  2223
```

<210> SEQ ID NO 89
<211> LENGTH: 740
<212> TYPE: PRT
<213> ORGANISM: Nicotiana tabacum

<400> SEQUENCE: 89

```
Met Asp Ser Ser Lys Asn Asn Ile Tyr Gln Pro Phe Leu Asp Asn Asn
1               5                   10                  15

Gly Asn Ser Ser Leu Ser Pro Gln Phe Ser Glu Thr His Asn Phe Glu
            20                  25                  30

Ser Ser Asn Glu Leu Glu Thr Val Leu Leu Asp Thr Glu Ile Pro Leu
        35                  40                  45

Trp Asn Lys Leu Arg Leu Ala Thr Trp Ile Glu Met Lys Leu Leu Phe
    50                  55                  60

His Leu Ala Ala Pro Ala Val Met Val Tyr Met Ile Asn Tyr Ile Met
65                  70                  75                  80

Ser Met Ser Thr Gln Ile Phe Ser Gly His Leu Gly Asn Leu Glu Leu
                85                  90                  95

Ala Ala Ala Ser Leu Gly Asn Thr Gly Ile Gln Val Phe Ala Tyr Gly
            100                 105                 110

Leu Met Leu Gly Met Gly Ser Ala Val Glu Thr Leu Cys Gly Gln Ala
        115                 120                 125

Phe Gly Ala Lys Lys Tyr Asp Met Leu Gly Val Tyr Leu Gln Arg Ser
    130                 135                 140

Thr Ile Leu Leu Thr Leu Thr Gly Ile Leu Leu Ala Phe Val Tyr Ile
145                 150                 155                 160

Phe Cys Lys Pro Ile Leu Ile Phe Leu Gly Glu Ser Glu Arg Ile Ala
                165                 170                 175

Ser Ala Ala Ala Leu Phe Val Tyr Gly Leu Ile Pro Gln Ile Phe Ala
            180                 185                 190

Tyr Ala Leu Asn Phe Pro Ile Gln Lys Phe Leu Gln Ala Gln Ser Ile
        195                 200                 205

Val Ala Pro Ser Ala Tyr Ile Ser Ala Ala Thr Leu Val Leu His Leu
    210                 215                 220

Val Met Ser Trp Val Val Ile Tyr Lys Ile Gly Leu Gly Leu Leu Gly
225                 230                 235                 240

Ala Ser Leu Ile Leu Ser Leu Ser Trp Trp Ile Ile Val Ile Gly Gln
                245                 250                 255

Phe Val Tyr Ile Val Lys Ser Glu Arg Cys Lys Gln Thr Trp Asn Gly
            260                 265                 270

Phe Ser Leu Gln Ala Phe Ser Gly Leu Pro Val Phe Lys Leu Ser
        275                 280                 285

Ala Ala Ser Ala Val Met Leu Cys Leu Glu Thr Trp Tyr Phe Gln Ile
    290                 295                 300

Val Val Leu Leu Ala Gly Leu Leu Glu Asn Pro Glu Leu Ser Leu Asp
305                 310                 315                 320

Ala Leu Ser Ile Cys Met Thr Ile Ser Gly Trp Val Phe Met Ile Ser
                325                 330                 335
```

```
Val Gly Phe Asn Ala Ala Ala Ser Val Arg Val Ser Asn Glu Leu Gly
                340                 345                 350

Ala Arg His Pro Lys Ser Ala Ala Phe Ser Val Val Val Thr Ser
            355                 360                 365

Trp Ser Phe Ile Leu Ser Val Ile Ala Ala Val Ile Val Leu Ala Leu
    370                 375                 380

Arg Asn Leu Ile Ser Tyr Ala Phe Thr Gly Gly Glu Val Val Ala Gln
385                 390                 395                 400

Ala Val Ser Asp Leu Cys Pro Leu Leu Ala Ile Ser Leu Ile Leu Asn
                405                 410                 415

Gly Ile Gln Pro Val Leu Ser Gly Val Ala Val Gly Cys Gly Trp Gln
            420                 425                 430

Thr Phe Val Ala Tyr Val Asn Val Gly Cys Tyr Tyr Ile Val Gly Val
        435                 440                 445

Pro Leu Gly Ala Leu Leu Gly Phe His Phe Lys Leu Gly Ala Lys Gly
    450                 455                 460

Ile Trp Ser Gly Met Leu Gly Gly Thr Val Met Gln Thr Ile Ile Leu
465                 470                 475                 480

Ile Trp Ile Thr Ala Arg Thr Asp Trp Asn Lys Glu Ala Lys Gly Leu
                485                 490                 495

Glu Phe Thr Leu Ser His Leu Ile Arg Leu Tyr Arg Pro Arg Leu Phe
            500                 505                 510

Arg Gly Leu Ile Lys Leu Gln His Arg Ser Thr Lys Ser Phe Phe Ala
        515                 520                 525

Ser Ile Asp Glu Asp Lys Asp Arg Gly Trp Met Ser Arg Phe Val Arg
    530                 535                 540

Val Arg Thr Cys Asp Leu Ile Pro Glu Glu Lys Leu Leu Phe Pro Glu
545                 550                 555                 560

Lys Trp Asn Pro Asp Pro Val Ala Trp Met Pro His Val Val Pro Asp
                565                 570                 575

Leu Glu Asp Trp Phe Glu Ser Trp Leu Gln Leu Pro Pro Met Pro Ser
            580                 585                 590

Ala Ala Gly Val Thr Trp Gln Gly Ala Asp Arg Arg Leu Arg Ile Ile
        595                 600                 605

Val Ser Ser Ser Cys Leu Gly Asp Val Ala Glu Ile Arg Pro Thr Ser
    610                 615                 620

Pro Gly Glu Glu Val Asp Pro Lys Pro Val Lys Asp Lys Lys Arg Arg
625                 630                 635                 640

Arg Ala Ser Pro Ser Asp Thr Pro Lys Ser Lys Lys Ile Lys Ala Arg
                645                 650                 655

Lys Leu Lys Asp Asp Ser Ala Thr Leu Ser Ala Asp Val Val Gln Gln
            660                 665                 670

Leu Arg Asp Glu Glu Glu Gly Asp Ala Gly Cys Asp Leu Val
        675                 680                 685

Pro Arg Lys Arg Gly Ser Val Glu Ala Pro Lys Ile Val Gly Pro Val
    690                 695                 700

Met Val Glu Glu Thr His Pro Trp Thr Glu Glu Ile Ser Glu Gly Thr
705                 710                 715                 720

Pro Ser Arg Val Pro Glu Ser Ser Gly Ala Gln Asp Ile Pro Val Val
                725                 730                 735

Met Lys Asn Arg
            740
```

<210> SEQ ID NO 90
<211> LENGTH: 1404
<212> TYPE: DNA
<213> ORGANISM: Nicotiana tabacum

<400> SEQUENCE: 90

```
atgcttgagc gagcctctgt tatagaattg aaaaatctat tccggctagc agccccatca      60
gttattgttt atttgctcaa caatatcact tcaatgtcta cccaactatt ctgtggtcat     120
ctcggtaatc ttgaactcgc tgctgcttcc cttggcaatg aaggtattca actcttggcc     180
tatggcgtca tgttagggat ggggagtgca gtggagacac tatgtgggca ggcatatgga     240
gctcacaagt atggaagtct tggaatatat cttcaaagat caactatcct cttgatgtta     300
tccggaatac cgataatggt ggcttactta ttctcaaagc caatttttaat tttttttagga     360
gaatcagaga agttgcatc agcagctgca ctatttgttt atggtttaat tcctcaaata     420
tttgcttatg ctgccaattt tcctatccaa aagttcttgc aagcccaaag tattgtaaat     480
cccagcgcat atatagcagc agcgacatta gtcctccatc ttttcctaac atggattgtg     540
ctttatgtat ttgagtgggg attgtttgga ggagccttgg ttctaagtat ttcgtggtgg     600
atagtagtca ttgcacaatt tatgtacata ttgtggagtg atacatgcaa gaaaacatgg     660
agtggattta gtctgcaagc gttttctggg ctgtgggatt tctttaagtt gtcagctgct     720
tcatctgtga tgttgtgttt ggaggcgtgg tactttcaga ttttggtttt agttgctggt     780
ttgctaccaa tcctgaagt ggcattggat tctctagctg tttgtaacac aattcttgga     840
tgtgtgttca tgttatctgt tggtttcaac gctgctgcaa gtgtaagggt gagcaatgaa     900
ttgggagctg acatccaaa atcagctgca ttttcagttg tggtggtaac attaagctcg     960
ttcgtgattc tgtagtcat tgccatagta gtgatgttgc ttcgcgatgt gatgagttat    1020
gcattcacag gcggggaaac cattgctaaa gcatcctcag aacttgcacc actcttggct    1080
gcctcagtag ttctcaatgg tattcaacct gttttatctg gggtggccgt tgggtgtgga    1140
tggcaaggtt ttgtagctta cgttaacgtc ggatgttact acgttgttgg cattccattg    1200
ggtgttcttc ttggtttcaa attcaaactc ggagctaagg ggattatggc tgggcatgtt    1260
tggaggaaca gccatacaaa ctctaatctt actatgggcc acttttcgaa ccaattggga    1320
cgacgaggtc aggtggagaa aacgaaaaat cgattaaata gtggcgaga tagcagtaaa    1380
accccattgt tgaacgaatc atga                                           1404
```

<210> SEQ ID NO 91
<211> LENGTH: 467
<212> TYPE: PRT
<213> ORGANISM: Nicotiana tabacum

<400> SEQUENCE: 91

```
Met Leu Glu Arg Ala Ser Val Ile Glu Leu Lys Asn Leu Phe Arg Leu
1               5                  10                  15

Ala Ala Pro Ser Val Ile Val Tyr Leu Leu Asn Asn Ile Thr Ser Met
            20                  25                  30

Ser Thr Gln Leu Phe Cys Gly His Leu Gly Asn Leu Glu Leu Ala Ala
        35                  40                  45

Ala Ser Leu Gly Asn Glu Gly Ile Gln Leu Leu Ala Tyr Gly Val Met
    50                  55                  60

Leu Gly Met Gly Ser Ala Val Glu Thr Leu Cys Gly Gln Ala Tyr Gly
65                  70                  75                  80
```

Ala His Lys Tyr Gly Ser Leu Gly Ile Tyr Leu Gln Arg Ser Thr Ile
            85                  90                  95

Leu Leu Met Leu Ser Gly Ile Pro Ile Met Val Ala Tyr Leu Phe Ser
        100                 105                 110

Lys Pro Ile Leu Ile Phe Leu Gly Glu Ser Glu Lys Val Ala Ser Ala
        115                 120                 125

Ala Ala Leu Phe Val Tyr Gly Leu Ile Pro Gln Ile Phe Ala Tyr Ala
        130                 135                 140

Ala Asn Phe Pro Ile Gln Lys Phe Leu Gln Ala Gln Ser Ile Val Asn
145                 150                 155                 160

Pro Ser Ala Tyr Ile Ala Ala Thr Leu Val Leu His Leu Phe Leu
                165                 170                 175

Thr Trp Ile Val Leu Tyr Val Phe Glu Trp Gly Leu Phe Gly Gly Ala
        180                 185                 190

Leu Val Leu Ser Ile Ser Trp Trp Ile Val Ile Ala Gln Phe Met
        195                 200                 205

Tyr Ile Leu Trp Ser Asp Thr Cys Lys Lys Thr Trp Ser Gly Phe Ser
        210                 215                 220

Leu Gln Ala Phe Ser Gly Leu Trp Asp Phe Phe Lys Leu Ser Ala Ala
225                 230                 235                 240

Ser Ser Val Met Leu Cys Leu Glu Ala Trp Tyr Phe Gln Ile Leu Val
                245                 250                 255

Leu Val Ala Gly Leu Leu Pro Asn Pro Glu Val Ala Leu Asp Ser Leu
        260                 265                 270

Ala Val Cys Asn Thr Ile Leu Gly Cys Val Phe Met Leu Ser Val Gly
        275                 280                 285

Phe Asn Ala Ala Ala Ser Val Arg Val Ser Asn Glu Leu Gly Ala Gly
290                 295                 300

His Pro Lys Ser Ala Ala Phe Ser Val Val Val Thr Leu Ser Ser
305                 310                 315                 320

Phe Val Ile Ala Val Ile Ala Ile Val Val Met Leu Leu Arg Asp
        325                 330                 335

Val Met Ser Tyr Ala Phe Thr Gly Gly Glu Thr Ile Ala Lys Ala Ser
        340                 345                 350

Ser Glu Leu Ala Pro Leu Leu Ala Ala Ser Val Val Leu Asn Gly Ile
        355                 360                 365

Gln Pro Val Leu Ser Gly Val Ala Val Gly Cys Gly Trp Gln Gly Phe
        370                 375                 380

Val Ala Tyr Val Asn Val Gly Cys Tyr Tyr Val Val Gly Ile Pro Leu
385                 390                 395                 400

Gly Val Leu Leu Gly Phe Lys Phe Lys Leu Gly Ala Lys Gly Ile Met
                405                 410                 415

Ala Gly His Val Trp Arg Asn Ser His Thr Asn Ser Asn Leu Thr Met
            420                 425                 430

Gly His Phe Ser Asn Gln Leu Gly Arg Arg Gly Gln Val Glu Lys Thr
        435                 440                 445

Lys Asn Arg Leu Asn Lys Trp Arg Asp Ser Ser Lys Thr Pro Leu Leu
450                 455                 460

Asn Glu Ser
465

<210> SEQ ID NO 92
<211> LENGTH: 353
<212> TYPE: PRT

<213> ORGANISM: Nicotiana tabacum

<400> SEQUENCE: 92

```
Met Glu His Pro Gly Leu Ser Thr Asn Met Arg Arg Ile Leu Leu Leu
1               5                   10                  15

Ile Ser Cys Leu Ile Leu Ala Val Gly Ile Cys Gly Gly Pro Leu Met
            20                  25                  30

Met Arg Leu Tyr Tyr Val Glu Gly Gly Ser Arg Ile Trp Leu Ser Ser
        35                  40                  45

Trp Leu Gln Thr Gly Gly Trp Pro Leu Thr Leu Ile Pro Leu Ala Ile
    50                  55                  60

Leu Tyr Tyr Tyr Arg Arg Lys Thr Glu Gly Ser Asn Ala Lys Phe Tyr
65                  70                  75                  80

Leu Met Thr Pro Arg Ile Phe Ile Ala Ser Phe Val Ile Gly Val Ala
                85                  90                  95

Thr Gly Leu Asp Asp Phe Leu Tyr Ser Trp Gly Gly Ser Lys Leu Pro
            100                 105                 110

Val Ser Thr Ser Ser Leu Leu Ala Ala Gln Leu Ala Phe Thr Ala
        115                 120                 125

Val Gly Ala Phe Phe Ile Val Lys Leu Lys Leu Ser Pro Phe Ser Ile
130                 135                 140

Asn Ala Val Val Leu Leu Thr Val Gly Ala Val Leu Leu Gly Ile Arg
145                 150                 155                 160

Ser Asn Gly Asp Arg Pro Glu Gly Val Thr Ser Lys Glu Tyr Ile Ile
                165                 170                 175

Gly Phe Met Met Thr Leu Leu Ala Ala Leu Tyr Gly Val Ile Leu
            180                 185                 190

Pro Cys Ile Glu Leu Ile Tyr Met Lys Ala Lys Gln Ala Ile Thr Ser
        195                 200                 205

Thr Leu Val Leu Glu Ile Gln Met Ile Met Ser Phe Ala Ala Thr Ala
    210                 215                 220

Phe Cys Thr Val Gly Met Ile Ala Asn Lys Asp Phe Gln Ala Met Ser
225                 230                 235                 240

Arg Glu Ala Lys Gln Phe Asn Val Gly Glu Ala Arg Tyr Tyr Thr Val
                245                 250                 255

Ile Val Cys Thr Ala Ala Ile Trp Gln Cys Phe Phe Val Gly Ile Ile
            260                 265                 270

Gly Val Ile Tyr Cys Ser Ser Ser Leu Met Ser Gly Val Met Ile Ala
        275                 280                 285

Val Leu Leu Pro Val Thr Glu Val Leu Ala Val Ile Phe Phe Lys Glu
    290                 295                 300

Asn Phe Ser Gly Glu Lys Gly Leu Ala Leu Phe Leu Ser Leu Trp Gly
305                 310                 315                 320

Phe Val Ser Tyr Phe Tyr Gly Glu Phe Arg Gln Thr Lys Lys Gln Lys
                325                 330                 335

Asn Thr Ser Pro Glu Ala Glu Met Thr Ile Thr Thr His Thr Glu Ser
            340                 345                 350

Val
```

<210> SEQ ID NO 93
<211> LENGTH: 352
<212> TYPE: PRT
<213> ORGANISM: Nicotiana tabacum

<400> SEQUENCE: 93

```
Met Glu His Pro Gly Leu Ser Thr Thr Met Arg Arg Ile Leu Leu Leu
1               5                   10                  15

Ile Ser Cys Leu Ile Leu Ala Val Gly Ile Cys Gly Gly Pro Leu Met
            20                  25                  30

Met Arg Leu Tyr Tyr Val Glu Gly Gly Ser Arg Ile Trp Leu Ser Ser
        35                  40                  45

Trp Leu Gln Thr Gly Gly Trp Pro Leu Thr Phe Ile Pro Leu Ala Phe
50                  55                  60

Leu Tyr Tyr Arg Arg Lys Ile Glu Gly Ser Asn Ala Lys Phe Tyr
65              70                  75                  80

Leu Met Thr Pro Arg Ile Phe Ile Ala Ala Phe Val Ile Gly Ile Ala
                85                  90                  95

Thr Gly Leu Asp Asp Phe Leu Tyr Ser Trp Gly Gly Ser Lys Leu Pro
            100                 105                 110

Val Ser Thr Ser Ser Leu Leu Leu Ala Ala Gln Leu Ala Phe Thr Ala
        115                 120                 125

Val Gly Ala Phe Phe Ile Val Lys Leu Lys Leu Ser Pro Phe Ser Ile
130                 135                 140

Asn Ala Val Val Leu Leu Thr Val Gly Ala Val Leu Leu Gly Ile Arg
145                 150                 155                 160

Ser Asn Gly Asp Arg Pro Glu Gly Val Thr Ser Lys Glu Tyr Ile Ile
                165                 170                 175

Gly Phe Met Met Thr Leu Leu Ala Ala Ala Leu Tyr Gly Val Ile Leu
            180                 185                 190

Pro Cys Ile Glu Leu Ile Tyr Met Lys Ala Lys Gln Ala Ile Thr Ala
        195                 200                 205

Thr Leu Val Leu Glu Ile Gln Met Ile Met Ser Phe Ala Ala Thr Ala
210                 215                 220

Phe Cys Thr Val Gly Met Ile Ala Asn Lys Asp Phe Gln Ala Met Ser
225                 230                 235                 240

Arg Glu Ala Lys Gln Phe Asn Leu Gly Glu Ala Arg Tyr Tyr Thr Val
                245                 250                 255

Ile Val Cys Thr Ala Ala Ile Trp Glu Cys Phe Phe Val Gly Ile Ile
            260                 265                 270

Gly Val Ile Tyr Cys Ser Ser Ser Leu Met Ser Gly Val Met Ile Ala
        275                 280                 285

Val Leu Leu Pro Val Thr Glu Val Leu Ala Val Ile Phe Phe Lys Glu
290                 295                 300

Lys Phe Ser Gly Glu Lys Gly Leu Ala Leu Phe Leu Ser Leu Trp Gly
305                 310                 315                 320

Phe Val Ser Tyr Phe Tyr Gly Glu Phe Arg Gln Thr Lys Lys Glu Lys
                325                 330                 335

Asn Lys Ser Pro Glu Ala Glu Met Thr Thr Thr His Thr Glu Ser Val
            340                 345                 350

<210> SEQ ID NO 94
<211> LENGTH: 1263
<212> TYPE: PRT
<213> ORGANISM: Solanum lycopersicum

<400> SEQUENCE: 94

Met Glu Asp Asn Asn Asn Asn Gly Glu Lys Lys Arg Asp Glu Asp Gln
1               5                   10                  15

Lys Val Ser Phe Tyr Lys Leu Phe Ser Phe Ala Asp Lys Phe Asp Ile
```

```
                20                  25                  30
Ala Leu Met Ile Ile Gly Thr Ile Gly Ala Ile Gly Asn Gly Leu Thr
            35                  40                  45
Gln Pro Leu Met Thr Leu Ile Phe Gly Gln Leu Val Asn Ser Phe Gly
        50                  55                  60
Ser Ser Asn Ser Asp Glu Val Val His Glu Ile Ser Lys Val Ser Ile
65                  70                  75                  80
Tyr Tyr Val Tyr Leu Ala Ile Gly Ala Gly Val Ala Ser Leu Leu Gln
                85                  90                  95
Met Ser Cys Trp Met Val Thr Gly Glu Arg Gln Ala Thr Arg Ile Arg
            100                 105                 110
Gly Leu Tyr Leu Lys Thr Ile Leu Arg Gln Asp Ile Ala Phe Phe Asp
        115                 120                 125
Thr Glu Thr Thr Thr Gly Glu Val Ile Gly Arg Met Ser Gly Asp Thr
    130                 135                 140
Ile Leu Ile Gln Asp Ala Leu Gly Glu Lys Val Gly Lys Phe Ile Gln
145                 150                 155                 160
Phe Ile Ser Thr Phe Val Gly Gly Phe Ile Val Ala Phe Phe Lys Gly
                165                 170                 175
Trp Leu Leu Ser Ile Val Leu Val Ser Cys Ile Pro Ala Leu Val Ile
            180                 185                 190
Ala Gly Gly Ala Met Ala Leu Ile Met Ser Lys Met Ser Ser Arg Gly
        195                 200                 205
Gln Val Ala Tyr Ala Gln Ala Gly Asn Val Val Glu Gln Thr Ile Gly
    210                 215                 220
Ala Ile Arg Thr Val Ser Ala Phe Thr Gly Glu Lys Leu Ala Ile Asp
225                 230                 235                 240
Lys Tyr Asp Ser Lys Leu Lys Ile Ala Cys Ala Ser Thr Val Gln Gln
                245                 250                 255
Gly Leu Val Ser Gly Ile Gly Leu Gly Thr Val Leu Leu Ile Val Phe
            260                 265                 270
Ser Thr Tyr Gly Leu Ala Val Trp Tyr Gly Ser Lys Leu Ile Ile Glu
        275                 280                 285
Arg Gly Tyr Asn Gly Gly Asp Val Ile Asn Val Ile Met Ala Ile Met
    290                 295                 300
Thr Gly Gly Met Ser Leu Gly Gln Thr Thr Pro Ser Leu Asn Ala Phe
305                 310                 315                 320
Ala Ala Gly Gln Ala Ala Ala Tyr Lys Met Phe Glu Thr Ile Asn Arg
                325                 330                 335
Lys Pro Leu Ile Asp Thr Ser Asp Thr Ser Gly Val Val Leu Glu Asn
            340                 345                 350
Ile Lys Gly Glu Ile Glu Leu Lys Asp Val Tyr Phe Lys Tyr Pro Ala
        355                 360                 365
Arg Pro Asp Val Gln Ile Phe Ser Gly Phe Ser Leu Val Val Pro Ser
    370                 375                 380
Gly Lys Thr Val Ala Leu Val Gly Gln Ser Gly Ser Gly Lys Ser Thr
385                 390                 395                 400
Val Ile Ser Leu Leu Glu Arg Phe Tyr Asp Pro Glu Ala Gly Glu Val
                405                 410                 415
Leu Ile Asp Gly Val Asn Leu Lys Lys Phe Gln Leu Lys Trp Leu Arg
            420                 425                 430
Gln Gln Met Gly Leu Val Ser Gln Glu Pro Ile Leu Phe Ala Thr Thr
        435                 440                 445
```

-continued

```
Ile Lys Glu Asn Ile Ser Tyr Gly Lys Glu Asn Ala Thr Glu Asp Glu
    450                 455                 460
Ile Lys Thr Ala Ile Glu Leu Ala Asn Ala Ala Lys Phe Leu Asp Lys
465                 470                 475                 480
Leu Pro Gln Gly Leu Asp Thr Met Val Gly Glu His Gly Thr Gln Leu
                485                 490                 495
Ser Gly Gly Gln Lys Gln Arg Leu Ala Ile Ala Arg Ala Ile Leu Lys
            500                 505                 510
Asn Pro Arg Ile Leu Leu Leu Asp Glu Ala Thr Ser Ala Leu Asp Ala
        515                 520                 525
Glu Ser Glu Arg Ile Val Gln Glu Ala Leu Glu Lys Val Met Ala Asn
    530                 535                 540
Arg Thr Thr Val Val Ala His Arg Leu Thr Thr Ile Arg Asn Ala
545                 550                 555                 560
Asp Leu Ile Ala Val Val Asn Ala Gly Lys Leu Leu Glu Lys Gly Thr
                565                 570                 575
His Thr Glu Leu Ile Gln Asp Pro Asn Gly Ala Tyr Ser Gln Leu Val
            580                 585                 590
Arg Met Gln Gly Gly Asn Arg Glu Glu Asn Met Lys Asn Ile Asp
        595                 600                 605
Leu Glu Lys Val Asp Leu Thr Thr Asp Phe Asp Asn Asn Leu Ser Arg
    610                 615                 620
Ser Ser Ser Gln Arg Leu Ser Ala Met Arg Arg Ser Thr Ser Gln Gly
625                 630                 635                 640
Ser Ser Arg His Ser Phe Thr Leu Asn Tyr Thr Val Pro Gly Leu Ile
                645                 650                 655
Gly Ile His Glu Ala Glu Ile Gly Asn Glu Asn Lys Gly Lys Glu Asp
            660                 665                 670
Lys Gly Ser Ser Lys Lys Arg Lys Lys Val Ser Ile Arg Arg Leu Ala
        675                 680                 685
Gly Leu Asn Lys Pro Glu Leu Pro Tyr Leu Leu Leu Gly Ser Leu Ala
    690                 695                 700
Ala Ile Ile His Gly Leu Ile Phe Pro Leu Phe Gly Leu Leu Leu Ser
705                 710                 715                 720
Thr Ala Ile Lys Ile Phe Phe Tyr Pro Pro Gln Lys Leu Arg Ile Glu
                725                 730                 735
Ser Arg Phe Trp Ala Leu Met Tyr Phe Gly Leu Gly Val Val Thr Leu
            740                 745                 750
Leu Val Val Pro Phe Gln Asn Tyr Leu Phe Gly Val Ala Gly Gly Lys
        755                 760                 765
Leu Ile Glu Arg Ile Arg Ser Leu Thr Phe Lys Lys Val Val His Gln
    770                 775                 780
Glu Ile Ser Trp Phe Asp Asp Pro Ala His Ser Ser Gly Ala Ile Gly
785                 790                 795                 800
Ala Arg Leu Ser Thr Asp Ala Ser Thr Val Arg Thr Leu Met Gly Asp
                805                 810                 815
Ala Leu Ala Leu Ile Val Gln Asn Ile Ala Thr Val Val Ala Gly Leu
            820                 825                 830
Val Ile Ala Phe Thr Ala Asn Trp Ile Leu Ala Leu Ile Ile Leu Leu
        835                 840                 845
Val Met Pro Leu Ile Gly Val Gln Gly Phe Leu Gln Thr Lys Met Tyr
    850                 855                 860
```

```
Lys Gly Phe Ser Ala Asp Ala Lys Val Met Tyr Glu Glu Ala Ser Gln
865                 870                 875                 880

Ile Ala Asn Asp Ala Val Gly Ser Ile Arg Thr Val Ala Ser Phe Cys
            885                 890                 895

Ala Glu Glu Lys Val Met Asp Met Tyr Gln Lys Lys Cys Glu Gly Pro
        900                 905                 910

Met Lys Gln Gly Val Lys Ile Gly Ile Val Ser Gly Ala Ser Leu Gly
    915                 920                 925

Phe Gly Ser Phe Ile Leu Tyr Cys Thr Asn Ala Phe Cys Phe Tyr Ile
930                 935                 940

Gly Ser Val Leu Ile Gln His Gly Leu Ala Ser Phe Gly Gln Val Phe
945                 950                 955                 960

Lys Val Phe Phe Ala Leu Thr Leu Ser Ala Val Gly Val Thr Gln Ser
                965                 970                 975

Thr Gly Met Ala Pro Asp Ala Asn Lys Ala Lys Asp Ser Ile Ala Ser
            980                 985                 990

Ile Phe Asp Ile Leu Asp Arg Lys Pro Glu Ile Asp Ser Ser Ser Asp
        995                 1000                1005

Val Gly Thr Thr Leu Ala Ala Val Arg Gly Asp Ile Glu Phe Lys His
    1010                1015                1020

Val Ser Tyr Arg Tyr Ala Thr Arg Pro Asp Val Gln Ile Phe Lys Asp
1025                1030                1035                1040

Leu Cys Leu Thr Ile Pro Ser Gly Lys Thr Val Ala Leu Val Gly Glu
                1045                1050                1055

Ser Gly Ser Gly Lys Ser Thr Val Ile Ser Leu Ile Glu Arg Phe Tyr
            1060                1065                1070

Asn Pro Glu Ser Gly Ser Ile Tyr Leu Asp Gly Val Glu Ile Arg Gln
        1075                1080                1085

Phe Lys Ile Ser Trp Leu Arg Gln Gln Met Gly Leu Val Ser Gln Glu
    1090                1095                1100

Pro Val Leu Phe Asn Glu Thr Ile Arg Asp Asn Ile Ala Tyr Ser Arg
1105                1110                1115                1120

Gln Gly His Ala Thr Glu Glu Glu Ile Ile Glu Ala Ala Lys Ser Ala
                1125                1130                1135

Asn Ala His Asn Phe Ile Ser Ser Leu Pro Gln Gly Tyr Asp Thr Ser
            1140                1145                1150

Val Gly Glu Arg Gly Ile Gln Leu Ser Gly Gly Gln Lys Gln Arg Ile
        1155                1160                1165

Ala Ile Ala Arg Ala Ile Leu Lys Asp Pro Lys Ile Leu Leu Leu Asp
    1170                1175                1180

Glu Ala Thr Ser Ala Leu Asp Ala Glu Ser Glu Arg Ile Val Gln Glu
1185                1190                1195                1200

Ala Leu Asp Arg Val Met Val Asn Arg Thr Thr Val Val Ala His
                1205                1210                1215

Arg Leu Thr Thr Ile Lys Gly Ala Asp Val Ile Ala Val Val Lys Asn
            1220                1225                1230

Gly Val Ile Ala Glu Glu Gly Arg His Asp Ala Leu Met Asn Ile Lys
        1235                1240                1245

Asp Gly Val Tyr Ala Ser Leu Val Ala Leu His Met Thr Ser Ala
    1250                1255                1260

<210> SEQ ID NO 95
<211> LENGTH: 500
<212> TYPE: PRT
```

<213> ORGANISM: Nicotiana tabacum

<400> SEQUENCE: 95

```
Met Gly Lys Ser Met Lys Ser Glu Val Glu Gln Pro Leu Leu Ile Ala
1               5                   10                  15

Ala His Gly Gly Ser Ser Glu Leu Glu Glu Val Leu Ser Asp Thr Gln
            20                  25                  30

Leu Pro Tyr Phe Arg Arg Leu Arg Tyr Ala Ser Trp Ile Glu Phe Gln
        35                  40                  45

Leu Leu Tyr Arg Leu Ala Ala Pro Ser Val Ala Val Tyr Met Ile Asn
50                  55                  60

Asn Ala Met Ser Met Ser Thr Arg Ile Phe Ser Gly Gln Leu Gly Asn
65                  70                  75                  80

Leu Gln Leu Ala Ala Ala Ser Leu Gly Asn Gln Gly Ile Gln Leu Phe
                85                  90                  95

Ala Tyr Gly Leu Met Leu Gly Met Gly Ser Ala Val Glu Thr Leu Cys
            100                 105                 110

Gly Gln Ala Tyr Gly Ala His Arg Tyr Glu Met Leu Gly Val Tyr Leu
        115                 120                 125

Gln Arg Ala Thr Val Val Leu Ser Val Thr Gly Ile Pro Leu Thr Val
130                 135                 140

Val Tyr Leu Phe Ser Lys Asn Ile Leu Leu Ala Leu Gly Glu Ser Lys
145                 150                 155                 160

Leu Val Ala Ser Ala Ala Ala Val Phe Val Tyr Gly Leu Ile Pro Gln
                165                 170                 175

Ile Phe Ala Tyr Ala Val Asn Phe Pro Ile Gln Lys Phe Leu Gln Ala
            180                 185                 190

Gln Ser Ile Val Ala Pro Ser Ala Phe Ile Ser Leu Gly Thr Leu Phe
        195                 200                 205

Val His Ile Leu Leu Ser Trp Val Val Tyr Lys Ile Gly Leu Gly
210                 215                 220

Leu Leu Gly Ala Ser Leu Val Leu Ser Phe Ser Trp Trp Ile Ile Val
225                 230                 235                 240

Val Ala Gln Phe Ile Tyr Ile Ile Lys Ser Glu Arg Cys Lys Ala Thr
                245                 250                 255

Trp Ala Gly Phe Arg Trp Glu Ala Phe Ser Gly Leu Cys Gln Phe Val
            260                 265                 270

Lys Leu Ser Ala Gly Ser Ala Val Met Leu Cys Leu Glu Thr Trp Tyr
        275                 280                 285

Met Gln Ile Leu Val Leu Leu Ser Gly Leu Leu Lys Asn Pro Glu Ile
290                 295                 300

Ala Leu Ala Ser Ile Ser Val Cys Leu Ala Val Asn Gly Leu Met Phe
305                 310                 315                 320

Met Val Ala Val Gly Phe Asn Ala Ala Ala Ser Val Arg Val Ser Asn
                325                 330                 335

Glu Leu Gly Ala Ala His Ser Lys Ser Ala Ala Phe Ser Val Phe Met
            340                 345                 350

Val Thr Phe Ile Ser Phe Leu Ile Ala Val Glu Ala Ile Ile Val
        355                 360                 365

Leu Ser Leu Arg Asn Val Ile Ser Tyr Ala Phe Thr Glu Gly Glu Ile
370                 375                 380

Val Ala Lys Glu Val Ser Glu Leu Cys Pro Phe Leu Ala Val Thr Leu
385                 390                 395                 400
```

```
Ile Leu Asn Gly Ile Gln Pro Val Leu Ser Gly Val Ala Val Gly Cys
                405                 410                 415

Gly Trp Gln Ala Phe Val Ala Tyr Val Asn Val Gly Cys Tyr Tyr Gly
            420                 425                 430

Val Gly Ile Pro Leu Gly Cys Leu Leu Gly Phe Lys Phe Asp Leu Gly
            435                 440                 445

Ala Lys Gly Ile Trp Thr Gly Met Ile Gly Gly Thr Val Met Gln Thr
        450                 455                 460

Val Ile Leu Leu Trp Val Thr Phe Arg Thr Asp Trp Asn Lys Lys Val
465                 470                 475                 480

Glu Cys Ala Lys Lys Arg Leu Asp Lys Trp Glu Asn Leu Lys Gly Pro
                485                 490                 495

Leu Asn Lys Glu
            500

<210> SEQ ID NO 96
<211> LENGTH: 1227
<212> TYPE: PRT
<213> ORGANISM: Solanum lycopersicum

<400> SEQUENCE: 96

Met Ser Ser Ser Thr Glu Lys Ala Phe Glu Asn Lys Asn Lys Asn Ser
1               5                   10                  15

Ile Gly Ile Ile Phe Arg Tyr Ala Asp Gly Lys Asp Ile Leu Leu Met
            20                  25                  30

Phe Leu Gly Thr Ile Gly Ala Ile Gly Asp Gly Ile Ser Thr Asn Cys
        35                  40                  45

Leu Leu Val Tyr Val Ser Gln Leu Phe Asn Ser Leu Gly Tyr Gly Lys
50                  55                  60

Thr Gln Gln Asn Asp His Asn Phe Met Glu Gln Ile Glu Lys Cys Ser
65                  70                  75                  80

Leu Tyr Phe Val Leu Leu Gly Leu Gly Val Met Val Val Ala Phe Met
                85                  90                  95

Glu Gly Tyr Cys Trp Ser Lys Thr Ser Glu Arg Gln Val Leu Lys Ile
            100                 105                 110

Arg Tyr Lys Tyr Leu Glu Ala Ile Leu Arg Gln Glu Val Gly Phe Phe
        115                 120                 125

Asp Ser Gln Glu Ala Thr Thr Ser Glu Ile Thr Asn Gly Ile Ser Lys
    130                 135                 140

Asp Thr Ser Leu Ile Gln Glu Val Leu Ser Glu Lys Val Pro Leu Phe
145                 150                 155                 160

Val Met His Thr Thr Val Phe Ile Ser Gly Val Val Phe Ser Ala Tyr
                165                 170                 175

Phe Ser Trp Arg Leu Ala Ile Val Ala Leu Pro Thr Ile Phe Leu Leu
            180                 185                 190

Ile Ile Pro Gly Leu Ile Tyr Gly Lys Tyr Leu Leu Tyr Leu Ser Gly
        195                 200                 205

Lys Ser Phe Lys Glu Tyr Ser Lys Ala Asn Gly Ile Val Glu Gln Ala
    210                 215                 220

Leu Ser Ser Ile Lys Thr Ile Tyr Ser Phe Thr Ala Glu Lys Ser Val
225                 230                 235                 240

Ile Glu Arg Tyr Ser Leu Ile Leu Asp Gly Thr Ile Lys Leu Gly Met
                245                 250                 255

Lys Gln Gly Ile Ala Lys Gly Leu Ala Val Gly Ser Thr Gly Leu Ser
            260                 265                 270
```

```
Phe Ala Ile Trp Ala Leu Leu Ala Trp Tyr Gly Ser His Leu Ile Met
            275                 280                 285

His Asn Gly Glu Ser Gly Gly Arg Ile Tyr Ala Ala Gly Val Ser Phe
    290                 295                 300

Val Leu Gly Gly Leu Ser Leu Gly Met Ala Leu Pro Glu Val Lys Tyr
305                 310                 315                 320

Phe Thr Glu Ala Ser Val Ala Ala Ser Arg Ile Phe Asp Arg Ile Asp
                325                 330                 335

Arg Val Pro Glu Ile Asp Gly Glu Asp Thr Arg Gly Leu Val Leu Glu
            340                 345                 350

Asp Ile Arg Gly Glu Val Glu Phe Arg Asn Val Lys Phe Thr Tyr Pro
            355                 360                 365

Ser Arg Pro Asp Thr Val Val Leu Lys Asp Phe Asn Leu Lys Ile Glu
    370                 375                 380

Ala Gly Lys Thr Val Ala Leu Val Gly Ser Ser Gly Ser Gly Lys Ser
385                 390                 395                 400

Thr Ala Ile Ala Leu Ile Gln Arg Phe Tyr Asp Ala Ser Ala Gly Ala
                405                 410                 415

Ile Cys Ile Asp Ser Val Glu Ile Lys Ser Leu Gln Leu Lys Trp Leu
            420                 425                 430

Arg Gly Lys Met Gly Leu Val Ser Gln Glu Asn Ala Leu Phe Gly Thr
            435                 440                 445

Ser Ile Lys Glu Asn Ile Met Phe Gly Lys Val Asp Ala Thr Met Asp
    450                 455                 460

Glu Val Val Ala Ala Ala Met Thr Ala Asn Ala His Asn Phe Ile Thr
465                 470                 475                 480

Gln Leu Pro Glu Gly Tyr Glu Thr Lys Ile Gly Glu Arg Gly Ala Leu
                485                 490                 495

Leu Ser Gly Gly Gln Lys Gln Arg Ile Ala Ile Ala Arg Ala Ile Ile
            500                 505                 510

Lys Asn Pro Val Ile Leu Leu Leu Asp Glu Ala Thr Ser Ala Leu Asp
    515                 520                 525

Ser Glu Ser Glu Thr Leu Val Gln Asn Ala Leu Asp Gln Ala Ile Val
    530                 535                 540

Gly Arg Thr Thr Leu Val Val Ala His Lys Leu Ser Thr Val Arg Asn
545                 550                 555                 560

Ala Asp Leu Ile Ala Val Val Ser Asn Gly Cys Ile Ser Glu Leu Gly
                565                 570                 575

Ala His Tyr Glu Leu Met Glu Lys Asp Gly Gln Tyr Ala Arg Leu Ala
            580                 585                 590

Lys Phe Gln Arg Gln Phe Ser Ser Ile Asp Gln Glu Gln Ser Ala Glu
            595                 600                 605

Pro Arg Ile Ser Ser Val Ala Arg Ser Ser Ala Gly Met Arg Ala Ser
    610                 615                 620

Pro Ala Val Ser Ala Ser Pro Leu Arg Ile Glu Asp Ser Pro Ile Gln
625                 630                 635                 640

Ala Ser Pro His Pro Pro Ser Phe Thr Arg Leu Leu Ser Leu Asn
                645                 650                 655

Leu Pro Glu Trp Lys Gln Gly Ile Ile Gly Ile Leu Ser Ala Ile Ala
            660                 665                 670

Phe Gly Ser Val Gln Pro Val Tyr Ala Leu Thr Ile Gly Gly Met Ile
            675                 680                 685
```

```
Ser Ala Phe Tyr Ser Pro Ser His Glu Glu Met Gln Ser Arg Ile Gln
690                 695                 700

Lys Tyr Cys Met Ile Phe Ile Ile Leu Cys Leu Val Ser Val Val Leu
705                 710                 715                 720

Asn Leu Cys Gln His Tyr Asn Phe Ala Tyr Met Gly Glu Arg Leu Thr
                725                 730                 735

Arg Arg Ile Arg Leu Gln Met Leu Glu Lys Ile Leu Ser Phe Glu Ala
            740                 745                 750

Ala Trp Phe Asp Glu Gln Asn Ser Ser Gly Ala Leu Cys Cys Arg
                755                 760                 765

Leu Ser Asn Glu Ala Ala Met Val Lys Ser Leu Val Ala Asp Arg Val
770                 775                 780

Ser Leu Leu Val Gln Ser Thr Ser Ala Val Thr Val Ala Met Val Met
785                 790                 795                 800

Gly Leu Ile Val Ala Trp Lys Leu Ala Leu Val Met Ile Val Val Gln
                805                 810                 815

Pro Leu Thr Ile Leu Cys Phe Tyr Thr Arg Lys Val Leu Leu Ser Thr
            820                 825                 830

Met Thr Ala Lys Phe Val Lys Ala Gln Cys Arg Ser Thr Gln Ile Ala
            835                 840                 845

Val Glu Ala Val Tyr Asn His Arg Ile Val Thr Ser Phe Gly Ser Ile
850                 855                 860

Asp Lys Val Leu Asp Ile Phe Asp Glu Ala Gln Asp Glu Pro Arg Lys
865                 870                 875                 880

Glu Ala Arg Lys Lys Ser Trp Leu Ala Gly Ile Gly Ile Gly Ser Ala
                885                 890                 895

Gln Gly Leu Thr Phe Ile Cys Trp Ala Leu Asp Phe Trp Tyr Gly Gly
            900                 905                 910

Lys Leu Val Asn Ala Gly Glu Ile Ser Ala Ala Asp Val Phe Lys Thr
            915                 920                 925

Phe Phe Ile Leu Val Ser Thr Gly Lys Val Ile Ala Glu Ala Gly Ser
930                 935                 940

Met Thr Ser Asp Leu Ala Lys Gly Ser Thr Val Val Ala Ser Ile Phe
945                 950                 955                 960

Ser Ile Leu Asp Arg Lys Ser Leu Ile Glu Gly Ser Asn Glu Ala Lys
                965                 970                 975

Asn Asn Ser Met Gly Thr Lys Met Thr Gly Arg Ile Glu Met Lys Lys
            980                 985                 990

Val Asp Phe Ala Tyr Pro Ser Arg Pro Asp Arg Leu Val Leu His Glu
            995                 1000                1005

Phe Ser Leu Glu Val Lys Ala Gly Thr Ser Ile Gly Leu Val Gly Lys
1010                1015                1020

Ser Gly Cys Gly Lys Ser Thr Val Ile Ala Leu Ile Gln Arg Phe Tyr
1025                1030                1035                1040

Asp Ala Asp Lys Gly Ser Leu Lys Ile Asp Gly Met Asp Ile Arg Leu
                1045                1050                1055

Leu Asp Leu Gly Trp Tyr Arg Arg Asn Met Ala Leu Val Ser Gln Glu
            1060                1065                1070

Pro Val Ile Tyr Ser Gly Ser Ile Arg Glu Asn Ile Leu Phe Gly Lys
            1075                1080                1085

Leu Asn Ala Ser Glu Asn Glu Val Val Glu Ala Ala Lys Ala Ala Asn
            1090                1095                1100

Ala His Glu Phe Ile Ser Ser Leu Lys Asn Gly Tyr Glu Thr Glu Cys
```

```
                1105                1110                1115                1120
Gly Asp Arg Gly Val Thr Ile Ser Gly Gly Gln Lys Gln Arg Ile Ala
                    1125                1130                1135
Ile Ala Arg Ala Ile Ile Arg Asn Pro Ser Ile Leu Leu Leu Asp Glu
            1140                1145                1150
Ala Thr Ser Ala Leu Asp Val Gln Ser Glu Gln Leu Val Gln Glu Ala
            1155                1160                1165
Leu Asp Gln Leu Met Val Gly Arg Thr Thr Val Val Ala His Arg
    1170                1175                1180
Leu Asn Thr Ile Arg Asn Leu Asp Ser Ile Ala Phe Ile Ser Glu Gly
1185                1190                1195                1200
Lys Val Leu Glu Lys Gly Thr Tyr Ser Tyr Leu Lys Asp Lys Arg Gly
                1205                1210                1215
Ala Phe Phe Asn Leu Val Asn Leu Gln Ser Thr
            1220                1225

<210> SEQ ID NO 97
<211> LENGTH: 276
<212> TYPE: PRT
<213> ORGANISM: Solanum lycopersicum

<400> SEQUENCE: 97

Met Thr Ser Val Ser His Thr His Pro Leu Val Tyr Thr Phe Gly Ile
1               5                   10                  15
Leu Gly Asn Leu Val Ser Phe Met Val Phe Ile Ala Pro Val Pro Thr
                20                  25                  30
Phe Tyr Arg Ile Val Lys Lys Lys Ser Ser Glu Gly Phe His Ser Leu
            35                  40                  45
Pro Tyr Val Val Gly Leu Phe Ser Ala Met Leu Trp Ile Tyr Tyr Ala
    50                  55                  60
Met Val Lys Thr Asn Val Thr Leu Leu Ile Thr Ile Asn Ser Phe Gly
65                  70                  75                  80
Cys Ile Ala Glu Thr Ile Tyr Val Ala Ile Tyr Phe Thr Tyr Ala Thr
                85                  90                  95
Lys Lys Ala Arg Met Lys Thr Leu Gly Leu Val Leu Leu Leu Asn Phe
            100                 105                 110
Gly Val Phe Gly Leu Ile Leu Phe Leu Thr Gln Ile Leu Cys Gln Gly
        115                 120                 125
Thr Lys Arg Ala Glu Val Ile Gly Trp Ile Cys Met Ala Phe Ser Ile
    130                 135                 140
Ser Val Phe Val Ala Pro Leu Ser Ile Met Gly Arg Val Ile Arg Thr
145                 150                 155                 160
Lys Ser Val Glu Phe Met Pro Phe Asn Leu Ser Leu Ala Leu Thr Val
                165                 170                 175
Ser Ala Val Met Trp Phe Leu Tyr Gly Leu Leu Leu Lys Asp Val Tyr
            180                 185                 190
Val Ala Val Pro Asn Ile Pro Gly Met Ile Leu Gly Val Leu Gln Met
        195                 200                 205
Ile Leu Tyr Gly Ile Tyr Arg Asn Ser Lys Ser Asn Asn Val Ala Thr
    210                 215                 220
Glu Lys Glu Leu Pro Ile Val Val Lys Val Asp Gln Glu Gln Pro Thr
225                 230                 235                 240
Lys Val Asn Ser Glu Val Tyr Pro Val Asn Ile Ser Ser Leu Asp Ser
                245                 250                 255
```

```
Glu Asn Gly Glu Ala Lys Asp Gly Lys Asn Leu Gln Asp Pro Gln Met
            260                 265                 270

Asn Ser Gln Val
        275
```